(12) United States Patent
Villongco

(10) Patent No.: US 12,048,488 B2
(45) Date of Patent: Jul. 30, 2024

(54) AUGMENTATION OF IMAGES WITH SOURCE LOCATIONS

(71) Applicant: Vektor Medical, Inc., Carlsbad, CA (US)

(72) Inventor: Christopher Villongco, Carlsbad, CA (US)

(73) Assignee: VEKTOR MEDICAL, INC., Carlsbad, CA (US)

( * ) Notice: Subject to any disclaimer, the term of this patent is extended or adjusted under 35 U.S.C. 154(b) by 488 days.

(21) Appl. No.: 17/318,245

(22) Filed: May 12, 2021

(65) Prior Publication Data
US 2021/0259610 A1 Aug. 26, 2021

Related U.S. Application Data

(63) Continuation of application No. PCT/US2019/058217, filed on Oct. 25, 2019, which is a continuation-in-part of application No. 16/247,463, filed on Jan. 14, 2019, now Pat. No. 11,259,871, and a continuation-in-part of application No. 16/206,005, filed on Nov. 30, 2018, now Pat. No. 10,860,754.

(60) Provisional application No. 62/760,561, filed on Nov. 13, 2018.

(51) Int. Cl.
*A61B 34/10* (2016.01)
*A61B 5/00* (2006.01)
(Continued)

(52) U.S. Cl.
CPC .......... *A61B 34/10* (2016.02); *A61B 5/0036* (2018.08); *A61B 5/287* (2021.01); *A61B 5/308* (2021.01);
(Continued)

(58) Field of Classification Search
CPC .......... A61B 5/361; A61B 5/363; A61B 5/366
See application file for complete search history.

(56) References Cited

U.S. PATENT DOCUMENTS 4,352,163 A 9/1982 Schultz et al.
5,458,116 A 10/1995 Egler
(Continued)

FOREIGN PATENT DOCUMENTS

CN 103829941 A 6/2014
CN 104680548 A 6/2015
(Continued)

OTHER PUBLICATIONS

Acharya Ur, Fujita H, Lih OS, Hagiwara Y, Tan JH, Adam M. Automated detection of arrhythmias using different intervals of tachycardia ECG segments with convolutional neural network. Information sciences. Sep. 1, 2017 ;405:81-90.
(Continued)

*Primary Examiner* — Oommen Jacob
(74) *Attorney, Agent, or Firm* — Perkins Coie LLP

(57) ABSTRACT

Systems are provided for generating data representing electromagnetic states of a heart for medical, scientific, research, and/or engineering purposes. The systems generate the data based on source configurations such as dimensions of, and scar or fibrosis or pro-arrhythmic substrate location within, a heart and a computational model of the electromagnetic output of the heart. The systems may dynamically generate the source configurations to provide representative source configurations that may be found in a population. For each source configuration of the electromagnetic source, the systems run a simulation of the functioning of the heart to generate modeled electromagnetic output (e.g., an electromagnetic mesh for each simulation step with a voltage at each point of the electromagnetic mesh) for that source configuration. The systems may generate a cardiogram for each source configuration from the modeled electromagnetic output of that source configuration for use in predicting the source location of an arrhythmia.

21 Claims, 71 Drawing Sheets

(51) Int. Cl.
*A61B 5/287* (2021.01)
*A61B 5/308* (2021.01)
*A61B 5/319* (2021.01)
*A61B 5/35* (2021.01)
*A61B 5/361* (2021.01)
*A61B 5/363* (2021.01)
*A61B 5/366* (2021.01)
*A61B 18/00* (2006.01)
*A61B 18/14* (2006.01)
*A61B 34/20* (2016.01)
*G06N 3/08* (2023.01)
*G16H 30/20* (2018.01)

(52) U.S. Cl.
CPC ............... *A61B 5/319* (2021.01); *A61B 5/35* (2021.01); *A61B 5/6858* (2013.01); *A61B 5/7203* (2013.01); *A61B 5/7267* (2013.01); *A61B 18/1492* (2013.01); *A61B 34/20* (2016.02); *G06N 3/08* (2013.01); *G16H 30/20* (2018.01); *A61B 5/361* (2021.01); *A61B 5/363* (2021.01); *A61B 5/366* (2021.01); *A61B 5/4836* (2013.01); *A61B 5/7253* (2013.01); *A61B 2018/00357* (2013.01); *A61B 2018/00577* (2013.01); *A61B 2018/00791* (2013.01); *A61B 2018/00904* (2013.01); *A61B 2034/107* (2016.02); *A61B 2034/2051* (2016.02)

(56) References Cited

U.S. PATENT DOCUMENTS

| | | |
|---|---|---|
| 5,596,634 A | 1/1997 | Fernandez et al. |
| 5,601,084 A | 2/1997 | Sheehan |
| 5,803,084 A | 9/1998 | Olson |
| 5,891,132 A | 4/1999 | Hohla |
| 6,269,336 B1 | 7/2001 | Ladd et al. |
| 6,292,783 B1 | 9/2001 | Rohler et al. |
| 6,324,513 B1 | 11/2001 | Nagai et al. |
| 6,370,412 B1 | 4/2002 | Armoundas et al. |
| 6,567,805 B1 | 5/2003 | Johnson et al. |
| 6,895,084 B1 | 5/2005 | Saylor et al. |
| 6,931,273 B2 | 8/2005 | Groenewegen et al. |
| 7,010,347 B2 | 3/2006 | Schecter |
| 7,286,866 B2 | 10/2007 | Okerlund et al. |
| 7,424,137 B2 | 9/2008 | Badilini et al. |
| 8,224,640 B2 | 7/2012 | Sharma et al. |
| 8,521,266 B2 | 8/2013 | Narayan |
| 8,838,203 B2 | 9/2014 | Van Dam et al. |
| 8,849,389 B2 | 9/2014 | Anderson et al. |
| 9,014,795 B1 | 4/2015 | Yang |
| 9,129,053 B2 | 9/2015 | Mansi et al. |
| 9,277,970 B2 | 3/2016 | Mansi et al. |
| 9,320,126 B2 | 4/2016 | Valcore, Jr. |
| 9,706,935 B2 | 7/2017 | Spector |
| 9,842,725 B2 | 12/2017 | Valcore, Jr. |
| 9,948,642 B2 | 4/2018 | Wang |
| 10,039,454 B2 | 8/2018 | Sapp, Jr. et al. |
| 10,311,978 B2 | 6/2019 | Mansi et al. |
| 10,319,144 B2 | 6/2019 | Krummen et al. |
| 10,342,620 B2 | 7/2019 | Kiraly et al. |
| 10,363,100 B2 | 7/2019 | Trayanova et al. |
| 10,556,113 B2 | 2/2020 | Villongco |
| 10,617,314 B1 | 4/2020 | Villongco |
| 10,713,790 B2 | 7/2020 | Adler |
| 10,860,754 B2 | 12/2020 | Villongco |
| 10,861,246 B2 | 12/2020 | Voth |
| 10,912,476 B2 | 2/2021 | Spector |
| 10,952,794 B2 | 3/2021 | Villongco |
| 10,998,101 B1 | 5/2021 | Tran |
| 11,065,060 B2 | 7/2021 | Villongco |
| 11,259,871 B2 | 3/2022 | Villongco |
| 11,338,131 B1 | 5/2022 | Krummen |
| 2001/0049688 A1 | 12/2001 | Fratkina et al. |
| 2002/0010679 A1 | 1/2002 | Felsher |
| 2002/0154153 A1 | 10/2002 | Messinger |
| 2002/0188599 A1 | 12/2002 | McGreevy |
| 2003/0182124 A1 | 9/2003 | Khan |
| 2004/0059237 A1* | 3/2004 | Narayan ............ A61B 5/35 607/9 |
| 2004/0083092 A1 | 4/2004 | Valles |
| 2004/0176697 A1 | 9/2004 | Kappenberger |
| 2007/0031019 A1 | 2/2007 | Lesage |
| 2007/0032733 A1 | 2/2007 | Burton |
| 2007/0060829 A1 | 3/2007 | Pappone |
| 2007/0219452 A1 | 9/2007 | Cohen et al. |
| 2008/0027908 A1* | 1/2008 | Durbeck ............ G06F 16/24568 |
| 2008/0077032 A1 | 3/2008 | Holmes et al. |
| 2008/0140143 A1 | 6/2008 | Ettori |
| 2008/0177192 A1 | 7/2008 | Chen |
| 2008/0205722 A1 | 8/2008 | Schaefer |
| 2008/0234576 A1 | 9/2008 | Gavit-Houdant et al. |
| 2008/0288493 A1 | 11/2008 | Yang et al. |
| 2009/0099468 A1 | 4/2009 | Thiagalingam |
| 2009/0275850 A1 | 11/2009 | Mehendale |
| 2010/0266170 A1 | 10/2010 | Khamene |
| 2011/0028848 A1 | 2/2011 | Shaquer |
| 2011/0118590 A1 | 5/2011 | Zhang |
| 2011/0251505 A1 | 10/2011 | Narayan |
| 2011/0307231 A1 | 12/2011 | Kirchner |
| 2012/0173576 A1 | 7/2012 | Gillam et al. |
| 2013/0006131 A1 | 1/2013 | Narayan |
| 2013/0096394 A1 | 4/2013 | Gupta |
| 2013/0131529 A1 | 5/2013 | Jia |
| 2013/0131629 A1 | 5/2013 | Jia |
| 2013/0150742 A1 | 6/2013 | Briggs |
| 2013/0197881 A1 | 8/2013 | Mansi et al. |
| 2013/0268284 A1 | 10/2013 | Heck |
| 2013/0304445 A1 | 11/2013 | Iwamura et al. |
| 2014/0005562 A1 | 1/2014 | Bunch |
| 2014/0088943 A1 | 3/2014 | Trayanova et al. |
| 2014/0107510 A1 | 4/2014 | Bogun et al. |
| 2014/0107511 A1 | 4/2014 | Banet |
| 2014/0122048 A1 | 5/2014 | Vadakkumpadan et al. |
| 2014/0200575 A1 | 7/2014 | Spector |
| 2014/0276152 A1 | 9/2014 | Narayan |
| 2015/0005652 A1 | 1/2015 | Banet et al. |
| 2015/0057522 A1 | 2/2015 | Nguyen |
| 2015/0216432 A1 | 8/2015 | Yang |
| 2015/0216434 A1 | 8/2015 | Ghosh |
| 2015/0216438 A1 | 8/2015 | Bokan et al. |
| 2015/0294082 A1 | 10/2015 | Passerini et al. |
| 2016/0008635 A1 | 1/2016 | Burdette |
| 2016/0038743 A1 | 2/2016 | Foster et al. |
| 2016/0113725 A1 | 4/2016 | Trayanova et al. |
| 2016/0135702 A1 | 5/2016 | Perez |
| 2016/0135706 A1 | 5/2016 | Sullivan |
| 2016/0143553 A1 | 5/2016 | Chien |
| 2016/0192868 A1 | 7/2016 | Levant et al. |
| 2016/0331337 A1 | 11/2016 | Ben-Haim |
| 2017/0027649 A1 | 2/2017 | Kiraly |
| 2017/0061617 A1 | 3/2017 | Cochet |
| 2017/0065195 A1 | 3/2017 | Nguyen |
| 2017/0068796 A1 | 3/2017 | Passerini et al. |
| 2017/0079542 A1 | 3/2017 | Spector |
| 2017/0112401 A1 | 4/2017 | Rapin |
| 2017/0150928 A1 | 6/2017 | del Alamo de Pedro |
| 2017/0156612 A1 | 6/2017 | Relan |
| 2017/0161439 A1 | 6/2017 | Raduchel et al. |
| 2017/0161896 A1 | 6/2017 | Blake, III |
| 2017/0178403 A1* | 6/2017 | Krummen ............ G06T 5/20 |
| 2017/0185740 A1 | 6/2017 | Seegerer |
| 2017/0202421 A1 | 7/2017 | Hwang et al. |
| 2017/0202521 A1 | 7/2017 | Urman et al. |
| 2017/0209698 A1 | 7/2017 | Villongco |
| 2017/0231505 A1 | 8/2017 | Mahajan |
| 2017/0273588 A1 | 9/2017 | He |
| 2017/0027465 A1 | 11/2017 | Blauer |
| 2017/0319089 A1 | 11/2017 | Lou |
| 2017/0319278 A1 | 11/2017 | Trayanova |
| 2017/0330075 A1 | 11/2017 | Tuysuzoglu |
| 2017/0367603 A1 | 12/2017 | Spector |

(56) References Cited

U.S. PATENT DOCUMENTS

| | | |
|---|---|---|
| 2018/0012363 A1 | 1/2018 | Seiler |
| 2018/0020916 A1 | 1/2018 | Ruppersberg |
| 2018/0032689 A1 | 2/2018 | Kiranyaz |
| 2018/0260706 A1 | 9/2018 | Galloway et al. |
| 2018/0279896 A1 | 10/2018 | Ruppersberg |
| 2018/0318606 A1 | 11/2018 | Robinson |
| 2018/0333104 A1 | 11/2018 | Sitek |
| 2019/0038363 A1 | 2/2019 | Adler |
| 2019/0060006 A1 | 2/2019 | Van Dam |
| 2019/0069795 A1 | 3/2019 | Kiranya |
| 2019/0104951 A1 | 4/2019 | Valys |
| 2019/0104958 A1 | 4/2019 | Rappel |
| 2019/0125186 A1 | 5/2019 | Ruppersberg |
| 2019/0216350 A1 | 7/2019 | Sullivan et al. |
| 2019/0223946 A1 | 7/2019 | Coates |
| 2019/0304183 A1 | 10/2019 | Krummen |
| 2019/0328254 A1 | 10/2019 | Villongco |
| 2019/0328257 A1 | 10/2019 | Villongco |
| 2019/0328457 A1 | 10/2019 | Villongco et al. |
| 2019/0328458 A1 | 10/2019 | Shmayahu |
| 2019/0332729 A1 | 10/2019 | Villongco |
| 2019/0333639 A1 | 10/2019 | Villongco |
| 2019/0333641 A1 | 10/2019 | Villongco |
| 2019/0333643 A1 | 10/2019 | Villongco |
| 2020/0324118 A1 | 10/2020 | Garner et al. |
| 2020/0405148 A1 | 12/2020 | Tran |
| 2021/0012868 A1 | 1/2021 | Wolf et al. |
| 2021/0015390 A1 | 1/2021 | Zhou et al. |
| 2021/0205025 A1 | 7/2021 | Erkamp et al. |
| 2021/0219923 A1 | 7/2021 | Eun Young Yang |
| 2021/0259560 A1 | 8/2021 | Venkatraman |
| 2021/0259610 A1* | 8/2021 | Villongco ............. A61B 5/308 |
| 2022/0047237 A1 | 2/2022 | Liu |

FOREIGN PATENT DOCUMENTS

| | | |
|---|---|---|
| CN | 105078440 A | 11/2015 |
| CN | 105194799 A | 12/2015 |
| CN | 105263405 | 1/2016 |
| CN | 106725428 | 5/2017 |
| CN | 113851225 | 12/2021 |
| CN | 114206218 | 3/2022 |
| JP | H4174643 A | 6/1992 |
| JP | H08289877 | 11/1996 |
| JP | 2007517633 A | 7/2007 |
| JP | 2008523929 A | 7/2008 |
| JP | 2012508079 | 4/2012 |
| JP | 2014530074 A | 11/2014 |
| JP | 2015163199 | 9/2015 |
| JP | 2017-140381 | 8/2017 |
| JP | 2018036996 A | 3/2018 |
| JP | 2019155093 A | 9/2019 |
| WO | 2006066324 A1 | 6/2006 |
| WO | 2014097063 A1 | 6/2014 |
| WO | 2015031576 A1 | 3/2015 |
| WO | 2015153832 | 10/2015 |
| WO | 2017112910 A1 | 6/2017 |
| WO | 2018190715 | 10/2018 |
| WO | 2019118640 | 6/2019 |
| WO | 2020101864 | 5/2020 |
| WO | 2020142539 | 7/2020 |

OTHER PUBLICATIONS

Bond et al., XML-BSPM: An XML Format for Storing Body Surface Potential Map Recordings, BMC Medical Informatics and Decision Making 2010, 10:28, http://www.biomedcentra.com/1472-6947/10/28, 27 pages.

Garg, et al., ECG Paper Records Digitization Through Image Processing Techniques, vol. 48, No. 13, Jun. 2012, 4 pages.

Goodfellow, Ian et al., Generative Adversarial Nets, Advances in Neural Information Processing Systems, pp. 2672-2680, 2014.

Halevy, A., Norvig, P., & Pereira, F. (2009). The unreasonable effectiveness of data. IEEE intelligent systems, 24(2), 8-12.

He, Zhenliang et al., Facial Attribute Editing by Only Changing What You Want, IEEE Transactions on Image Processing, 2018.

Hershey S, Chaudhuri S, Ellis DP, Gemmeke JF, Jansen A, Moore RC, Plakal M, Platt D, Saurous RA, Seybold B, Slaney M. CNN architectures for large-scale audio classification. In2017 ieee international conference on acoustics, speech and signal processing (icassp) Mar. 5, 2017 (pp. 131-135). IEEE.

Kiranyaz S, Ince T, Hamila R, Gabbouj M. Convolutional neural networks for patient-specific ECG classification. In2015 37th Annual International Conference of the IEEE Engineering in Medicine and Biology Society (EMBC) Aug. 25, 2015 (pp. 2608-2611 ). IEEE.

Lee H, Kwon H. Going deeper with contextual CNN for hyperspectral image classification. IEEE Transactions on Image Processing, Jul. 11, 2017;26(10):4843-55.

Li D, Zhang J, Zhang Q, Wei X. Classification of ECG signals based on 1 D convolution neural network. In2017 IEEE 19th International Conference on e-Health Networking, Applications and Services (Healthcom) Oct. 12, 2017 (pp. 1-6). IEEE.

Ravichandran et al., Novel Tool for Complete Digitization of Paper Electrocardiography Data, vol. 1, 2013, 7 pages.

Sapp, John L. et al., "Real-Time Localization of Ventricular Tachycardia Origin From the 12-Lead Electrocardiogram" JACC: Clinical Electrophysiology by the Amercian College of Cardiology Foundation, vol. 3, 2017, pp. 687-699.

Sharma, et al., Digitalization of ECG Records, International Journal of Engineering Research and Applications, www.ijera.com, ISSN: 2248-9622, vol. 10, Issue 6, (Series-VIII) Jun. 2020, pp. 01-05.

Shin HC, Roth HR, Gao M, Lu L, Xu Z, Nogues I, Yao J, Mollura D, Summers RM. Deep convolutional neural networks for computer-aided detection: CNN architectures, dataset characteristics and transfer learning. IEEE transactions on medical imaging. Feb. 11, 2016 ;35(5): 1285-98.

Therrien R, Doyle S. Role of training data variability on classifier performance and generalizability. In Medical Imaging 2018: Digital Pathology Mar. 6, 2018 (vol. 10581, p. 1058109). International Society for Optics and Photonics.

Zentara, et al., ECG Signal Coding Methods in Digital Systems, Communication Papers of the Federated Conference on Computer Science and Information Systems,DOI: 10.15439/2018F108, ISSN 2300-5963 ACSIS, vol. 17, pp. 95-102.

Zhu X, Vondrick C, Fowlkes CC, Ramanan D. Do we need more training data?. International Journal of Computer Vision.Aug. 2016;119(1):76-92.

Zubair M, Kim J, Yoon C. An automated ECG beat classification system using convolutional neural networks. In2016 6th international conference on IT convergence and security (ICITCS) Sep. 26, 2016 (pp. 1-5). IEEE.

Andreu et al., "Integration of 3D Electroanatomic Maps and Magnetic Resonance Scar Characterization Into the Navigation System to Guide Ventricular Tachycardia Ablation", Circ Arrhythm Electrophysiol, Oct. 2011, 4(5), pp. 674-683.

Acharya et al., "A deep convolutional neural network model to classify heartbeats," Computers in Biology and Medicine (Oct. 1, 2017) vol. 89, pp. 389-396.

Acharya et al., "Deep convolutional neural network for the automated detection and diagnosis of seizure using EEG signals," Computers in Biology and Medicine (Sep. 1, 2018, Epub Sep. 27, 2017) 100:270-278.

Carrault, Guy, et al. "A model-based approach for learning to identify cardia arrhythias," Joint European Conference on Artificial Intelligence in Medicine and Medicine Decision Making. Springer, Berline Heidelberg, 1999.

Carrualt, Guy, et al. "Temporal abstraction and inductive logic programming for arrhythima recognition from electrocardiograms." Artificial intelligence in medicine 28.3 (2003): 231-263.

Cobb, Leonard A., et al. "Changing incidence of out-of-hospital ventricular fibrillation, 1980-2000." Jama 288.23 (2002): 3008-3013.

Cuculich, Phillip S. et al., "Noninvasive Cardiac Radiation for Ablation of Ventricular Tachycardia" New England Journal of Medicine, 377; 24, pp. 2325-2336, Dec. 14, 2017.

(56) References Cited

OTHER PUBLICATIONS

Dandu Ravi Varma, "Managing DICOM images: Tips and tricks for the radiologist", Indian J Radiol Imaging., Jan.-Mar. 2012; 22(1), pp. 4-13.
Extended European Search Report issued in European Patent Application No. 19215701.4 and dated Apr. 17, 2020, 9 pages.
Extended European Search Report issued in European Patent Application No. 19792821.1 and dated Mar. 15, 2021. 10 pages.
Frank, Ernest, "An Accurate, Clinically Practical System for Spatial Vectorcardiography," American Heart Association, Inc., downloaded from http://circ.ahajournals.org/ at Cons California Dig Lib on Mar. 12, 2014.
Gonzales, Matthew J., et al. "Structural contributions to fibrillatory rotors in a patient-derived computational model of the atria." EP Europace 16.suppl 4 (2014): iv3-iv10.
Graham, Adam J. et al., "Evaluation of ECG Imaging to Map Haemodynamically Stable and Unstable Ventricular Arrhythmias" downloaded from http://ahajournals.org on Jan. 22, 2020.
Hren, Rok, et al. "Value of simulated body surface potential maps as templates in localizing sites of ectopic activation for radiofrequency ablation" Physiol. Meas. 18 (1997) 373-400. Mar. 7, 1997.
International Search Report and Written Opinion issued for PCT/US16/68449 mailed on Mar. 29, 2017.
International Search Report and Written Opinion issued for PCT/US2019/029181 mailed Sep. 16, 2019.
International Search Report and Written Opinion issued for PCT/US2019/029184 mailed Sep. 24, 2019.
International Search Report and Written Opinion issued for PCT/US2019/058217 mailed Feb. 7, 2020, 9 pages.
International Search Report and Written Opinion issued for PCT/US2019/069136 mailed May 11, 2020, 13 pages.
International Search Report and Written Opinion issued in PCT/US2020/036754 mailed Oct. 15, 2020, 13 pages.
International Searching Authority, International Search Report and Written Opinion, PCT Patent Application PCT/US2021/057616, mailed Jan. 28, 2022, 9 pages.
Jacquemet, V., "Lessons from Computer Simulation of Ablation of Atrial Fibrillation", J Physiol. 594(9): 2417-2430, May 1, 2016.
Kiranyaz et al., Real-time patient-specific EDG classification by 1-D convolutional neural networks, IEEE Transactions on Biomedical Engineering (Mar. 2016) 63:664-675.
Kors, J.A., et al., "Recontruction of the Frank vectorcardiogram from standard electrocardiogramads: diagnostic comparison of different methods," European Heart Journal, vol. 11, Issue 12, Dec. 1, 1990, pp. 1083-1092.
Krishnamurthy, Adarsh, et al. "CRT Response is Greater in Patients With Larger Fraction of the Myocardium Performing Negative Regional Work." Circulation 128.Suppl 22 (2013): A11135-A11135, Abstract only.
Krishnamurthy, Adarsh, et al. "Patient-specific models of cardiac biomechanics." Journal of computational physics 244 (2013): 4-21.
Krummen, David E., et al. "Rotor stability separates sustained ventricular fibrillation from selfterminating episodes in humans." Journal of the American College of Cardiology 63.24 (2014): 2712-2721.
Light, D., E., et al. "Two Dimensional Arrays for Real Time Volumetric and Intracardiac Imaging with Simultaneous Electrocardiagram", 1196-2000 IEEE Ultrasonics Symposium, retrieved on Sep. 24, 2021.
Lyon, et al. J.R. Soc Interface vol. 15:1-18. (2017).
Nash, Martyn P., et al. "Evidence for multiple mechanisms in human ventricular fibrillation." Circulation 114.6 (2006): 536-542.
Potse, Mark et al., "Continuos Localization of Cardian Activation Sites Using a Database of Multichannel ECG Recordings" IEEE Transactions of Biomedical Engineering, vol. 47, No. 5, May 2000, pp. 682-689.
Rahhal et al., Convolutional neural networks for electrocardiogram classification, Journal of Medical and Biological Engineering (Mar. 30, 2018) 38: 1014-1025.
Sapp et al., "Real-Time Localization of Ventricular Tachycardia Origin From the 12-Lead Electrocardiogram", JACC Clinical Electrophysiology, vol. 3, No. 7, Jul. 2017.
Si, Hang, "TetGen, a Delaunay-Based Quality Tetrahedral Mesh Generator," ACM Transactions on Mathematical Software, vol. 41, No. 2, Article 11, Jan. 2015, 36 pages.
Siregar, P. "An Interactive Qualitative Model in Cardiology" Computers and Biomedical Research 28, pp. 443-478, May 16, 1994.
Taggart, Peter, et al. "Developing a novel comprehensive framework for the investigation of cellular and whole heart electrophysiology in the in situ human heart: Historical perspectives, current progress and future prospects."   Progress in biophysics and molecular biology  115.2-3 (2014): 252-260.
Tajbakhsh, Nima et al., "Convolutional Neural Networks for Medical Image Analysis: Full Training or Fine Tuning?" IEEE Transactions on Medical Imaging (2016) vol. 35, e-pp. 1-17).
Ten Tusscher et al. "A model for human ventricular tissue." American Journal of PhysioloQy—Heart and Circulatory PhysioloQy 286.4 (2004): H1573-H1589.
Thakor and Tong (Annual Reviews in Biomedicine and Engineering (2004) vol. 6, 453-495).
Tobon, Catalina, et al. "Dominant frequency and organization index maps in a realistic three-dimensional computational model of atrial fibrillation." Europace; 14, suppl_5 (2012): v25-v32.
Tomašić, Ivan et al., "Electrocardiograms With Reduced Numbers of Leads—Synthesis of the 12-Lead ECG," IEEE Reviews in Biomedical Engineering, vol. 7, 2014, pp. 126-142.
Vadakkumpadan, Fijoy, et al. "Image-based estimation of ventricular fiber orientations for personalized modeling of cardiac electrophysiology."  IEEE-TMI31.5 (2012): 1051-1060.
Villongco, Christopher T., et al. "Patient-specific modeling of ventricular activation pattern using surface ECG-derived vectorcardiogram in bundle branch block." Progress in biophysics and molecular bioloQy 115.2 (2014): 305-313.
Vozda, M. et al., "Methods for derivation of orthogonal leads from 12-lead electrocardiogram: A review," Elsevier, Biomedical Signal Processing and Control 19 (2015), 23-34.
Xiong et al. Computing and Cardiology vol. 44: pp. 1-4. (2017).
Zhang, C., et al. "Patient-Specific ECG Classification Based on Recurrent Neural Networks and Clustering Technique," Proceedings of the IASTED International Conference in Biomedical Engineering (Bio Med 2017); Feb. 20-21, 2017 in Innsbruck, Austria, 5 pages.
Zhou, Shijie et al. "Localization of ventricular activation origin using patient-specific geometry: Preliminary results" J. Carciovasc Electrophysiol, 2018; 29: pp. 979-986.
Zhou, Shijie et al. "Rapid 12-lead automated localization method: Comparison to electrocardiogramaging (ECGI) in patient-specific geometry", Journal of Electrocardiology, vol. 51, 2018, pp. S92-S97.

* cited by examiner

AUGMENTATION OF IMAGES WITH SOURCE LOCATIONS

CROSS-REFERENCE TO RELATED APPLICATIONS

This application is a continuation of International Application No. PCT/US2019/058217 filed Oct. 25, 2019, which is a continuation in part of U.S. patent application Ser. No. 16/247,463 filed Jan. 14, 2019 and of U.S. patent application Ser. No. 16/206,005 filed Nov. 30, 2018, and claims the benefit of U.S. Provisional Application No. 62/760,561 filed Nov. 13, 2018.

BACKGROUND

Many heart disorders can cause symptoms, morbidity (e.g., syncope or stroke), and mortality. Common heart disorders caused by arrhythmias include inappropriate sinus tachycardia ("IST"), ectopic atrial rhythm, junctional rhythm, ventricular escape rhythm, atrial fibrillation ("AF"), ventricular fibrillation ("VF"), focal atrial tachycardia ("focal AT"), atrial microreentry, ventricular tachycardia ("VT"), atrial flutter ("AFL"), premature ventricular complexes ("PVCs"), premature atrial complexes ("PACs"), atrioventricular nodal reentrant tachycardia ("AVNRT"), atrioventricular reentrant tachycardia ("AVRT"), permanent junctional reciprocating tachycardia ("PJRT"), and junctional tachycardia ("JT"). The sources of arrhythmias may include electrical rotors (e.g., ventricular fibrillation), recurring electrical focal sources (e.g., atrial tachycardia), anatomically based reentry (e.g., ventricular tachycardia), and so on. These sources are important drivers of sustained or clinically significant episodes. Arrhythmias can be treated with ablation using different technologies, including radiofrequency energy ablation, cryoablation, ultrasound ablation, laser ablation, external radiation sources, directed gene therapy, and so on by targeting the source of the heart disorder. Since the sources of heart disorders and the locations of the source vary from patient to patient, even for common heart disorders, targeted therapies require the source of the arrhythmia to be identified.

Unfortunately, current methods for reliably identifying the source locations of the source of a heart disorder can be complex, cumbersome, and expensive. For example, one method uses an electrophysiology catheter having a multi-electrode basket catheter that is inserted into the heart (e.g., left ventricle) intravascularly to collect from within the heart measurements of the electrical activity of the heart, such as during an induced episode of VF. The measurements can then be analyzed to help identify a possible source location. Presently, electrophysiology catheters are expensive (and generally limited to a single use) and may lead to serious complications, including cardiac perforation and tamponade. Another method uses an exterior body surface vest with electrodes to collect measurements from the patient's body surface, which can be analyzed to help identify an arrhythmia source location. Such body surface vests are expensive, are complex and difficult to manufacture, and may interfere with the placement of defibrillator pads needed after inducing VF to collect measurements during the arrhythmia. In addition, the vest analysis requires a computed tomography ("CT") scan and is unable to sense the interventricular and interatrial septa where approximately 20% of arrhythmia sources may occur.

DETAILED DESCRIPTION

Figure 1:
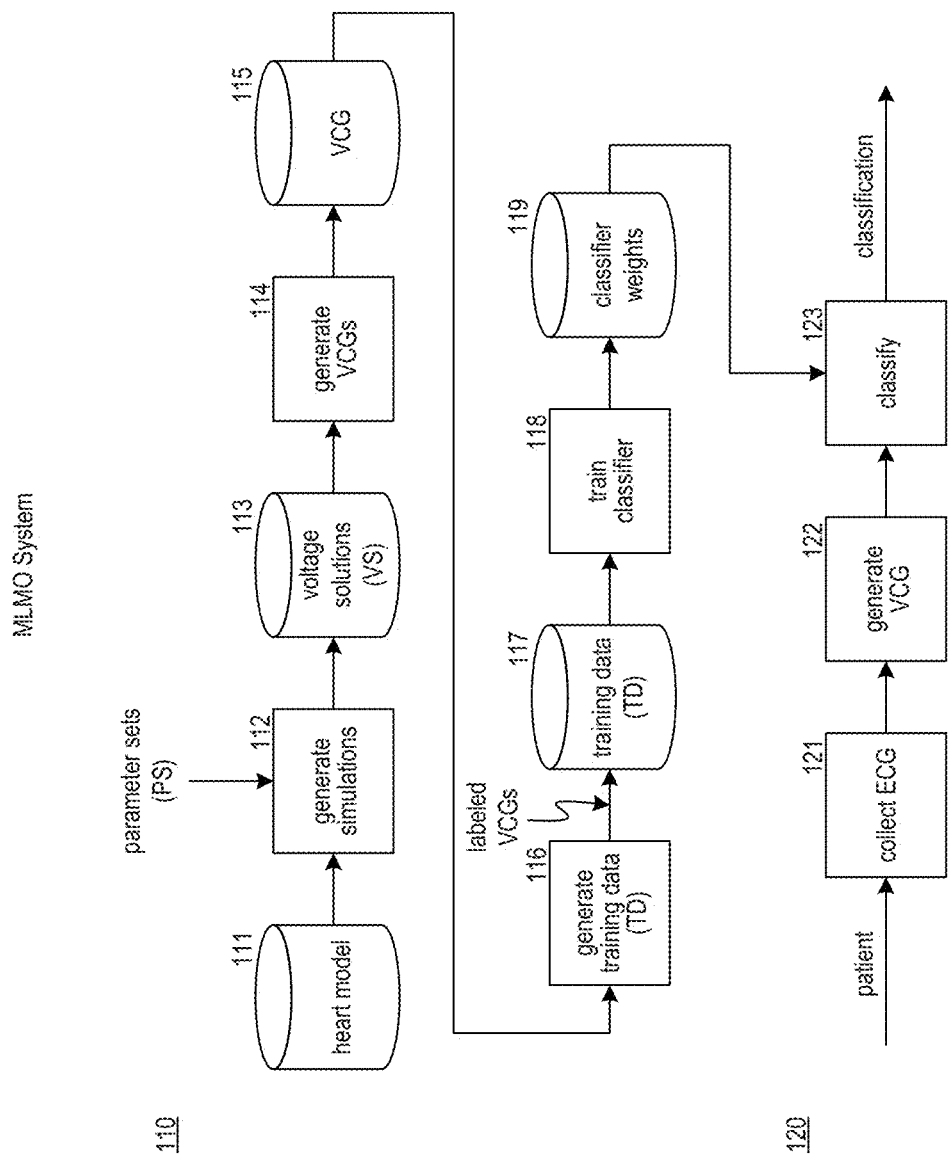
FIG. 1 is a block diagram that illustrates the overall processing of the MLMO system in some embodiments.

Methods and systems are provided for generating data representing electromagnetic states (e.g., normal sinus rhythm versus ventricular fibrillation) of an electromagnetic source (e.g., a heart) within a body for various purposes such as medical, scientific, research, and engineering purposes. The systems generate the data based on source configurations (e.g., dimensions of, and scar or fibrosis or proarrhythmic substrate location within, a heart) of the electromagnetic source and a computational model of the electromagnetic output of the electromagnetic source. The systems may dynamically generate the source configurations to provide representative source configurations that may be found in a population. For each source configuration of the electromagnetic source, the systems run a simulation of the functioning of the electromagnetic source to generate modeled electromagnetic output for that source configuration. The systems generate derived electromagnetic data (e.g., a vectorcardiogram) for each source configuration from the modeled electromagnetic output of that source configuration. The system may then use the modeled electromagnetic output for various purposes such as identifying locations of disorders within the electromagnetic source of a patient's body, guiding a procedure to repair (e.g., directed gene therapy) or modify (e.g., ablate) the electromagnetic source, predicting results of a procedure on the electromagnetic source, analyzing genetic defects, and so on. The systems may include a machine learning based on modeled output system and a model library generation system, which are described below.

Machine Learning Based on Modeled Output System

A method and a system are provided for generating a classifier for classifying electromagnetic data derived from an electromagnetic source within a body. A body may be, for example, a human body, and the electromagnetic source may be a heart, a brain, a liver, a lung, a kidney, or another part of the body that generates an electromagnetic field that can be measured from outside or inside the body. The electromagnetic fields can be measured by various measuring devices (e.g., electrocardiograph and electroencephalograph) using, for example, one or more (e.g., 12) leads connected to electrodes attached to or adjacent to (e.g., via a smart watch device) a patient's body, a body surface vest worn by a patient, an intra-electromagnetic source device (e.g., a basket catheter), a cap worn by a patient, and so on. The measurements can be represented via a cardiogram such as an electrocardiogram ("ECG") and a vectorcardiogram ("VCG"), an electroencephalogram ("EEG"), and so on. In some embodiments, a machine learning based on modeled output ("MLMO") system is provided to generate a classifier by modeling electromagnetic output of the electromagnetic source for a variety of source configurations and using machine learning to train a classifier using derived electromagnetic data that is derived from the modeled electromagnetic output as training data. The MLMO system is described below primarily to generate a classifier for electromagnetic data of the heart.

In some embodiments, the MLMO system employs a computational model of the electromagnetic source to generate training data for training the classifier. A computational model models electromagnetic output of the electromagnetic source over time based on a source configuration of the electromagnetic source. The electromagnetic output may represent electrical potential, a current, a magnetic field, and so on. When the electromagnetic ("EM") source is a heart, the source configuration may include any subset of the group consisting of information on geometry and muscle fibers of the heart, torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, other normal and pathophysiologic feature distributions, and so on, and the EM output is a collection of the electric potentials at various heart locations over time. To generate the EM output, a simulation may be performed for simulation steps of a step size (e.g., 1 ms) to generate an EM mesh for that step. The EM mesh may be a finite-element mesh that stores the value of the electric potential at each heart location for that step. For example, the left ventricle may be defined as having approximately 70,000 heart locations with the EM mesh storing an electromagnetic value for each heart location. If so, a three-second simulation with a step size of 1 ms would generate 3,000 EM meshes that each include 70,000 values. The collection of the EM meshes is the EM output for the simulation. A computational model is described in C. T. Villongco, D. E. Krummen, P. Stark, J. H. Omens, & A. D. McCulloch, "Patient-specific modeling of ventricular activation pattern using surface ECG-derived vectorcardiogram in bundle branch block," *Progress in Biophysics and Molecular Biology*, Volume 115, Issues 2-3, August 2014, Pages 305-313, which is hereby incorporated by reference. In some embodiments, the MLMO system may generate values for points between the vertices as the mesh, rather than just at the vertices. For example, the MLMO system may calculated the values for such points using a Gaussian quadrature technique.

In some embodiments, the MLMO system generates the training data by running many simulations, each based on a different source configuration, which is a set of different values for the configuration parameters of the computational model. For example, the configuration parameters for the heart may be cardiac geometry, rotor location, focal source location, ventricular orientation in the chest, ventricular myofiber orientation, cardiomyocyte intracellular potential electrogenesis and propagation, and so on. Each configuration parameter may have a set or range of possible values. For example, the rotor location may be 78 possible parameter sets corresponding to different locations within a ventricle. Since the MLMO system may run a simulation for each combination of possible values, the number of simulations may be in the millions.

In some embodiments, the MLMO system uses EM outputs of the simulations to train the classifier for the generation of a classification based on EM data collected from a patient. The MLMO system may generate derived EM data for each EM output of a simulation. The derived EM data correspond to EM data generated based on measurements that would be collected by an EM measuring devices that use, for example, 12 leads to generate an ECG or a VCG, a body surface vest, an intra-electromagnetic source device, and so on. The ECG and VCG are equivalent source representations of the EM output. The MLMO then generates a label (or labels) for each derived EM data to specify its corresponding classification. For example, the MLMO system may generate a label that is the value of a configuration parameter (e.g., rotor location) used when generating the EM output from which the EM data was derived. The collection of the derived EM data, which correspond to feature vectors, and their labels compose the training data for training the classifier. The MLMO system then trains the classifier. The classifier may be any of a variety or combination of classifiers including neural networks such as fully-connected, convolutional, recurrent, autoencoder, or restricted Boltzmann machine, a support vector machine, a Bayesian classifier, and so on. When the classifier is a deep neural network, the training results in a set of weights for the activation functions of the deep neural network. The classifier selected may be based on the type of disorder to be identified. For example, certain types of neural networks may be able to effectively train based on focal sources, but not rotor sources.

In some embodiments, the MLMO system may augment the training data with additional features from the configuration parameters of the source configuration used to generate the training data. For example, the MLMO system may generate additional features to represent the geometry of the heart, the orientation of the heart, scar or fibrosis or pro-arrhythmic substrate location or locations, ablation location, ablation shape, and so on. The MLMO system may input these additional features into the fully connected layer along with the output generated by the layer before the fully connected layer of a convolutional neural network ("CNN"), which is described below. The output of the layer before the fully connected layer (e.g., pooling layer) may be "flattened" into a one-dimensional array, and the MLMO system may add the additional features as further elements of the one-dimensional array. The output of the fully connected layer may provide a probability for each label used in the training data. The probabilities will thus be based on the combination of the derived EM data and the additional features. The classifier will be able to output different probabilities even when the derived EM data is the same or similar to reflect, for example, that the same or similar EM data may be generated for patients with different heart geometries and different scar or fibrosis or pro-arrhythmic substrate locations. The MLMO system may alternatively employ an additional classifier that (1) inputs the probabilities generated by the CNN based only on the derived EM data and (2) inputs the additional features and then outputs a final probability for each classification that factors in the additional features. The additional classifier may be, for example, a support vector machine. The CNN and the additional classifier may be trained in parallel.

In some embodiments, the MLMO system normalizes the VCGs of each cycle of the training data in both the voltage and time axes. A cycle may be defined as a time interval (e.g., start time to end time) defining a single unit or beat of periodic electrical activity during normal or abnormal rhythms. Cycles facilitate beat-by-beat analysis of source configuration evolution over time and enable subsequent voltage and time normalization over each cycle. Normalization preserves salient features of voltage-time dynamics and improves generalizability of the training data to variations in source configuration parameters (e.g., torso conductivities, lead placement and resistance, myocardial conduction velocity, action potential dynamics, overall heart size, etc.) anticipated in real patients. The MLMO system may normalize the voltages to a range between −1 and 1 and the time to a fixed range of 0 to 1 in increments of milliseconds or percentages. To normalize the voltages for a cycle, the MLMO system may identify the maximum magnitude of the vectors across the axes. The MLMO system divides each voltage by the maximum magnitude. To normalize the time axis, the MLMO system performs an interpolation from the number of points in the VCG, which may be more or less than 1000, to the 1000 points of the normalized cycle.

In some embodiments, after the classifier is trained, the MLMO system is ready to generate classifications based on EM and other routinely available clinical data collected from patients. For example, an ECG may be collected from a patient, and a VCG may be generated from the ECG. The VCG is input to the classifier to generate a classification indicating, for example, a rotor location for the patient. As a result, even though the geometry of the patient's heart is not known or no simulation was based on the same geometry as the patient's heart, the MLMO system can be used to generate a classification. If other patient measurements such as cardiac dimensions and orientation, scar or fibrosis or pro-arrhythmic substrate configuration, etc. are available, they may be included as input with the EM data to improve accuracy. This allows the classifier to effectively learn complex hidden features in various clinical data that are not directly represented by the training data.

In some embodiments, the MLMO system may classify source stability (i.e., the beat-to-beat consistency of a dominant arrhythmia source localized to a particular region in the heart) by generating training data that is based on sequences of consecutive cycles that have similar EM features. A technique for determining the stability of arrhythmia sources is described in Krummen, D., et al., Rotor Stability Separates Sustained Ventricular Fibrillation from Self-Terminating Episodes in Humans, Journal of American College of Cardiology, Vol. 63, No. 23, 2014, which is hereby incorporated by reference. This reference demonstrates the efficacy of targeted ablation at stable source sites for preventing recurring arrhythmic episodes. For example, given a VCG, the MLMO system may identify the cycles and then identify sequences of two consecutive cycles, three consecutive cycles, four consecutive cycles, and so on in which all the VCG cycles in the sequence are of similar morphology to each other. Each identified sequence may be labeled based on the value of a parameter of the source configuration used to generate the VCG. The MLMO system may then train a separate classifier for each sequence length (e.g., 2, 3, 4, and so on) using the training data for the sequences of that sequence length. For example, the MLMO system may train a classifier for sequences of two cycles and a separate classifier for sequences of three cycles. To generate a classification for a patient, the MLMO system may identify sequences of similar cycles of varying sequence lengths in the VCG of the patient and input those sequences into the classifier for the appropriate sequence length. The MLMO system may then combine the classifications from all the classifiers to arrive at a final classification or may simply output all the classifications.

Although a classifier could be trained using actual patient ECGs or VCGs and corresponding intracardiac basket catheter measurements of source location, the cost of collecting, preparing, and labeling a sufficient number of data may currently be very expensive although advances in technology may significantly reduce the cost. Also, training data based on actual patients may currently be too sparse and noisy to be particularly effective at training a classifier for a large population although advances in collecting and storing of medical records may result in use of actual patient data being more effective. In some embodiments, the MLMO system could be trained using a combination of actual patient VCGs and VCGs derived from simulations. The training data collected from actual patients may be collected using various devices such as flexible electronics (e.g., an epidermal electronic system), smart clothing, and so on.

In some embodiments, the MLMO system could be trained using a combination of actual patient VCGs and VCGs derived from simulations.

FIG. 1 is a block diagram that illustrates the overall processing of the MLMO system in some embodiments. The MLMO system includes classifier generation components 110 and classification components 120. The computational model for a heart is a heart model that may include data and code stored in a heart model data store 111. A generate simulations component 112 inputs the heart model and the parameter sets for the simulations. The parameter sets, also referred to as source configurations, may include a parameter set for each combination of possible values of the parameters or may specify how to generate (e.g., via a computer code) the parameter sets. For example, the computer code for the rotor location parameter may include a list of possible rotor locations and for the ventricle orientation parameter may dynamically generate the values from a base orientation axis along with code for generating possible tilt angles from that base orientation such as an x-axis and a y-axis increment. The output of the generate simulations component is stored in a voltage solutions data store 113 where a voltage solution is an EM output. A voltage solution is an example of an EM mesh. A generate VCGs component 114 generates a VCG from the voltage solutions and stores the VCG in a VCG data store 115. The generate VCGs component may generate an ECG from the voltage solutions and then generate a VCG from the ECG. The generation of a VCG from an ECG is described in J. A. Kors, G. Van Herpen, A. C. Sittig, & J. H. Van Bemmel, "Reconstruction of the Frank vectorcardiogram from standard electrocardiographic leads: diagnostic comparison of different methods," *European Heart Journal*, Volume 11, Issue 12, 1 Dec. 1990, Pages 1083-1092, which is hereby incorporated by reference. A generate training data component 116 inputs the VCGs and labels each VCG with a label or labels that may be derived from the parameter sets and stores the training data in a training data store 117. A label may be, for example, the value of a parameter of the parameter set used to generate the EM output from which the VCG is derived. A train classifier component 118 inputs the training data, trains a classifier, and stores the weights (e.g., of activation functions of a convolutional neural network) in a classifier weights data store 119. To generate a classification, a collect ECG component 121 inputs an ECG collected from a patient. A generate VCG component 122 generates a VCG from the ECG. A classify component 123 inputs the VCG and generates a classification using the classifier weights of the trained classifier.

The computing systems (e.g., network nodes or collections of network nodes) on which the MLMO system and the other described systems may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based servers, desktop computers, laptops, tablets, e-readers, personal digital assistants, smartphones, gaming devices, servers, and so on. For example, the simulations and training may be performed using a high-performance computing system, and the classifications may be performed by a tablet. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the MLMO system and the other described systems. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The MLMO system and the other described systems may be described in the general context of computer-executable instructions, such as program modules and components, executed by one or more computers, processors, or other devices. Generally, program modules or components include routines, programs, objects, data structures, and so on that perform tasks or implement data types of the MLMO system and the other described systems. Typically, the functionality of the program modules may be combined or distributed as desired in various examples. Aspects of the MLMO system and the other described systems may be implemented in hardware using, for example, an application-specific integrated circuit ("ASIC") or field programmable gate array ("FPGA").

Figure 2:
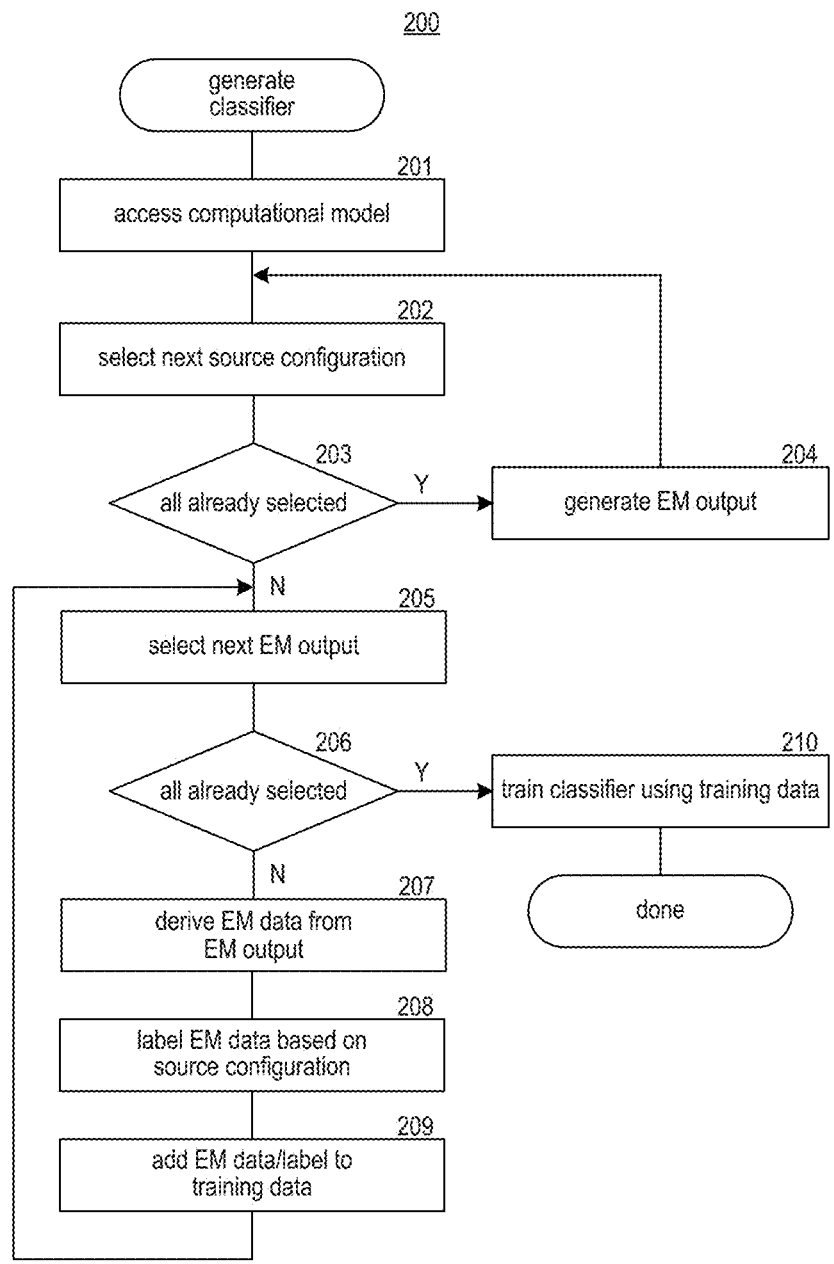
FIG. 2 is a flow diagram that illustrates the overall processing of generating a classifier by the MLMO system in some embodiments.

FIG. 2 is a flow diagram that illustrates the overall processing of generating a classifier by the MLMO system in some embodiments. A generate classifier component 200 is executed to generate a classifier. In block 201, the component accesses the computational model to be used to run the simulations. In block 202, the component selects the next source configuration (i.e., parameter set) to be used in a simulation. In decision block 203, if all the source configurations have already been selected, then the component continues at block 205, else the component continues at block 204. In block 204, the component runs the simulation using the selected source configuration to generate an EM output for the simulation and then loops to block 202 to select the next source configuration. In block 205, the component selects the next EM output that was generated by a simulation. In decision block 206, if all the EM outputs have already been selected, then the component continues at block 210, else the component continues at block 207. In block 207, the component derives the EM data from the EM output. For example, the EM output may be a collection of EM meshes, and the EM data may be an ECG or a VCG derived from the electromagnetic values of the EM mesh. In some embodiments, the component may in addition identify cycles (periodic intervals of arrhythmic activity) within the ECG or VCG. A cycle may be delimited by successive crossings from a negative voltage to a positive voltage ("positive crossings") or successive crossings from a positive voltage to a negative voltage ("negative crossings") with respect to a spatial direction or set of directions comprising a reference frame or set of reference frames. A reference frame may coincide with anatomical axes (e.g., left-to-right with x, superior-to-inferior with y, anterior-to-posterior with z), imaging axes (e.g., CT, MR, or x-ray coordinate frames), body-surface lead vectors, principal axes computed by principal component analysis of measured or simulated EM source configurations and outputs, or user-defined directions of interest. For example, a three-second VCG may have three cycles, and each cycle may be delimited by the times of the positive crossings along the x-axis. Alternatively, the cycles may be delimited by crossings along the y-axis or z-axis. In addition, cycles may be defined by negative crossings. Thus, in some embodiments, the component may generate training data from a single VCG based on various cycle definitions that are various combinations of positive crossings and negative crossings with the cycles for all the axes being defined by crossings on one of the x-axis, y-axis, and z-axis or the cycles for each defined by crossings on that axis. Moreover, the training data may include cycles identified based on all possible cycle definitions or a subset of the cycle definition. For example, the training data may include, for each axis, a cycle defined by positive crossings of the x-axis, negative crossings of they-axis, and positive crossings of that axis itself. Cycles definitions may also be defined by the timing of electrical events derived from the values stored in the EM mesh. For example, a point or set of points in the mesh may periodically cross voltage thresholds signifying electrical activation and deactivation. Thus, a cycle may be defined by activation-deactivation, or successive activation-activation or deactivation-deactivation intervals corresponding to a point or set of points within the mesh. The resulting timings of these intervals can be co-localized to the ECG or VCG for cycles identification. In block 208, the component labels the EM data based on the source configuration (e.g., a source location). When cycles are identified, the component may label each cycle with the same label. For example, the component may label the identified cycles with the same rotor location. In block 209, the component adds the EM data along with the label to the training data and then loops to block 205 to select the next EM output. In block 210, the component trains the classifier using the training data and then completes.

Figure 3:
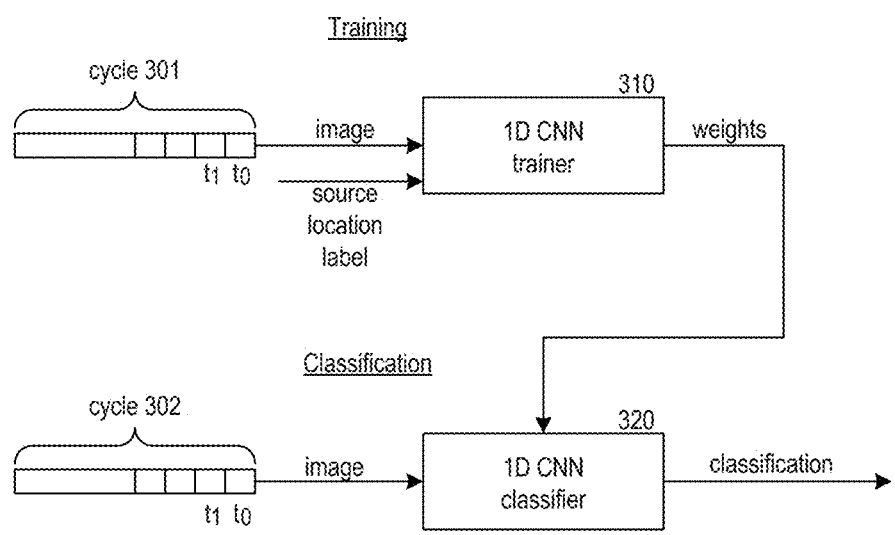
FIG. 3 is a block diagram that illustrates training and classifying using a convolutional neural network in some embodiments.

FIG. 3 is a block diagram that illustrates training and classifying using a convolutional neural network in some embodiments. The convolutional neural network may be one-dimensional in the sense that it inputs an image that is a single row of pixels with each pixel having a red, green, and blue ("RGB") value. The MLMO system sets the values of the pixels based on the voltages of a VCG of the training data. The image has the same number of pixels as vectors of a VCG of the training data. The MLMO system sets the red, green, and blue values of a pixel of the image to the x, y, and z values of the corresponding vector of the VCG. For example, if a cycle of a VCG is 1 second long, and the VCG has a vector for each millisecond, then the image is 1 by 1000 pixels. The one-dimensional convolutional neural network ("1D CNN") trainer 310 learns the weights of activation functions for the convolutional neural network using the training data 301. To generate a classification for a patient, the MLMO system provides the VCG 302 for the patient as a one-dimensional image. The 1D CNN 320 then classifies the VCG based on the weights and outputs the classification, such as rotor location.

CNNs are a type of neural network that has been developed specifically to process images. A CNN may be used to input an entire image and output a classification of the image. For example, a CNN can be used to automatically determine whether a scan of a patient indicates the presence of an anomaly (e.g., tumor). The MLMO system considers the derived EM data to be a one-dimensional image. A CNN has multiple layers such as a convolution layer, a rectified linear unit ("ReLU") layer, a pooling layer, a fully connected ("FC") layer, and so on. Some more complex CNNs may have multiple convolution layers, ReLU layers, pooling layers, and FC layers.

A convolution layer may include multiple filters (also referred to as kernels or activation functions). A filter inputs a convolution window of an image, applies weights to each pixel of the convolution window, and outputs an activation value for that convolution window. For example, if the image is 256 by 256 pixels, the convolution window may be 8 by 8 pixels. The filter may apply a different weight to each of the 64 pixels in a convolution window to generate the activation value also referred to as a feature value. The convolution layer may include, for each filter, a node (also referred to as a neuron) for each pixel of the image assuming a stride of one with appropriate padding. Each node outputs a feature value based on a set of weights for the filter that are learned during a training phase for that node. Continuing with the example, the convolution layer may have 65,566 nodes (256*256) for each filter. The feature values generated by the nodes for a filter may be considered to form a convolution feature map with a height and width of 256. If an assumption is made that the feature value calculated for a convolution window at one location to identify a feature or characteristic (e.g., edge) would be useful to identify that feature at a different location, then all the nodes for a filter can share the same set of weights. With the sharing of weights, both the training time and the storage requirements can be significantly reduced. If each pixel of an image is represented by multiple colors, then the convolution layer may include another dimension to represent each separate color. Also, if the image is a 3D image, the convolution layer may include yet another dimension for each image within the 3D image. In such a case, a filter may input a 3D convolution window.

The ReLU layer may have a node for each node of the convolution layer that generates a feature value. The generated feature values form a ReLU feature map. The ReLU layer applies a filter to each feature value of a convolution feature map to generate feature values for a ReLU feature map. For example, a filter such as max(0, activation value) may be used to ensure that the feature values of the ReLU feature map are not negative.

The pooling layer may be used to reduce the size of the ReLU feature map by downsampling the ReLU feature map to form a pooling feature map. The pooling layer includes a pooling function that inputs a group of feature values of the ReLU feature map and outputs a feature value. For example, the pooling function may generate a feature value that is an average of groups of 2 by 2 feature values of the ReLU feature map. Continuing with the example above, the pooling layer would have 128 by 128 pooling feature map for each filter.

The FC layer includes some number of nodes that are each connected to every feature value of the pooling feature maps. For example, if an image is to be classified as being a cat, dog, bird, mouse, or ferret, then the FC layer may include five nodes whose feature values provide scores indicating the likelihood that an image contains one of the animals. Each node has a filter with its own set of weights that are adapted to the type of the animal that the filter is to detect.

In the following, the MLMO system is described in reference to the following data structures. The brackets indicate an array. For example, VCG[2].V[5].x represents the voltage for the x-axis for the fifth time interval in the second VCG. The data structures are further described below when first referenced.

VCG Data Structures

VCG[ ]
  size
  V[ ]
    x
    y
    x
nVCG
  V[ ]
    x
    y
    z

Cycles Data Structure

C
C[ ]
  start
  end

Training Data Structure

TD
TD[ ]
  nVCG[ ]
  label(s)

Figure 4:
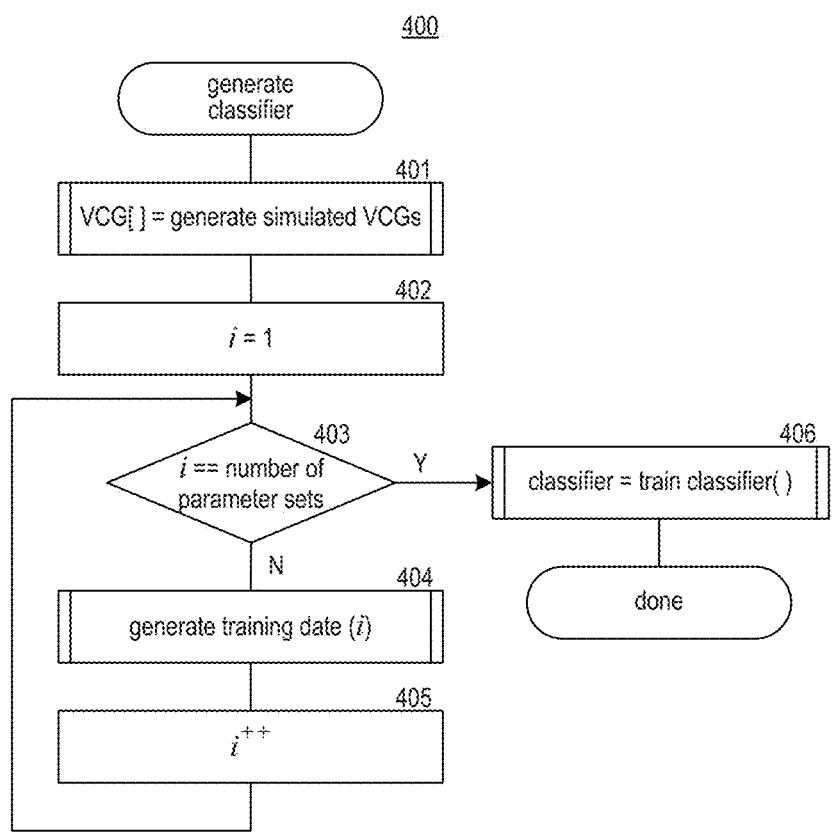
FIG. 4 is a flow diagram that illustrates processing of a generate classifier component of the MLMO system in some embodiments.

FIG. 4 is a flow diagram that illustrates detailed processing of the generate classifier component of the MLMO system in some embodiments. The generate classifier component 400 is invoked to generate a classifier. In block 401, the component invokes a generate simulated VCGs component to simulate VCGs (VCG[ ]) for a variety of parameter sets. In blocks 402-405, the component loops, generating the training data for each simulation. In block 402, the component sets an index i to 1 for indexing the parameter sets. In decision block 403, if index i is equal to the number of parameter sets, then all the training data has been generated and the component continues at block 406, else the component continues at block 404. In block 404, the component invokes a generate training data component, passing an indication of the indexed parameter set. In block 405, the component increments index i and then loops to block 403. In block 406, the component invokes a train classifier component to train the classifier based on the generated training data and then completes.

Figure 5:
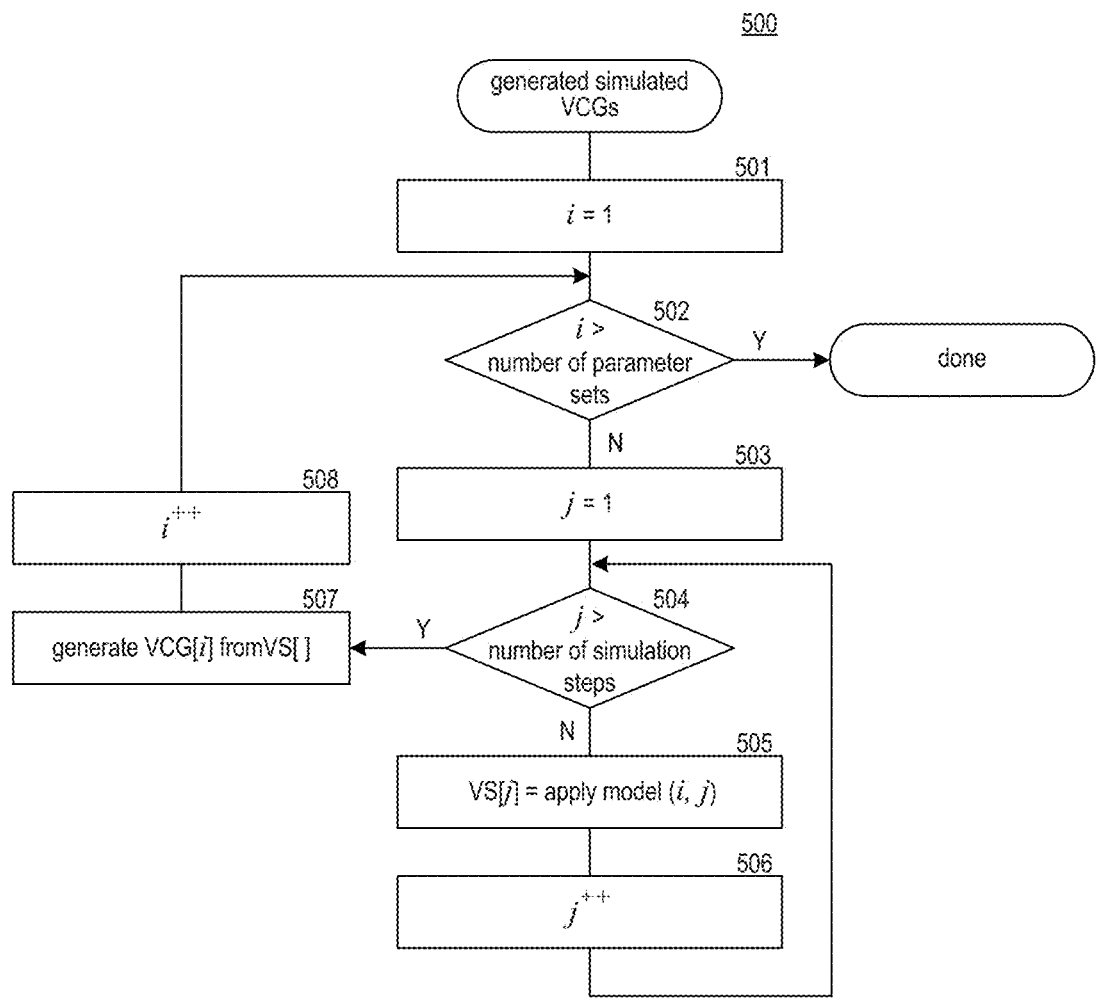
FIG. 5 is a flow diagram that illustrates the processing of a generate simulated VCGs component of the MLMO system in some embodiments.

FIG. 5 is a flow diagram that illustrates the processing of a generate simulated VCGs component of the MLMO system in some embodiments. The generate simulated VCGs component 500 is invoked to generate a simulated VCG for each parameter set. In block 501, the component sets an index i to 1 for indexing through the parameter sets. In decision block 502, if index i is greater than the number of parameter sets, then the component completes, else the component continues at block 503. In block 503, the component sets an index j to 1 for indexing through the simulation steps. In decision block 504, if index j is greater than the number of simulation steps, then the simulation for the indexed parameter set is complete and the component continues at block 507, else the component continues at block 505. In block 505, the component applies the computational model based on the indexed parameter set and the indexed simulation step to generate a voltage solution (VS[/]) for the indexed simulation step. In block 506, the component increments index j and then loops to block 504 to process the next simulation step. In block 507, the component generates a VCG (VCG[i]) for the indexed parameter set from the voltage solution (VS[ ]) that was calculated for the parameter set. In block 508, the component increments index i and then loops to block 502 to process the next parameter set.

Figure 6:
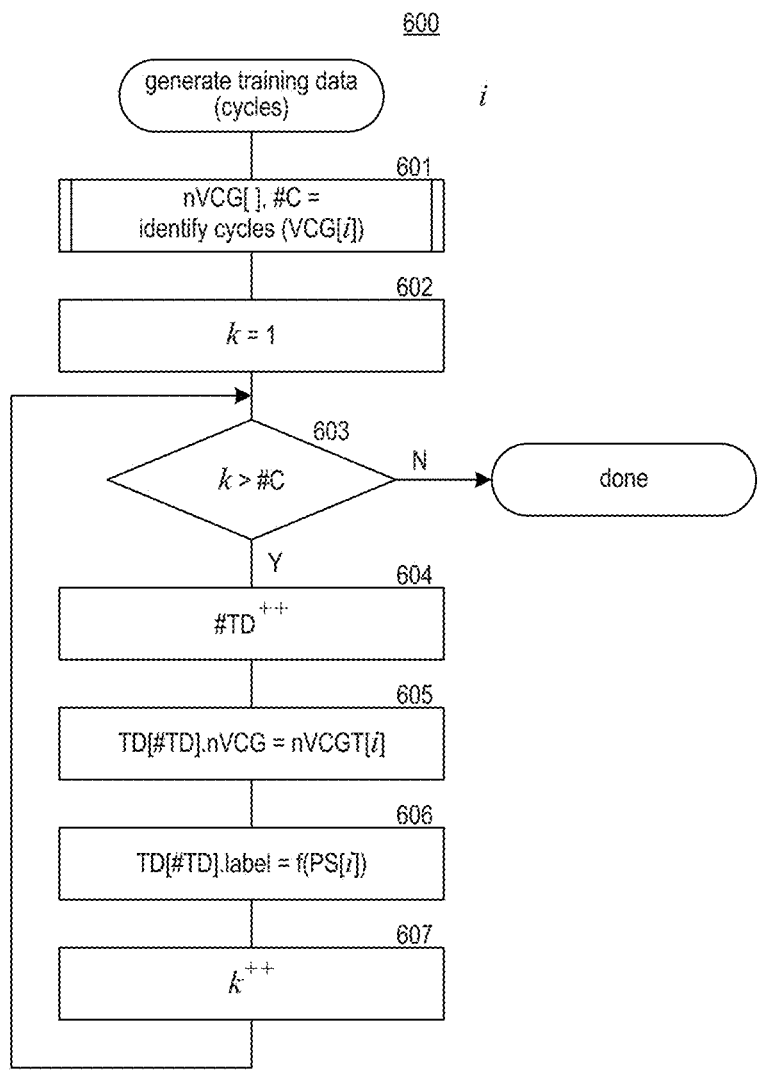
FIG. 6 is a flow diagram that illustrates the processing of a generate training data component for cycles of the MLMO system in some embodiments.

FIG. 6 is a flow diagram that illustrates the processing of a generate training data component for cycles of the MLMO system in some embodiments. The generate training data component 600 is invoked, passing an index i, that indexes a VCG generated for a parameter set and generates the training data from the VCG. In block 601, the component invokes an identify cycles component, passing an indication of the indexed VCG (VCG[i]) and receiving a normalized VCG (nVCG[ ]) for each cycle along with a count (#C) of the cycles that were identified. In block 602, the component sets an index k to 1 for indexing through the cycles. In decision block 603, if index k is greater than the count of the cycles, then the training data for all the cycles of the indexed VCG has been generated and the component completes, else the component continues at block 604. In block 604, the component increments a running count (#TD) of the training data (TD) that is used as an index into the training data. In block 605, the component sets the normalized nVCG of the indexed training data (TD[#TD].nVCG) to the portion of the VCG specified by the indexed cycle. The component extracts the portion from the x-axis, y-axis, and z-axis as defined by the start and end points of the cycle. In block 606, the component sets the label(s) of the indexed training data based on the function of the indexed parameter set (e.g., rotor location). In block 607, the component increments index k to index to the next cycle and then loops to block 603 to process the next cycle.

Figure 7:
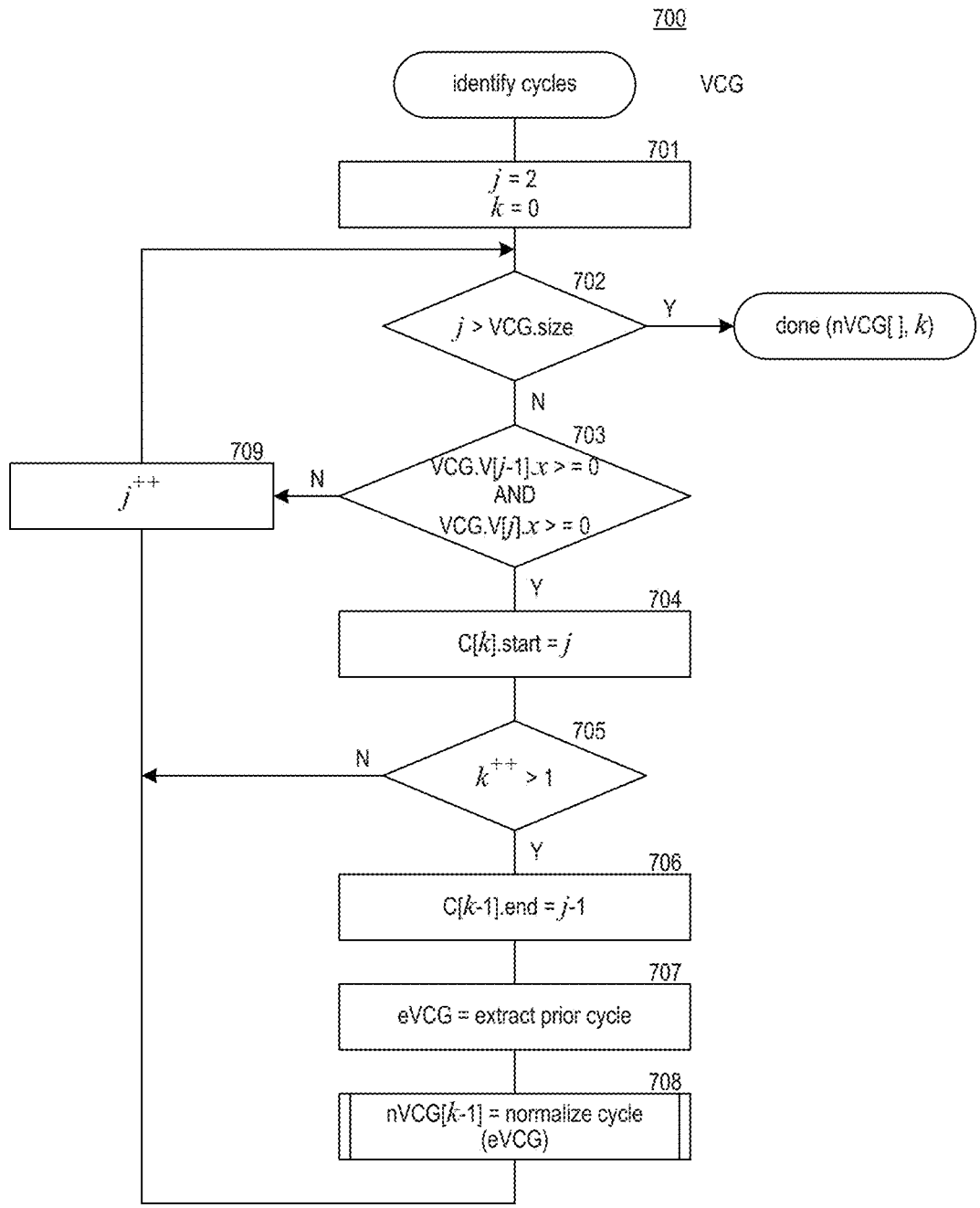
FIG. 7 is a flow diagram that illustrates the processing of an identify cycles component of the MLMO system in some embodiments.

FIG. 7 is a flow diagram that illustrates the processing of an identify cycles component of the MLMO system in some embodiments. The identify cycles component 700 is invoked to identify the cycles within a VCG and provides the normalized VCGs (nVCG[ ]) for the cycles. In block 701, the component initializes an index j to 2 for indexing through the VCG and sets an index k to 0 for indexing through the identified cycles. In decision block 702, if index j is greater than the size of the VCG, then the component has identified all the cycles and the component completes, providing the normalized nVCG, else the component continues at block 703. In block 703, if the prior voltage of the x-axis of the VCG (VCG.V[j−1].x) is greater than or equal to zero and the indexed voltage of the x-axis of the VCG (VCG.V[j].x) is less than zero (i.e., a negative crossing of the x-axis), then the start of a possible cycle has been identified and the component continues at block 704 to identify the cycle, else the component continues at block 709. In block 704, the component sets the start of the indexed cycle (C[k].start) equal to index j. In decision block 705, if at least one cycle has already been identified, then the end of the prior cycle is known and the component increments index k and continues at block 706, else the component increments index k and continues at block 709. In block 706, the component sets the end of the prior cycle to index j−1. In block 707, the component extracts the VCG (eVCG) for the prior indexed cycle delimited by the start and the end of the prior cycle. In block 708, the component invokes a normalize cycle component, passing an indication of the extracted VCG (eVCG), and receives the normalized cycle (nVCG). In block 709, the component increments the index j for indexing through the VCG and loops to block 702.

Figure 8:
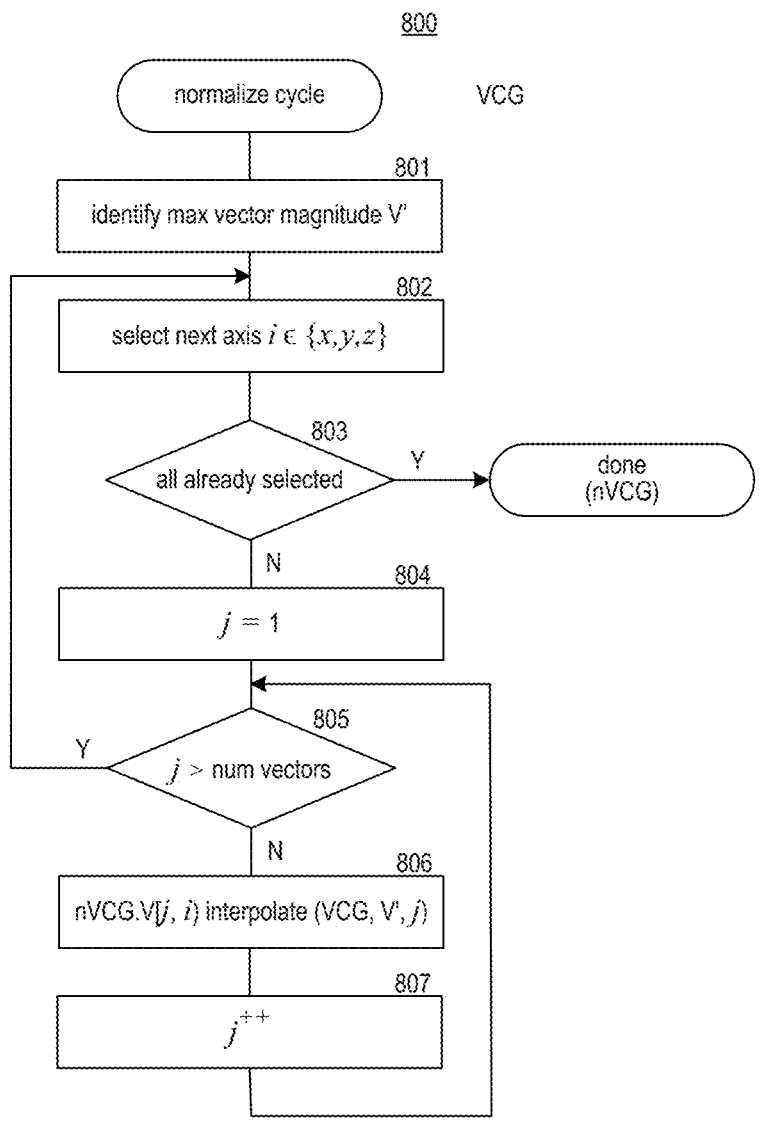
FIG. 8 is a block diagram that illustrates the processing of a normalize cycle component of the MLMO system in some embodiments.

FIG. 8 is a block diagram that illustrates the processing of a normalize cycle component of the MLMO system in some embodiments. The normalize cycle component 800 is invoked, passing an indication of the VCG of a cycle, and normalizes the cycle. In block 801, the component identifies the maximum vector magnitude V' of the vectors in the cycle. For example, a vector magnitude of a vector may be calculated by taking the square root of the sum of the squares of the x, y, and z values of the vector. In block 802, the component sets index i to index a next axis of the VCG. In decision block 803, if all the axes have already been selected, then the component completes, providing the normalized VCG, else the component continues at block 804. In block 804, the component initializes an index j to 1 for indexing through the vectors of a normalized cycle. In decision block 805, if index j is greater than the number of vectors of a normalized cycle, then the component loops to block 802 to select the next axis, else the component continues at block 806. In block 806, the component sets the normalized VCG for the indexed vector for the indexed axis to an interpolation of the passed VCG, the indexed vector, and the maximum vector magnitude V'. The interpolation effectively compresses or expands the VCG to the number of vectors in the normalized VCG and divides the x, y, and z values of the vector by the maximum vector magnitude V'. In block 807, the component increments the index j and then loops to block 805.

Figure 9:
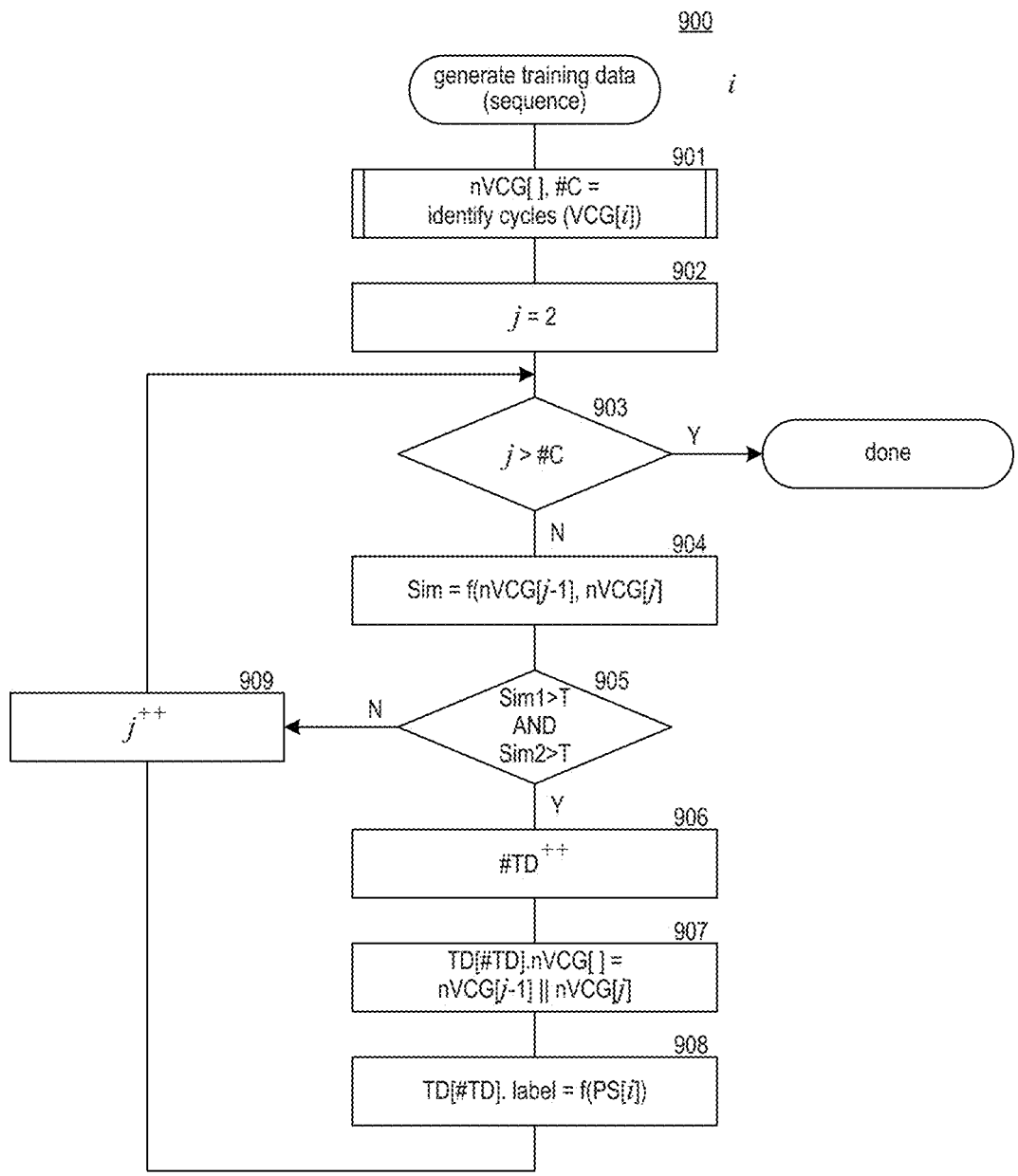
FIG. 9 is a flow diagram that illustrates processing of a generate training data for a sequence of similar cycles component of the MLMO system in some embodiments.

FIG. 9 is a flow diagram that illustrates processing of a generate training data for a sequence of similar cycles component of the MLMO system in some embodiments. The generate training data for a sequence of similar cycles component 900 is invoked to identify sequences of two consecutive cycles of the VCG indexed by the passed index i that are similar and generate training data based on the identified sequences of similar cycles. The cycles in a sequence are similar according to a similarity score that reflects the stability of the cycles. In block 901, the component invokes the identify cycles component to identify the cycles (nVCG[ ]) for the VCG. In block 902, the component sets an index j to 2 for indexing through the identified cycles. In decision block 903, if index j is greater than the number of identified cycles, then all the cycles have been indexed and then component completes, else the component continues at block 904. In block 904, the component generates a similarity score for the cycles indexed by j−1 and j. The similarity score may be based on, for example, a cosine similarity, a Pearson correlation, and so on. In decision block 905, if similarity score is above a similarity score threshold (T) indicating similar cycles, then a sequence of similar cycles has been identified and the component continues at block 906, else the component continues at block 909. In block 906, the component increments a running count (#TD) of the training data. In block 907, the component sets the training data to the sequence of similar cycles. In block 908, the component sets the label for the training data to a label derived from the parameter set (PS[i]) used to generate the VCG and then continues at block 909. In block 909, the component increments index i to select the next sequence of cycles and loops to block 903.

Figure 10:
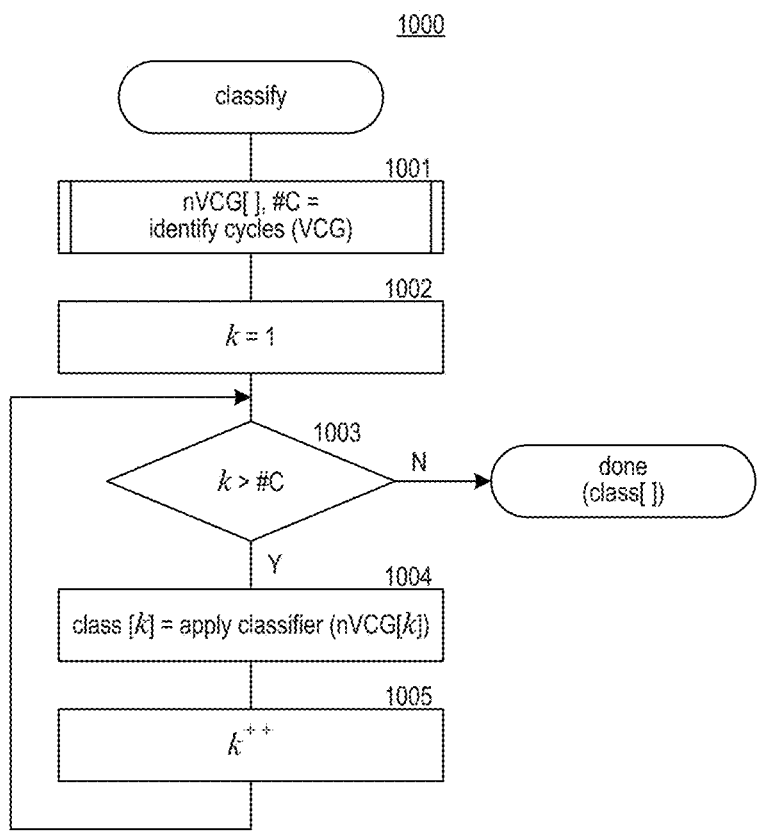
FIG. 10 is a flow diagram that illustrates the processing of a classify component of the MLMO system in some embodiments.

FIG. 10 is a flow diagram that illustrates the processing of a classify component of the MLMO system in some embodiments. The classify component 1000 is invoked, passing a VCG derived from a patient, and outputs a classification. In block 1001, the component invokes the identify cycles component, passing an indication of the VCG, and receives the normalized VCGs for the cycles and a count of cycles. In block 1002, the component sets an index k to 1 for indexing through the cycles. In decision block 1003, if index k is greater than the number of cycles, then the component completes with the classifications, else the component continues at block 1004. In block 1004, the component applies the classifier to the indexed cycle to generate the classification. In block 1005, the component increments the index and then loops to block 1003 to process the next cycle. A different classification (e.g., different rotor location) may be generated for each cycle. In such a case, the overall classification may be derived from the combination of the different classifications (e.g., average of the rotor locations).

Model Library Generation System

A method and system for generating a model library of models of an EM source within a body is provided. In some embodiments, a model library generation ("MLG") system generates models based on source configurations with configuration parameters that include anatomical parameters and electrophysiology parameters for the EM source. The anatomical parameters specify dimensions or overall geometry of the EM source. When the EM source is a heart, then the models may be arrhythmia models based on anatomical parameters that may include any subset of the group consisting of thickness of a heart wall (e.g., thickness of the endocardium, myocardium, and epicardium), dimensions of chambers, diameters, ventricular orientation in the chest, torso anatomy, fiber architecture, the location(s) of scar, fibrosis, and pro-arrhythmia substrate, scar shape and so on. The geometry of a heart may be measured when maximal chamber volume and minimal wall thickness and activation occur. With normal sinus, activation occurs at the time of the end-diastolic portion of a beat. With an arrhythmia, activation may occur at a different time during a beat. Therefore, the MLG system may allow the geometry to be specified at times other than the end-diastolic portion. The torso anatomy may be used tailor the EM output based on the size, shape, composition, and so on of the torso. The electrophysiology parameters are the non-anatomical parameters that may include any subset of the group consisting of inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions, action potential dynamics, conductivities, arrhythmia source location, and so on. The configuration parameters that are selected for a simulation may be based on the machine learning algorithm employed. For example, the fiber architecture parameter may be selected for a convolutional neural network, but not for other types of neural networks. The MLG system generates source configurations from which the arrhythmia models are generated. For each source configuration, the MLG system generates an arrhythmia model that includes a mesh and model parameter such as variable weights for the arrhythmia model. The MLG system generates the mesh based on the anatomical parameters. After the computational mesh is generated, the MLG generates model parameters of the arrhythmia model at point within the mesh based on the electrophysiology parameters of that source configuration. The electrophysiology parameters control the modeling of, for example, the electromagnetic propagation at that point based on the electrophysiology parameters. The collection of arrhythmia models forms an arrhythmia model library. The MLMO system can then generate a modeled EM output for each arrhythmia model and use the modeled EM outputs to train a classifier. The arrhythmia model library may be used for other purposes such as studying the efficacy of different types of ablations.

In some embodiments, the MLG system generates sets of anatomical parameters for the heart, with each set having a value (e.g., scalar, vector, or tensor) for each anatomical parameter. A set of anatomical parameters specifies an anatomy of a heart. The MLG system generates simulated anatomies that are based on a set of seed anatomies (specifying values for the dimensions of the EM source) and sets of weights that include a weight for each seed anatomy. The seed anatomies may also include values for features derived from the specified values such as the mass, the volume, ratios of length and width, the sphericity, and so on of a chamber. The seed anatomies may represent extreme anatomies found in patients. For example, the seed anatomies may be generated from ultrasound, computed tomography, and magnetic resonance imaging scans of patients who have extreme heart conditions such as an enlarged right ventricle, a very thick or thin endocardium, and so on. The MLG system generates a simulated anatomy for each set of weights. Each weight in a set of weights indicates the contribution of the anatomical parameters of a seed anatomy to a simulated anatomy. For example, if four seed anatomies are specified, then the weights may be 0.4, 0.3, 0.2, and 0.1. The MLG system sets the value of each anatomical parameter for a simulated anatomy for a set of weights to a weighted average of the values of each anatomical parameter of the seed anatomies. The MLG system may use various techniques for generating the sets of weights, such as defining a fixed interval (e.g., 0.001), randomly selecting weights that add to 1.0, using a design-of-experiments technique, and so on. The MLG system may also validate the simulated anatomies based on comparison of the anatomical parameters to actual anatomical parameters of actual patients. For example, if the combination of a height, width, and depth of a heart chamber results in a volume that has not been seen in an actual patient (e.g., not found in a patient population), then the MLG system may discard that simulated anatomy as it is unlikely to appear in an actual patient.

In some embodiments, the MLG system may employ a bootstrapping technique to speed up the generating of the modeled EM output based on the arrhythmia models. Since a mesh for a left ventricle may have 70,000 vertices, a simulation to generate the modeled EM output for an arrhythmia model for the left ventricle would require the calculation of 70,000 values per EM mesh. If the simulation is for three seconds with a step size of 1 ms, then $70 \times 10^6$ values for the vertices would need to be calculated. If the arrhythmia model library includes a million arrhythmia models, then the number of values that need to be calculated would be $70 \times 10^{12}$. In addition, the calculation of a single value may involve many mathematical operations, and multiple values may be calculated for each vertex. To help reduce the number of values that need to be calculated, the MLG system effectively shares some of the values for the EM meshes generated for one simulation based on one arrhythmia model with another simulation that is based on another arrhythmia model. For example, when a simulation is started, it may take approximately one second before some of the values of the EM mesh have an appreciable effect on the values. For example, at the one-second point in simulations, the EM meshes for simulations based on arrhythmia models with the same source configuration except for scar or fibrosis or pro-arrhythmic substrate location may have very similar values. To reduce the number of values that need to be calculated, the MLG system groups together arrhythmia models with source configurations that are the same or nearly the same except for their scar or fibrosis or pro-arrhythmic substrate locations. The groupings may also not factor in conduction velocity and action potential parameters. The MLG system then runs the simulation for a representative arrhythmia model of the group (e.g., one without a scar or fibrosis or pro-arrhythmic substrate location). To run the simulations for the other arrhythmia models, the MLG system sets the values of the initial EM meshes to the values of the EM mesh at the one-second point in the simulation for the representative arrhythmia model. The MLG system then runs the other simulations for two seconds starting with the values of the initial EM mesh. The modeled EM output for each other arrhythmia model includes the EM meshes for the first second of the representative arrhythmia model and the EM meshes for the two seconds of that other arrhythmia model. In this way, the MLG system can significantly reduce the number of values (e.g., approximately by one-third) that need to be calculated during some of the simulations, which can significantly speed up the generating of the model EM output or voltage solutions for an arrhythmia model library.

In some embodiments, the MLG system may employ other bootstrapping techniques to speed up the generating of modeled EM output. One bootstrapping technique may allow for rapid generation for different configuration parameters such as different geometries, different action potentials, and different conductivity parameters. For example, for a given focal or rotor source location and a set of set of other configuration parameters, a simulation may be run for two seconds. The EM mesh from that simulation is then modified based on a different geometry, or the model parameters are adjusted based on different action potentials or conductivity parameters. The simulation is then continued. It may take a second or so for the activation potentials to stabilize based on the different configuration parameters. Another bootstrapping technique speeds up the generation for a rotor anchored to a different scar location. For example, for a given anchoring scar location, the simulation may be run for two seconds. After the first second, the rotor may stabilize anchored to the scar location. During the second, sufficient modeled EM output is simulated to generate a cardiogram. The EM mesh from that simulation is then modified to have the anchoring scar location moved nearby and possibly modified based on a different geometry. The simulation is then continued. The simulation will allow the rotor to detach from the prior anchoring scar location and attach to the new anchoring scar location. Once attached, the modeled EM output for the next second or so can be used to generate ECGs or VCGs. Also, rather than modifying the anchoring scar location, an ablation shape and pattern can be added to the EM mesh to simulate the effect of that ablation, or the configuration of the anchoring scar may be modified to rapidly simulate the effect of that configuration.

In some embodiments, the MLG system may speed up the generating of derived EM data that is derived from the modeled EM outputs generated for the arrhythmia models of the arrhythmia model libraries. The derived EM data may be a VCG (or other cardiogram) generated from a modeled EM output (e.g., 3,000 EM meshes). The MLG system may group together arrhythmia models with source configurations that have similar anatomical parameters. Each arrhythmia model in a group will thus have similar electrophysiology parameters and different anatomical parameters. The MLG system then runs the simulation for a representative arrhythmia model of the group. The MLG system, however, does not need to run the simulations for the other arrhythmia models in the group. To generate the VCG for one of the other arrhythmia models, the MLG system inputs the modeled EM output of the representative arrhythmia model and the anatomical parameters of the other arrhythmia model. The MLG system then calculates the VCG values for the other arrhythmia model based on the values of the modeled EM output with adjustments based on differences in the anatomical parameters of the representative arrhythmia model and the other source configuration. In this way, the MLG system avoids running any simulations except for the representative arrhythmia model of each group of arrhythmia models.

In some embodiments, the MLG system converts the arrhythmia models based on one polyhedral model to arrhythmia models based on another polyhedral model. Different finite-mesh problem solvers may be based on different polyhedral models. For example, one polyhedral model may be a hexahedral model, and another polyhedral model may be a tetrahedral model. With a hexahedral model, a mesh is filled with hexahedrons. With a tetrahedral model, a mesh is filled with tetrahedrons. If an arrhythmia model library is generated based on a hexahedral model, that arrhythmia library cannot be input to a tetrahedral problem solver. A separate arrhythmia model library based on a tetrahedral model could be generated based on the source configurations, but it would be computationally expensive to do so. To reduce this computational expense of generating a tetrahedral arrhythmia model library, the MLG system converts hexahedral arrhythmia models to tetrahedral arrhythmia models. To convert a tetrahedral arrhythmia model, the MLG system generates a surface representation of the tetrahedral arrhythmia model, for example, based on the surface faces of the mesh of the hexahedral arrhythmia model. The MLG system then populates the volume formed by the surface representation with tetrahedrons to generate a tetrahedral mesh. The MLG system then generates a value for each vertex of the tetrahedral mesh by interpolating the values of the vertices of the hexahedral mesh that are proximate to that vertex of the tetrahedral mesh. In this way, the MLG system can use an arrhythmia model library for one type of polyhedron to generate an arrhythmia model library for another type of polyhedron and avoid the computational expense of generating the arrhythmia model library for the other type of polyhedron from source configurations. The MLG system may also convert an arrhythmia model from one polyhedral model to another polyhedral model for display of the electromagnetic source. For example, the MLG system may run a simulation using a hexahedral ventricular mesh and then, for display, convert to a surface-triangle ventricular mesh to provide a more realistic looking display of the ventricle.

Figure 11:
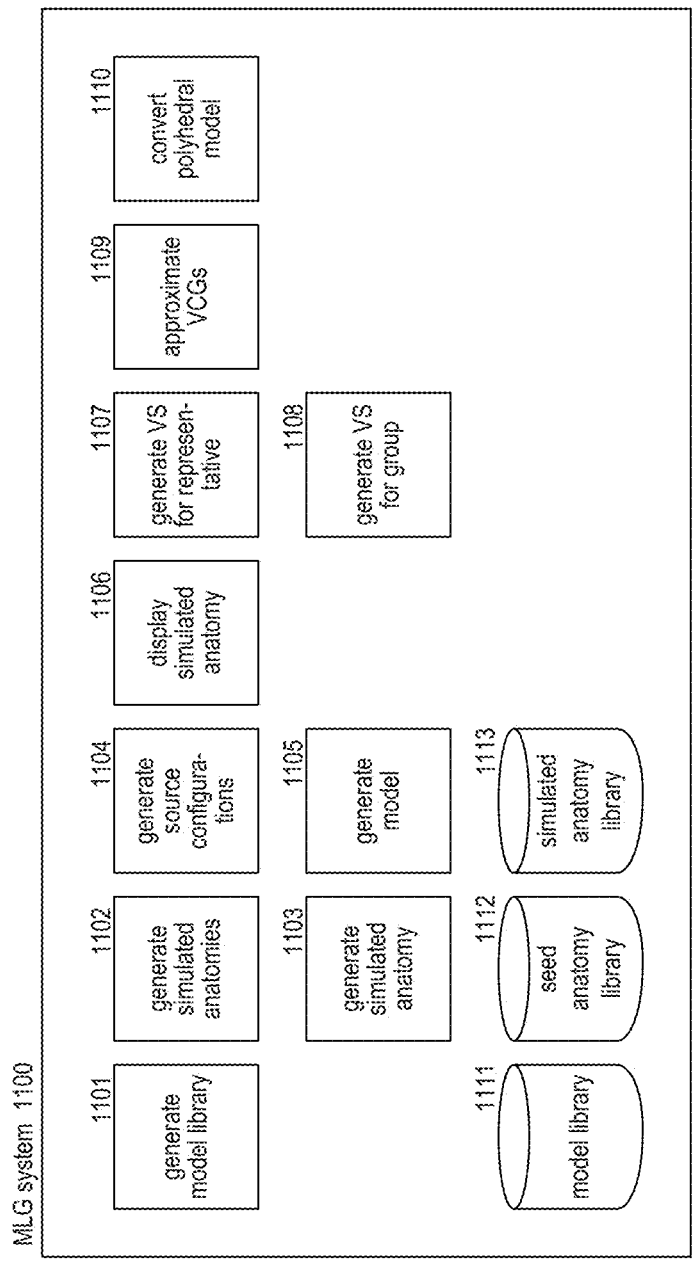
FIG. 11 is a block diagram illustrating components of the MLG system in some embodiments.

FIG. 11 is a block diagram illustrating components of the MLG system in some embodiments. The MLG system 1100 includes a generate model library component 1101, a generate simulated anatomies component 1102, a generate simulated anatomy component 1103, a generate source configurations component 1104, a generate model component 1105, a display simulated anatomy component 1106, a generate voltage solution for representative component 1107, a generate voltage solution for group component 1108, an approximate VCGs component 1109, and a convert polyhedral model component 1110. The MLG system also includes a model library 1111 that stores arrhythmia models, a seed anatomy library 1112, which stores seed anatomies (for example, of a heart), and a simulated anatomy library 1113, which stores simulated anatomies (for example, of a heart). The generate model library component controls the overall generation of the model library. The generate simulated anatomies component generates the simulated anatomies for various sets of weights by invoking the generate simulated anatomy component for each set of weights. The generate source configurations component generates various source configurations based on the simulated anatomies and possible values for electrophysiology parameters. The generate model component generates a model based on a source configuration. The display simulated anatomy component may provide an application programming interface or a user experience for specifying the sets of weights and viewing seed and simulated anatomies. The generate voltage solution for representative component generates a voltage solution for a representative source configuration of a group. The generate voltage solution for group component generates voltage solutions for source configurations in a group based on bootstrapping using the voltage solution for a representative source configuration. The approximate VCGs component generates an approximate VCG based on a voltage solution for similar source configuration but with different anatomical parameters. The convert polyhedral model component converts a hexahedral model to a tetrahedral model.

Figure 12:
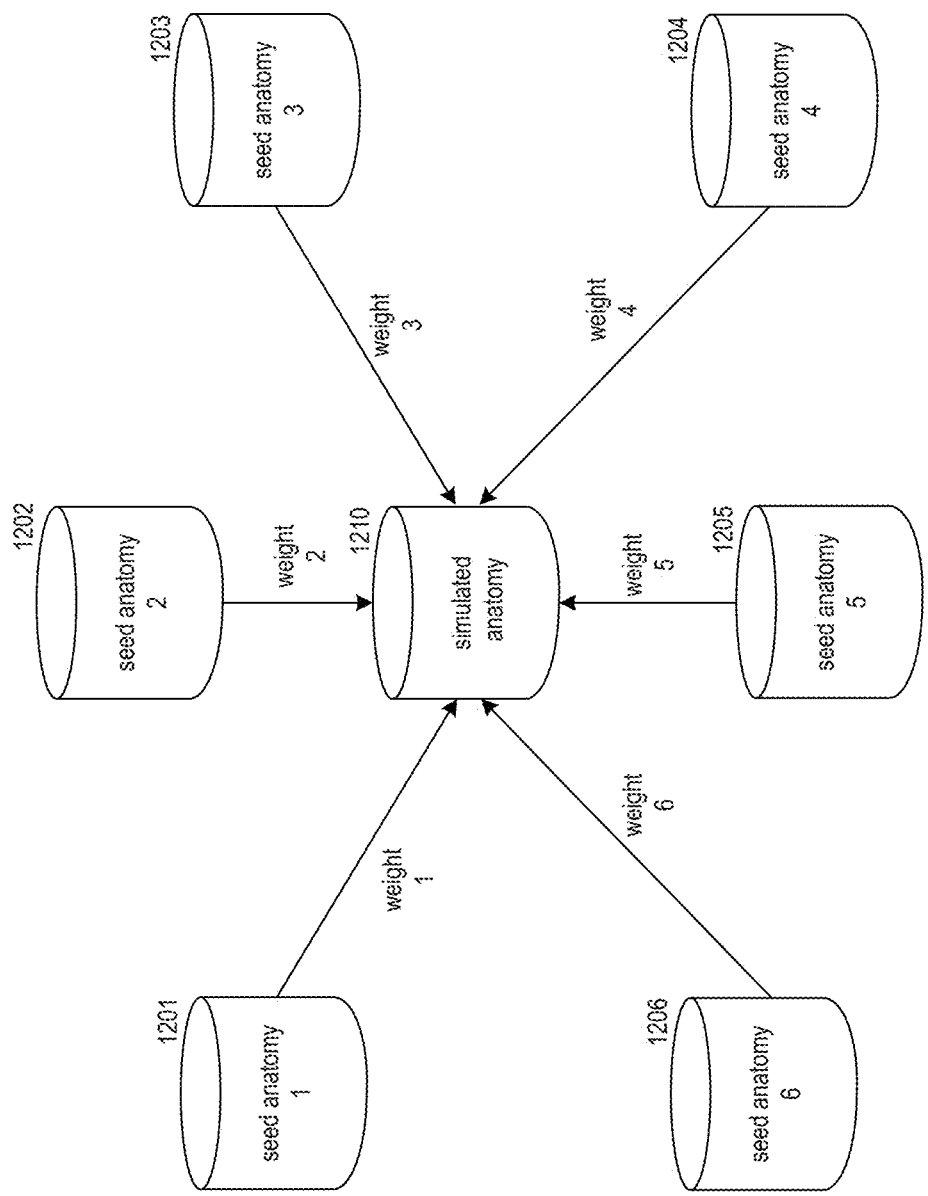
FIG. 12 is a block diagram that illustrates the generating of a simulated anatomy from seed anatomies.

FIG. 12 is a block diagram that illustrates the generating of a simulated anatomy from seed anatomies. In this example, seed anatomies 1201-1206 are used to generate a simulated anatomy 1210. Each seed anatomy has an associated weight that specifies the contribution of the seed anatomy to the simulated anatomy. The weights may sum to 1.0. In some embodiments, rather than a single weight for each seed anatomy, the MLG system may employ a weight for each anatomy parameter of the seed geometry. For example, the weights may include a weight for dimensions of a heart chamber, a weight for the thickness of a heart wall, and so on. The weights for an anatomy parameter of the seed anatomies may sum to 1.0. For example, the weights of seed anatomies 1201-1206 may be 0.1, 0.1, 0.1, 0.1, 0.3, and 0.3, respectively, for the dimensions of the left ventricle and 0.2, 0.2, 0.2, 0.2, 0.1, and 0.1, respectively, for the thickness of an endocardium, myocardium, and epicardium. Alternatively, the weights for the seed anatomies or an anatomical parameter of the seed anatomies need not sum to 1.0.

Figure 13:
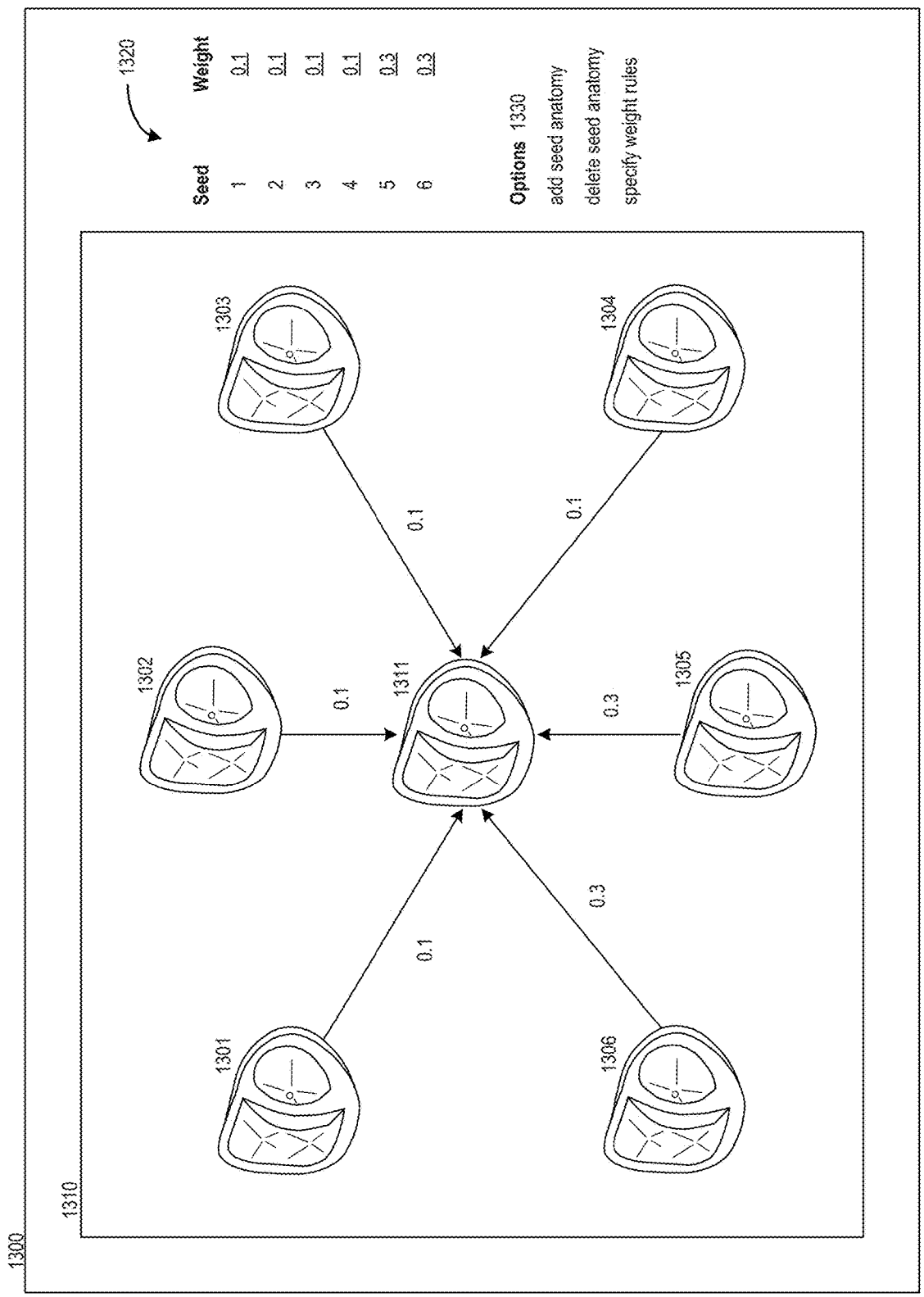
FIG. 13 is a display page that illustrates a user experience for viewing simulated anatomies in some embodiments.

FIG. 13 is a display page that illustrates a user experience for viewing simulated anatomies in some embodiments. A display page 1300 includes a graphics area 1310, a weights area 1320, and an options area 1330. The graphics area displays a graphic of each seed anatomy of a heart and the weights along with a graphic of the simulated anatomy of the heart based on those weights. A user can use the weights area to specify the weight of each seed anatomy. The user may use the options area to add additional seed anatomies, delete a seed anatomy, and specify weight rules based on a user interface (not illustrated) for each option. The MLG system may specify a data structure for storing the anatomical parameters of a seed anatomy. A user can upload the data structure when adding a new seed anatomy. The MLG system may also allow a user to create a library of seed anatomies that can be used to generate simulated anatomies. A weight rule specifies how to generate sets of weights for a library of simulated anatomies. For example, a weight rule may specify to generate every combination of sets of unnormalized weights that range between 0.0 and 1.0 in increments of 0.2 and then normalize the weights so that the weights in each set of weights sums to 1.0. Given this weight rule and six seed anatomies, $5 \times 10^6$ sets of weights are specified. The graphics may be generated using a 3D computer graphics software toolset such as Blender.

Figure 14:
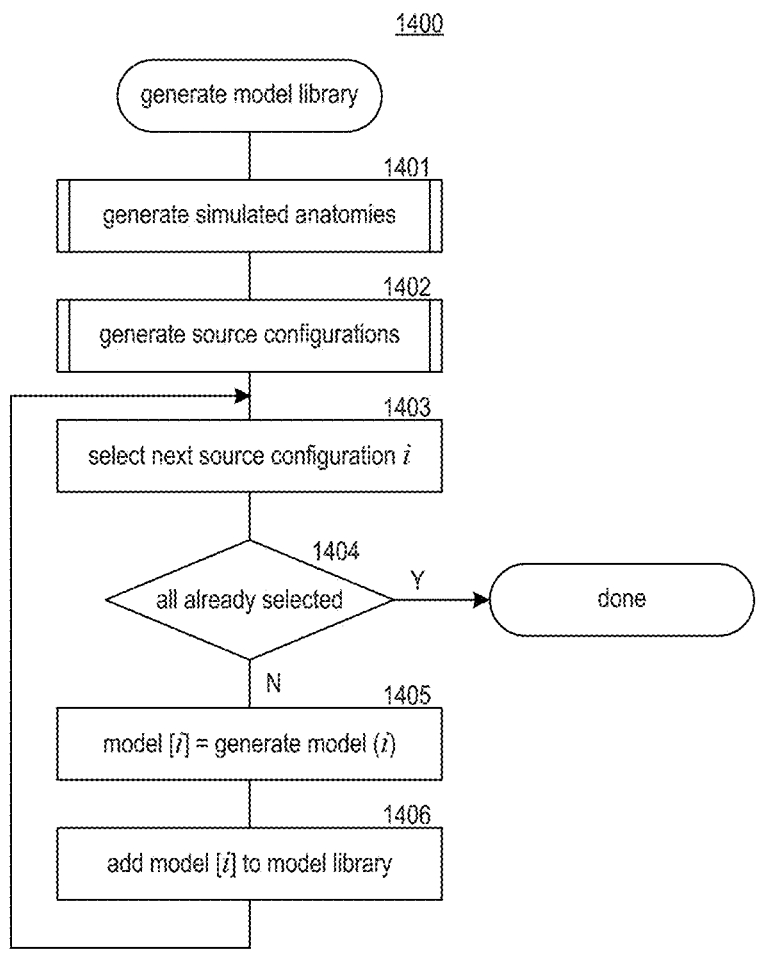
FIG. 14 is a flow diagram that illustrates the processing of a generate model library component of the MLG system in some embodiments.

FIG. 14 is a flow diagram that illustrates the processing of a generate model library component of the MLG system in some embodiments. The generate model library component 1400 is invoked to generate a model library, such as an arrhythmia model library, based on seed anatomies and, for each model, a set of weights for the seed anatomies for generating the anatomical parameters along with electrophysiology parameter specifications that specify the range of values for each electrophysiology parameter. The component generates source configurations from combinations of the anatomical parameters and electrophysiology parameters. In block 1401, the component invokes a generate simulated anatomies component to generate the simulated anatomies from the seed anatomies. In block 1402, the component invokes a generate source configurations component to generate the source configurations based on the anatomical parameters of the simulated anatomies and the electrophysiology parameter specifications. In blocks 1403-1406, the component loops, generating a model for each source configuration. In block 1403, the component selects the next source configuration i. In decision block 1404, if all the source configurations have already been selected, then the component completes, else the component continues at block 1405. In block 1405, the component invokes a generate model component, passing an indication of the source configuration i, to generate a model (model[i]) for that source configuration. In block 1406, the component adds the generated model to the model library and then loops to block 1403 to select the next source configuration.

Figure 15:
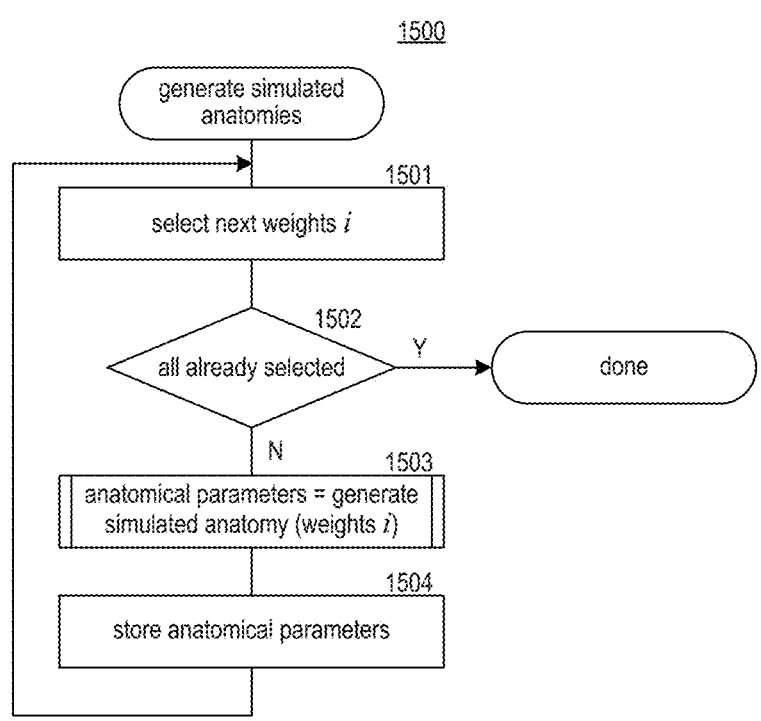
FIG. 15 is a flow diagram that illustrates the processing of a generate simulated anatomies component of the MLG system in some embodiments.

FIG. 15 is a flow diagram that illustrates the processing of a generate simulated anatomies component of the MLG system in some embodiments. The generate simulated anatomies component 1500 is invoked to generate simulated anatomies based on seed anatomies and associated sets of weights. In block 1501, the component selects the next set of weights i. In decision block 1502, if all the sets of weights have already been selected, then the component completes, else the component continues at block 1503. In block 1503, the component invokes the generate simulated anatomy component, passing an indication of the selected set of weights i and receiving an indication of the anatomical parameters for the simulated anatomy. In block 1504, the component stores the anatomical parameters and then loops to block 1501 to select the next set of weights.

Figure 16:
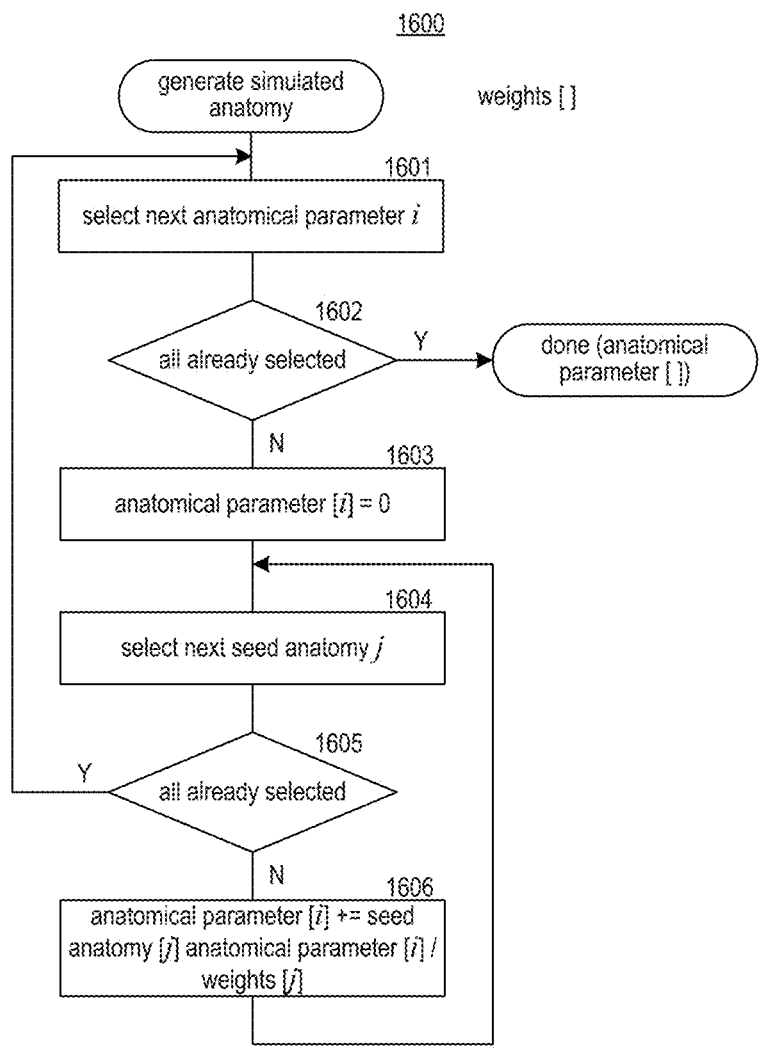
FIG. 16 is a flow diagram that illustrates the processing of a generate simulated anatomy component of the MLG system in some embodiments.

FIG. 16 is a flow diagram that illustrates the processing of a generate simulated anatomy component of the MLG system in some embodiments. The generate simulated anatomy component 1600 is invoked, passing an indication of a set of weights, and generates a simulated anatomy based on that set of weights. In block 1601, the component selects the next anatomical parameter i. In decision block 1602, if all the anatomical parameters have already been selected, then the component returns an indication of the anatomical parameters for the simulated anatomy, else the component continues at block 1603. In block 1603, the component initializes the selected anatomical parameter i. In blocks 1604-1606, the component loops, adjusting the selected anatomical parameter based on the weights and the value for that anatomical parameter for each seed anatomy. In block 1604, the component selects the next seed anatomy j. In decision block 1605, if all the seed anatomies have already been selected, then the component loops to block 1601 to select the next anatomical parameter, else the component continues at block 1606. In block 1606, the component sets the selected anatomical parameter i to the sum of the selected anatomical parameter i and that anatomical parameter i for the selected seed anatomy j divided by the weight for the selected seed anatomy. The component then loops to block 1604 to select the next seed anatomy.

Figure 17:
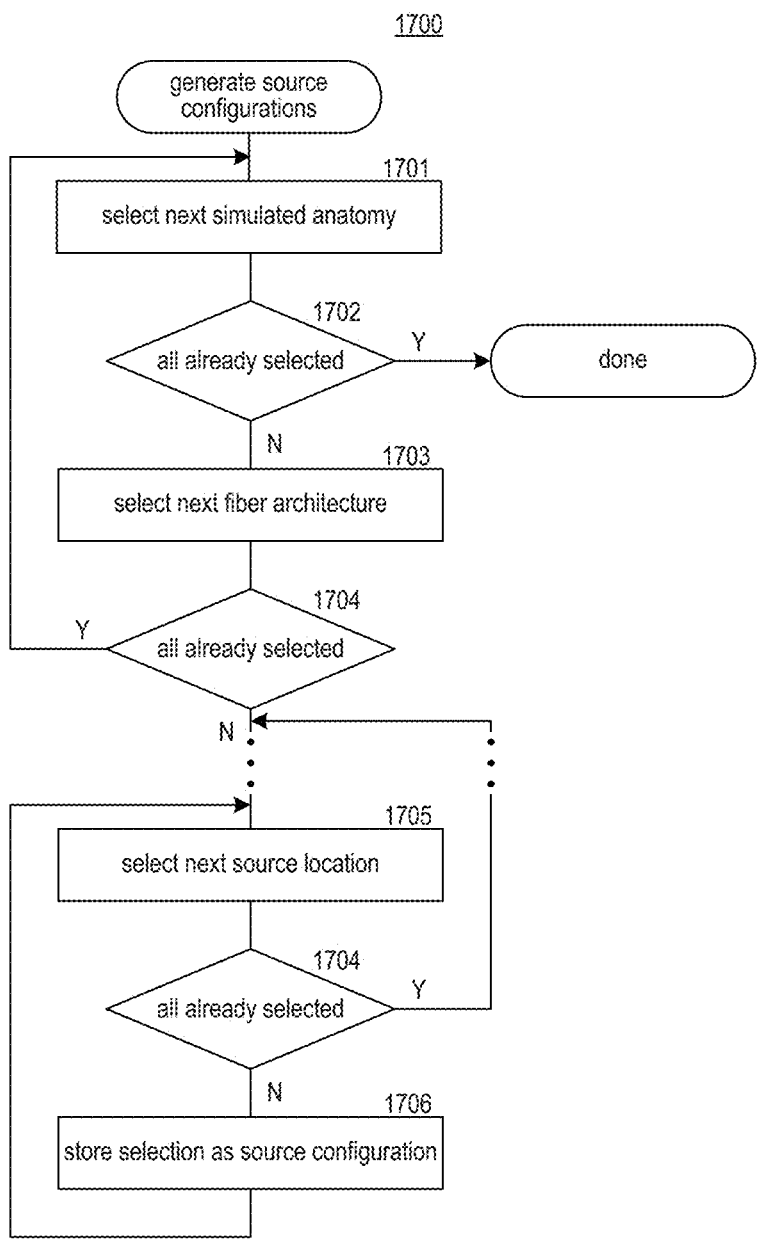
FIG. 17 is a flow diagram that illustrates the processing of a generate source configurations component of the MLG system in some embodiments.

FIG. 17 is a flow diagram that illustrates the processing of a generate source configurations component of the MLG system in some embodiments. The generate source configurations component 1700 is invoked to generate source configurations for use in generating a model library. A source configuration is specified by a simulated anatomy and a combination of values of anatomical parameters. In block 1701, the component selects a next simulated anatomy. In decision block 1702, if all the simulated anatomies have already been selected, then the component completes, else the component continues at block 1703. In blocks 1703-1707, the component loops, selecting sets of anatomical parameters for the selected simulated anatomy. In block 1703, the component selects the next value for the fiber architecture anatomical parameter. In decision block 1704, if all the values for the fiber architecture anatomical parameter have already been selected for the selected simulated anatomy, then all the source configurations for the selected simulated anatomy have been generated and the component loops to block 1701 to select the next simulated anatomy, else the component continues to select a value for each of the other anatomical parameters, as illustrated by the ellipsis. In block 1705, the component selects the next source location for the selected simulated anatomy and set of values for the other anatomical parameters. In decision block 1706, if all the source locations have already been selected for the selected simulated anatomy and set of values for the other anatomical parameters, then the component loops to block 1705 to select a new set of values. In block 1707, the component stores an indication of the selected simulated anatomy and the set of selected values for the anatomical parameters as a source configuration and then loops to block 1705 to select the next source location.

Figure 18:
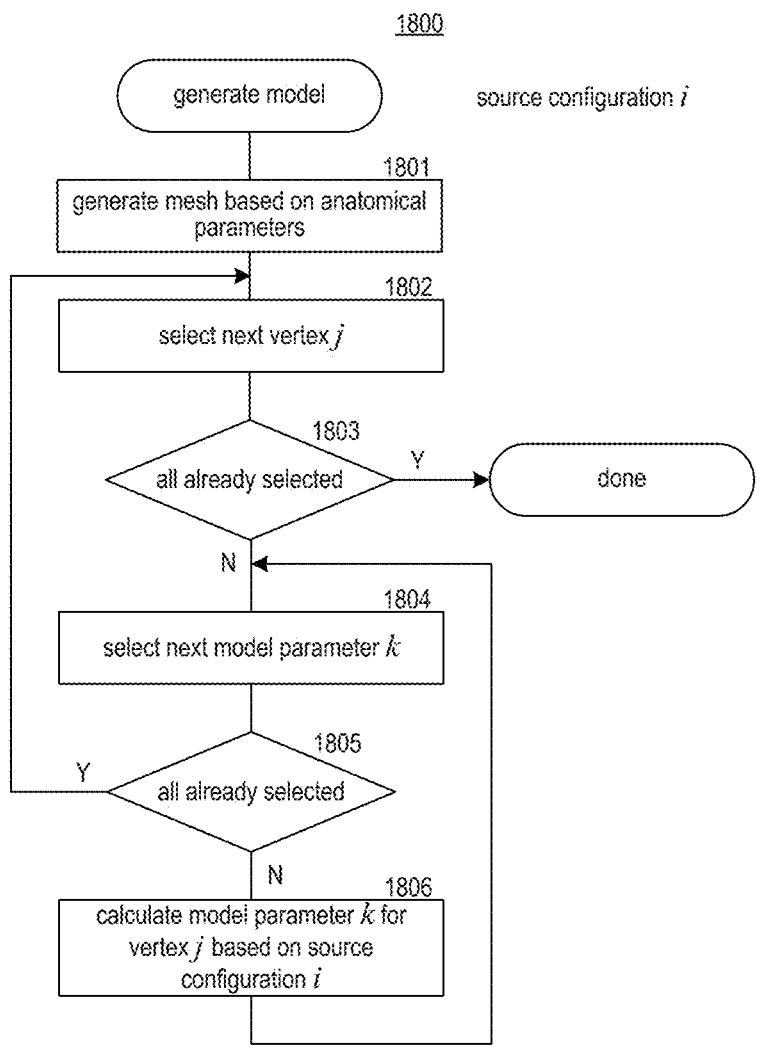
FIG. 18 is a flow diagram that illustrates the processing of a generate model component of the MLG system in some embodiments.

FIG. 18 is a flow diagram that illustrates the processing of a generate model component of the MLG system in some embodiments. The generate model component 1800 is invoked, passing an indication of a source configuration i, and generates a model. The model includes one or more model parameters for each vertex of a mesh representing the simulated anatomy of the source configuration. In block 1801, the component generates the mesh based on the anatomical parameters. The mesh may be represented by a data structure that includes, for each vertex, a reference to its adjacent vertices explicitly or implicitly along with a value for one or more model parameters for use in generating, for example, a voltage for that vertex. In block 1802, the component selects the next vertex j. In decision block 1803, if all the vertices have already been selected, then the component completes, else the component continues at block 1804. In block 1804, the component selects the next model parameter k of the computational model for the selected vertex. In decision block 1805, if all the model parameters have already been selected, then the component loops to block 1802 to select the next vertex, else the component continues at block 1806. In block 1806, the component calculates the selected model parameter k for the selected vertex j based on the source configuration i and then loops to block 1804 to select the next model parameter.

Figure 19:
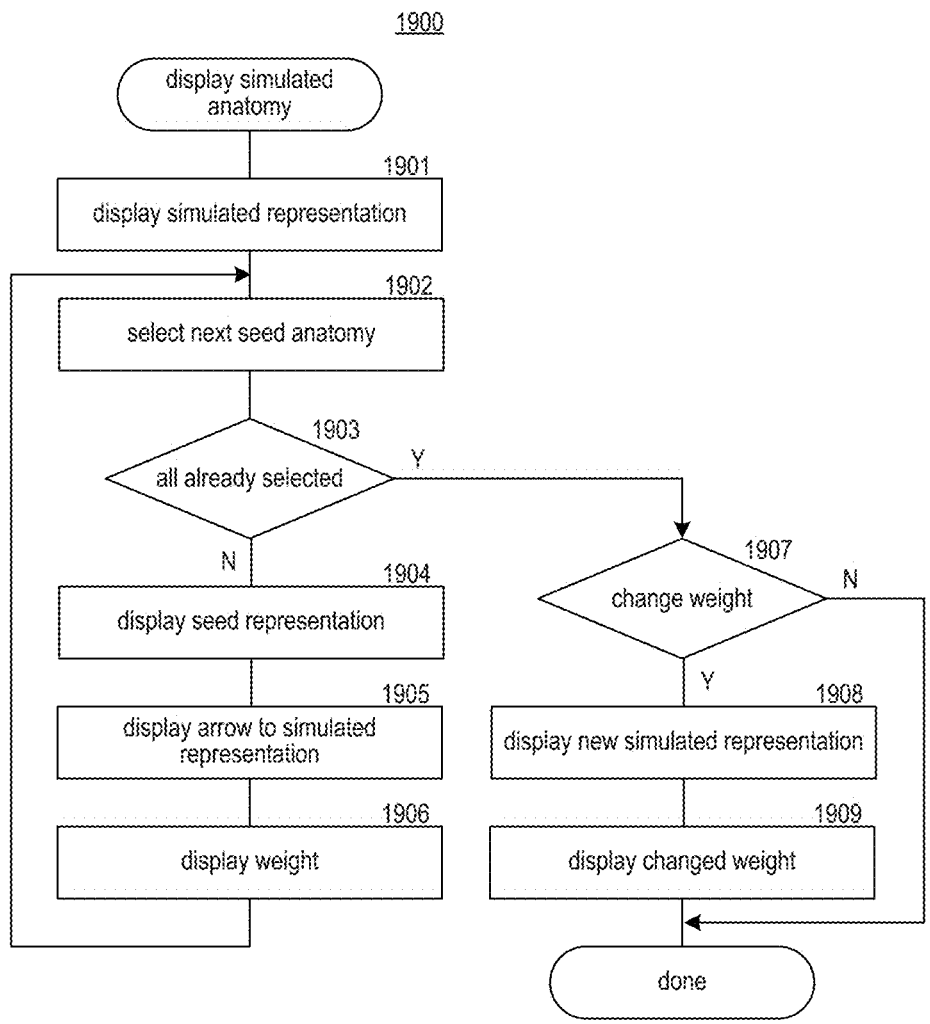
FIG. 19 is a flow diagram that illustrates the processing of a display simulated anatomy component of the MLG system in some embodiments.

FIG. 19 is a flow diagram that illustrates the processing of a display simulated anatomy component of the MLG system in some embodiments. The display simulated anatomy component 1900 is invoked to display a simulated anatomy that has been generated based on seed anatomies. In block 1901, the component displays a simulated representation of a simulated anatomy, such as graphic 1311. In blocks 1902-1906, the component loops, displaying a seed representation of each seed anatomy. In block 1902, the component selects the next seed anatomy that was used to generate the simulated anatomy. In decision block 1903, if all the seed anatomies have already been selected, then the component continues at block 1907, else the component continues at block 1904. In block 1904, the component displays a seed representation of the selected seed anatomy, such as graphics 1301-1306. In block 1905, the component displays an arrow from the seed representation to the simulated representation. In block 1906, the component displays the weight associated with the seed anatomy adjacent to the arrow and then loops to block 1902 to select the next seed anatomy. In decision block 1907, if a user indicates to change the weight, then the component continues at block 1908, else the component completes. In block 1908, the component displays a new simulated representation of a simulated anatomy that is based on the changed weight. The component may invoke the generate simulated anatomy component to generate the simulated anatomy and a component to generate the graphic for the simulated anatomy. In block 1909, the component displays the changed weight near the arrow from the seed representation of the seed anatomy whose weight has been changed and then completes.

Figure 20:
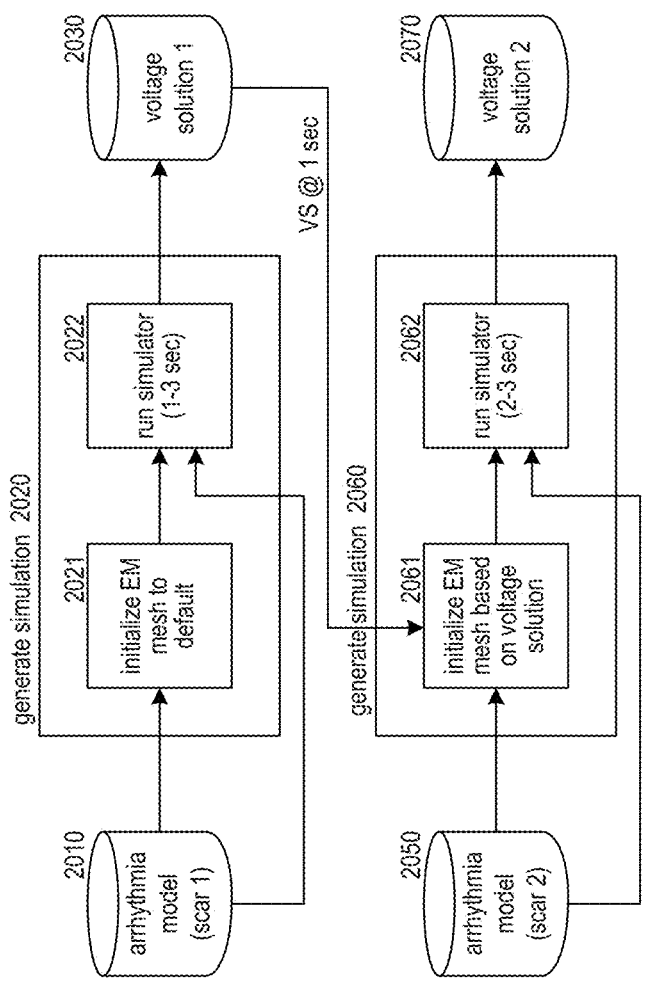
FIG. 20 is a block diagram that illustrates the process of bootstrapping a simulation based on an EM mesh of a prior simulation with similar anatomical parameters.

FIG. 20 is a block diagram that illustrates the process of bootstrapping a simulation based on an EM mesh of a prior simulation with similar anatomical parameters. The simulation may be bootstrapped based on a prior simulation that in turn is based on an arrhythmia model for the same source configuration except for different scar or fibrosis or pro-arrhythmic substrate locations. To generate the initial EM mesh, a generate simulation component 2020 inputs an arrhythmia model 2010 with a first scar or fibrosis or pro-arrhythmic substrate location and outputs a voltage solution 2030. The generate simulation component 2020 includes an initialize mesh to default component 2021 and a run simulation component 2022. The initialize EM mesh component initializes an EM mesh with default values for the voltages of the vertices. The run simulation component 2022 runs a simulation (e.g., for 3 seconds) based on the initialized EM mesh and the arrhythmia model 2010 to generate a voltage solution (e.g., 3,000 EM meshes) and outputs the voltage solution 2030. To bootstrap a simulation, a generate simulation component 2060 inputs an arrhythmia model 2050 with a second scar or fibrosis or pro-arrhythmic substrate location and outputs a voltage solution 2070. The generate simulation component 2060 includes an initialize EM mesh based on voltage solution component 2061 and a run simulation component 2062. The initialize EM mesh based on voltage solution component 2061 inputs the voltage solution 2030 and initializes the EM mesh to, for example, the EM mesh corresponding to the one-second point of the voltage solution 2030. The run simulation component 2062 runs a simulation based on the initialized EM mesh. For example, if the simulations are three seconds and the initialized EM mesh is based on an EM mesh at the one-second point, then the run simulation component 2062 runs a simulation for two additional seconds. The run simulation component 2062 stores the voltage solution in a voltage solution store 2070.

Figure 21:
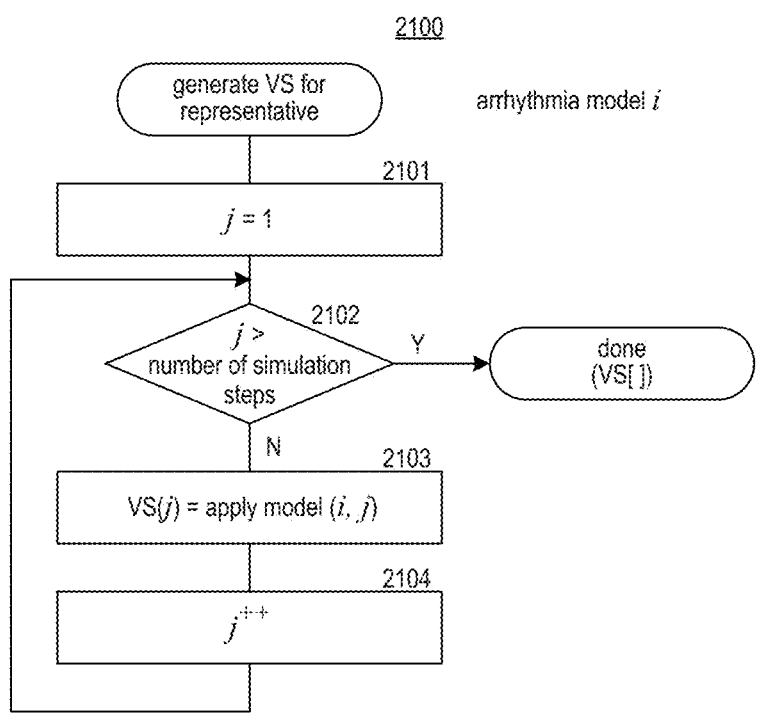
FIG. 21 is a flow diagram that illustrates the processing of a component to generate a voltage solution for a representative arrhythmia model of a group of the MLG system in some embodiments.

FIG. 21 is a flow diagram that illustrates the processing of a component to generate a voltage solution for a representative arrhythmia model of a group of the MLG system in some embodiments. The generate voltage solution for representative component 2100 generates a voltage solution for an arrhythmia model i. In block 2101, the component initializes an index j to track the number of simulation steps. In decision block 2102, if the index j is greater than the number of simulation steps, then the component completes, indicating the voltage solution, else the component continues at block 2103. In block 2103, the component applies the computational model based on the arrhythmia model and the selected simulation step to generate a voltage solution for the selected simulation step. In block 2104, the component increments to the next simulation step and loops to block 2102.

Figure 22:
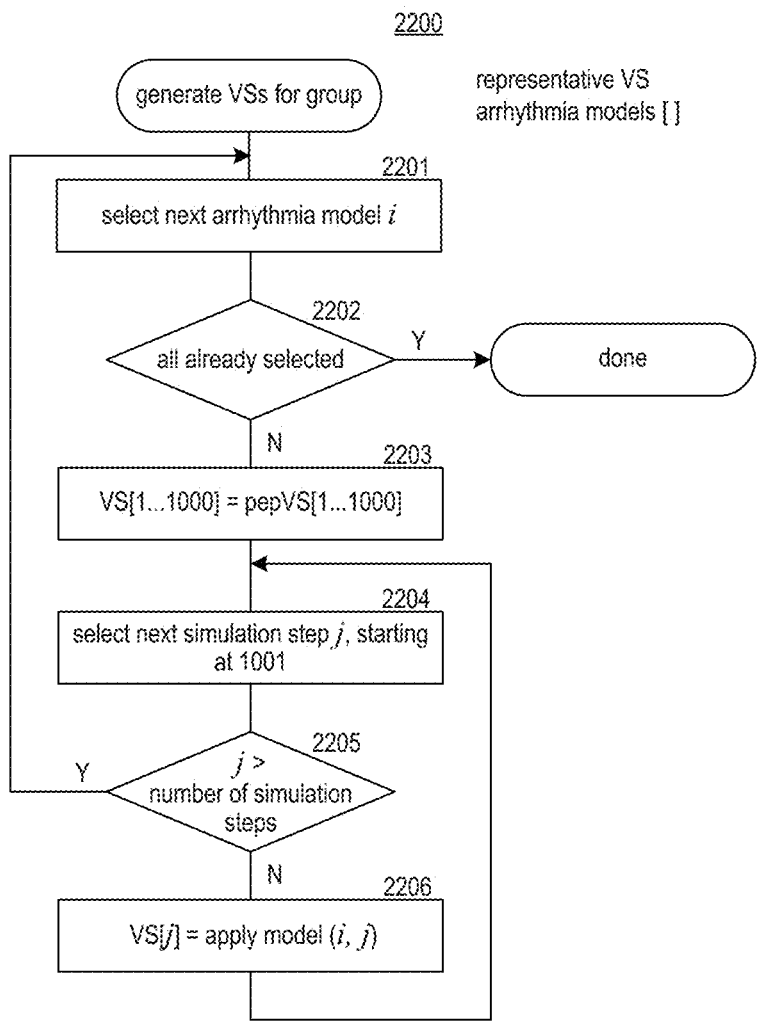
FIG. 22 is a flow diagram that illustrates the processing of a generate voltage solution component for a group of arrhythmia models based on a representative voltage solution of the MLG system in some embodiments.

FIG. 22 is a flow diagram that illustrates the processing of a generate voltage solution component for a group of arrhythmia models based on a representative voltage solution of the MLG system in some embodiments. The generate voltage solution for group component 2200 is passed an indication of a representative voltage solution and a set of arrhythmia models. In block 2201, the component selects the next arrhythmia model i. In decision block 2202, if all the arrhythmia models have already been selected, then the component completes, else the component continues at block 2203. In block 2203, the component initializes the voltage solution for the selected arrhythmia model to the representative voltage solution for the first 1000 simulation steps. In blocks 2204-2206, the component loops, running the simulation starting at simulation step 1001 and continuing to the end of the simulation. In block 2204, the component selects the next simulation step j, starting at simulation step 1001. In decision block 2205, if the current simulation step is greater than the number of simulation steps, then the component loops to block 2201 to select the next arrhythmia model, else the component continues at block 2206. In block 2206, the component applies the arrhythmia model based on the simulation step to generate a voltage solution for the simulation step and then loops to block 2204 to select the next simulation step.

Figure 23:
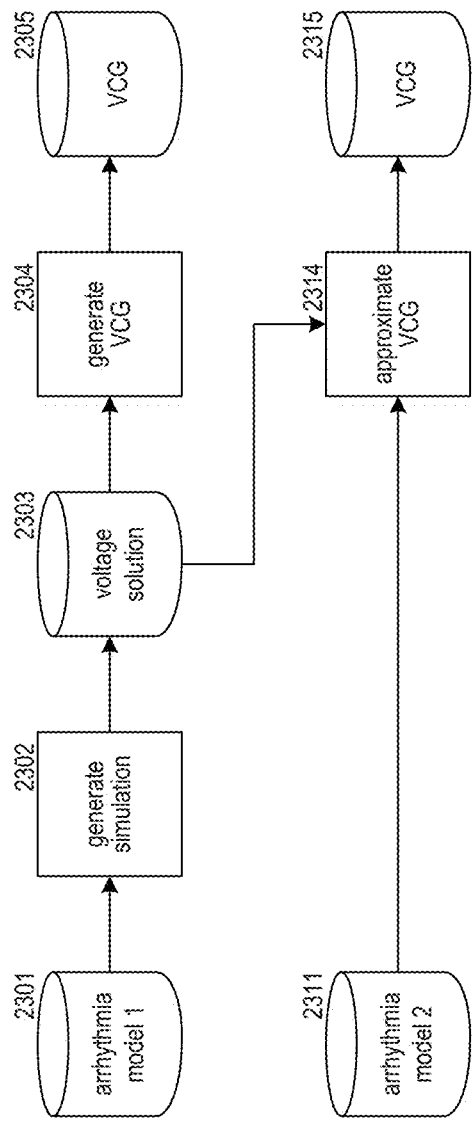
FIG. 23 is a block diagram that illustrates the process of approximating a cardiogram based on a voltage solution for an arrhythmia model with different anatomical parameters.

FIG. 23 is a block diagram that illustrates the process of approximating a vectorcardiogram based on a voltage solution for an arrhythmia model with different anatomical parameters. To generate the voltage solution for an arrhythmia model 2301 based on a first set of anatomical parameters, a generate simulation component 2302 inputs the arrhythmia model and outputs a voltage solution 2303. A generate VCG component 2304 then generates a VCG from the voltage solution and stores it in a VCG store 2305. To approximate a VCG for an arrhythmia model based on a similar source configuration but with different anatomical parameters, an approximate VCG component 2314 inputs an arrhythmia model 2311, generates an approximate VCG, and outputs the VCG 2315.

Figure 24:
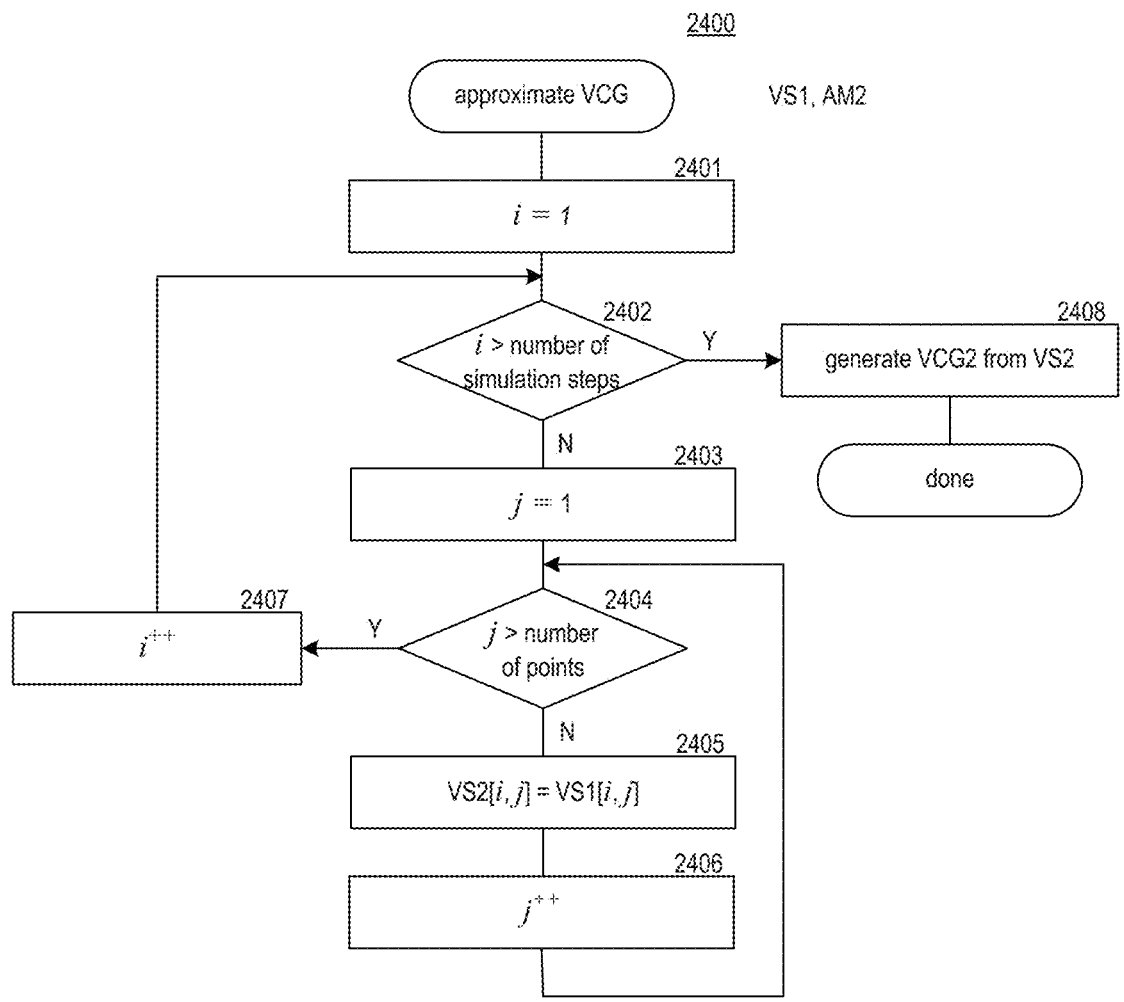
FIG. 24 is a flow diagram that illustrates the processing of an approximate VCG component of the MLG system in some embodiments.

FIG. 24 is a flow diagram that illustrates the processing of an approximate VCG component of the MLG system in some embodiments. The approximate VCG component 2400 inputs a voltage solution ("VS1") generated based on a first arrhythmia model with first anatomical parameters and approximates a VCG for a second arrhythmia model with second anatomical parameters. In block 2401, the component sets an index i for indexing through the simulation steps. In decision block 2402, if index i is greater than the number of simulations steps, then the component continues at block 2408, else the component continues at block 2403. In block 2403, the component sets an index j for indexing through the points (e.g., vertices or Gaussian points) of the mesh of an arrhythmia model. In decision block 2404, if index j is greater than the number of points, then the component continues at block 2407, else the component continues at block 2405. In block 2405, the component sets the value for the voltage solution ("VS2") for the second arrhythmia model at the index simulation step and point to the corresponding value for the voltage solution of the first arrhythmia model. In block 2405, the component increments index j and loops to block 2404. In block 2407, the component increments index i and loops to block 2402. In block 2408, the component generates the VCG for the second arrhythmia model based on the generated voltage solution VS2 and then completes.

Figure 25:
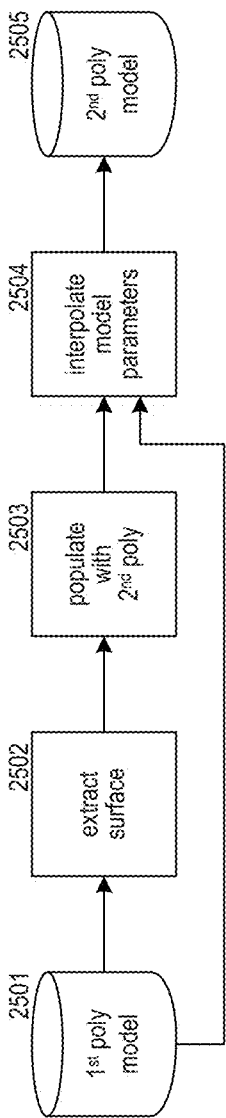
FIG. 25 is a block diagram that illustrates the process of converting an arrhythmia model based on a first polyhedron to an arrhythmia model based on a second polyhedron in some embodiments.

FIG. 25 is a block diagram that illustrates the process of converting an arrhythmia model based on a first polyhedron to an arrhythmia model based on a second polyhedron in some embodiments. A first polyhedron arrhythmia model of a first polyhedron arrhythmia model 2501 is input to an extract surface component 2502. The extract surface component extracts the surface of the mesh of the arrhythmia model. A populate with second polyhedrons component 2303 inputs the surface and populates the volume within the surface with the second type of polyhedrons. An interpolate model parameters component 2504 inputs the second polyhedron mesh and the first polyhedral model and generates model parameters of the second polyhedral model and outputs the second polyhedral model 2505.

Figure 26:
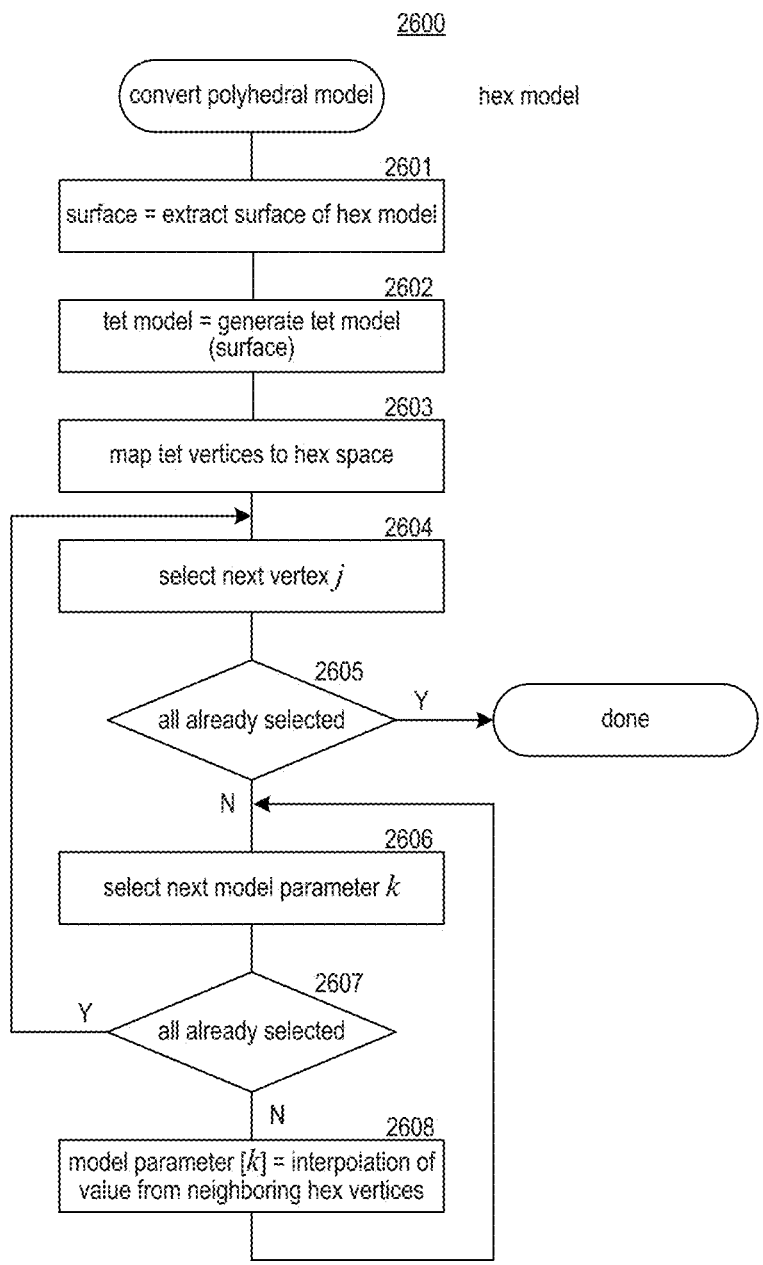
FIG. 26 is a flow diagram that illustrates the processing of a convert polyhedral model component of the MLG system in some embodiments.

FIG. 26 is a flow diagram that illustrates the processing of a convert polyhedral model component of the MLG system in some embodiments. A convert polyhedral model component 2600 is invoked to convert a hexahedral model to a tetrahedral model. In block 2601, the component extracts the surface from the hexahedral model. In block 2602, the component generates a tetrahedral mesh based on the surface of the hexahedral model. In block 2603, the component maps the vertices of the tetrahedral mesh to the space of the hexahedral mesh of the hexahedral model, for example, setting the locations of the vertices relative to the same origin. In block 2604, the component selects the next vertex j of the tetrahedral mesh. In decision block 2605, if all such vertices have already been selected, then the component completes, else the component continues at 2606. In block 2606, the component selects the next model parameter k. In decision block 2607, if all the model parameters have already been selected for the selected vertex, then the component loops to block 2604 to select the next vertex, else the component continues to block 2608. In block 2608, the component sets the selected model parameter based on interpolation of the values of the selected model parameter of neighboring vertices in the hexahedral model. The component then loops to block 2606 to select the next model parameter.

Patient Matching System

Methods and systems for identifying attributes or classification of an EM source within a body based on patient matching that is matching a patient source configuration to model source configurations of the EM source are provided. In some embodiments, a patient matching ("PM") system uses the matching model source configurations to speed up the process of identifying the attributes for the patient or to provide a more accurate classification for the patient using a classifier. To identify an attribute (e.g., arrhythmia source location) for a patient, the PM system generates a mapping of each model source configuration used to generate simulated (or modeled) EM output to the derived EM data that is derived from the simulated EM output generated based on that model source configuration. Each derived (or modeled) EM data is also mapped to an attribute associated with the EM source having the model source configuration. For example, when the EM source is a heart, the model source configurations include configuration parameters such as anatomical parameters and electrophysiology parameters. The configuration parameters may include the source location of an arrhythmia, a rotor type, type of disorder or condition, and so on. One of the configuration parameters, such as arrhythmia source location, may be designated as an attribute parameter, which represents the attribute to be identified for a patient. The PM system generates the mappings of model source configurations to modeled VCGs and generates the mappings of modeled VCGs to their corresponding source location of the arrhythmia. The mappings of modeled VCGs to source locations may be generated in a manner similar to how the training data is generated by the MLMO system with the attribute corresponding to the label. In some embodiments, the mappings of derived electromagnetic data to source configurations and attributes may be based on data collected from actual patients rather than data input to and generate by a simulation.

In some embodiments, the PM system uses the mappings to identify the attribute for a patient based on a combination of the patient source configuration of the patient and a patient VCG of the patient. The attribute can be identified by comparing the patient VCG to each modeled VCG to identify the most similar modeled VCG and by identifying the attribute of that most similar modeled VCG as the patient attribute of the patient. It can, however, be computationally very expensive to compare the patient VCG to each modeled VCG because the number of modeled VCGs may be in the millions. The PM system may employ various techniques to reduce the computational expense. With one technique, the PM system uses the patient source configuration to reduce the number of modeled VCGs to which the patient VCG needs to be compared. The PM system may allow a user to provide the patient source configuration for a patient. It would be preferable if a value for each configuration parameter of the patient source configuration could be provided. In practice, however, it may be that the values of only certain configuration parameters are known for a patient. In such cases, the PM system performs the comparison based on the known values of the configuration parameters, rather than all the configuration parameters. The anatomical parameters for a patient may be calculated based on imaging scans. The action potentials may be calculated based on output of a basket catheter inserted into the patient's heart or the patient's history of anti-arrhythmic drug or gene therapy, and the conductivity may be calculated based on analysis of the patient's ECG. The configuration parameters may also include electrophysiology parameters to indicate whether the action potential and/or conductivity represents a diseased state. In such a case, if the action potential or conductivity of a patient is not available, the configuration parameters indicate whether the action potential or conductivity represent a disease state. The PM system may use various techniques to assess the similarity between a patient source configuration and a model source configuration such as one based on least squares, cosine similarity, and so on. The PM system may generate a similarity score for each model source configuration and identify as matching model source configurations those with a similar score that is above a matching threshold.

In some embodiments, after the matching model source configurations are identified, the PM system compares the patient VCG to the modeled VCGs to which the matching model source configurations are mapped. The PM system may generate a similarity score for each modeled VCG (e.g., using a Pearson correlation technique) and identify as matching modeled VCGs those with a similarity score above a threshold similarity. The PM system then identifies the attribute(s) for the patient based on the attributes of the matching modeled VCGs. For example, if the attribute is source location of an arrhythmia, the PM system may generate an average of the source locations weighted based on the similarity scores of the matching model VCGs. In this way, the PM system avoids the computational expense of comparing a patient VCG to every modeled VCG.

In some embodiments, the PM system may employ other techniques for reducing the computational expense of comparing the patient VCG to every modeled VCG. For example, the PM system may identify features of VCGs such as area, maximum dimensions, and so on. The PM system then may generate an index that maps values of the features to the modeled VCGs having those values. To identify modeled VCGs that match a patient VCG, the PM system identifies the features of the patient VCG and uses the index to identify matching modeled VCGs. For example, the PM system may identify for, each feature, a set of the modeled VCGs that match that feature of the patient VCG. The PM system can then identify the modeled VCGs that are common to each set (e.g., intersection of the sets) or most common to the sets as the matching modeled VCGs. The PM system can then compare those matching modeled VCGs to the patient VCG as described above to identify the attribute.

In some embodiments, the PM system may employ patient matching to improve the classification of VCGs based on a trained classifier. The PM system may generate clusters of similar model source configurations using various clustering techniques. The clustering techniques may include a centroid-based clustering technique (e.g., k-means clustering), a supervised or unsupervised learning clustering technique (e.g., using a neural network), and so on. With a centroid-based clustering technique, the PM system generates clusters by successively adding each model source configuration to the current cluster of model source configurations to which it is most similar. The PM system may combine and split clusters dynamically, for example, based on the number of model source configuration in each cluster, the similarity of the model source configurations of one cluster to another, and so on. After the clusters are identified, the PM system may employ components of the MLMO system to generate a classifier for each cluster. The PM system trains the classifier for a cluster based on the modeled VCGs for the model source configurations of that cluster as the training data for the classifier.

In some embodiments, to generate a classification for a patient, the PM system identifies the cluster with model source configurations that best matches the patient source configuration. For example, the PM system may generate a similarity score for each cluster based on similarity between a representative model source configuration (e.g., with average values of a cluster) of that cluster and the patient source configuration. The PM system then selects the classifier for the cluster with the highest similarity score and applies that classifier to the patient VCG to generate the classification for the patient. Because each classifier is trained based on a cluster of similar model source configurations, each classifier is adapted to generate classifications based only on the differences, which may be subtle, in those similar model source configurations. In contrast, a classifier trained based on all model source configurations may not be able to factor in subtle differences between similar model source configurations. As such, a classifier trained based on a cluster of similar model source configurations may provide a more accurate classification than a classifier trained based on all model source configurations.

In some embodiments, the PM system may generate the modeled EM output for the model source configurations assuming a standard orientation of a heart. If a patient, however, has a heart with a somewhat different orientation, then the matching modeled VCGs may not have attributes or classifications that would apply to the patient because of the differences in the orientations. In such a case, the PM system may perform a VCG rotation prior to comparing the patient VCG to the modeled VCGs. The PM system may rotate either each modeled VCG or the patient VCG. The PM system may generate a rotation matrix based on the difference in orientations. The PM system then performs a matrix multiplication between each point (e.g., x, y, and z values) of a VCG and the rotation matrix (e.g., a 3-by-3 matrix) to generate a rotated point for the rotated VCG. The MLMO system may also rotate VCGs based on difference in orientations.

Figure 27:
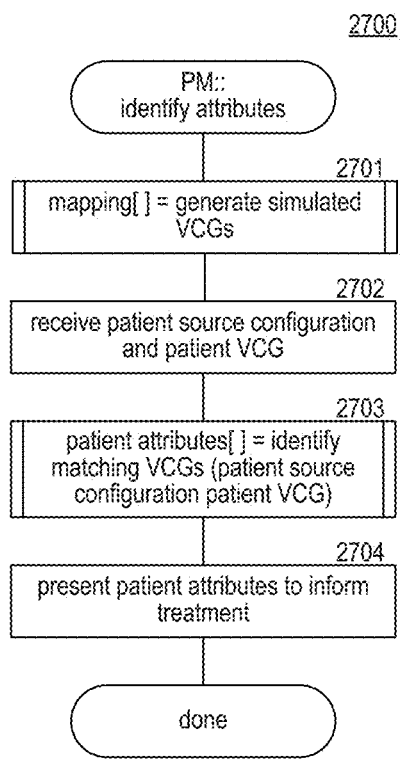
FIG. 27 is a flow diagram that illustrates the processing of an identify attributes component of the PM system in some embodiments.

FIGS. 27-30 are flow diagrams that illustrates the processing of components of the PM system in some embodiments. FIG. 27 is a flow diagram that illustrates the processing of an identify attributes component of the PM system in some embodiments. The identify attributes component 2700 identifies patient attributes of a patient based on a patient source configuration and a patient cardiogram (e.g., the VCG). In block 2701, the component invokes the generate simulated VCGs component of the MLMO system to generate the modeled VCGs and then maps them to the model source configurations from which they were generated. In block 2702, the component retrieves the patient source configuration and the patient VCG. In block 2703, the component invokes the identify matching VCGs component passing an indication of the patient source configuration and the patient VCG to identify patient attributes based on the matching VCGs. In block 2704, the component presents the patient attributes to inform treatment on the patient and then completes.

Figure 28:
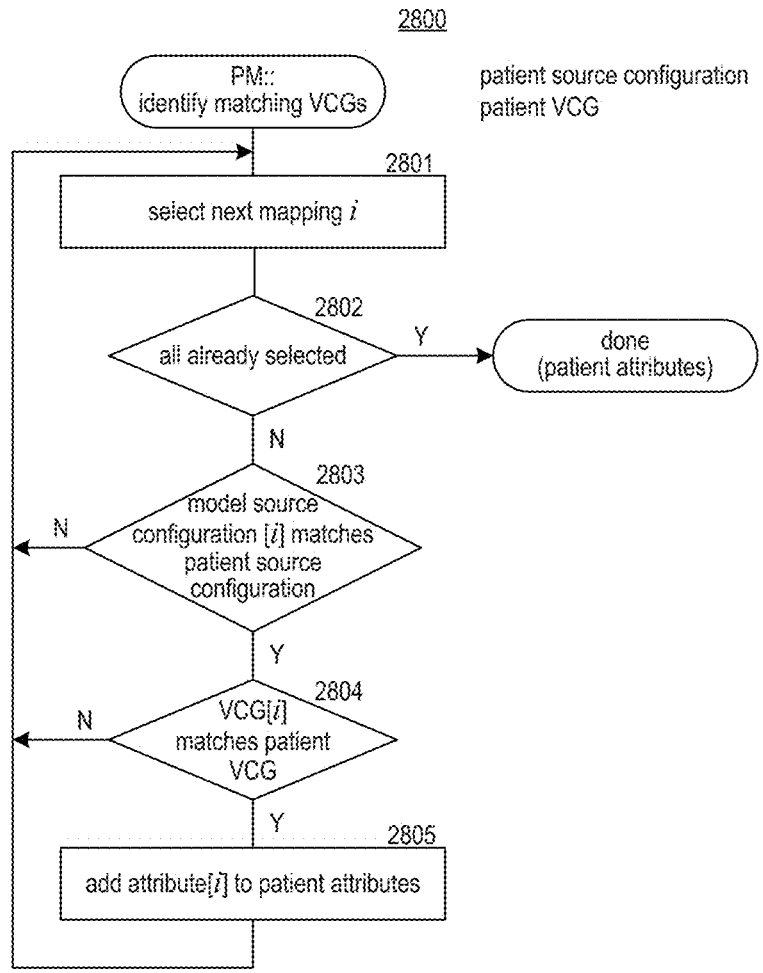
FIG. 28 is a flow diagram that illustrates the processing of an identify matching VCGs component of the PM system in some embodiments.

FIG. 28 is a flow diagram that illustrates the processing of an identify matching VCGs component of the PM system in some embodiments. The identify matching VCGs component 2700 is passed a patient source configuration and a patient VCG and identifies the patient attributes. In block 2801, the component selects the next mapping of a model source configuration to a modeled VCG. In decision block 2802, if all the mappings have already been selected, then the component completes indicating the patient attributes, else the component continues at block 2803. In decision block 2003, if the selected model source configuration matches the patient source configuration, then the component continues at block 2804, else the component loops to block 2801 to select the next mapping. In decision block 2804, if the modeled VCG for the selected mapping matches the patient VCG, then the component continues at block 2805, else the component loops to block 2801 to select the next mapping. In block 2805, the component adds the attribute for the selected modeled VCG to the patient attributes and then loops to block 2801 to select the next mapping. In some embodiments, the PM system may include components to identify other types of matching measurements such as an EEG and measurements corresponding to those collected by a body surface vest, a basket catheter, a cap worn by a patient, and so on.

Figure 29:
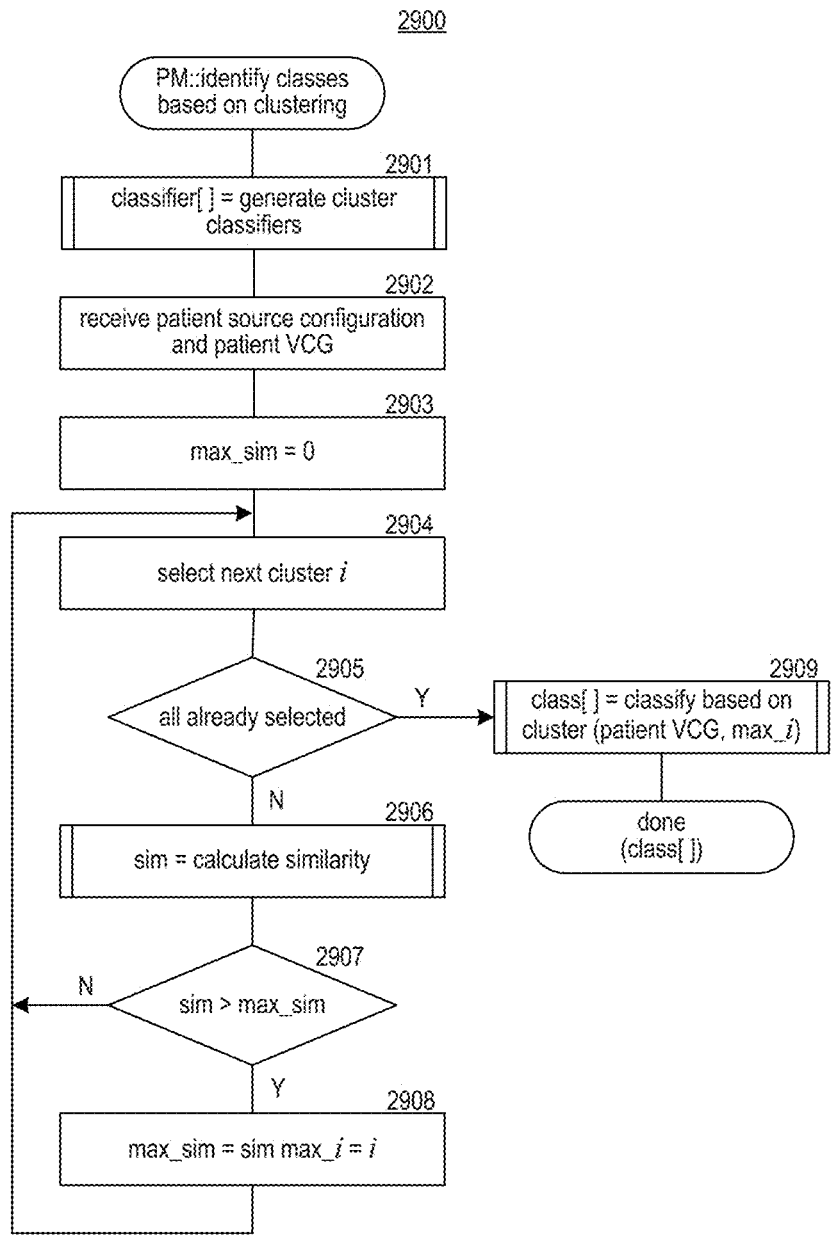
FIG. 29 is a flow diagram that illustrates the processing of an identify classes based on clustering component of the PM system in some embodiments.

FIG. 29 is a flow diagram that illustrates the processing of an identify classes based on clustering component of the PM system in some embodiments. The identify classes based on clustering component 2900 identifies the classes for a patient based on classifiers trained using clusters of similar model source configurations. In block 2901, the component invokes a generate cluster classifiers component to generate classifiers for clusters of similar model source configurations. In block 2902, the component receives a patient source configuration and a patient VCG. In blocks 2903-2908, the component loops selecting clusters to identify the cluster with model source configurations that are most similar to the patient source configuration. In block 2903, the component initializes the variable to track the maximum similarity calculated so far. In block 2904, the component selects the next cluster. In decision block 2905, if all the clusters have already been selected, then the component continues at block 2909, else the component continues at block 2906. In block 2906, the component invokes a calculate similarity component to calculate the similarity between the model source configurations of the selected cluster and the patient source configuration. In decision block 2907, if the similarity is greater than the maximum similarity calculated so far, then the component continues at block 2908, else the component loops to block 2904 to select the next cluster. In block 2908, the component sets the maximum similarity to the similarity calculated for the selected cluster and sets a variable to indicate the index of the cluster with the maximum similarity calculated so far. The component then loops to block 2904 to select the next cluster. In block 2909, the component invokes a classify based on cluster component to identify the classes for the patient VCG based on the cluster with the maximum similarity. The classify based on cluster component may correspond to the classify component of the MLMO system that has been adapted to input the classifier to use. The component then completes indicating the classes.

Figure 30:
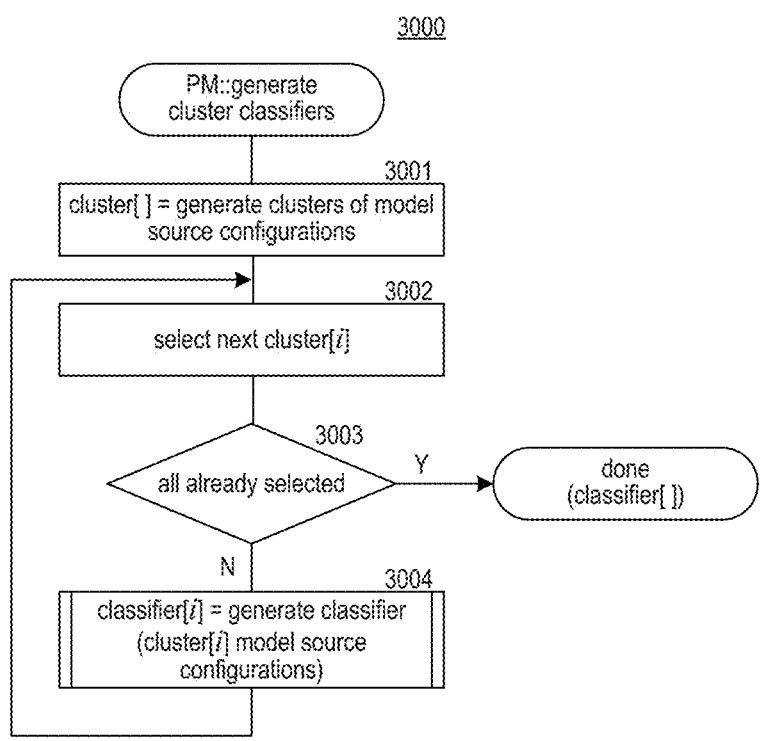
FIG. 30 is a flow diagram that illustrates the processing of a generate cluster classifiers component of the PM system in some embodiments.

FIG. 30 is a flow diagram that illustrates the processing of a generate cluster classifiers component of the PM system in some embodiments. The generate cluster classifiers component 3000 is invoked to cluster the model source configurations and generate a classifier based on each cluster. In block 2001, the component generates the clusters of the model source configurations. In block 3002, the component selects the next cluster. In decision block 3003, if all the clusters have already been selected, then the component completes indicating the classifiers, else the component continues at block 3004. In block 3004, the component invokes a generate classifier component of the MLMO system passing an indication of the model source configurations of the selected cluster to generate a classifier for that cluster. The component then loops to block 3002 to select the next cluster.

Machine Learning Based on Clinical Data

Methods and systems are provided to adapt the MLMO system to generate classifiers based on actual patient data. In some embodiments, a machine learning based on clinical data ("MLCD") system is provided that generates (1) a patient classifier based on patient training data associated with actual patients using transference of model classifier weights and (2) generates a patient-specific model classifier based on model training data that is selected based on similarity to a patient. The patient classifier is generated by a patient classifier system of the MLCD system, and patient-specific model classifier is generated by a patient-specific model classifier system. The term "patient classifier" refers to a classifier that is generated based on patient training data generated based on data of patients, and the term "model classifier" refers to a classifier that is generated based on model training data generated based on a computational model of an EM source.

Patient Classifier System

In some embodiments, the patient classifier ("PC") system generates a patient classifier for classifying derived EM data derived from EM output of an EM source within a body. For example, the patient classifier classifies VCGs derived from ECGs. The PC system accesses a model classifier such as one generated using the MLMO system. The model classifier is generated using model training data generated using a computational model of an EM source. The model classifier includes model classifier weights that are learned when the model classifier is trained such as the weights of the activation functions of a CNN. The PC system also accesses patient training data that includes, for each of a patient, patient derived EM data (e.g., VCGs) and a patient classification for that patient such as rotor location and prior ablation procedure outcome. An example prior ablation procedure outcome may be that a patient was arrhythmia free for a certain time period after being ablated at a certain location with a certain burn pattern. To train the patient classifier, the PC system initializes patient classifier weights of the patient classifier based on the model classifier weights of the model classifier and then trains the patient classifier with the patient training data and with the initialized patient classifier weights. Normally, the weights of a classifier are initialized to default values such as all to a certain value (e.g., 0.0, 0.5, or 1.0) or to random values. The learning of the weights for the classifier is thus considered to be from "scratch." The process of initializing the values of the weights based on previously learned weights is referred to as "transference" of knowledge. The knowledge gained by the previous training of a prior classifier is transferred to the training of a new classifier. The goal of transference is to both speed up the training of and increase the accuracy of the new classifier.

In some embodiments, the PC system uses the patient classifier to classify patients. For example, when the EM source is a heart, the PC system may receive a cardiogram (e.g., ECG or VCG) of a patient and apply the patient classifier to that cardiogram. Depending on the patients selected for training the patient classifier, the patient classifier may be a more accurate classifier than a model classifier trained on model training data generated using a computational model. Moreover, if the patient is similar to the patients used to train the patient classifier, then the accuracy of the classifier may be even more accurate. The PC system may also identify clusters of similar patients and train a separate patient classifier for each cluster, referred to as a cluster patient classifier. The similarity of the patients may be determined in various ways such as based on comparison of various characteristics such one or more of derived EM data (e.g., cardiograms) collected from the patients, patient source configurations of the patients (e.g., anatomical parameters, electrical dynamic properties), patient demographic information, and so on. The cluster patient classifier for each cluster may be trained based on the VCGs and corresponding labels of the patients in that cluster. When a target patient is to be classified, the PC system identifies the cluster of patients to which the target patient is most similar. The PC system then applies the cluster patient classifier of the identified cluster to VCG of the target patient.

Patient-Specific Model Classifier System

In some embodiments, a patient-specific model classifier ("PSMC") system generates a patient-specific model classifier for classifying derived EM data of an EM source within a body. The PSMC system identifies models that are similar to a patient. The PSMC system identifies similar models based on a patient-model similarity. The patient-model similarity may be based on similarity between model source configuration of a model and patient source configuration of the patient and/or similarity between modeled derived EM data (e.g., VCGs) of a model and corresponding patient derived EM data of the patient. For example, the PSMC system may base the similarity on anatomical parameters (e.g., dimensions of a right ventricle), certain electrophysiology parameters, and so on. The PSMC system then may use the MLMO system to generate a patient-specific model classifier using the model source configurations of the similar models. The PSMC system may generate the patient-specific model classifier by first applying a computational model of the EM source to generate modeled EM output of the EM source based on the model source configurations of the similar models. The PSMC system then generates model training data that includes modeled derived EM data (e.g., VCGs) from the generated modeled EM output and labels for the models. Alternatively, if the model training data has already been generated for the similar models, then the PSMC system need not regenerate the model training data. The PSMC system then trains the patient-specific model classifier based on the model training data.

In some embodiments, after a patient-specific model classifier is generated, the PSMC system applies the patient-specific model classifier to derived EM data (e.g., VCG) of the patient to generate a classification for the patient. Because the patient-specific model classifier is trained using model training data that is selected based on the patient, the patient-specific model classifier provides classification that is more accurate than a classification that would be provided by a model classifier trained based on a collection of model training data that is not specific to the patient.

In some embodiments, the PSMC system may generate a cluster-specific model classifier for a cluster of target patients. To generate a cluster-specific model classifier, the PSMC system identifies models that are overall similar to the target patients of the cluster and then trains a cluster-specific model classifier based on the similar models. The PSMC system can then apply the cluster-specific model classifier to generate a classification for the target patients of the cluster. The PSMC system may also generate clusters of target patients and generate a cluster-specific model classifier for each cluster. The PSMC system can then generate a classification for each target patient using the cluster-specific model classifier for the cluster to which that target patient is a member. The PSMC system may even use a cluster-specific model classifier to generate a classification for a new target patient. The PSMC system identifies the cluster to which a new target patient is most similar and applies the cluster-specific model classifier for that identified cluster to the patient derived EM data for the new target patient to generate the classification for the new target patient.

Figure 31:
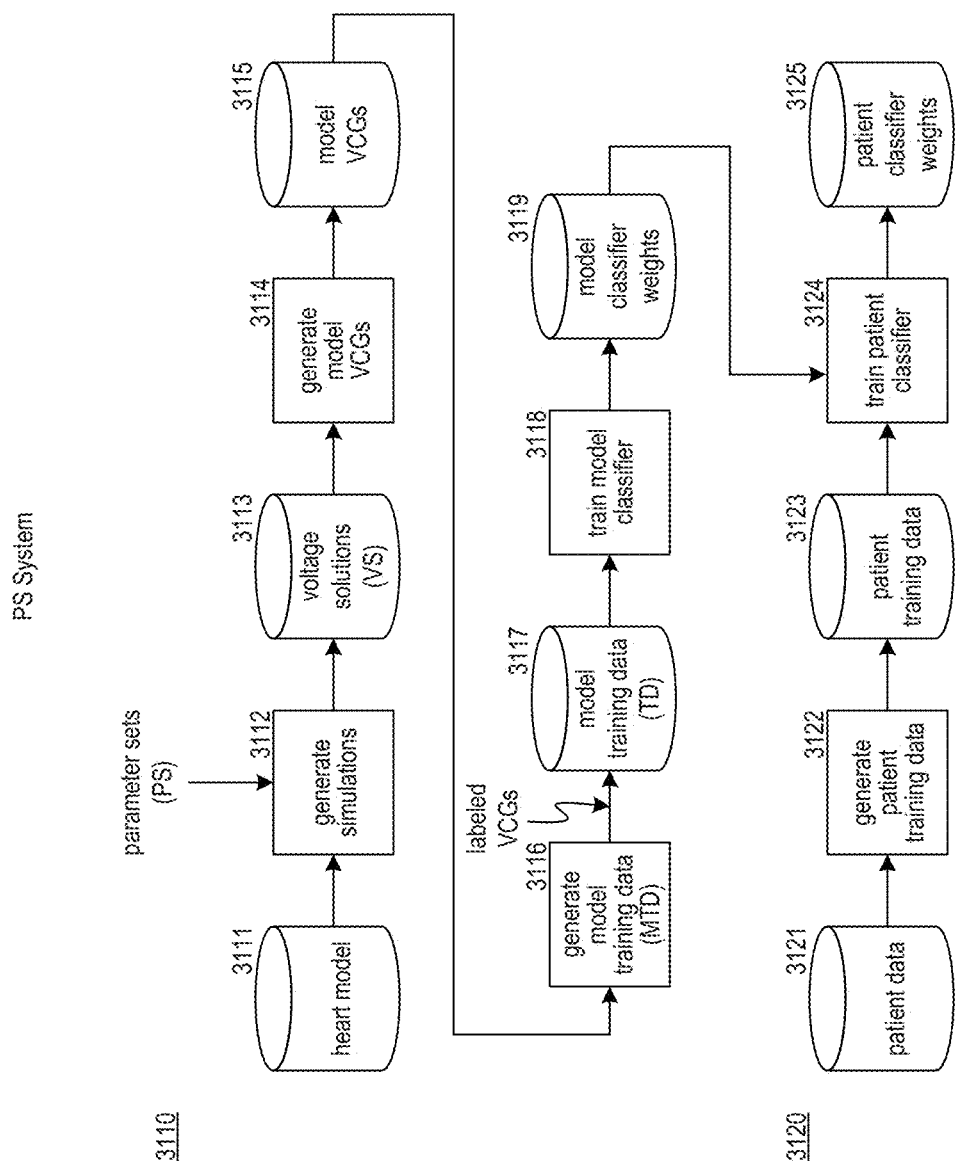
FIG. 31 is a block diagram that illustrates the overall processing of a patient classifier system of a MLCD system in some embodiments.

FIG. 31 is a block diagram that illustrates the overall processing of a patient classifier system of a MLCD system in some embodiments. Classifier components 3110 (i.e., components 3111-19) are similar to classifier components 110 of FIG. 1. The term "model" has been inserted in various components to emphasize that the components are used to generate a classifier based on models represented by simulated source configurations or parameter sets. Components 3120 include a patient data store 3121, a generate patient training data component 3122, a patient training data store 3123, a train patient classifier component 3124, and a patient classifier weights store 3125. The patient data store may include ECGs collected from patients and corresponding labels such as locations of a heart disorder. The generate patient training data component generates patient training data from the patient data, for example, by generating VCGs from the ECGs and labeling the VCGs and storing the training data in the patient training data store. The train patient classifier component inputs the model classifier weights from a model classifier weights store 3119 as transference of knowledge from the model classifier and trains the patient classifier based on the patient training data. The train patient classifier then stores the patient classifier weights in the patient classifier weights store.

Figure 32:
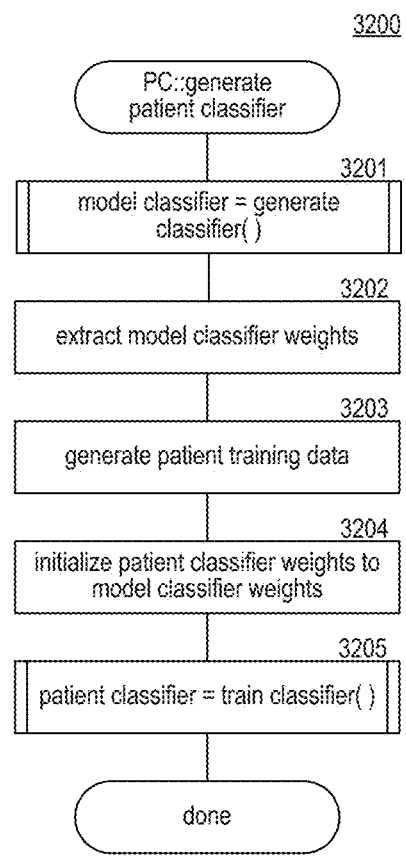
FIG. 32 is a flow diagram that illustrates the processing of a generate patient classifier component of the patient classifier system in some embodiments.

FIG. 32 is a flow diagram that illustrates the processing of a generate patient classifier component of the patient classifier system in some embodiments. The generate patient classifier component 3200 generates a patient classifier for a collection of patients using transference of knowledge from a model classifier. In block 3201, the component invokes a generate classifier component to generate a model classifier based on model training data if the model classifier has not already been generated. The generate classifier component generates model classifier weights for the model classifier. In block 3202, the component extracts the model classifier weights of the model classifier. In block 3203, the component generates the patient training data, for example, by generating VCGs and labeling the VCGs. In block 3204, the component initializes the patient classifier weights of the patient classifier to the model classifier weights. In block 3205, the component invokes a train classifier component to train a patient classifier based on the patient training data and the initialized patient classifier weights. The component then completes.

Figure 33:
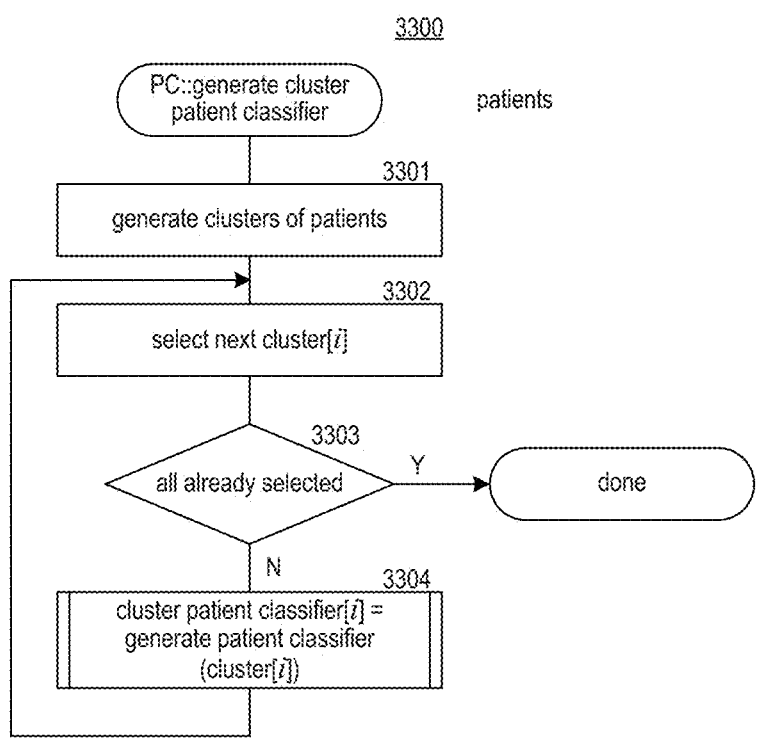
FIG. 33 is a flow diagram that illustrates the processing of a generate cluster patient classifier of the patient classifier system in some embodiments.

FIG. 33 is a flow diagram that illustrates the processing of a generate cluster patient classifier of the patient classifier system in some embodiments. The generate cluster patient classifier 3300 generates a cluster patient classifier for clusters of patients. In block 3301, the component generates clusters of patients, for example, based on similarity of their clinical features, source configurations, or VCGs. In block 3302, the component selects the next cluster. In decision block 3303, if all the clusters have already been selected, then the component completes, else the component continues at block 3304. In block 3304, the component invokes a generate patient classifier component passing an indication of the selected cluster to generate a cluster patient classifier for the patients in the selected cluster and then loops to block 3302 to select the next cluster. When the generate patient classifier component is invoked, it does not need to generate a model classifier for each invocation because it can reuse the same model classifier weights for each invocation.

Figure 34:
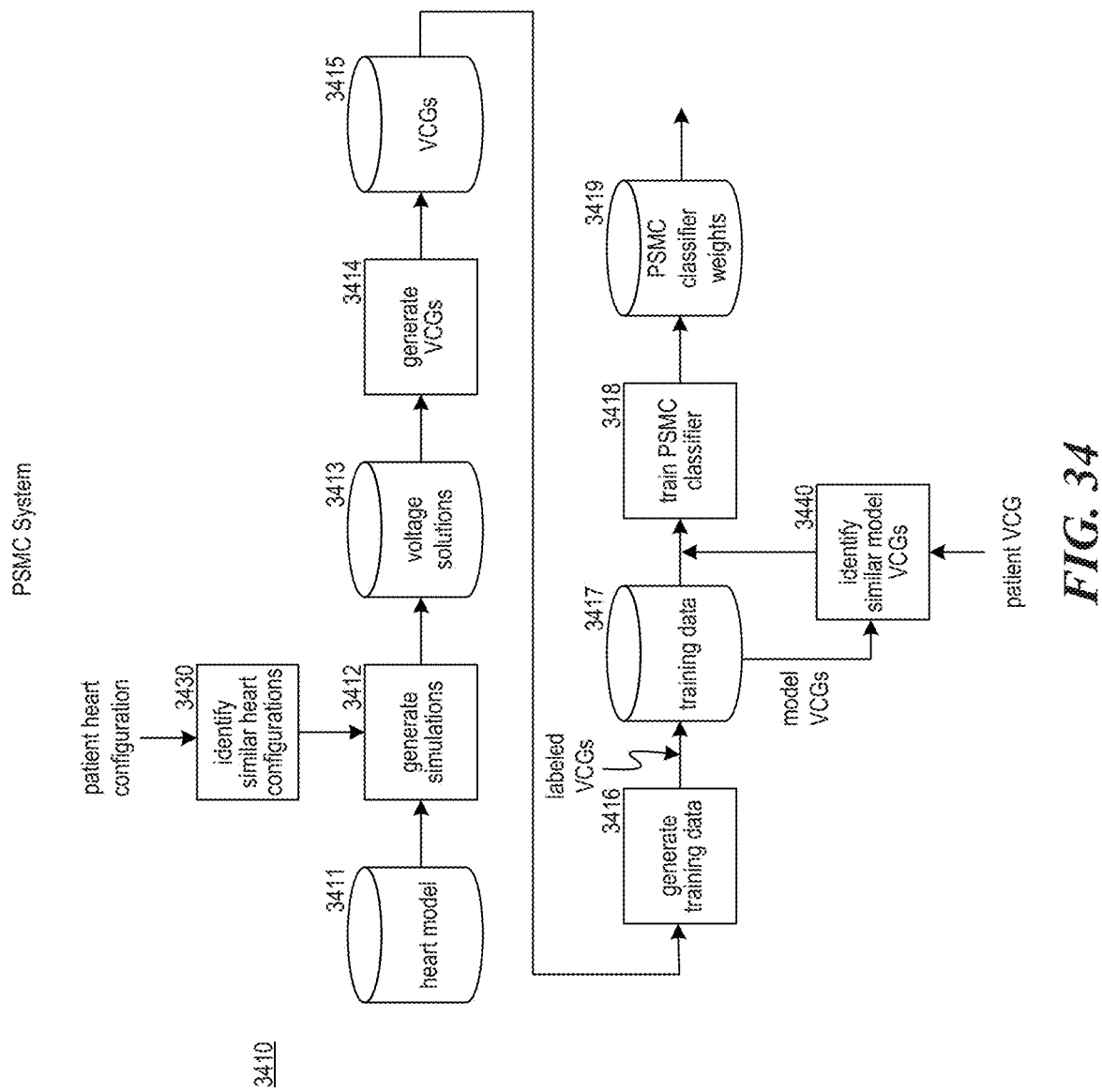
FIG. 34 is a block diagram that illustrates components of a patient-specific model classifier system of a MLCD system in some embodiments.

FIG. 34 is a block diagram that illustrates components of a patient-specific model classifier system of a MLCD system in some embodiments. The PSMC system includes components 3410 (components 3411-19) are similar to components 110 of FIG. 1. The PSMC system also includes an identify similar heart configurations component 3430 and an identify similar VCGs component 3440, which represent two different embodiments of the PSMC system. In a first embodiment, the identify similar hearts configuration component inputs a patient heart configuration and model heart configurations and identifies the model heart configurations that are similar to the patient heart configuration. The similar model heart configurations are then input to the generate simulations component to generate the voltage solutions and ultimately train the patient-specific model classifier. In a second embodiment, the identify similar VCGs component inputs a patient VCG and the training data and identifies VCGs of the training data that are similar to the patient VCG. The training data for the similar VCGs is an input to the train PSMC classifier component 3418 to train the patient-specific model classifier. Although not illustrated, the train PSMC classifier may use transference to initialize the PSMC classifier weights. Also, the first and second embodiments may be both used to generate training data based on similar heart configurations and then select similar VCGs for training.

Figure 35:
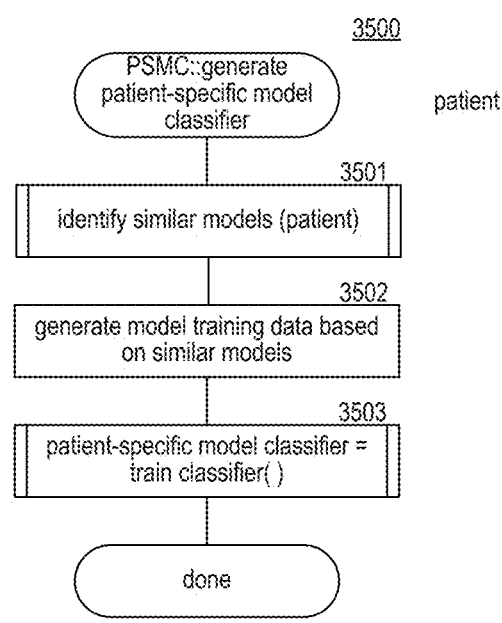
FIG. 35 is a flow diagram that illustrates processing of a generate patient-specific model classifier component of the PSMC system in some embodiments.

FIG. 35 is a flow diagram that illustrates processing of a generate patient-specific model classifier component of the PSMC system in some embodiments. The generate patient-specific model component 3500 generates a patient-specific model classifier for a target patient. In block 3501, the component invokes an identify similar models component passing an indication of the target patient to identify similar models. In block 3502, the component generates model training data based on the identified similar models. The component may employ the MLMO system to generate the training data based on the model heart configurations of the identified similar models or, if already generated, retrieve the training data based on similar VCGs. In block 3503, the component invokes the train classifier component to train the patient-specific model classifier based on the model training data for the similar models and then completes.

Figure 36:
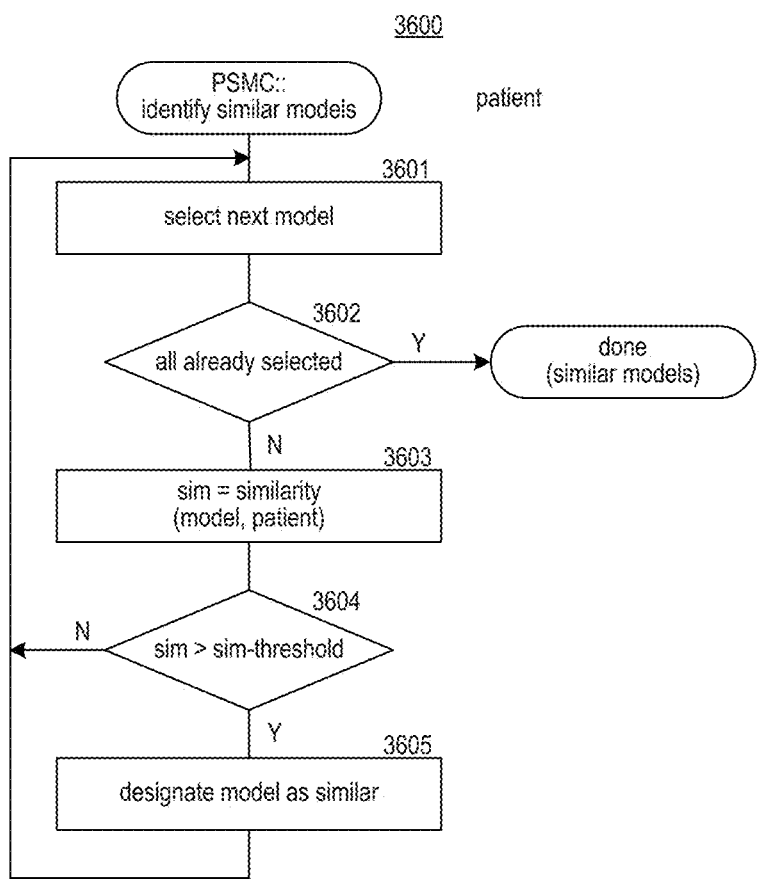
FIG. 36 is a flow diagram that illustrates the processing of an identify similar models component of the PSMC system in some embodiments.

FIG. 36 is a flow diagram that illustrates the processing of an identify similar models component of the PSMC system in some embodiments. The identify similar models component 3600 identifies models that are similar to a patient. In block 3601, the component selects the next model. In decision block 3602, if all the models have already been selected, then the component completes indicating the similar models, else the component continues at block 3603. In block 3603, the component generates a similarity score between the selected model and the patient. The patient-model similarity score may be based on heart configurations, cardiograms, or both. In decision block 3604, if the similarity score is above a similarity threshold, then the component continues at block 3605, else the component loops to block 3601 to select the next model. In block 3605, the component designates the model as similar to the patient and loops to block 3601 to select the next model.

Patient-Specific Model Display

Methods and systems are provided to adapt the MLMO system to support generating and displaying a representation of an EM source of a patient that is based on modeled EM output for a model that is similar to the patient. In some embodiments, a patient-specific model display ("PSMD") system identifies a model for the EM source that is deemed similar to the EM source of a patient. The PSMD system then generates a graphical representation of patient's EM source based on clinical parameters for the patient such as infarction and drug history. For example, if the EM source is a heart, the PSMD system may generate a map representing an anatomical model of the patient's heart. The PSMD system then populates the map with display values that are derived from the modeled EM output for the similar model. For example, the PSMD system may select an EM mesh of that modeled EM output and set each the value of each vertex of the map based on the corresponding voltage of that EM mesh. The PSMD system may also map the modeled EM output from the polyhedral mesh used in the simulation to another polyhedral mesh to produce a more realistic looking display such as a hexahedral mesh to a surface-triangle mesh. The PSMD system may set the values corresponding to high voltages to varying intensities of the color red (or grey scale shading) and the values corresponding to low voltages to varying intensities of the color green. As another example, the PSMD system may select a cycle of the model EM output and set the values based on the differences or delta between voltages of the first EM mesh in the cycle and the last EM mesh in the cycle. The PSMD system may also set the values based on an accumulation, which may be weighted, of the deltas over successive EM meshes in a cycle. The PSMD system then displays (e.g., using a rasterization technique) the map as the representation of activity of the patient's EM source. The PSMD system may also display an outlined image of a heart based on the anatomical parameters of the patient. The outlined image may illustrate boundaries of the chambers of the heart.

In some embodiments, the PSMD system may identify a model that is similar to a patient by comparing model source configurations and modeled derived EM data to the patient source configuration and the patient derived EM data. The comparison may be based on the processing represented by the processing of the identify matching VCGs component illustrated in FIG. 28. That component, however, may be adapted to generate a similarity score for each matching VCG so that the PSMD system may select the VCG, and thus the model, that is most similar to the patient. Alternatively, the PSMD system may generate values for the pixels of the map based on a weighted combination (e.g., an average) of the values of the EM mesh for all the matching models. The PSMD system may also weight the values based on the similarity scores of the matching models.

In some embodiments, the PSMD system may generate a sequence of maps for display as a video representation of activation of patient's EM source over time. For example, the PSMD may divide the cycle into 30 display intervals and generate a map for each display interval based on values of an EM mesh corresponding to that display interval. The PSMD system may then display the 30 maps in sequence over the time of the cycle to provide a video based on the actual cycle time or in sequence over a time longer than the cycle to provide a slow-motion effect. The PSMD system may also achieve a slow-motion effect by generating more maps per second of simulation time than the maximum frame rate for the display. For example, if the maximum frame rate is 60 frames-per-second, then generating 120 maps per second of simulation will result in one second of simulation time being displayed over two seconds. The slowest and smoothest slow-motion effect may be achieved by generating a map from the voltage solution for each simulation time.

Figure 37:
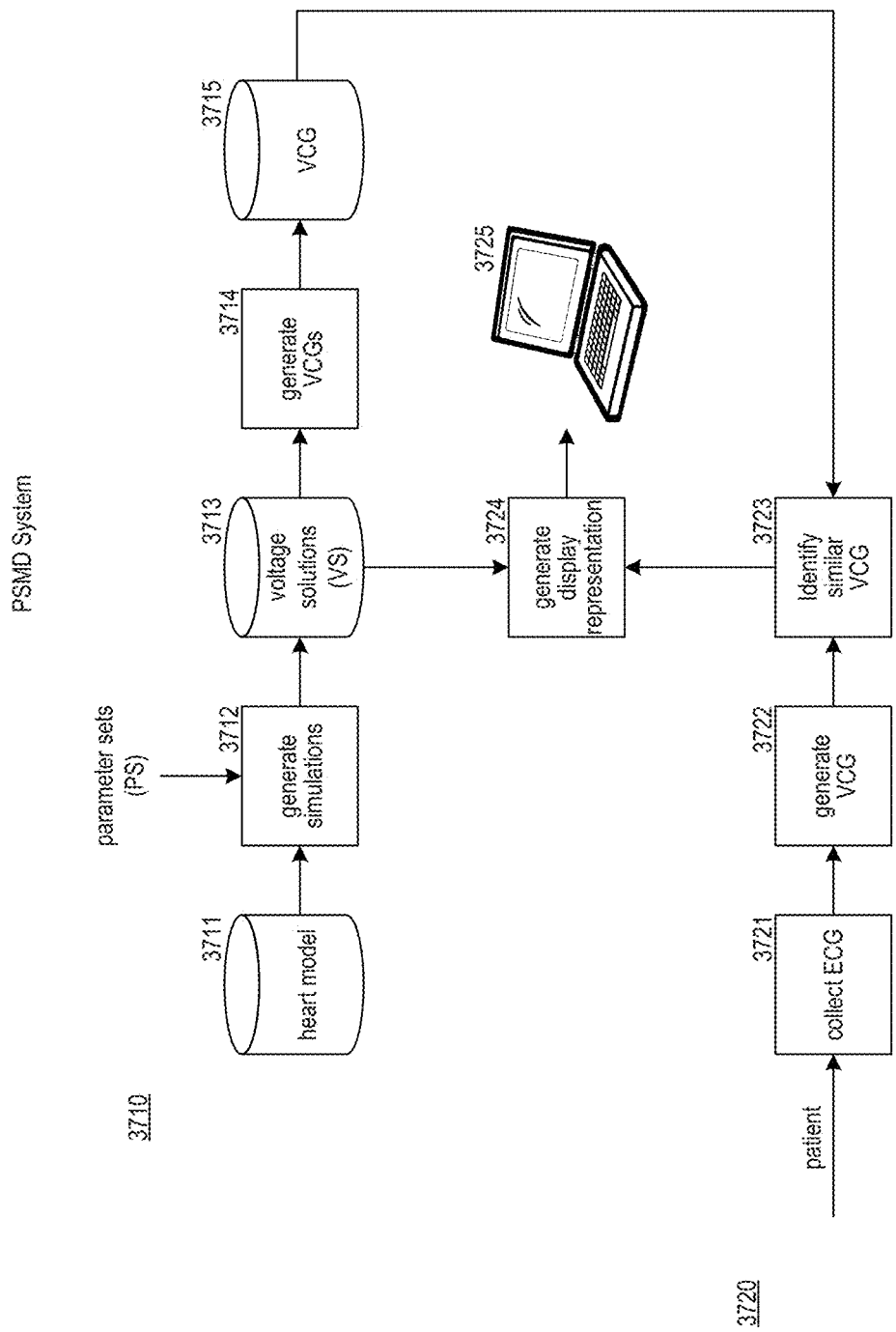
FIG. 37 is a block diagram that illustrates the overall processing of a patient-specific model display system in some embodiments.

FIG. 37 is a block diagram that illustrates the overall processing of a patient-specific model display system in some embodiments. Components 3710 (i.e., components 3711-15) are similar to components 111-115 of FIG. 1. Components 3720 include a collect ECG component 3721, a generate VCG component 3722, an identify similar VCG component 3723, a generate display representation component 3724, and a display device 3725. The collect ECG component receives an ECG for the patient whose heart is to be represented by the output of the PSMD system. The generate VCG component receives the patient's ECG and generates a VCG for the patient. The identify similar VCG component compares the patient VCG to the modeled VCGs of the VCG store to identify a modeled VCG that is similar to the patient VCG. Similar VCGs may be identified based on comparison of cycles of the VCGs. Thus, the identify similar VCG component may invoke an identify cycles component to identify the cycles of each VCG. The generate display representation component inputs the similar modeled VCG and generates a display representation of the patient's heart based on the voltage solutions from which the similar modeled VCG was derived. The generate display representation component then outputs the display representation to the display device.

Figure 38:
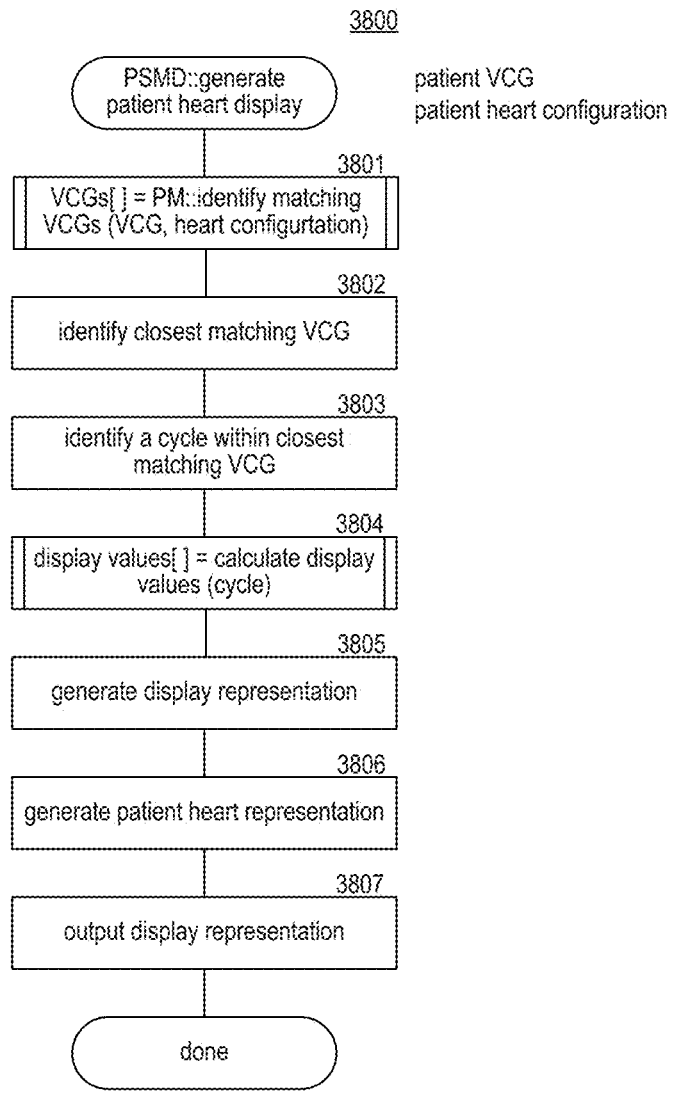
FIG. 38 is a flow diagram that illustrates the processing of a generate patient heart display component of the PSMD system in some embodiments.

FIG. 38 is a flow diagram that illustrates the processing of a generate patient heart display component of the PSMD system in some embodiments. The generate patient heart display component 3800 is provided a patient VCG and a patient heart configuration and generates an output representation of the patient's heart. In block 3801, the component invokes an identify matching VCGs component of the patient matching system passing an indication of the patient VCG and the patient heart configuration to identify one or more matching VCGs. In block 3802, the component identifies the closest matching of the VCGs. In block 3803, the component identifies a cycle within the closest matching VCG. In block 3804, the component invokes the calculate display values component passing an indication of the identified cycle to generate display values for map. In block 3805, the component generates the display representation by storing the display values in the map. In block 3805, the component display values in the map to represent an outline of the patient's heart based on anatomical parameters of that patient. In block 3807, the component outputs the map and completes.

Figure 39:
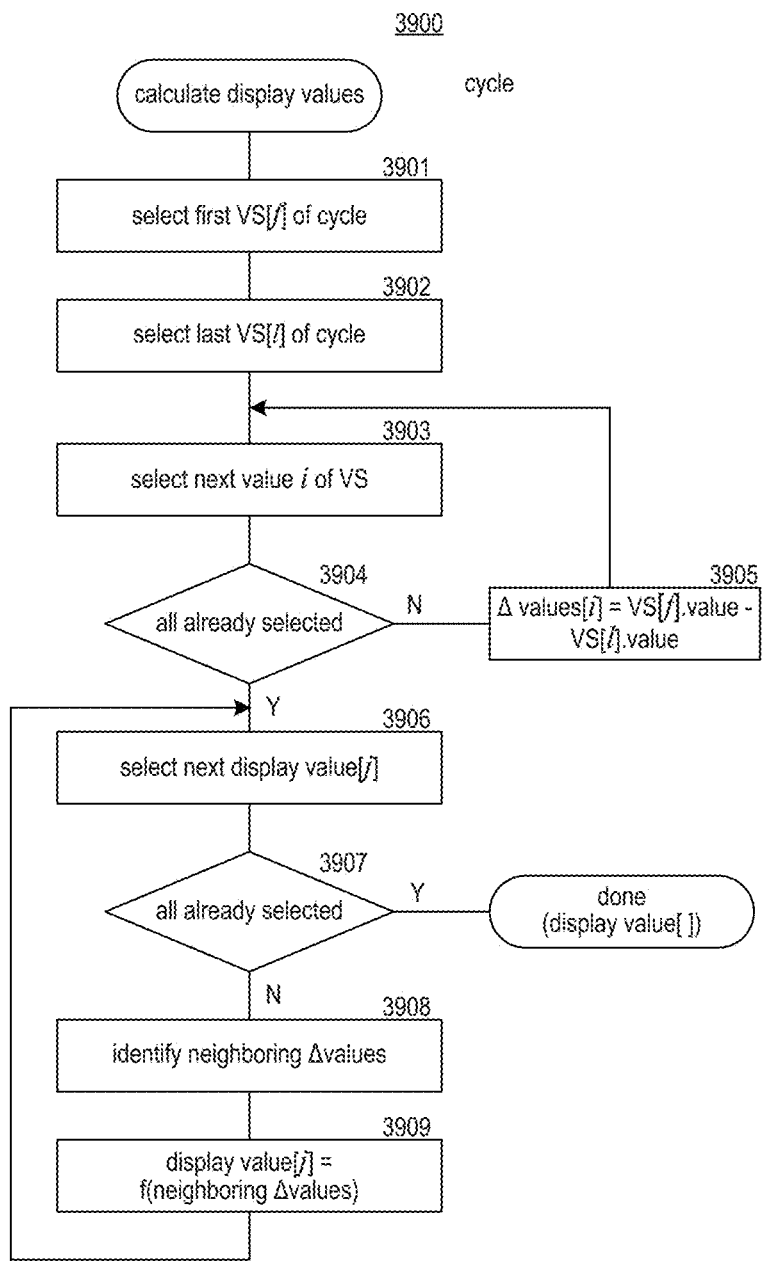
FIG. 39 is a flow diagram that illustrates the processing of a calculate display values component of the PSMD system in some embodiments.

FIG. 39 is a flow diagram that illustrates the processing of a calculate display values component of the PSMD system in some embodiments. The calculate display values component 3900 is passed an indication of a cycle and generates display values based on EM meshes of that cycle. In block 3901, the component selects the first voltage solution of the cycle. In block 3902, the component selects another voltage solution of the cycle such as the last voltage solution. In block 3903, the component selects the next value of a voltage solution. In decision block 3904, if all the values of already been selected, then the component continues at block 3906, else the component continues at block 3905. In block 3905, the component sets a delta value for the selected value to the difference between the value for the first voltage solution and the last voltage solution of the cycle. The delta value may alternatively be weight accumulation of the differences over a cycle. The component then loops to block 3903 to select the next value of the voltage solution. In block 3906, the component selects the next display value of the map. In decision block 3907, if all the display values have already been selected, then the component completes indicating the display values, else the component continues at block 3908. In block 3908, the component identifies neighboring delta values that are near the display value. In block 3910, the component sets the display value to a function of the neighboring delta values and then loops to block 3906 to select the next display value. The function may take the average of the neighboring delta values, a weighted average based on distance between the location of the voltage solution and the location and the patient heart that the display value represents, and so on.

Display of an Electromagnetic Force

Methods and systems for generating a visual representation of an electromagnetic force generated by an electromagnetic source within a body is provided. In some embodiments, an electromagnetic force display ("EFD") system generates a "surface representation" of the electromagnetic force from a sequence of vectors representing magnitude and direction of the electromagnetic force over time. For example, when the electromagnetic source is a heart, the sequence of vectors may be a vectorcardiogram. The vectors are relative to an origin, which may be located within the electromagnetic source. To generate the surface representation, the EFD system, for pairs of vectors adjacent in time, identifies a region based on the origin and the pair of vectors. For example, if a vector has the values (1.0, 2.0, 2.0) for its x, y, and z coordinates and the adjacent vector has values (1.1, 2.0, and 2.0), then the region is the area bounded by the triangle with the vertices at (0.0, 0.0, 0.0), (1.0, 2.0, 2.0), and (1.1, 2.0, and 2.0). The EFD system then displays a representation of each region to form the surface representation of the electromagnetic force. Since the regions will unlikely lie in one plane, the EFD system may provide shading or coloring to help illustrate that the regions lie in different planes. The EFD system may also display a representation of the electromagnetic source so that the surface representation visually emanates from the electromagnetic source. For example, the EFD system may display a heart that is based on the anatomical parameters of a patient from whom the VCG was collected. When the electromagnetic force has cycles, the regions for a cycle form a surface representation for that cycle. The EFD system may simultaneously display surface representations for multiple cycles. For example, when the electromagnetic source is a heart, the cycle may be based on an arrhythmia. The EFD system may also display the surface representation of each cycle in sequence (e.g., centered at the same location on the display) illustrate changes in the electromagnetic force over time. The EFD system may display each region of a surface representation in sequence to illustrate the times associated with the vectors. The EFD system may be used display either simulated VCGs or VCGs collected from patients.

Figure 40:
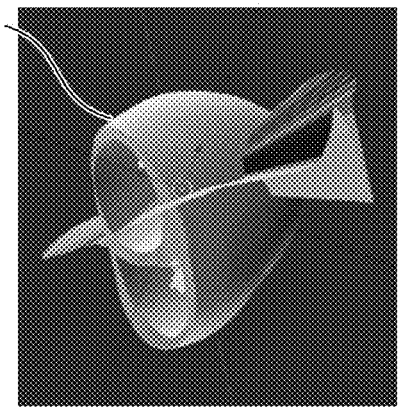
FIG. 40 illustrates various surface representations of vectorcardiograms.
Figure 40:
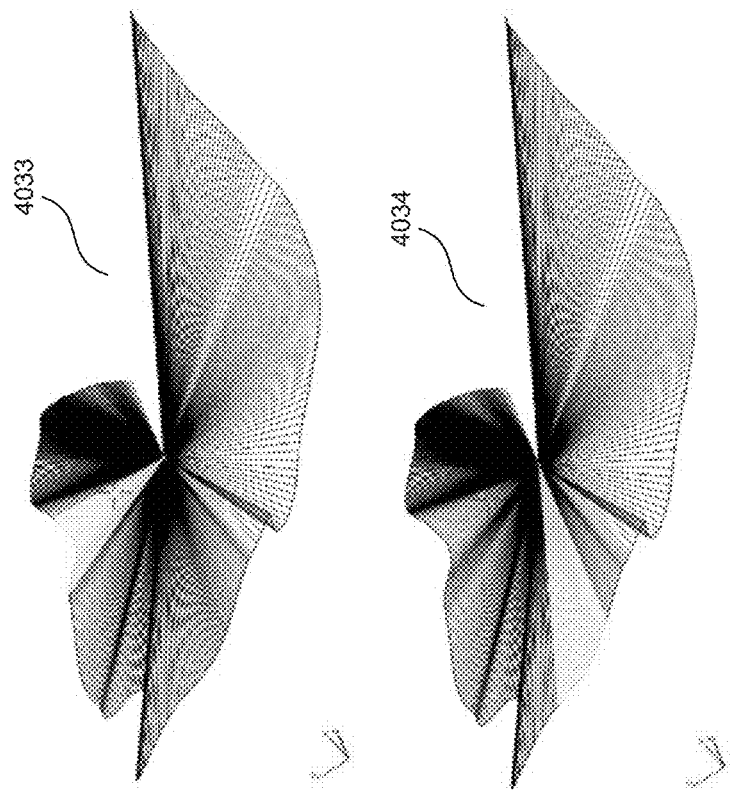
Figure 40:
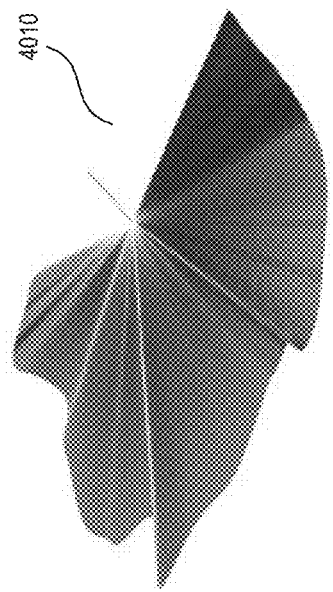
Figure 40:
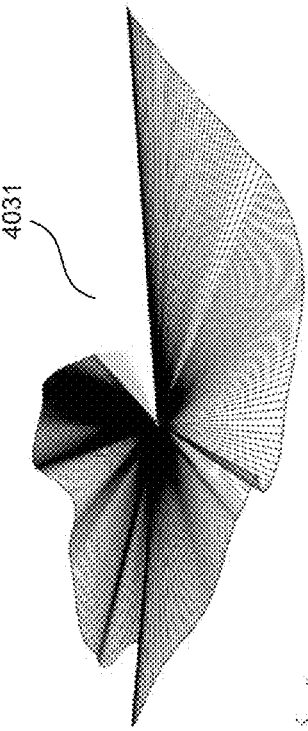
Figure 40:
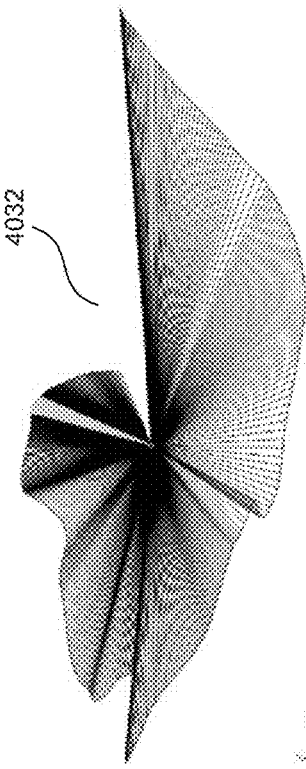

FIG. 40 illustrates various surface representations of vectorcardiograms. Image 4010 illustrates a display of a surface representation of a vectorcardiogram based on a perspective view. Image 4020 illustrates a display of a surface representation of vectorcardiogram shown as emanating from a heart. Images 4031-34 illustrate display of the surface representation over time to illustrate changes in the electromagnetic force.

In some embodiments, the EFD system may employ a variety of animation techniques to assist a user in analyzing a VCG. For example, the EFD system may animate the display of the surface representation by displaying each region in sequence with a timing that is the same as the actual timing of the VCG. If a cycle is 1000 ms, then EFD system would display the regions in sequence over 1000 ms. When displaying the surface representations for multiple cycles in sequence and the next region to display would overlap a region previously displayed, then the EFD system may first remove the region that would be overlapped and then display the next region. The EFD system may also allow the user to specify that only a portion of the surface representation for a cycle be displayed. For example, the user may specify to display a portion corresponding to 250 ms of the surface representation. In such a case, the EFD system may animate the display of the portion by removing the tail region when adding a head region. The EFD system may also allow the user to speed up or slow down the display of the surface representations.

Figure 41:
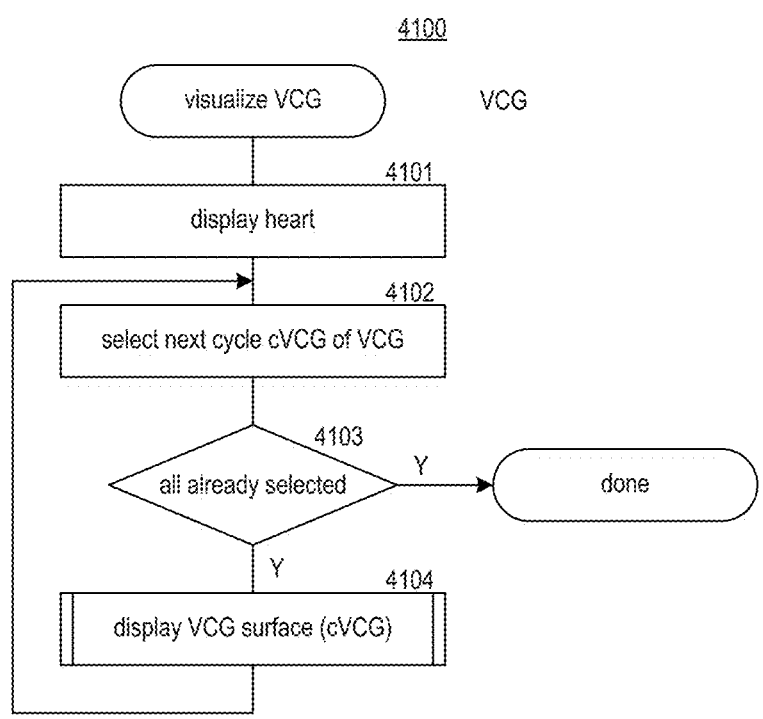
FIG. 41 is a flow diagram that illustrates the processing of a visualize VCG component of the EFD system in some embodiments.

FIG. 41 is a flow diagram that illustrates the processing of a visualize VCG component of the EFD system in some embodiments. The visualize VCG component 4100 is passed a VCG and generates a surface representation for each portion (e.g., cycle) of the VCG. In block 4101, the component displays a representation of a heart. In block 4102, the component selects the next cycle of the VCG. In decision block 4103, if all the cycles have already been selected, then the component completes, else the component continues at block 4104. In block 4104, the component invokes a display VCG surface representation component to display a surface representation for the selected cycle and then loops to block 4102 to select the next cycle.

Figure 42:
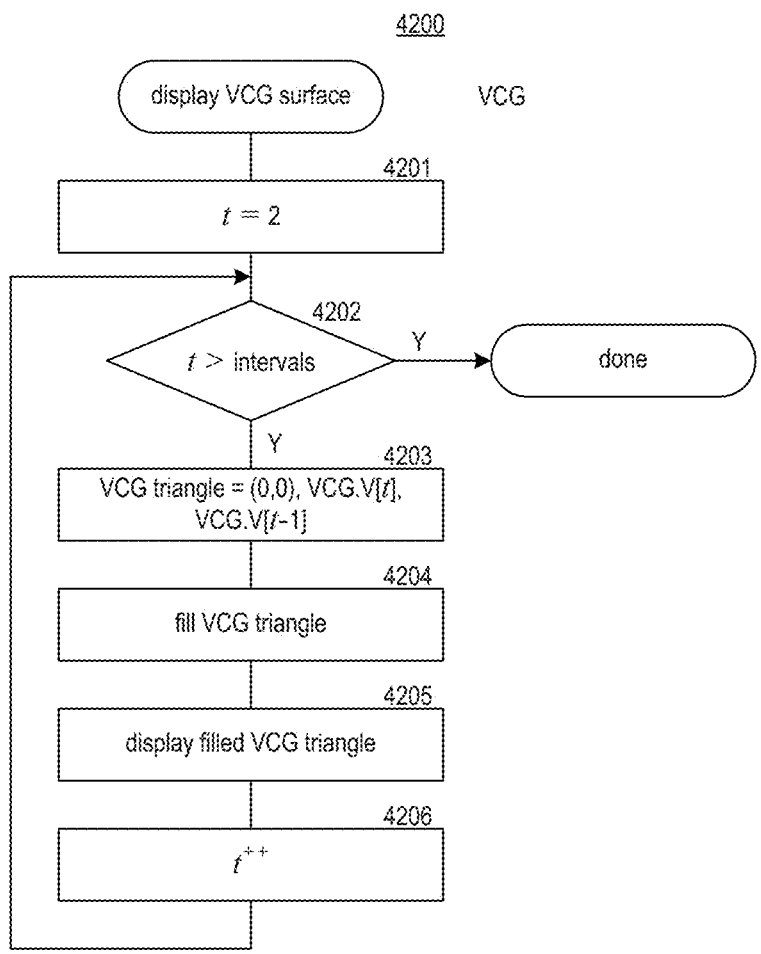
FIG. 42 is a flow diagram that illustrates the processing of a display VCG surface representation component of the EFD system in some embodiments.

FIG. 42 is a flow diagram that illustrates the processing of a display VCG surface representation component of the EFD system in some embodiments. The display VCG surface representation component 4200 is passed a vectorcardiogram and generates a surface display representation of the VCG. In block 4201, the component sets an index t to 2 for indexing through the time intervals of the VCG. In decision block 4002, if the index t is greater than the number of time intervals, then the component completes, else the component continues at block 4203. In block 4203, the component generates a VCG triangle based on the origin, the indexed interval t, and the prior interval t−1. In block 4204, the component fills the VCG triangle with a shading that may vary based on the plane of the triangle. In block 4205, the component displays the filled VCG triangle. In block 4206, the component increments the index t. In decision block 4207, if the index t is greater than the display span $t_{span}+1$, then the component continues at block 4208, else the component loops to block 4202. In block 4208, the component removes from the display the VCG triangle at the beginning of the currently displayed span and loops to block 4202.

Calibration of Simulations

Methods and system performed by a computing system for generating a calibrated collection of simulated cardiograms, also referred to as model cardiograms, based on morphological similarity such as orientation similarity and/or electrophysiological similarity to patient cardiograms are provided. Morphological similarity may be determined based on analysis of "raw trace" data (e.g., voltage vs. time) that represents a ECG and/or VCG data of a patient. The calibrated collection may be further generated based on similarity of additional configuration parameters used to generate the simulated cardiograms to configuration parameters of the patient. In some embodiments, a calibrate simulated cardiograms ("CSC") system generates the calibrated collection. Because the CSC system generates the calibrated collection based on similarity to patient cardiograms, the calibrated collection represents a patient-specific collection of simulated cardiograms. The simulated cardiograms of the calibrated collection can be used to train a patient-specific model classifier with each simulated cardiogram labeled with a configuration parameter used to generate that simulated cardiogram. The simulated cardiograms may be labeled with a configuration parameter that is not collected from the patient, such as a source location of a rotor. The patient-specific model classifier can then be used to determine that configuration parameter for the patient. The CSC system, like the PSMC system, generates a patient-specific model classifier, but uses various similarity measurements such as morphological similarity.

In some embodiments, the CSC system inputs simulated cardiograms and the simulated configuration parameters used in generating each simulated cardiogram. The simulated cardiograms may be generated by the MLMO system as illustrated by the generate simulation component 112 and the generated VCGs component of FIG. 1. The CSC system also inputs the patient cardiograms and patient configuration parameters. The CSC system identifies pacing-similar simulated cardiograms whose simulated pacings are similar to the patient pacing(s) used when collecting the patient cardiograms. To collect the patient cardiograms, an electrophysiologist (or other care provider) may place a catheter in the patient's heart at different locations, such as near the coronary sinus. For each location, the patient's heart is paced, for example, at 1 Hz for 10 beats followed by an extra-stimulus beat after a certain delay. The same process of pacing at 1 Hz is then repeated multiple times with different delays of the extra-stimulus beat. The same pacing process is then repeated but with different pacing rates (e.g., 2 Hz and 4 Hz). The result is a collection of patient electrocardiograms collected based on different locations, pacing rates, and extra-stimulus delays. The electrocardiogram for normal sinus rhythm beats may also be collected.

In some embodiments, the pacing locations include at least two sites, which may be distant sites, in the target chamber that is a target of the pacings or a clinical procedure. For example, if the target chambers are the ventricles, the pacing locations may include one location in the posterior right ventricle and one pacing location in the lateral left ventricle. Such, pacing locations are commonly accessed and easily accessible with a catheter. However, other pacing locations may be used. For example, if the only target chamber is the left ventricle, the pacing locations may include one pacing location in the lateral left ventricle wall near the base (at the level of the heart valves) and one pacing location in the left ventricle septal wall near the apex. As another example, if target chambers are the atria, then only one pacing location may be used such as a pacing location in the coronary sinus in the left atrium. This pacing location can be paired with a normal P-wave located at the sinoatrial node in the right atrium. Generally, the effectiveness of the calibration increases with more pacing locations and with pacing locations that are distant.

The CSC system identifies simulated cardiograms that are morphologically-similar to patient cardiograms. Morphological similarity includes both orientation similarity and electrophysiological similarity, and electrophysiological similarity includes both action potential and conduction velocity similarity. The CSC system identifies, from the pacing-similar cardiograms, orientation-similar simulated cardiograms of a simulated heart with a simulation orientation that is similar to a patient orientation of the patient's heart. To determine orientation similarity, the CSC system generates QRS complex and T-wave vectors for ventricular beats and P-wave vectors for atrial beats of the patient. The vectors may represent the mean spatial orientation of the total electrical dipole at that cycle phase (e.g., QRS complex) of the cardiac cycle. Alternatively, rather than the mean vectors, the CSC system may use a time series of vectors, that is the raw VCG signals. The CSC system labels each vector with its pacing (e.g., pacing location and pacing rate) and cycle phase. The CSC system generates corresponding simulated vectors from the simulated cardiograms of the pacing-similar simulated collection. The CSC system then calculates the orientation difference between the patient vectors and each simulated vector for the same pacing and cycle phase. For example, the CSC system may calculate the dot products between vectors at the left ventricle ("LV") apex, LV lateral wall, LV posterior wall, and LV anterior wall during the QRS complex and the T-wave. The CSC system then identifies the set of simulated cardiograms whose total orientation difference (e.g., weighted average of the dot products) is minimal. To calculate the orientation difference, the CSC system generates a rotation matrix representing the difference in orientation between the patient orientation and each of the simulated orientations of the identified set. To generate the rotation matrix, the CSC system may apply a least-squares fit of the patient vectors to simulated vectors of the set. The CSC system selects, as the orientation-similar simulated cardiograms, the simulated cardiograms with the smallest simulated orientation difference as indicated by the rotation matrix. In some embodiments, the CSC system may determine orientation similarity based on features of the raw trace data (e.g., voltage vs. time) other than vectors derived from the QRS complex, T-wave, and P-wave of the ECGs or VCGs.

The CSC system identifies, from the morphologically-similar simulated cardiograms, action-potential-similar simulated cardiograms that represent action potentials that are similar to the action potential represented by the patient cardiograms. To determine action potential similarity, the CSC system normalizes the ECGs of the simulated cardiograms and the patient cardiograms both in time and magnitude. For example, each ECG may be normalized to one second and to a certain peak QRS complex or P-wave signal. The CSC system estimates action potential parameters that control the time duration of activated myocardial tissue (action potential duration), which change the relative durations of the ECG and/or VCG cycle phases. The action potential characteristics are heterogenous throughout the anatomy and may depend on various attributes of the cardiac tissue (e.g., location in the anatomy, type of cardiac cell, and healthy/disease classification). The time durations of the cardiac cycled in the ECG and/or VCG represent the global effect of the local distribution of action potential parameters on the overall cardiac dipole. The CSC system may compare a patient VCG to a simulated VCG at the same pacing rate and pacing location. The action potentials are considered similar based on similarity between the relative magnitudes and deflections between the X, Y, and Z values of the QRS complex, T-wave, and P-wave even if the absolute timing of the cycles differ. The relative timings indicate the shape and duration of the electrical waves in the myocardium (wavefront, waveback, and wavelength). The CSC system may adjust the time of the simulated VCGs based on one or more of 1) selecting a better matching geometry to the patient, 2) adjusting a bulk myocardial conductivity parameter, and 3) adjusting parameters (i.e., time constants) in the ionic model that govern the duration of the action potential. The latter two parameters may be varied such that the errors between absolute and relative timings are below some threshold (e.g. 10 ms, or 5%). The CSC system then calculates the action potential similarity between each simulated cardiogram and each patient cardiogram (e.g., using a Pearson correlation). The CSC system then selects the most similar simulated cardiograms (e.g., action potential similarity above a threshold) as the action-potential-similar simulated cardiograms.

The CSC system identifies, from the action-potential-similar simulated cardiograms, conduction-velocity-similar simulated cardiograms that represent conduction velocities that are similar to the conduction velocities represented by the patient cardiogram. The CSC system identifies the conduction-velocity-similar simulated cardiograms in a manner similar to that of identifying action-potential-similar simulated cardiograms except that the cardiograms are normalized in magnitude but not in time.

The CSC system may also identify simulated cardiograms based on cardiac geometry similarity and disease substrate similarity. The cardiac geometry similarity may be based on structural disease similarity that is based on the extent of structural disease in a certain chamber (e.g., severe cardiomyopathy in the ventricles) and measurement similarity based on comparison of measurements of the patient's heart (e.g., collected via CT or ultrasound) to configuration parameters of the simulated cardiograms. The disease substrate may be based on location and size of the patient's myocardial scars. The size and location of the patient's scars may be identified by a person designating the scarred portions of the patient's heart (based on a voltage map) on a geometric representation of the patient's heart. Disease substrate similarity is based on the extent of overlap of the patient's scars and the scars of the simulated cardiogram.

The CSC system may determine cardiac geometry similarity (e.g., structural disease similarity and measurement similarity), orientation similarity, electrophysiological similarity (e.g., action potential similarity and conduction velocity similarity), and disease substrate similarity in any order. In particular, with a given order of determining similarity, the CSC system may determine similarity based on the set of simulated cardiograms that are determined to be similar based on the prior determination of similarity—effectively successively filtering the set of simulated cardiograms. The CSC system may also identify from the collection of simulated cardiograms a set that is most similar for each similarity metric and then identify the most similar simulated cardiograms from those sets. For example, the CSC system may combine the similarity scores using a weighted average into a final similarity score for each simulated cardiogram.

The CSC system may also identify a calibrated collection of simulated cardiograms using various machine learning ("ML") techniques such as linear regression techniques, neural networks, and so on. To generate a ML calibrated collection, the CSC system identifies a training set of simulated cardiograms that match the patient cardiograms based on the similarity of configuration parameters (e.g., morphological parameters) to the corresponding parameters of the patient and based on similarity of pacing locations. For example, for each pacing location of a patient cardiogram, the CSC identifies, from those simulated cardiograms with that pacing location, a set of simulated cardiograms with configuration parameters that are similar to the patient parameters.

The CSC system then trains a mapping function that maps the simulated cardiograms to the patient cardiograms. For example, the mapping function may be a neural network whose weights are learned based on the training set. The weights represent a non-linear transformation of the simulated cardiograms to the patient cardiograms that tends to minimize the difference between the configuration parameters and the patient parameters. To train the mapping function, the CSC system may derive various features from the simulated cardiograms and use those features as training data. The features may be based on the magnitude of voltages of cardiac segments, the timing of cardiac segments, and so on. Once the mapping function is trained, the CSC system applies to the mapping function to a set of simulated cardiograms that match the patient cardiograms to generate ML transformed simulated cardiograms. The ML transformed simulated cardiograms form the ML calibrated collection of simulated cardiograms.

The ML calibrated collection can then be used to generate a patient-specific model classifier. The mapping function can be used in combination with the various techniques described above to identify simulated cardiograms that match the patient cardiograms. For example, the matching simulated cardiograms may be identified based on orientation similarity and electrophysiological similarity.

In some embodiments, the CSC system may also generate a calibrated collection of simulated cardiograms based on patient-specific source configuration (e.g. geometry, disease substrate or scar, action potentials). To identify the calibrated collection, the CSC system identifies simulations based on their source configurations and/or cardiograms such as VCGs being similar that of the patient. The CSC system then employs a bootstrapping technique similar to one described above that is used to speed up generating of the model library. For each identified simulation, the CSC system uses the values of the EM mesh at some point of the simulation to bootstrap a patient-specific simulation. The CSC system then continues the simulation using the patient-specific source configuration of the patient, rather than the source configuration of the identified simulation. For example, if the simulations are for four seconds, the CSC system may initialize the patient-specific simulations with the values from the three second point and run a patient-specific simulation for one second. The CSC system then generates patient-specific simulated VCGs from the patient-specific simulations. The CSC system identifies as the calibrated collection the patient-specific simulations with their corresponding source configurations and patient-specific VCGs as the calibrated collection of simulated cardiograms. The calibrated collection may be used as training data for a patient-specific classifier or for other purposes such as using the source configurations of the simulations in the collection directly to identify a source location.

In some embodiments, the CSC system may also identify a calibrated collection of simulated cardiograms based on patient-specific simulated cardiograms such as VCGs. To identify the calibrated collection, the CSC system identifies simulations based on their source configurations being similar that of the patient. For example, the similarity may be based on geometry and scar locations. The CSC system then uses the EM data or EM output of each identified simulation and the geometry of the patient's heart to generate a patient-specific VCG for that simulation. To generate the VCG, the CSC system effectively assumes that the EM data or EM output was generated using a geometry that matches that of the patient when generating the patient-specific VCG. The CSC system then identifies the simulations with VCGs that best match the patient-specific VCG as the calibrated collection of simulated cardiograms. The calibrated collection may be used as training data for a patient-specific classifier or for other purposes such as using the source configurations of the simulations in the collection directly to identify a source location.

In some embodiments, the CSC system may perform additional calibration based on the identified simulated VCGs that best match the patient-specific VCGs via linear or non-linear transformation of pairs of simulated and patient-specific VCGs. A pair of simulated and patient-specific VCGs comprises two VCGs with similar source configuration (e.g. geometry, scar locations, electrophysiology properties, source location, etc.) and electromagnetic data (e.g., cardiogram morphology). The CSC system may compute a linear transformation from a least-squares fit of at least one pair of simulated and patient-specific VCG, such that the transformation applied to the simulated VCG improves the similarity score with the patient-specific VCG. The CSC system may also apply non-linear transformations using a neural network trained on pairs of simulated and patient-specific VCGs or other machine learning technologies to transform the simulated VCGs to better match the patient-specific VCGs.

Figure 43:
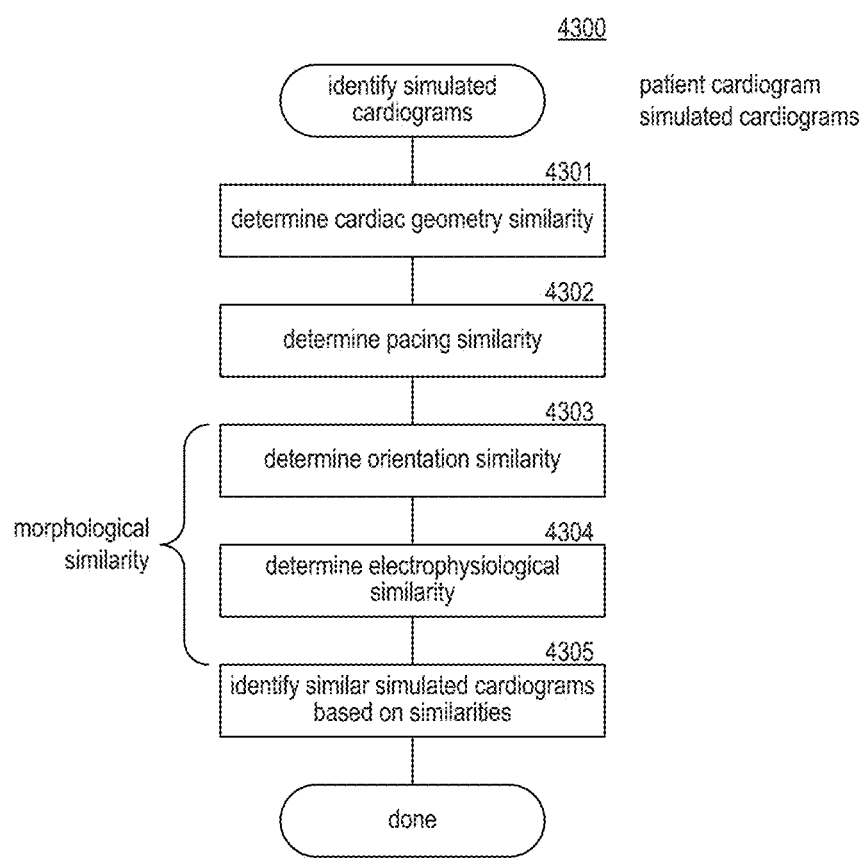
FIG. 43 is a flow diagram that illustrates processing of an identify simulated cardiograms component of the CSC system in some embodiments.

FIG. 43 is a flow diagram that illustrates processing of an identify simulated cardiograms component of the CSC system in some embodiments. The identify simulated cardiograms component 4300 is passed patient cardiograms and simulated cardiograms and identifies the simulated cardiograms that are similar to each patient cardiogram. In block 4301, the component determines the cardiac geometry similarity (e.g., structural disease similarity and/or measurement similarity) between each patient cardiogram and each simulated cardiogram. In block 4302, the component determines pacing similarity between each patient cardiogram and each simulated cardiogram. Pacing similarity may be based on how close a pacing location and a pacing rate of a simulated cardiogram is to that of a patient cardiogram. In block 4303, the component determines orientation similarity between each patient cardiogram and each simulated cardiogram. In block 4304, the component determines electrophysiological similarity between each patient cardiogram and each simulated cardiogram. In block 4305, the component identifies the simulated cardiograms as the calibrated simulated cardiograms based on the determined similarities and then completes. Although not illustrated, the component may also determine disease substrate similarity for identifying similar simulated cardiograms. The configuration parameters used to generate the simulated cardiograms are considered to be associated with those cardiograms. For example, a cardiogram may be considered to have a pacing location and a disease substrate used in generating a simulated cardiogram or a patient cardiogram.

Figure 44:
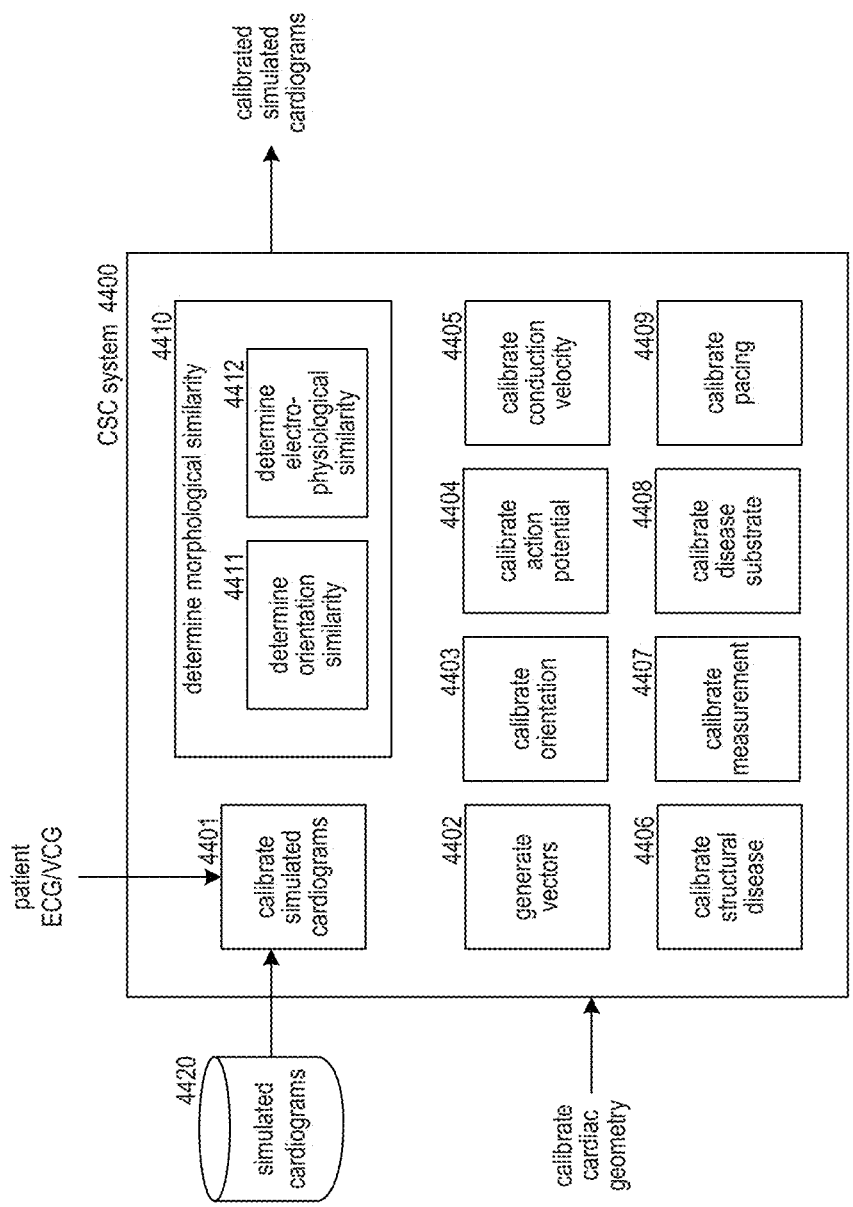
FIG. 44 is a block diagram that illustrates components of the CSC system in some embodiments.

FIG. 44 is a block diagram that illustrates components of the CSC system in some embodiments. The CSC system 4400 includes a calibrate simulated cardiograms component 4401. The CSC system includes calibrate orientation components that include a generate vectors component 4402 and a determine morphological similarity component 4410 with a determine orientation similarity component 4411 and a determine electrophysiological component 4412. The CSC system includes an identify orientation-similar component 4403 and calibrate electrophysiology components that include a calibrate action potential component 4404 and a calibrate conduction velocity component 4405. The CSC system includes cardiac geometry components that include a calibrate structural disease component 4406 and a calibrate measurement component 4407. The CSC system includes a calibrate disease substrate component 4408 and a calibrate pacing component 4409. The CSC system accesses simulation store 4420 and outputs calibrated simulated cardiograms. The calibrate simulated cardiograms component invokes the calibrate orientation components, the calibrate electrophysiology components, the cardiac geometry components, the calibrate disease substrate component, and the calibrate pacing component to identify the calibrated simulated cardiograms. The calibrate orientation components, the calibrate action potential component, and the calibrate cardiac geometry components are described in flow diagrams.

Figure 45:
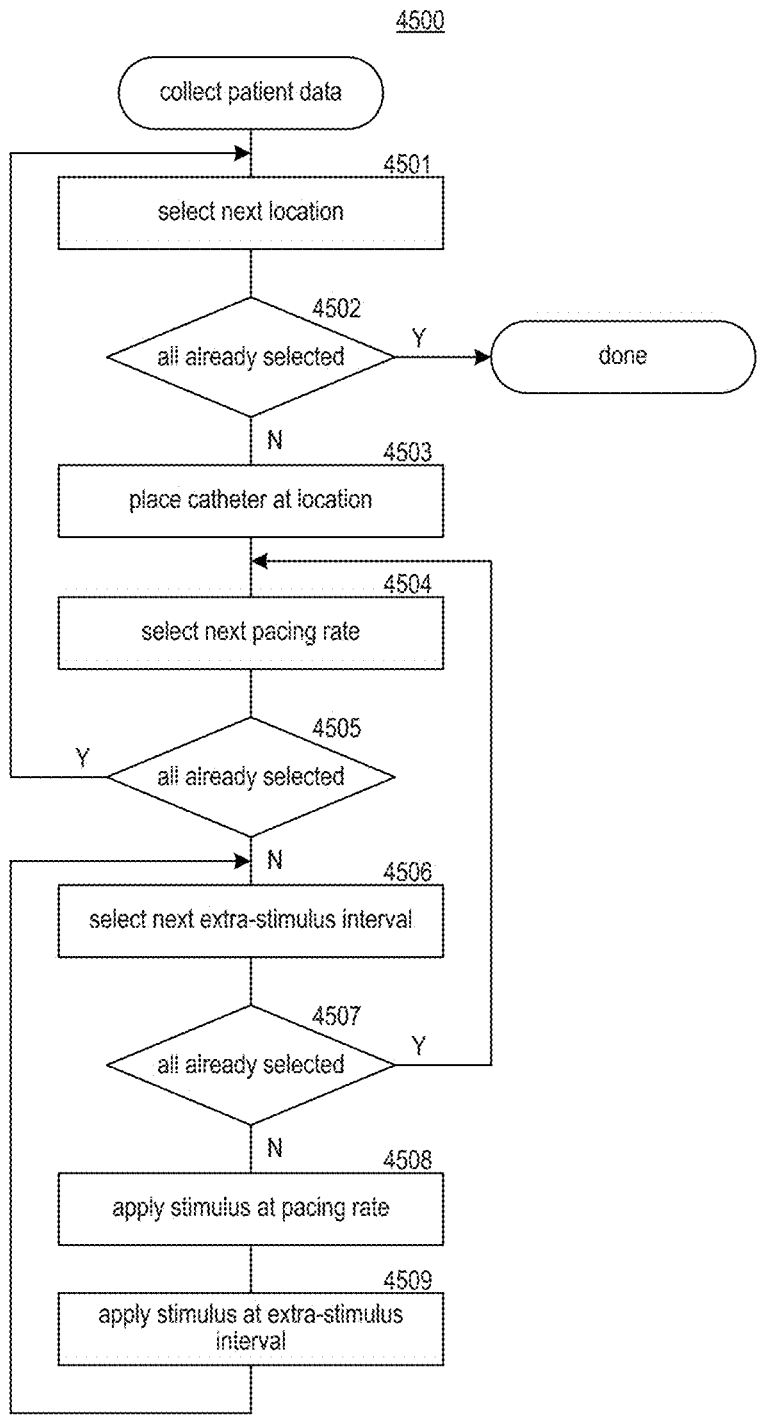
FIG. 45 is a flow diagram that illustrates the processing performed by an electrophysiologist ("EP") to collect patient data.

FIG. 45 is a flow diagram that illustrates the processing performed by an electrophysiologist ("EP") to collect patient data. In block 4501, the EP selects the next pacing location. In decision block 4502, if all the pacing locations have already been selected, then the processing completes, else the processing continues at block 4503. In block 4503, the EP places the catheter at the pacing location. In block 4504, the EP selects the next pacing rate. In decision block 4505, if all the pacing rates have already been selected for the selected pacing location, then the processing loops to block 4501 to select the next pacing location, else the processing continues at block 4506. In block 4506, the EP selects the next extra-stimulus interval. In decision block 4507, if all the extra-stimulus intervals have already been selected for the selected pacing location and pacing rate, then the processing loops block 4504 to select the next pacing rate, else the processing continues at block 4508. In block 4508, the EP applies a stimulus at the selected pacing rate. In block 4509, the stimulus is applied at the extra-stimulus interval and the processing loops to block 4506 to select the next extra-stimulus interval.

Figure 46:
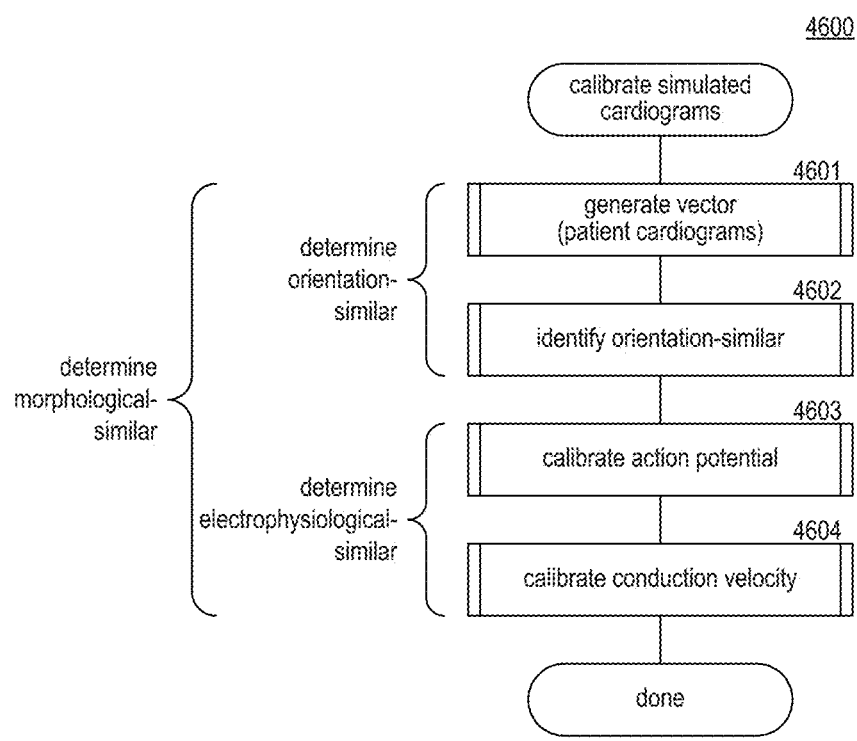
FIG. 46 is a flow diagram that illustrates processing of a calibrate simulated cardiograms component of the CSC system in some embodiments.

FIG. 46 is a flow diagram that illustrates processing of a calibrate simulated cardiograms component of the CSC system in some embodiments. The calibrate simulated cardiograms component 4600 is passed an indication of the patient cardiograms and the simulated cardiograms and identifies simulated cardiograms that are similar to the patient cardiograms. In block 4601, the component invokes the generate vectors component passing an indication of the patient cardiograms to generate the patient vectors for each patient cardiogram. In block 4602, the component invokes an identify orientation-similar simulated cardiograms passing an indication of the simulated cardiograms and the measured vectors for each patient cardiogram and receives an indication of the orientation-similar simulated cardiograms in return. Blocks 4601 and 4602 represent processing to determine the orientation-similar simulated cardiograms. In block 4603, the component invokes a calibrate action potential component passing an indication of the orientation-similar simulated cardiograms and the patient cardiograms and receives an indication of the action-potential-similar simulated cardiograms in return. In block 4604, the component invokes a calibrate conduction velocity component passing an indication of the action-potential-similar simulated cardiograms and the patient cardiograms and receives an indication of conduction-velocity-similar simulated cardiograms in return. Blocks 4603 and 4604 represent processing to determine the electrophysiological similarity.

Figure 47:
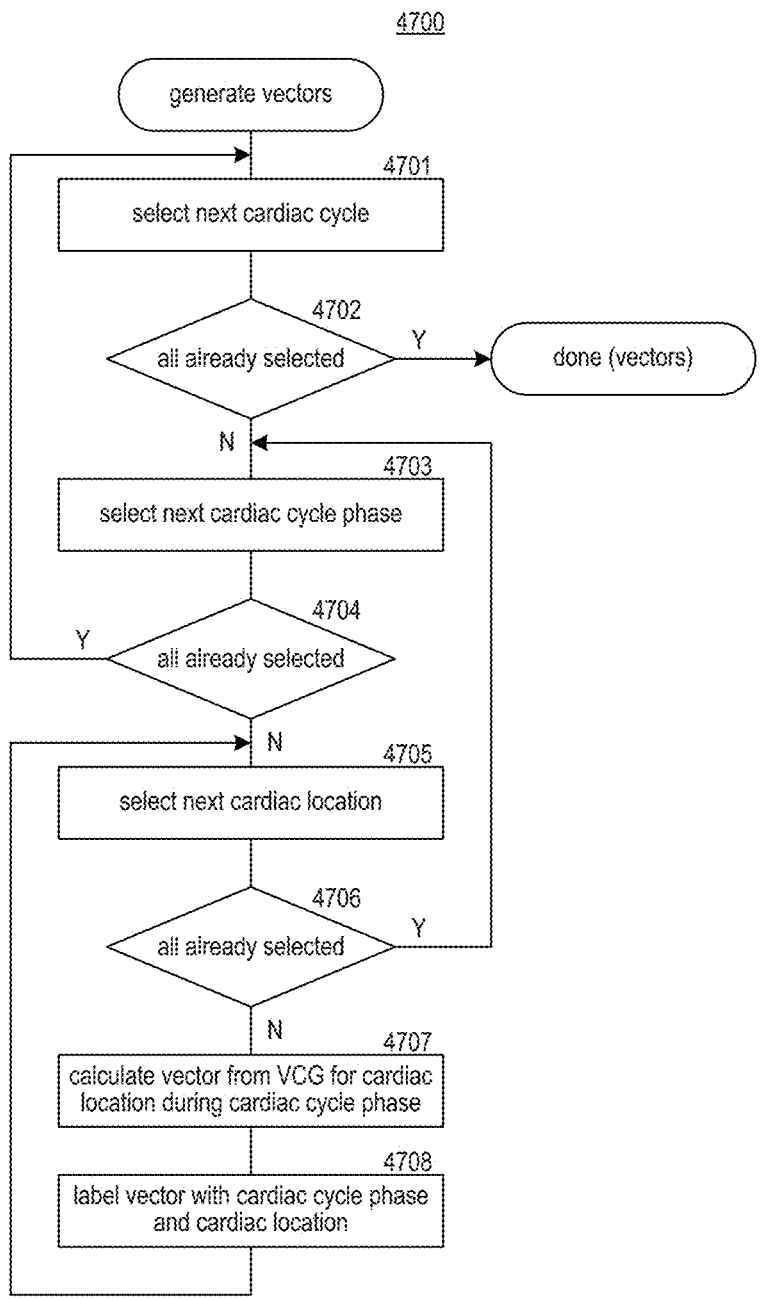
FIG. 47 is a flow diagram that illustrates the processing of a generate vectors components of the CSC system in some embodiments.

FIG. 47 is a flow diagram that illustrates the processing of a generate vectors component of the CSC system in some embodiments. The generate vectors component is invoked to generate the vectors for each cardiogram that is passed. Although not illustrated, the processing of blocks 4701-4708 are performed for each cardiogram. In block 4701, the component selects the next cardiac cycle of the cardiogram. In decision block 4702, if all the cardiac cycles have already been selected, then the component completes, else the component continues at block 4703. In block 4703, the component selects the next cardiac cycle phase for the selected cardiac cycle. In decision block 4704, if all the cardiac cycle phases have already been selected, then the component loops to block 4701 to select the next cardiac cycle, else the component continues at block 4705. In block 4705, the component selects the next cardiac location. In decision block 4706, if all the cardiac locations have already been selected, then the component continues at block 4703 to select the next cardiac cycle phase, else the component continues at block 4707. In block 4707, the component calculates the vector from the cardiogram for the cardiac location during the cardiac cycle phase. In block 4708, the component labels the vector with the cardiac cycle phase and cardiac location and then loops to block 4705 to select the next cardiac location.

Figure 48:
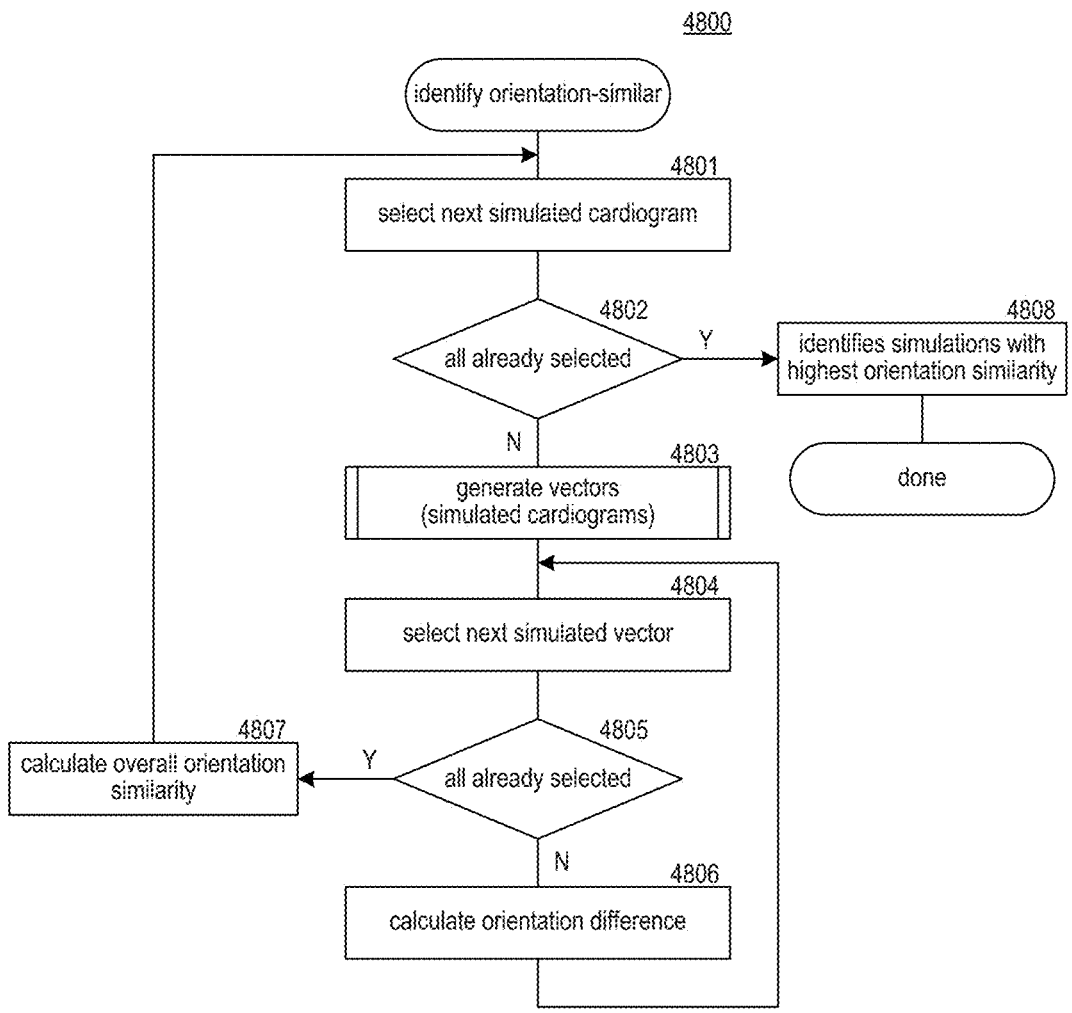
FIG. 48 flow diagram that illustrates the processing of the identify orientation-similar component of the CSC system in some embodiments.

FIG. 48 is a flow diagram that illustrates the processing of the identify orientation-similar component of the CSC system in some embodiments. The identify orientation-similar component 4800 is invoked passing an indication of the simulated cardiogram and the patient vectors for each patient cardiogram. Although not illustrated, blocks 4801-4807 are performed for each patient cardiogram. In block 4801, the component selects the next simulated cardiogram. In decision block 4802, if all the simulated cardiograms have already been selected, then the component continues at block 4808, else the component continues at block 4803. In block 4803, the component invokes the generate vectors component passing an indication of the simulated cardiogram and receives the simulated vectors in return. In block 4804, the component selects the next simulated vector. In decision block 4805, if all the simulated vectors have already been selected, then the component continues at block 4807, else the component continues at block 4806. In block 4806, the component calculates the orientation difference between the selected simulated vector and the corresponding patient vector and loops to block 4804 to select the next simulated vector. In block 4807, the component calculates orientation similarity for the selected simulation cardiogram and then loops to block 4801 to select the next simulated cardiogram. In block 4808, the component identifies and returns the simulated cardiograms with the highest orientation similarity and then completes.

Figure 49:
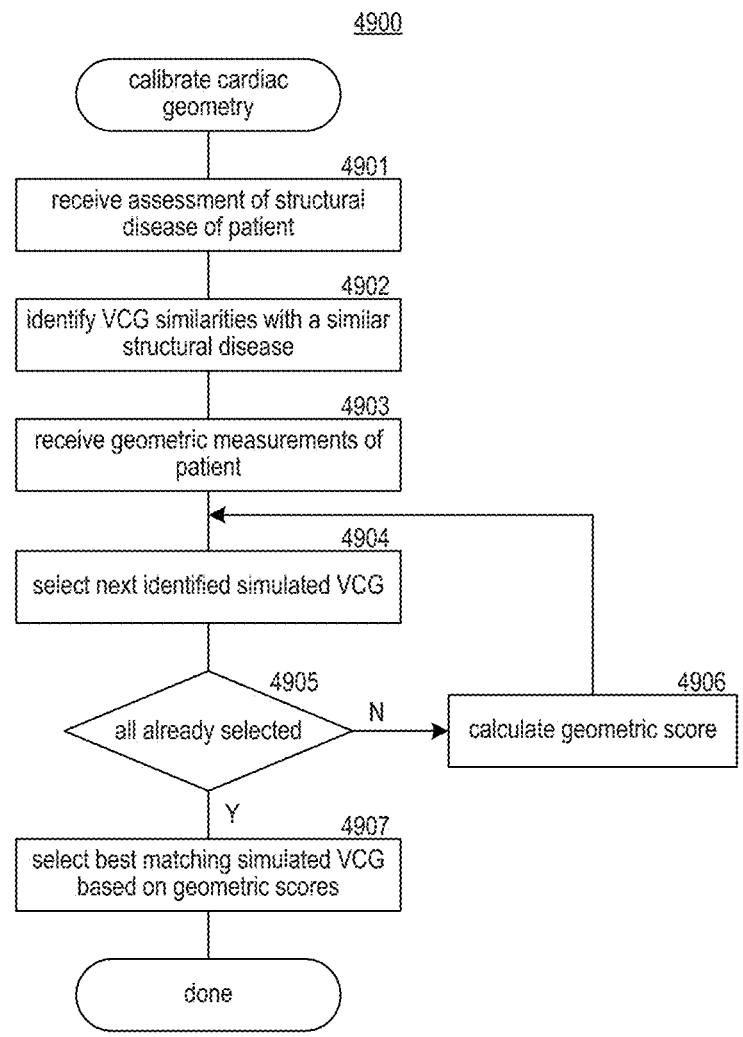
FIG. 49 is a flow diagram that illustrates the processing of a calibrate cardiac geometry component of the CSC system in some embodiments.

FIG. 49 is a flow diagram that illustrates the processing of a calibrate cardiac geometry component of the CSC system in some embodiments. The calibrate cardiac geometry component 4900 is invoked to identify simulated cardiograms that are cardiac-geometry-similar to the patient cardiograms. In block 4901, the component receives an assessment of the structural disease of the patient. In block 4902, the component identifies simulated cardiograms with a similar structural disease. In block 4903, the component receives the geometric measurements of the patient. In block 4904, the component selects the next identified simulated cardiogram. In decision block 4905, if all the simulated cardiograms have already been selected, then the component continues at block 4907, else the component continues at block 4906. In block 4906, the component calculates a geometric score between the selected simulated cardiograms and the patient, and then loops to block 4904 to select the next identified simulated cardiogram. In block 4907, the component selects and returns the best matching simulated cardiograms based on geometric scores as the cardiac-geometry-similar simulated cardiograms.

Figure 50:
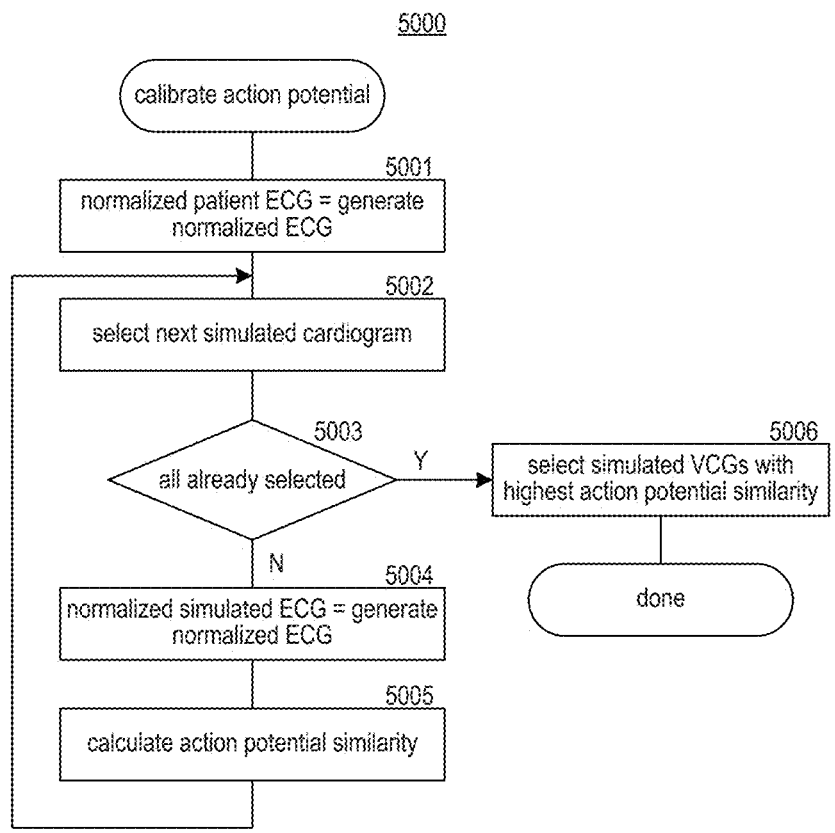
FIG. 50 is a flow diagram that illustrates the processing of a calibrate action potential component of the CSC system in some embodiments.

FIG. 50 is a flow diagram that illustrates the processing of a calibrate action potential component of the CSC system in some embodiments. The calibrate action potential component 5000 identifies simulated cardiograms whose action potential are similar to the patient cardiograms. Although not illustrated, the processing of blocks 5001-5006 are performed for each patient cardiogram. In block 5001, the component generates a normalized ECG for the patient cardiogram. In block 5002, the component selects the next simulated cardiogram. In decision block 5003, if all the simulated cardiograms have already been selected, then the component continues at block 5006, else the component continues at block 5004. In block 5004, the component generates a normalized simulated ECG for the selected simulated cardiogram. In block 5005, the component calculates the action potential similarity between the normalized patient ECG and the simulated ECG and then loops to block 5002 to select the next simulated cardiogram. In block 5006, the component selects and returns the simulated cardiograms with the highest action potential similarity.

Figure 51:
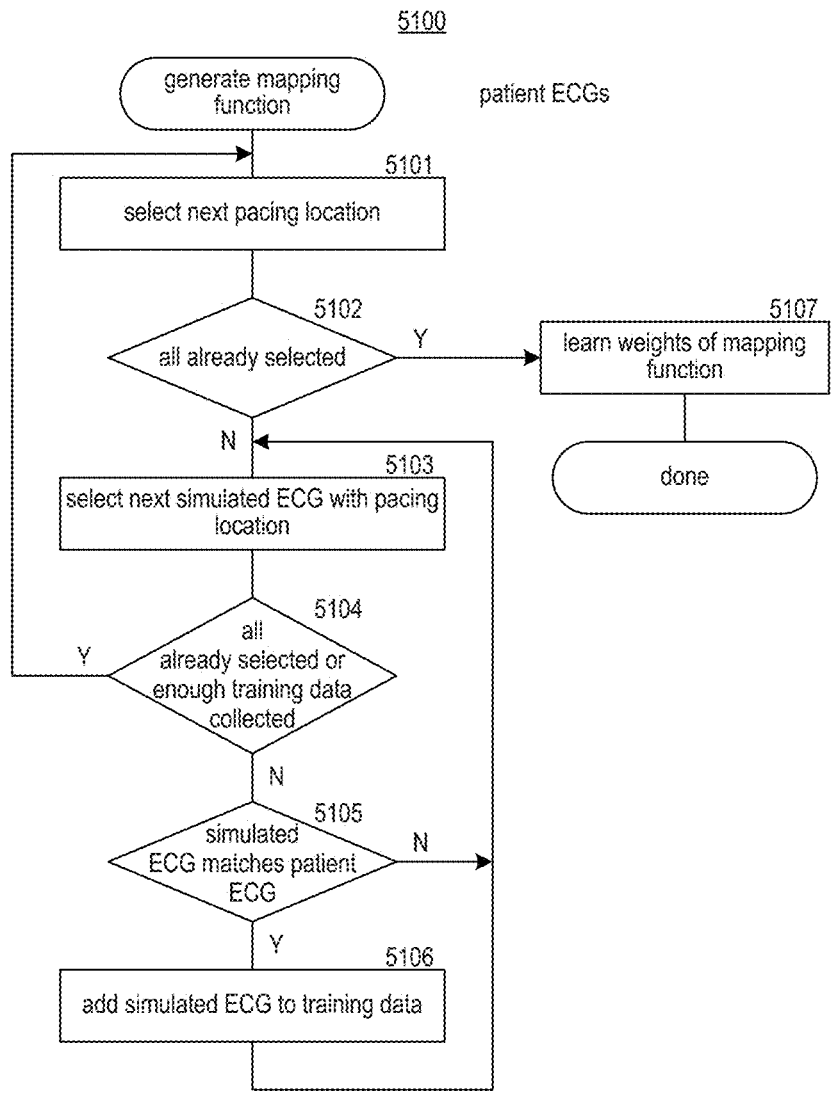
FIG. 51 is a flow diagram that illustrates the processing of a generate mapping function component of the CSC system in some embodiments.

FIG. 51 is a flow diagram that illustrates the processing of a generate mapping function component of the CSC system in some embodiments. The generate mapping function component 5100 identifies a set of simulated cardiograms that match the patient cardiograms to be used as training data and then trains the mapping function. In block 5101, the component selects the next pacing location of the patient cardiograms. In decision block 5102, if all the pacing locations have already been selected, then the component continues at block 5107, else the component continues at block 5103. In block 5103, the component selects the next simulated cardiogram with that pacing location. In decision block 5104, if all such simulated cardiograms have already been selected, then the component loops to block 5101 to select the next pacing location, else the component continues at block 5105. In decision block 5105, if the configuration parameters of the simulated cardiogram match the patient configuration parameters, then the component continues at block 5106, else the component loops to block 5103 to select the next simulated cardiogram. In block 5106, the component adds the simulated cardiogram to the training data and loops to block 5106 to select the next simulated cardiogram. In block 5107, the component trains the mapping function to map the simulated cardiograms of the training data to the patient cardiograms and then completes.

Figure 52:
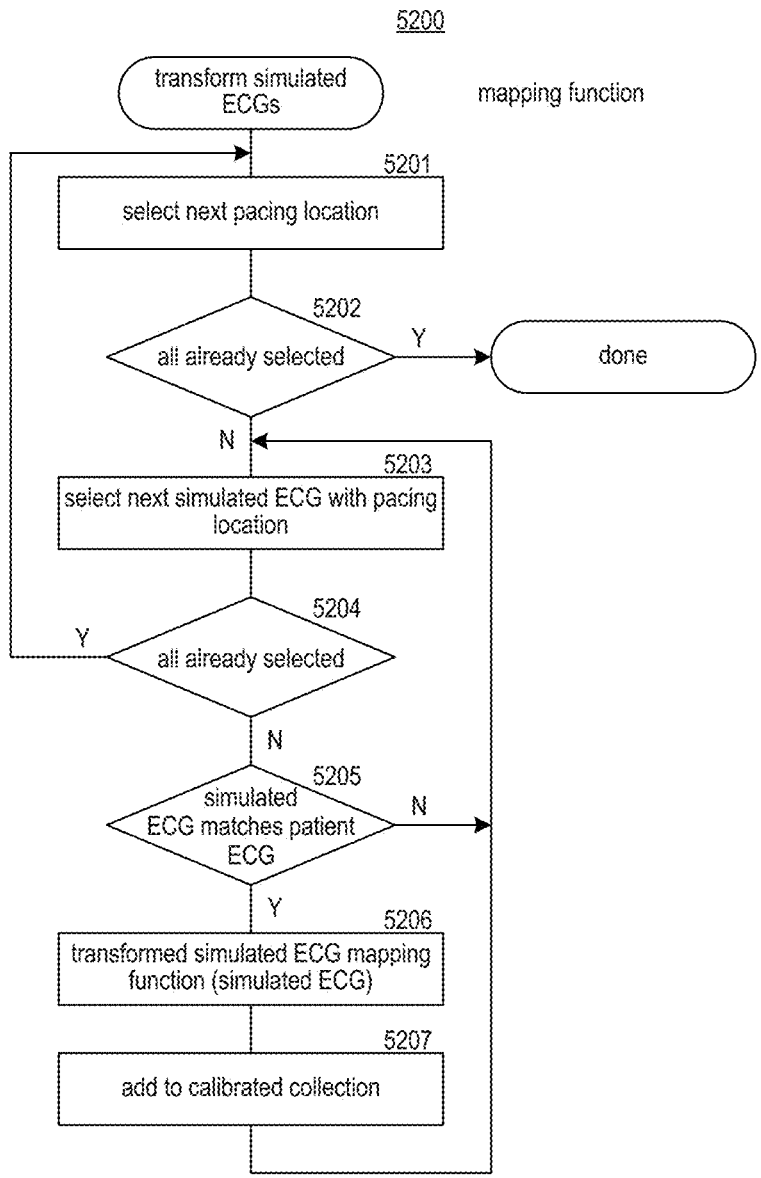
FIG. 52 is a flow diagram that illustrates the processing of a transform simulated cardiograms component of the CSC system in some embodiments.

FIG. 52 is a flow diagram that illustrates the processing of a transform simulated cardiograms component of the CSC system in some embodiments. The transform simulated cardiograms component 5200 applies the mapping function to simulated cardiograms to generate a ML calibrated collection of simulated cardiograms. In block 5201, the component selects the next pacing location of the patient cardiograms. In decision block 5202, if all the pacing locations have already been selected, then the component completes, else the component continues at block 5203. In block 5203, the component selects the next simulated cardiogram with that pacing location. In decision block 5204, if all such simulated cardiograms have already been selected, then the component loops to block 5201 to select the next pacing location, else the component continues at block 5205. In decision block 5205, if the configuration parameters of the simulated cardiogram match the patient configuration parameters, then the component continues at block 5206, else the component loops to block 5203 to select the next simulated cardiogram. In block 5206, the component applies the mapping function to the simulated cardiogram to generate a ML transformed simulated cardiogram. In block 5207, the component adds the ML transformed simulated cardiogram to the ML calibrated collection and loops to block 5203 to select the next simulated cardiogram.

Although described primarily in the context of an electromagnetic source that is a heart, the CSC system may be used to calibrate simulated electromagnetic outputs for other electromagnetic sources with a body. The CSC system and the other systems described herein may be used, for example, when the body is a human body or body of another animal and when the electromagnetic source is a heart, a brain, a liver, a lung, a kidney, a muscle, or another part of the body that generates an electromagnetic field that can be measured from outside or inside the body. Also, the patient pacing may be performed using an invasive pacing device that administers electromagnetic pulses from inside the electromagnetic source such as a catheter. The patient pacing may be performed using a non-invasive pacing device that administers electromagnetic pulses from outside the electromagnetic source such as a magnetic resonance scanner. A non-invasive pacing device may generate an electromagnetic field to pace the electromagnetic source of the patient.

User Interface for Calibrating Orientation

In some embodiments, the user interface calibrating ("UIC") system of the CSC system provides a user interface for manual calibration of the orientation of a patient VCG to a simulated VCG. The UIC system accessing patient ECGs collected during normal sinus rhythm and/or based on pacing at various pacing locations that may be identified based on study imaging data (e.g., from a chest x-ray or a catheter system localization system). The UIC system then extracts segments whose activation source location are known from the ECGs and then denoises the segments. The UIC system then generates VCGs from the segments. The UIC system then selects simulated cardiograms with source locations similar to those of the accessed patient ECGs.

Figure 53:
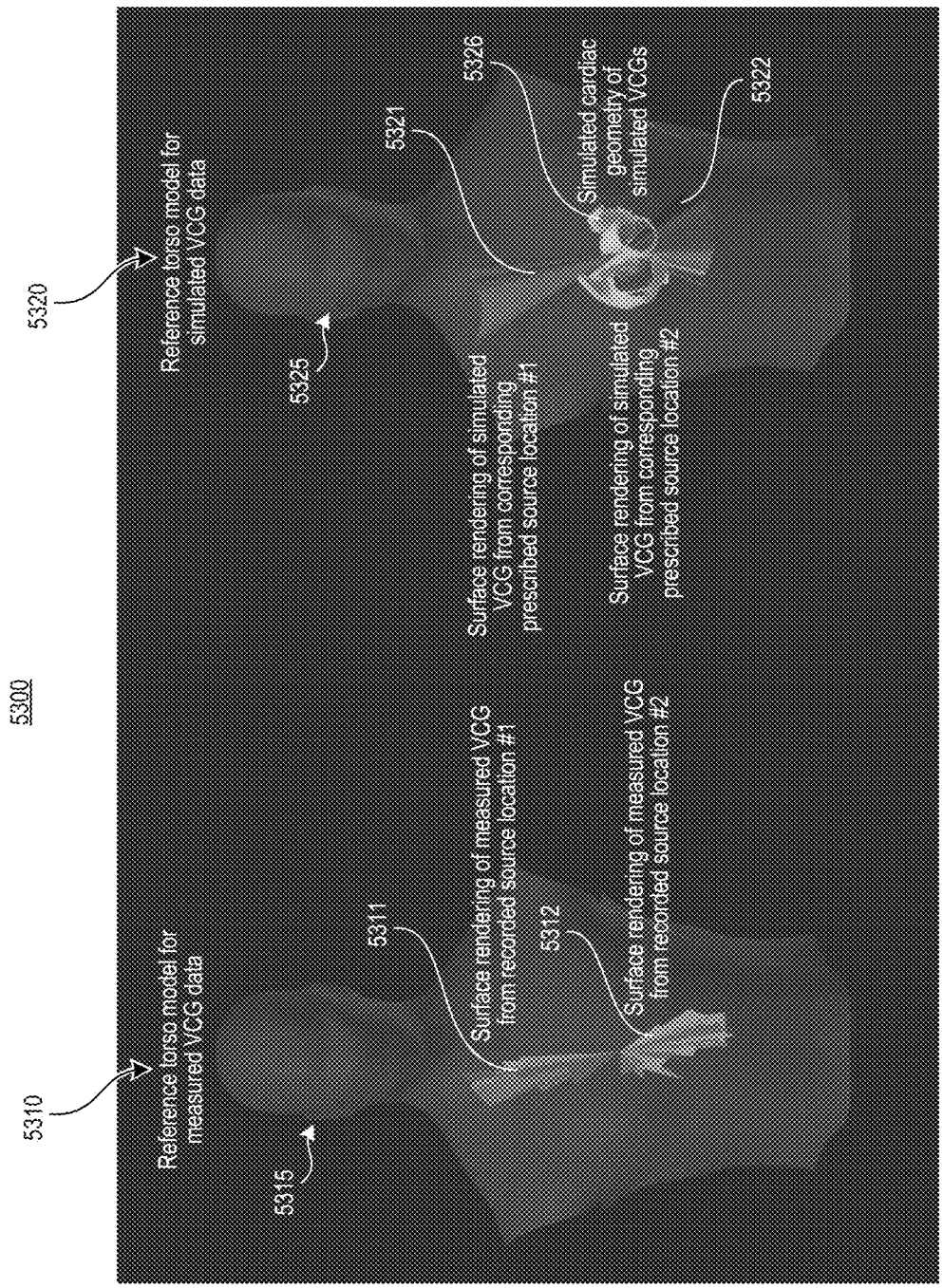
FIG. 53 illustrates the user interface for manually calibrating orientation.

FIG. 53 illustrates the user interface for manually calibrating orientation. Display 5300 includes a patient representation 5310 and a simulated representation 5320. To generate the patient representation, the UIC system renders patient VCGs 5311 and 5312 for patient source locations as three-dimensional ("3D") surfaces. The patent VCGs may be superimposed on a torso model 5315 to provide an anatomical reference frame such as a coronal view and/or an orthogonal view, which can be rotated in 3D. To generate the simulated representation, the UI system renders simulated VCGs 5321 and 5322 from the selected simulated cardiograms with simulated source locations similar to the patient source locations which may also be superimposed on a torso model 5325. The UIC system may also superimpose a representation of a heart 5326 based on the cardiac geometry of the simulated cardiograms. A user can then rotate the cardiac geometry with the simulated VCGs, which rotates with the cardiac geometry, to align the simulated VCGs to the patient VCGs (based on a visual comparison). To assist in the alignment, the UIC system may also generate an alignment score (e.g., based on a least square fit) indicating closeness of the alignment of the rotated, simulated VCGs to the patient VCGs. When the user determines that the VCGs are aligned, the UIC system then generates a rotation matrix based on the amount of rotation of the cardiac geometry needed to align the simulated VCGs to the patient VCGs. The CSC system can use the rotation matrix to identify orientation-similar cardiograms.

Identify Ablation Patterns

Methods and computing systems for identifying an ablation pattern and methods for treating a patient based on the identified ablation pattern are provided. In some embodiments, an ablation pattern identification ("API") system identifies an ablation pattern for treating an EM source of a patient. The API system accesses a patient EM output of the EM source (e.g., a heart or brain). The API system identifies non-ablation pattern information of a non-ablation pattern simulation based on a simulated source configuration and not based on an ablation pattern. For example, the non-ablation pattern information may be simulated EM output (e.g., a simulated ECG) generated from a non-ablation pattern simulation. The API system identifies the non-ablation pattern information based on similarity of simulated EM output of a non-ablation pattern simulation to the patient EM output. The API system then identifies an ablation pattern based on the identified non-ablation pattern information and ablation pattern information associated with an ablation pattern simulation. For example, the ablation pattern may be identified based on a mapping of simulated EM output to ablation patterns used in ablation pattern simulations. Each ablation pattern simulation is generated based on a simulated source configuration and an ablation pattern. The API system then outputs an indication of the identified ablation pattern as the potential ablation pattern for the EM source of the patient.

In some embodiments, the API system accesses a model library of non-ablation pattern simulations and simulated derived EM data generated from the simulated EM output of the model library. The model library may be generated by the MLMO system. This model library is referred to as a "non-ablation pattern model library" and the simulations are referred as "non-ablation pattern simulations" because the simulations are based on simulated source configurations that do not include ablation patterns. For example, if the EM source is a heart, then the non-ablation pattern simulations may be based on a simulated source location of an arrhythmia without assuming an ablation pattern and the simulated derived EM data may be a VCG. The API system also generates an ablation pattern model library that may include one or more ablation pattern simulations for each simulated source configuration used to generate the non-ablation pattern model library. For each simulated source configuration, the API system performs an ablation pattern simulation for each of a set of ablation patterns. Each ablation pattern simulation is used to identify the results of that ablation pattern applied to the simulated source location of the simulated source configuration. If an ablation pattern simulation results in no arrhythmia, the ablation pattern is identified as being successful for stopping the arrhythmia for the simulated source configuration. Otherwise, it is identified as being unsuccessful. For example, if the set of ablation patterns includes 10 ablation patterns, the API system generates 10 ablation pattern simulations for each simulated source configuration. The number of successful ablation patterns for the simulated source configurations may vary from 0 to 10. For example, one of the simulated source configurations may have 2 successful ablation patterns and another may have 7 successful ablation patterns.

In some embodiments, the API system identifies one or more potential ablation patterns for a patient by comparing the patient EM output (or patient-derived EM data) to the simulated EM outputs (or simulated derived EM data) to identify a matching simulated EM output. The API system selects the simulated source configuration used in the non-ablation pattern simulation from which the matching simulated EM output was generated. The API system then identifies the ablation pattern simulations based on that selected simulated source configuration. The API system selects the successful ablation patterns of those ablation pattern simulations as the potential ablation patterns. For example, if the EM source is a heart of a patient and the patient-derived data is a VCG, the API system uses the patient VCG to select the simulated source configuration of the non-ablation pattern simulation used to generate the best matching simulated VCG. The API system then identifies the ablation pattern simulations based on the selected simulated source configuration resulting in a successful ablation pattern. The API system then outputs the successful ablation patterns as the potential ablation patterns for the patient.

In some embodiments, the API system is used to assist with a method of treating a patient, for example, when treating a patient with an arrhythmia (or more generally a tachycardia). An ablation assist ("AA") system is used to assist a physician in treating the patient. A patient VCG of the patient collected during the arrhythmia is input to the AA system. The AA system then provides the patient VCG to the API system. In response, the API system outputs an indication of one or more potential ablation patterns for the ablation and may output one or more target sites for the ablation. The physician then selects a potential ablation pattern and target site. To assist in the selection, the AA system may display an ablation pattern superimposed at the target site on a representation of the patient's heart. The displayed representation may be based on the anatomical characteristics of the patient's heart. When using a stereotactic body radiation therapy ("SBRT") device, anatomical characteristics of the patient can be determined from images collected as part of the therapy (e.g. "scout" images). The AA system may provide the selected ablation pattern and the source location to an ablation device (e.g., an SBRT device) for automatic positioning. Alternatively, the physician may manually position the ablation device (e.g., catheter). When the patient is ready for the ablation, the energy is activated to perform the ablation based on the selected ablation pattern. The ablation device may be an SBRT device, an ablation catheter, a cryoablation catheter, an implantable pulse generator, and so on.

Figure 54:
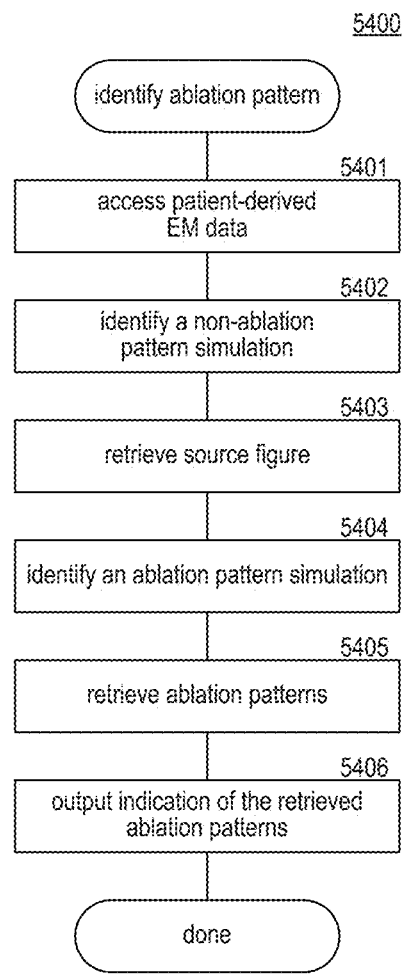
FIG. 54 is a flow diagram that illustrates the overall processing of the API system in some embodiments.

FIG. 54 is a flow diagram that illustrates the overall processing of the API system in some embodiments. An identify ablation pattern component 5400 identifies an ablation pattern based on patient-derived EM data. In block 5401, the component accesses the derived EM data (e.g., VCG). In block 5402, the component identifies a non-ablation pattern simulation of the model library based on the simulated derived EM data that best matches the patient-derived EM data. In block 5403, the component retrieves the simulated source configuration used to generate the identified non-ablation pattern simulation. In block 5404, the component identifies the ablation pattern simulation performed using the retrieved simulated source configuration. In block 5405, the component retrieves the ablation patterns associated with the identified ablation simulation. In block 5406, the component outputs an indication of the retrieved ablation patterns and then completes.

Figure 55:
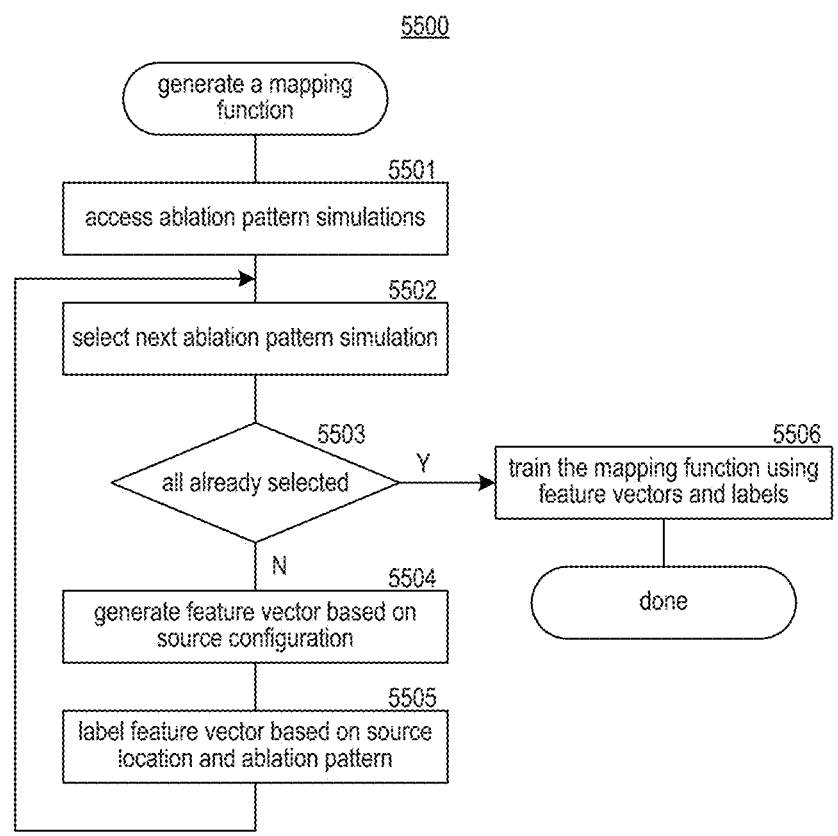
FIG. 55 is a flow diagram that illustrates the processing of a generate mapping function of the API system in some embodiments.

FIG. 55 is a flow diagram that illustrates the processing of a generate mapping function of the API system in some embodiments. The generate mapping function 5500 generates a mapping function that may be used to identify a potential source location and potential ablation pattern. In block 5501, the component accesses the ablation pattern simulations. In block 5502, the component selects the next ablation pattern simulation. In decision block 5503, if all the ablation pattern simulations have already been selected, then the component continues at block 5506, else the component continues at block 5504. In block 5504, the component generates a feature vector based on the simulated source configuration of the selection ablation pattern simulation. The features of the vector may include all the simulated source configurations or a subset of the simulated source configurations that is particularly relevant to identifying a source location and an ablation pattern along with other information such as a simulated EM data generated from the non-ablation pattern simulation that used the simulated source configuration. In block 5505, the component labels the feature vector based on the simulated source location and the ablation pattern of the selected ablation pattern simulation and then loops to block 5502 to select the next ablation pattern simulation. In block 5506, the component trains the mapping function using the feature vectors and labels and then completes.

Figure 56:
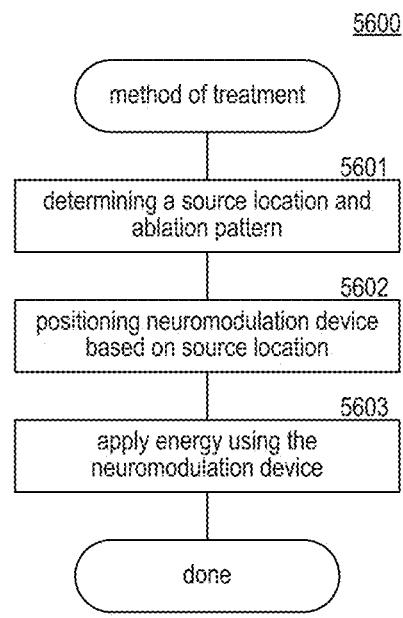
FIG. 56 is a block diagram that illustrates the processing of a method for treating a patient during an ablation in some embodiments.

FIG. 56 is a block diagram that illustrates the processing of a method for treating a patient during an ablation in some embodiments. The method 5600 accesses patient-derived EM data (e.g., VCG) as an initial step in the processing. In step 5601, the method identifies a source location and ablation pattern to be used. This identification may be made by generating a feature vector based on features derived from a patient source configuration of the patient and patient-derived EM data and then applying the mapping function trained by the API system. Alternatively, the identification may be made by identifying a non-ablation pattern simulation with simulated EM data that best matches the patient EM data and then using the simulated source configuration to identify an ablation pattern simulation generated using that simulated source configuration. In step 5602, the method positions or directs (i.e., aims) an ablation device (e.g., neuromodulation device) based on the identified source location. In step 5603, the method applies or directs energy using the ablation device (e.g. neuromodulation device) at a target site derived from the identified source location and based on the identified ablation pattern.

Figure 57:
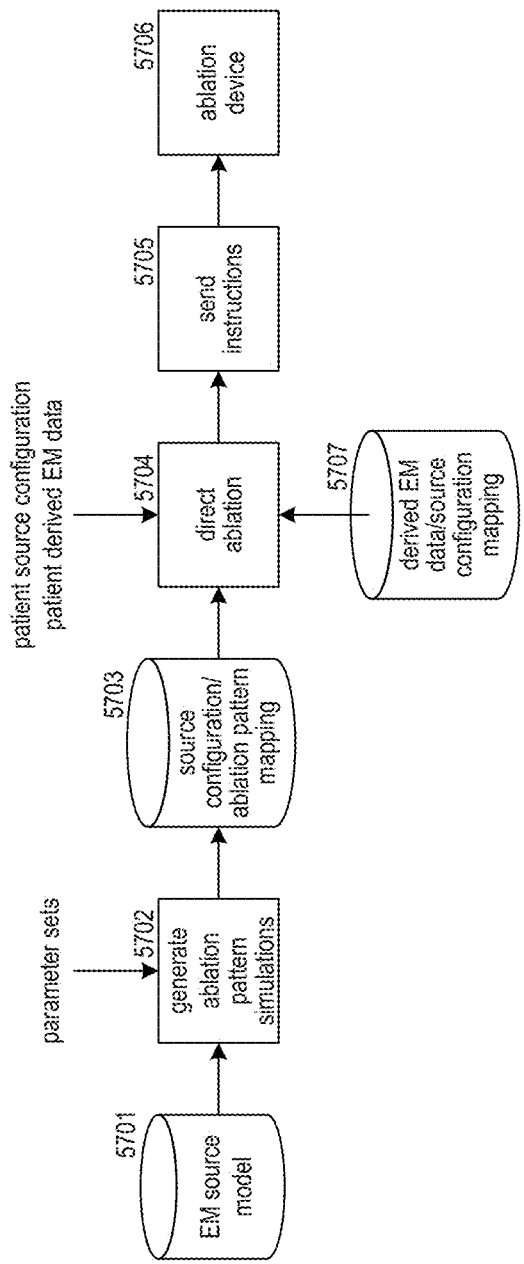
FIG. 57 is a block diagram that illustrates components of the API system in some embodiments.

FIG. 57 is a block diagram that illustrates components of the API system in some embodiments. A generate ablation pattern simulations component 5702 inputs an EM source model 5701 and parameter sets of source configurations and performs simulations based on the source configurations using the heart models. The ablation pattern simulation component then stores a mapping of the source configurations to the ablation patterns in a source configuration/ablation pattern mapping store 5703. A direct ablation component 5704 inputs the patient source configuration and patient-derived EM data and accesses a derived EM data/source configuration mapping store 5707 and the source configuration/ablation pattern mapping store to identify a source location and an ablation pattern and controls the performing of an ablation. A send instructions component 5705 inputs the source location and ablation pattern and sends instructions to an ablation device 5706.

Figure 58:
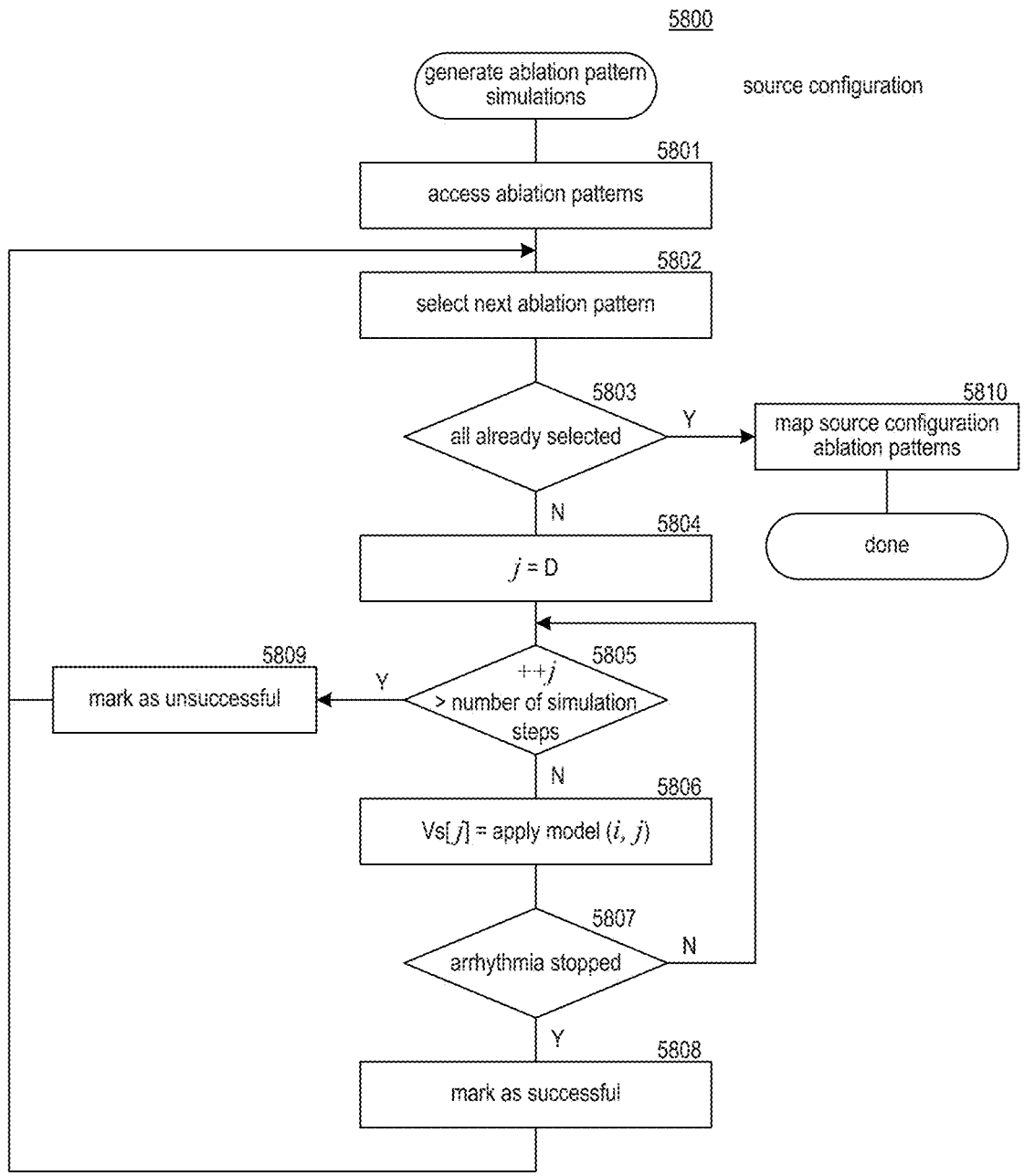
FIG. 58 is a flow diagram that illustrates the processing of a generate ablation pattern simulations component of the API system in some embodiments.

FIG. 58 is a flow diagram that illustrates the processing of a generate ablation pattern simulations component of the API system in some embodiments. The generate ablation pattern simulations component 5800 inputs a source configuration and maps the source configuration to successful ablation patterns. The component is invoked for each source configuration. In block 5801, the component accesses ablation patterns to be used in the ablation pattern simulations. The API system may use the same ablation patterns for each source configuration. Alternatively, the API system may select the ablation patterns based on the source location because different ablation patterns may be more effective at different source locations. In block 5802, the component selects the next ablation pattern and sets a variable i to the selected ablation pattern. In decision block 5803, if all the ablation patterns have already been selected, then the component continues at block 5810, else the component continues at block 5804. In block 5804, the component initializes the variable j to zero to track each step of the ablation pattern simulation. In decision block 5805, the component increments the variable j and determines whether the variable j is greater than the number of simulation steps, indicating that the ablation pattern simulation is complete. If complete, the component continues at block 5809, else the component continues at block 5806 to perform the next step of the simulation. In block 5806, the component applies the model to the selected ablation pattern for the next step of the ablation pattern simulation. In decision block 5807, if the ablation pattern simulation indicates that the arrhythmia has stopped, then the component continues at block 5808, else the component loops to block 5805 to perform the next step of the simulation. In block 5808, the component marks the ablation pattern as successful and loops to block 5802 to select the next ablation pattern. In block 5809, the component marks the ablation pattern as unsuccessful because the ablation simulation has been completed but the arrhythmia has not been stopped. The component then loops to block 5802 to select the next ablation pattern. In block 5810, the component maps the source configuration to the ablation patterns that are successful and completes.

Figure 59:
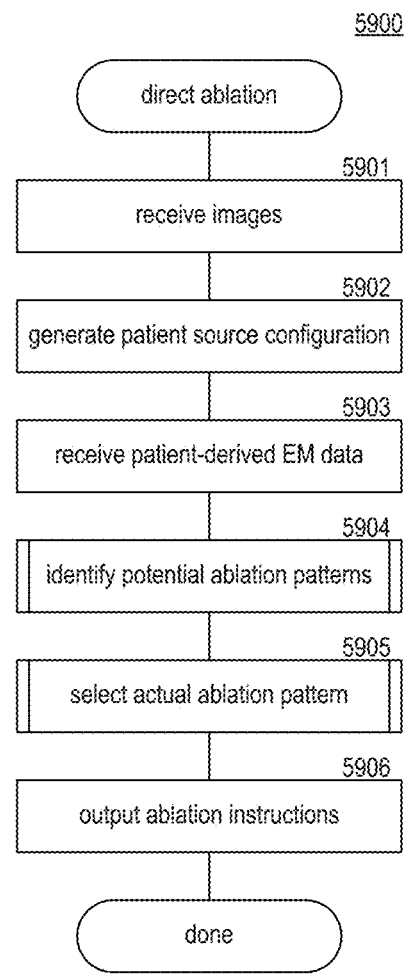
FIG. 59 is a block diagram illustrating the processing of a direct ablation component of the API system in some embodiments.

FIG. 59 is a block diagram illustrating the processing of a direct ablation component of the API system in some embodiments. The direct ablation component 5900 is invoked to direct the ablation for a patient. In block 5901, the component receives images of the EM source of the patient. In block 5902, the component generates a patient source configuration based on the image and other information provided about the patient such as scar location, prior ablations, current medications, and so forth. In block 5903, the component receives the patient-derived EM data (e.g., VCG). In block 5904, the component invokes an identify potential ablation patterns component. In block 5905, the component invokes a select actual ablation pattern component to select an ablation pattern for use in the ablation. In block 5906, the component outputs ablation instructions generated based on the actual ablation pattern. The ablation instructions may be provided directly to an ablation device or displayed to a physician. The component then completes.

Figure 60:
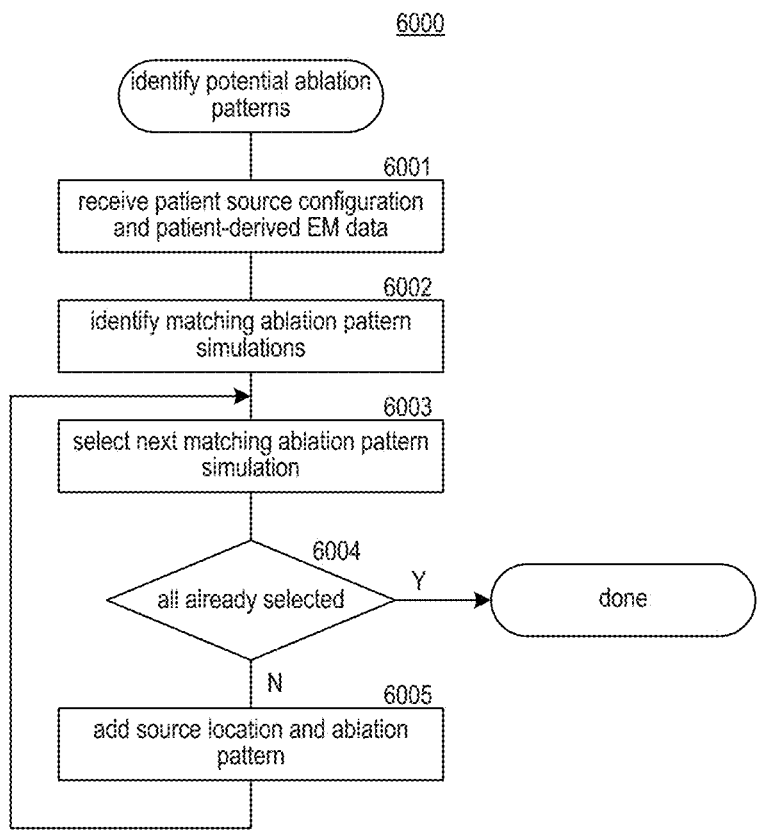
FIG. 60 is a flow diagram that illustrates the processing of an identify potential ablation patterns component of the API system in some embodiments.

FIG. 60 is a flow diagram that illustrates the processing of an identify potential ablation patterns component of the API system in some embodiments. The identify potential ablation pattern component 6000 is invoked to identify potential ablation patterns for the ablation. In block 6001, the component receives the patient source configuration and the patient-derived EM data. In block 6002, the component identifies one or more ablation pattern simulations based on the patient source configuration and the patient-derived EM data. In block 6003, the component selects the next matching ablation pattern simulation. In decision block 6004, if all the matching ablation pattern simulations have already been selected, then the component completes, else the component continues at block 6005. In block 6005, the component adds to a set of instructions the matching ablation pattern and the source location of the selected matching ablation pattern simulations. The component may also add a target volume to the ablation instructions. The target volume may be a parameter of the source configuration used when generating the non-ablation pattern simulations. The component then loops to block 6003 to select the next matching ablation pattern.

Figure 61:
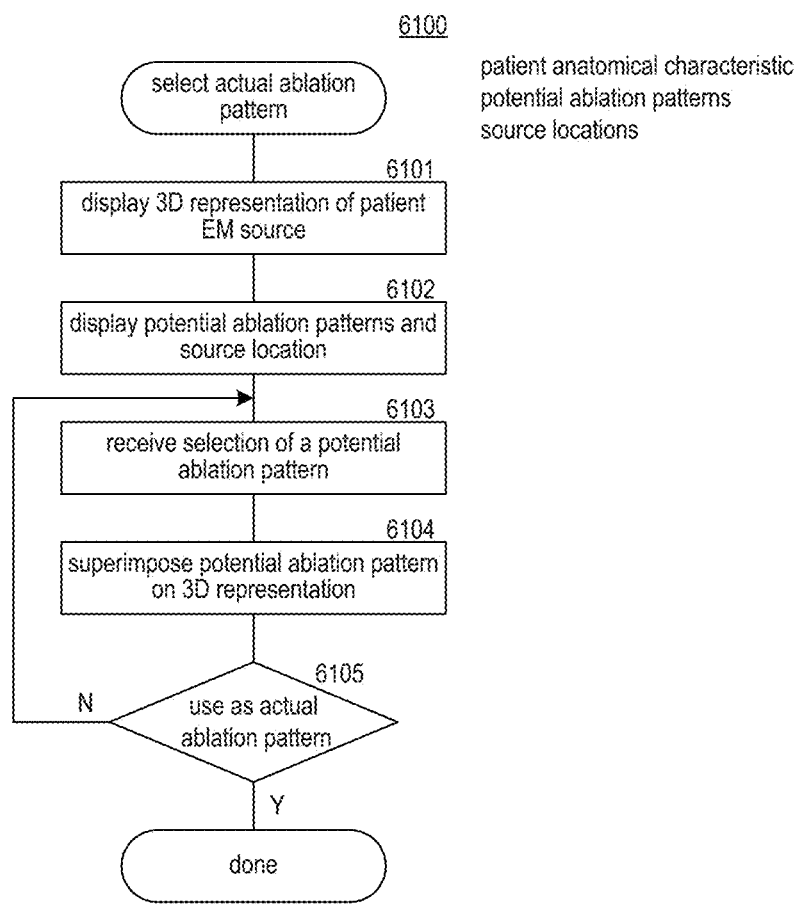
FIG. 61 is a flow diagram that illustrates the processing of a select actual ablation pattern component of the API system in some embodiments.

FIG. 61 is a flow diagram that illustrates the processing of a select actual ablation pattern component of the API system in some embodiments. The select actual ablation pattern component 6100 is invoked passing an indication of patient anatomical characteristics, potential ablation patterns, and corresponding source locations. The component identifies an actual ablation pattern to be used in the ablation. In block 6101, the component displays a 3D representation of the patient EM source based on the patient anatomical characteristics. In block 6102, the component displays a list of the potential ablation patterns and corresponding source locations. In block 6103, the component receives a selection of a potential ablation pattern. In block 6104, the component superimposes the selected partial ablation pattern and source location on the 3D representation. In decision block 6105, if the physician has indicated to use the selected potential ablation pattern as the actual ablation pattern, the component completes, else the component loops to block 6103 to display another potential ablation pattern.

Remote Collection of EM Data

In some embodiments, a remote EM data collection ("REMDC") system may receive EM data of an EM source collected from a patient who is not in a clinical setting. For example, a patient may visit a clinic to be fitted with a portable EM data collection ("PEMDC") device (e.g., a Holter monitor) that collects the EM data (e.g., ECG). Additionally, non-prescribed PEMDC devices may be used (e.g., a wearable device such as a smart watch; an external mobile device equipped with electromagnetic sensors; epidermial-, dermial-, or hypodermial-embedded electromagnetic sensors; smart clothing with embedded electromagnetic sensors). When the patient leaves the clinic, the PEMDC device may collect EM data of the patient on a periodic or continuous basis. The PEMDC device allows the collected EM data to be transmitted to the REMDC system when the patient is remote from the clinic. For example, the PEMDC device may include a wireless interface to transmit the collected EM data using a WiFi, cellular, Bluetooth, or other connection. When using a WiFi connection, the PEMDC device may transmit the collected EM data directly to the REMDC system whenever the PEMDC device can connect to a WiFi network that has internet access. When using a cellular connection (e.g., cellular transmitter/receiver embedded in the PEMDC device), the PEMDC device may transmit the collected EM data directly to the REMDC system whenever the PEMDC device is within range of a cellular network. When using a Bluetooth connection (e.g., a Bluetooth transmitter/receiver embedded in the PEMDC device), the PEMDC device may transmit the collection EM data to a smart phone, smart watch, desktop computer, or other Bluetooth enabled device. The PEM DC device may also have a wired interface to transmit the collected EM data via a wire (e.g., a universal serial bus ("USB") cable) to a computing device (e.g., laptop), which forwards the collected EM data to the REMDC system. The PEMDC device may transmit the collected data on a scheduled basis (e.g., once an hour), as soon as collected, when requested by the REMDC system, or some other criteria such as based on an analysis of the collected EM data perform by a program installed on the PEMDC.

When the REMDC system receives the collected EM data, the collected EM data may be processed by any of the systems described herein. For example, when the EM data is an ECG, the REMDC system may use the classifier generated by the MLMO system to identify a source location based on the collected ECG. As another example, the REMDC system may use the PSMC system to generate a patient-specific model classifier that can then be used to identify a source location. As another example, the REMDC system may use the CSC system to generate a calibrated collection of simulations.

Because the REMDC system can process the collected EM data before the patient returns to the clinic, a care provider will be able to analyze the outputs of the various systems and identify a course of action (e.g., recommending a procedure, an ablation and an ablation pattern) before the patient returns. In such a case, the delay associated with the various systems processing EM data after the EM data is collected while the patient is in the clinic can be avoided. In addition, the cost of the computational resources needed process the EM data can be much less when the EM data is collected before the patient returns to the clinic. Also, prior to a patient returning to the clinic, the care provider can review the outputs of the various systems and ask the patient to return earlier or later than expected based on that review. Finally, using the results of the collected EM data, the care provider can better allocate and execute the necessary time and other medical resources needed to administer optimal patient care.

Recording Patient Study Results in a Distributed Ledger

A method and a system are provided for storing in a distributed ledger study results of procedures performed on patients. In some embodiments, a distributed ledger for study results ("DLSR") system stores study (or procedure) results of procedures performed on an electromagnetic source of patients. A computational targeting procedure may be used to identify a procedure target for a procedure based on mappings of electromagnetic data derived from the electromagnetic source to procedure targets. The computational targeting procedure may be a classifier trained using the mappings generated to identify a procedure target. The MLMO system may be used to generate such classifiers. The computational targeting procedure may alternatively identify the electromagnetic data of a mapping that is most similar to the electromagnetic data of a patient and identify the procedure target of that mapping for use in the procedure. The electromagnetic data of the mappings may be simulated or actual patient data. In the following, an embodiment of the computational target procedure is described as using a classifier to identify procedure targets.

In some embodiments, the electromagnetic source may be a heart, and the procedure may be an ablation procedure performed by a physician based on an ablation target identified using a classifier. The DLSR system may apply classifiers to identify ablation targets of hearts based on electrocardiograms of patients. Each classifier may be trained using training data generated from modeled electrocardiograms for a plurality of heart configurations. The modeled electrocardiograms may be generated using a computational model of the heart that models electromagnetic output of the heart over time based on a heart configuration. The DLSR system selects a classifier based on the electrocardiogram of a patient matching a modeled electrocardiogram. The DLSR system receives results of ablation procedures performed on the patients based on the identified ablation targets. For each ablation procedure, the DLSR system generates an ablation procedure record of the result of the ablation procedure. The ablation procedure record identifies the patient and any other interested parties (e.g., physicians, insurance companies, regulator, and healthcare providers) in the ablation procedure and includes a reference to the result of the ablation procedure. The DLSR system publishes each ablation procedure record for recording in a distributed ledger for access by permissioned parties.

In some embodiments, the distributed ledger is a blockchain. Distributed ledgers and specifically blockchains are described below. The reference to the result of an ablation procedure and an electronic medical record of the patient may be stored by interested parties. An interested party that stores the result of ablation procedure may control access by a party to the result. A party may be provided access to classifiers trained using training data generated from modeled electrocardiograms based on the quantity and quality of ablation procedures records that the party stores in the blockchain. An ablation procedure may be one of several ablation procedures performed on the patient during an ablation study, and the ablation procedures records for the patient may be stored in the same block of the distributed ledger. Each block of the distributed ledger may store ablation procedure records for only one patient. The computational resources needed to maintain the distributed ledger may be provided by miners of the distributed ledger. The miners may be provided access to classifiers trained using training data generated from modeled electrocardiograms for a plurality of heart configurations based on the mining performed by the miner. A miner for mining a block may be selected based on a proof-of-stake consensus algorithm.

Figure 62:
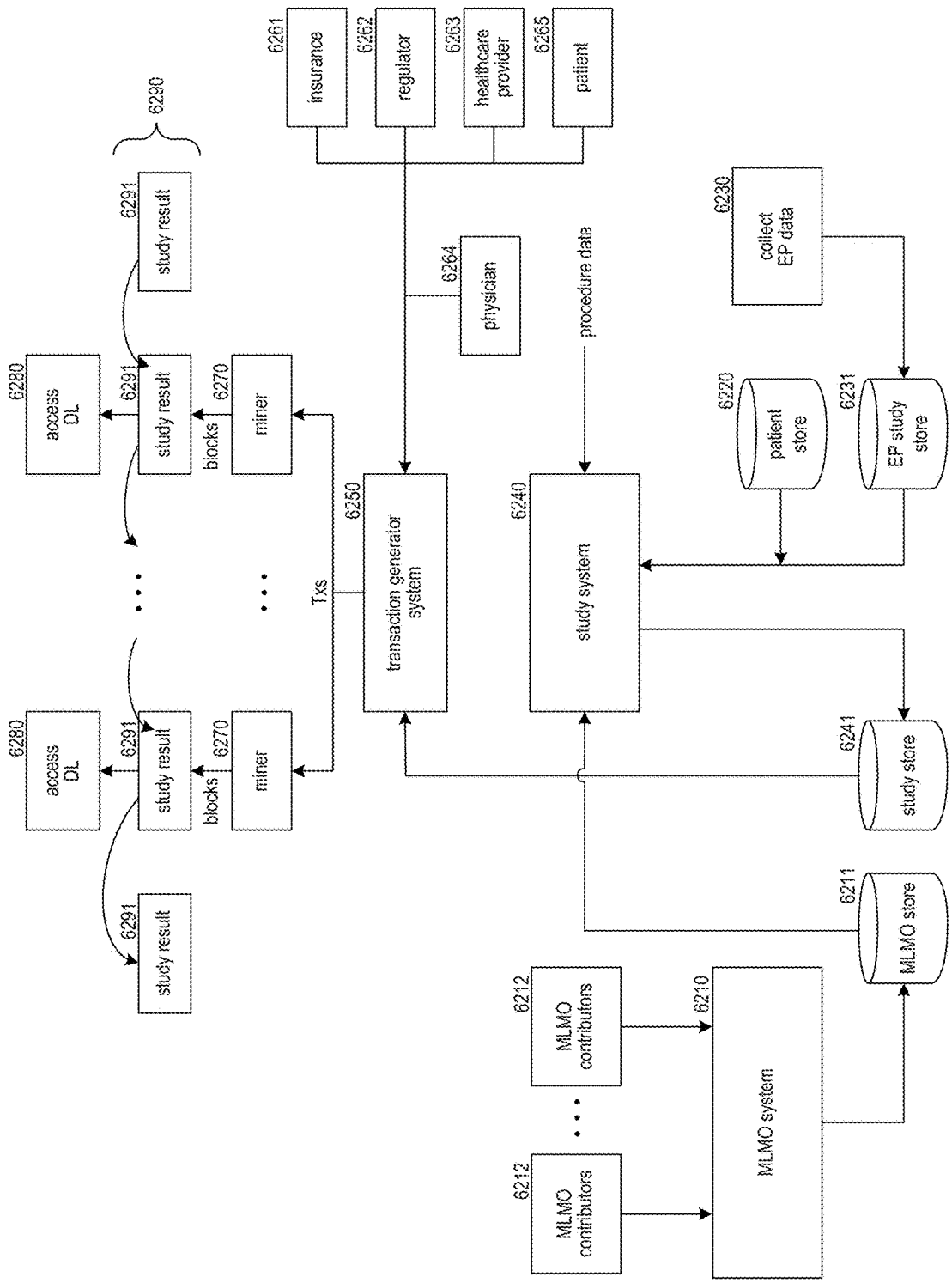
FIG. 62 is a block diagram that illustrates components of the DLSR system in some embodiments.

FIG. 62 is a block diagram that illustrates components of the DLSR system in some embodiments. The DLSR system comprises a MLMO system 6210, a collect electrophysiology ("EP") data component 6230, a study system 6240, a transaction generator system 6250, interested party systems 6261-64, miner systems 6270, access distributed ledger systems 6280, and distributed ledger 6290. In some embodiments, the MLMO system generates heart configurations, applies computational modeling of the heart to simulate function of the heart, and generates the electrocardiogram based on the simulated function. The MLMO system stores the results in MLMO store 6211. The MLMO store may store a mapping of modeled electrocardiograms to source locations.

In some embodiments, the MLMO system may define tasks relating to supporting the MLMO system such as running simulations and mining for the distributed ledger. A task may be implemented as a container that is deployed and orchestrated by a container-based system such as one based on an Amazon Web Services ("AWS") Elastic Container Repository or AWS batch. The MLMO system may allow miners or other contributors to run tasks on the servers of the MLMO system. For example, a miner may run a mining task. A report may be generated that identifies each contributor who runs a task and the computational resources used to run the task. A contributor may be charged for the computational resources (e.g., CPU, storage) used and may be rewarded with task tokens as an incentive to run tasks. For example, a miner who runs a mining task to mine a block or a contributor who runs a simulation task is rewarded, based on the computational resources used to run the task, with one or more task tokens that are recorded in the distributed ledger. The owner of a task token can then exchange the task token for access to various resources tracked in the distributed ledger. For example, a task token may be exchanged for access to results of certain studies. The number of task tokens rewarded to a miner may also be used in a proof-of-stake consensus algorithm to select a miner to mine a block. (In a similar manner, a party that submits procedure records for recording in the blockchain may be awarded record tokens, which may be exchanged for access to resources.) To support the running of simulations, the MLMO system may maintain a queue of simulation tasks to run or to complete. When a simulation task is to run, the code of the container removes the simulation task from the top of the queue and runs the simulation task. For example, if a simulation is not yet complete, the queue would contain a simulation task for completing that simulation task. Whenever a simulation is not completed by a simulation task (e.g., because the contributor signed up to expend a certain amount of computational resource that was not sufficient to complete the simulation task), the container that ran that simulation task would add to the queue (e.g., front of the queue or more precisely a doubly ended queue or deque) a new simulation task to continue the simulation. In addition to simulation tasks, the MLMO system may add pre-simulation tasks and post-simulation tasks to the queue. The pre-simulation task may relate to constructing a model or simulation initialization. The post-simulation tasks may relate to training a classifier (or other machine learning), validation of the simulation results, and making inferences based on the simulations.

The patient store 6220 stores electronic medical records of patients. Although illustrated as a single database, the electronic medical record of a single patient may be housed by various entities such as hospitals, physicians, laboratories, and so on. In addition, the electronic medical records may be accessible via a distributed ledger system that is either a permissioned distributed ledger system or a public distributed ledger system that complies with various regulations such as the Health Insurance Portability and Accountability Act ("HIPPA"). The collect EP data system 6230 collects electrophysiology data of patients and stores the electrophysiology data in EP study store 6231. The study system 6240 inputs electrophysiology data for an EP study of the patient and information from an electronic medical record of the patient, selects a classifier from the MLMO store, applies the classifier to the patient data to identify an ablation target, and stores study information in study store 6241.

A transaction generator system 6250 accesses the study store and generates records (e.g., transactions) for storing in the distributed ledger. The transaction generator system may also receive information from an insurance system 6261, a regulator system 6262, the healthcare provider system 6263, and a physician system 6264. Once a record is generated, the interested parties may sign the record using their private key. In such a case, the transaction generator system may send a record to the insurance system, the regulator system, the healthcare provider system, and/or the physician system for signing. The transaction generator system then publishes a record to the miner systems 6270. The miner systems may implement a proof-of-stake consensus algorithm or some other consensus algorithm for identifying which miner system is to generate a block storing a distributed ledger 6290. The distributed ledger includes blocks 6291 that each may represent a study for a single patient that includes a transaction for each procedure performed as part of that study. The access distributed ledger systems 6280 may have access to the distributed ledger based on permissions. For example, a certain class of access distributed ledger systems may be configured with a private key for accessing certain records that have been encrypted with a public key. Alternatively, the access ledger systems may access a front-end system to the distributed ledger that controls access to the blockchain distributed ledger.

Figure 63:
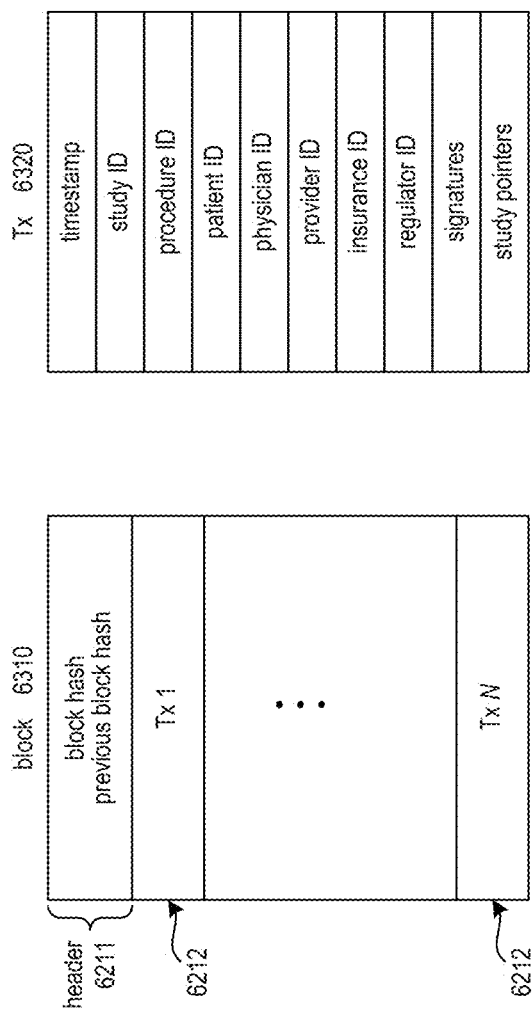
FIG. 63 is a block diagram that illustrates the structure of a block and records within the block in some embodiments.

FIG. 63 is a block diagram that illustrates the structure of a block and records within the block in some embodiments. A block 6310 includes a block header 6211 and transactions 6212. The block header may include a block hash that is a hash of data of the block including the previous block hash of the previous block in the blockchain and the hash of the root node of a Merkle tree of the hashes of the transactions. The structure of a blockchain is described below in detail. A transaction 6320 may include a timestamp of when the transaction is generated, a study identifier, a procedure identifier, a patient identifier, a physician identifier, a healthcare provider identifier, an insurance provider, and a regulator identifier. The transaction may also include signatures on various interested parties verifying transaction. The transaction may also include various pointers to information relating to the study such as a pointer to the study store and a pointer to summary information generated from the study store, the patient store, and the EP study store.

Figure 64:
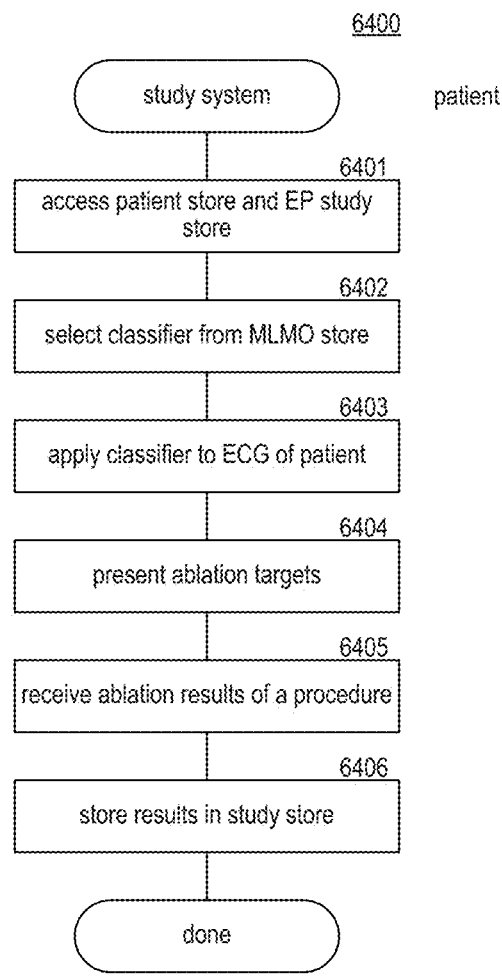
FIG. 64 is a flow diagram that illustrates the processing of a study system in some embodiments.

FIG. 64 is a flow diagram that illustrates the processing of a study system in some embodiments. A study system component 6400 is passed an indication of the patient and coordinates the performing by a physician a procedure on the patient. In block 6401, the component accesses the patient store and the EP study store to retrieve information relating to the patient. In block 6402, the component selects the classifier from the MLMO store based on matching with patient data and the electrophysiology data. In block 6403, the component applies the classifier to electrocardiogram of patient. In block 6404, the component presents the ablation target for targets to the physician. In block 6405, the component receives ablation result of the procedure. In block 6406, the component stores the result in the study store and then completes.

Figure 65:
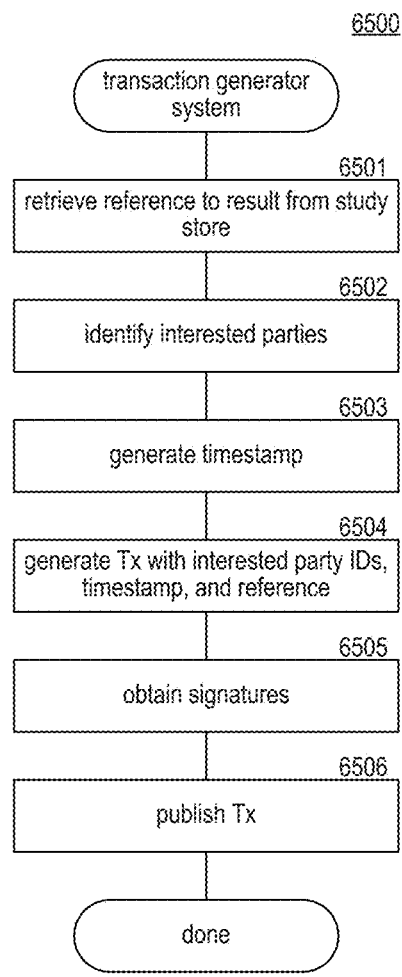
FIG. 65 is a flow diagram that illustrates the processing of a transaction generator system in some embodiments.

FIG. 65 is a flow diagram that illustrates the processing of a transaction generator system in some embodiments. A transaction generator system component 6500 may run periodically to generate a transaction for storing in the distributed ledger. In block 6501, the component retrieves a reference to a result of the procedure from the study store. In block 6502, the component identifies the interested parties to procedure based on the patient identified in the result. In block 6503, the component may generate a timestamp. In 6504, the component generates a transaction that identifies the interested parties, a timestamp, and a reference to the results stored in the study store. In block 6505, the component may obtain signatures from interested parties. The permissions of the interested parties may be needed to record a transaction in the distributed ledger. In block 6506, the component publishes the transaction to the miner systems and then completes.

Figure 66:
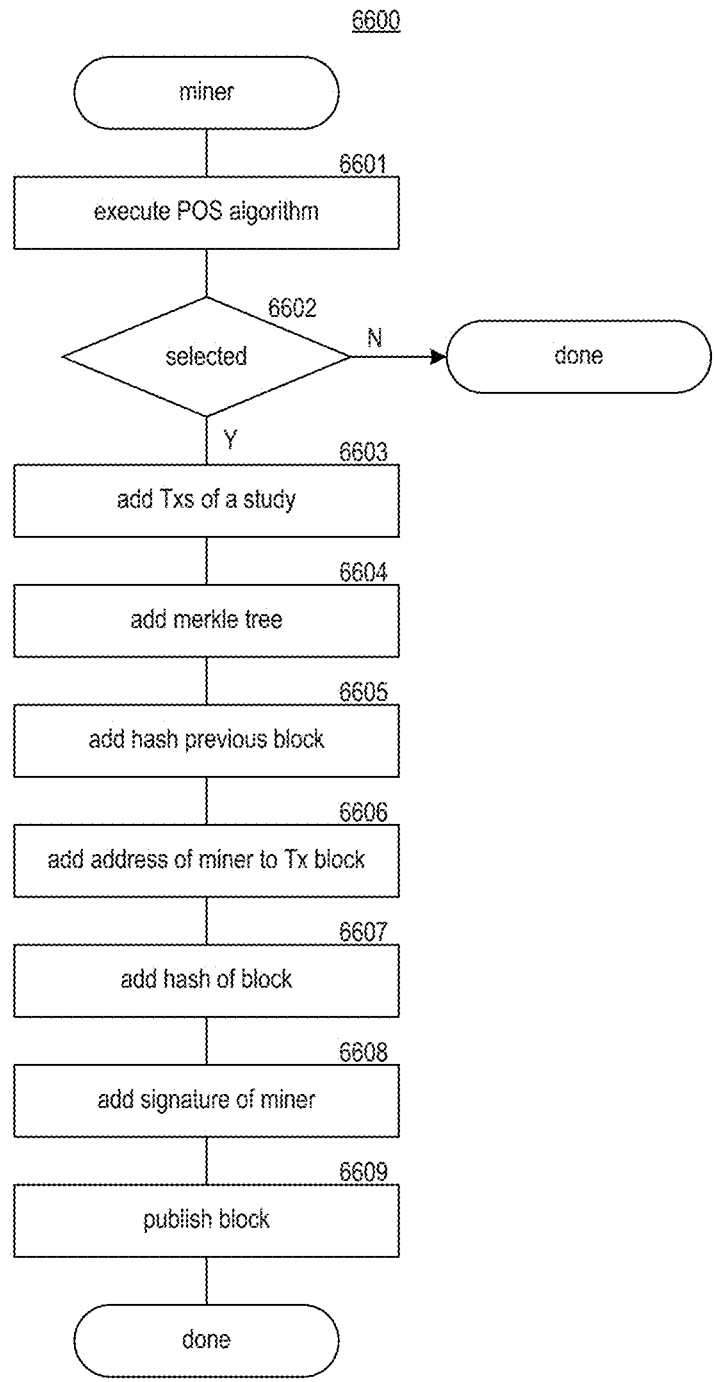
FIG. 66 is a flow diagram that illustrates the processing of a miner system in some embodiments.

FIG. 66 is a flow diagram that illustrates the processing of a miner system in some embodiments. A miner component 6600 may be invoked periodically to generate a block or blocks of procedures to store in the distributed ledger. In block 6601, the component executes a proof-of-stake consensus algorithm to determine whether the miner system is selected to generate the next block. In decision block 6602, if selected, the component continues at block 6603, else the component completes. In block 6603, the component adds the transactions of a study to a block. In block 6604, the component generates and adds a Merkle tree to the block. In block 6605, the component adds the hash of the previous block to the block. In block 6606, the component adds the address of the miner to the block. In block 6607, the component adds a hash of the entire block to the block. In block 6608, the component adds a signature of the miner to the block. In block 6609, the component publishes the block and then completes. The component may also add a creation timestamp for the block that may be used when other miner systems verify that the block was created by the miner identified by the proof-of-stake algorithm.

Distributed Ledger

Distributed ledgers are currently being used in a wide variety of business applications. The bitcoin system is an example of a distributed ledger. The bitcoin system was developed to allow electronic cash to be transferred directly from one party to another without going through a financial institution, as described in the white paper entitled "Bitcoin: A Peer-to-Peer Electronic Cash System" by Satoshi Nakamoto. A bitcoin (e.g., an electronic coin) is represented by a chain of transactions that transfers ownership from one party to another party. To transfer ownership of a bitcoin, a new transaction is generated and added to a stack of transactions in a block. The new transaction, which includes the public key of the new owner, is digitally signed by the owner with the owner's private key to transfer ownership to the new owner, as represented by the new owner public key. The signing by the owner of the bitcoin is an authorization by the owner to transfer ownership of the bitcoin to the new owner via the new transaction. Once the block is full, the block is "capped" with a block header that is a hash digest of all the transaction identifiers within the block. The block header is recorded as the first transaction in the next block in the chain, creating a mathematical hierarchy called a "blockchain." To verify the current owner, the blockchain of transactions can be followed to verify each transaction from the first transaction to the last transaction. The new owner need only have the private key that matches the public key of the transaction that transferred the bitcoin. The blockchain creates a mathematical proof of ownership in an entity represented by a security identity (e.g., a public key), which in the case of the bitcoin system is pseudo-anonymous.

To ensure that a previous owner of a bitcoin did not double-spend the bitcoin (i.e., transfer ownership of the same bitcoin to two parties), the bitcoin system maintains a distributed ledger of transactions. With the distributed ledger, a ledger of all the transactions for a bitcoin is stored redundantly at multiple nodes (i.e., computers) of a blockchain network. The ledger at each node is stored as a blockchain. In a blockchain, the transactions are stored in the order that the transactions are received by the nodes. Each node in the blockchain network has a complete replica of the entire blockchain. The bitcoin system also implements techniques to ensure that each node will store the identical blockchain, even though nodes may receive transactions in different orderings. To verify that the transactions in a ledger stored at a node are correct, the blocks in the blockchain can be accessed from oldest to newest, generating a new hash of the block and comparing the new hash to the hash generated when the block was created. If the hashes are the same, then the transactions in the block are verified. The bitcoin system also implements techniques to ensure that it would be infeasible to change a transaction and regenerate the blockchain by employing a computationally expensive technique to generate a nonce that is added to the block when it is created. A bitcoin ledger is sometimes referred to as an Unspent Transaction Output ("UTXO") set because it tracks the output of all transactions that have not yet been spent.

Although the bitcoin system has been very successful, it is limited to transactions in bitcoins or other cryptocurrencies. Blockchains have been developed to support transactions of any type, such as those relating to the sale of vehicles, sale of financial derivatives, sale of stock, payments on contracts, and so on. Such transactions use identity tokens to uniquely identify something that can be owned or can own other things. An identity token for a physical or digital asset is generated using a cryptographic one-way hash of information that uniquely identifies the asset. Tokens also have an owner that uses an additional public/private key pair. The owner public key or hash of the owner public key is set as the token owner identity, and when performing actions against tokens, ownership proof is established by providing a signature generated by the owner private key and validated against the public key or hash of the public key listed as the owner of the token. A person can be uniquely identified, for example, using a combination of a user name, social security number, and biometric (e.g., fingerprint). The creation of an identity token for an asset in a blockchain establishes provenance of the asset, and the identity token can be used in transactions (e.g., buying, selling, insuring) involving the asset stored in a blockchain, creating a full audit trail of the transactions.

To enable more complex transactions than bitcoin can support, some systems use "smart contracts." A smart contract is a decentralized computer program that comprises code and a state. A smart contract can perform virtually any type of processing such as sending money, accessing external databases and services (e.g., oracles), and so on. A smart contract may be executed in a secure platform (e.g., Ethereum platform, which provides a virtual machine) that supports recording transactions in a blockchain. The smart contract code itself may be recorded as a transaction in the blockchain using an identity token that is a hash of the smart contract code so that it can be authenticated. When deployed, a constructor of the smart contract executes, initializing the smart contract and its state. In Ethereum, a smart contract is associated with a contract account. There are two types of accounts in Ethereum: externally owned accounts ("EOA"), which are controlled by private keys, and contract accounts, which are controlled by computer code. Accounts contain the following fields: a balance, code (if present), and a storage (empty by default). The code of a smart contract is stored as the code in a contract account, and the state of the smart contract is stored in the contract account's storage, which the code can read from and write to. An EOA has no code and does not need a storage, so those two fields are empty in an EOA. Accounts have a state. The state of an EOA comprises only a balance, whereas the state of a contract account comprises both a balance and a storage. The states of all accounts are the state of the Ethereum network, which is updated with every block and about which the network needs to reach a consensus. An EOA can send transactions to other accounts by signing the transactions with the private key of the EOA account. A transaction is a signed data package that contains a message to be sent from an EOA to the recipient account identified in the transaction. Like an EOA, a contract account, under control of its code, can also send messages to other accounts. However, a contract account can send messages only in response to transactions that it has received. Therefore, all action in the Ethereum blockchain is triggered by transactions sent from EOAs. A message sent by a contract account differs from a transaction sent by an EOA in that a message sent by a contract account does not include a cryptographic signature since a contract account is not controlled by a private key. When a contract account receives a message, every mining node that maintains a replica of the blockchain executes the code of the contract account as part of the block validation process. So if a transaction is added into a block, all nodes that validate the block executes the code whose execution is triggered by that transaction. Although the execution of the computer code at each node helps ensure the authenticity of the blockchain, it requires large amounts of computer resources to support such redundant execution of computer code.

Although blockchains can effectively store transactions, the large amount of computer resources, such as storage and computational power, needed to maintain all the replicas of the blockchain can be problematic. To overcome this problem, some systems for storing transactions do not use blockchains, but rather have each party to a transaction maintain its own copy of the transaction. One such system is the Corda system developed by R3, Ltd., which provides a decentralized distributed ledger platform in which each participant in the platform has a node (e.g., computer system) that maintains its portion of the distributed ledger. When parties agree on the terms of a transaction, a party submits the transaction to a notary, which is a trusted node, for notarization. The notary maintains an UTXO database of unspent transaction outputs. When a transaction is received, the notary checks the inputs to the transaction against the UTXO database to ensure that the outputs that the inputs reference have not been spent. If the inputs have not been spent, the notary updates the UTXO database to indicate that the referenced outputs have been spent, notarizes the transaction (e.g., by signing the transaction or a transaction identifier with a public key of the notary), and sends the notarization to the party that submitted the transaction for notarization. When the party receives the notarization, the party stores the notarization and provides the notarization to the counterparties.

Augmentation of Images with Source Locations

Methods and systems for augmenting an image of an organ of a patient with a patient source location of a disorder of the organ are provided. In some embodiments, an augment image with source location ("AISL") system receives image data that includes an image of the organ of a patient, receives derived EM data that is derived from EM output of the organ of the patent, identifies a patient source location of a disorder of the organ based on the derived EM data, and augments the image data with the patient source location. For example, the image data may be a 3D image of a heart that is an image file in a Digital Imaging and Communications in Medicine ("DICOM") format or another format. The derived EM data may be a cardiogram. The image data that is received may also include a patient substrate location of a substrate of the heart of the patient. After identifying the patient source location, the AISL system adds the patient source location to the image data. For example, the patient source location may be added as metadata to a DICOM file or superimposed (e.g., an indication added) on the 3D image. The AILS system may then provide the augmented DICOM file to a planning system to inform treatment (e.g., an ablation procedure) of the patient. Because the augmented DICOM file includes the source location, a more informed treatment plan for the patient may be developed.

In some embodiments, the identification of the patient source location may be based on mappings of derived EM output to source locations. For example, the mappings may be generated by running simulations for a variety of non-patient specific configuration parameters or for patient-specific configuration parameters. The running of the simulations may be performed by the MLMO system as described above. Derived EM data for each simulation is mapped to a source location used in the simulation. The AISL system may identify a patient source location by comparing the derived EM data of the patient to the derived EM data of the simulations to identify a match and selecting the source location of matching derived EM data as the patient source location. The AISL system may also identify a patient source location using a classifier that is trained by the MLMO system using the mappings as training data. In addition, prior to identifying the patient source locations, the AISL system may calibrate the mappings using the CSC system as described above.

Although the AISL system is described primary in the context of an organ that is a heart and a patient that is a human, the AISL system may be used for other organs (e.g., brains and livers) and non-humans (e.g., horses and primates). When the organ is a heart, the disorder, for example, may be arrythmia, tachycardia, or fibrillation and the source location may be of a rotor or focal source.

Figure 67:
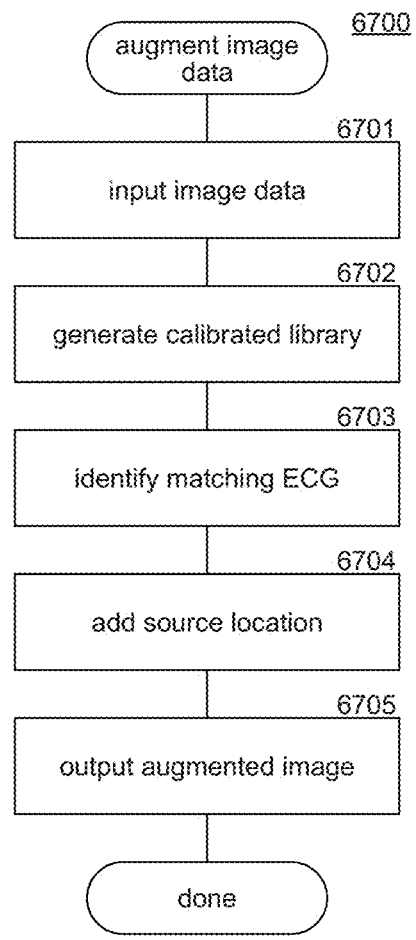
FIG. 67 is a flow diagram that illustrates the overall process of the AISL system in some embodiments.

FIG. 67 is a flow diagram that illustrates the overall processing of the AISL system in some embodiments. An augment image data component 6680 generates augmented image data. In block 6681, the component inputs image data such as 3D image of the heart of a patient in the DICOM format along with a patient substrate location such as a scar location. The substrate location may have been provided by an electrophysiologist manually superimposing an indication of the substrate location on the 3D image or adding the substrate location as metadata of the image data. The combination of the 3D image and the patient substrate location may be referred to as a substrate map. In block 6682, the component may employ the CSC system to generate a library of calibrated mappings, for example, based on mappings associated with substrate locations and heart geometries that are similar to those of the patient. In block 6683, the component identifies an ECG of the calibrated mappings that matches the ECG of the patient. In block 6684, the component adds the source location of the matching ECG to the image data as the patient source location to generate the augmented image data. In block 6685, the component outputs the augmented image data and then completes.

Figure 68:
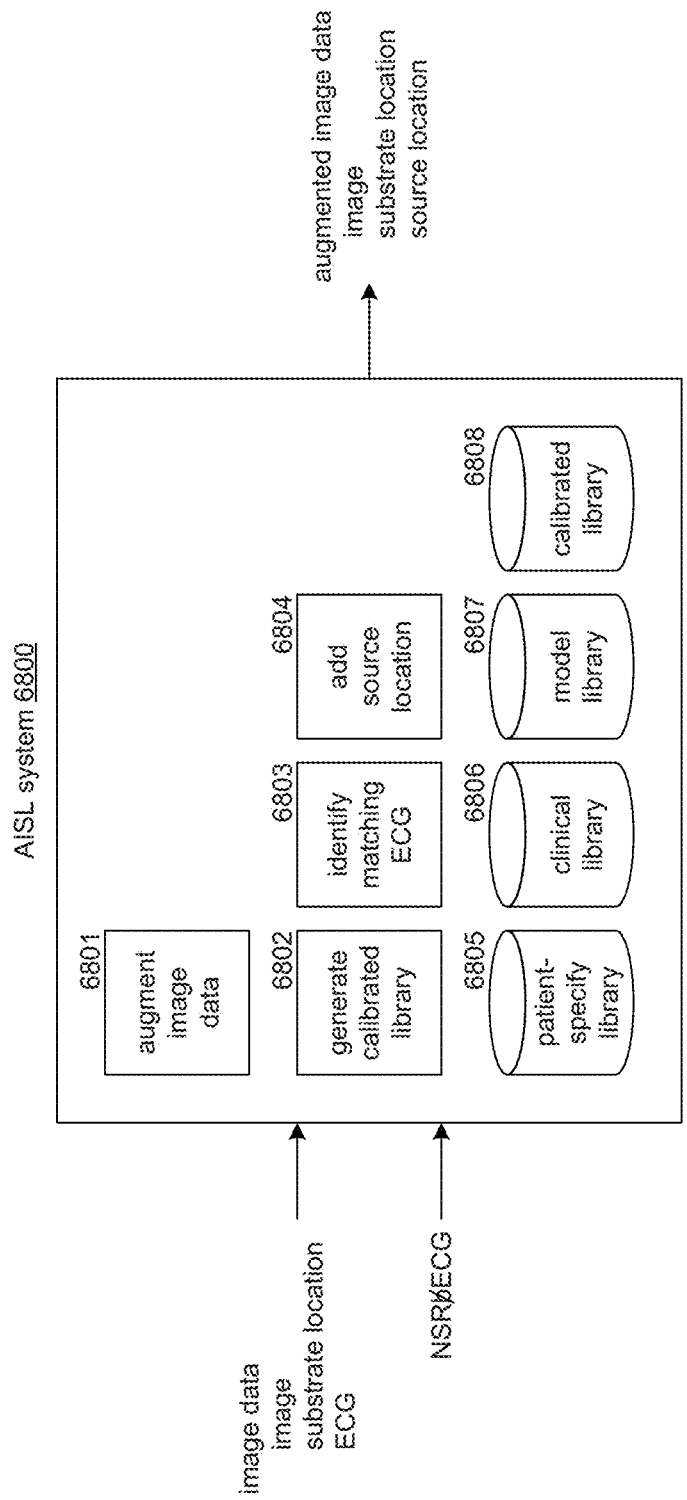
FIG. 68 is a block diagram that illustrates components of the AISL system in some embodiments.

FIG. 68 is a block diagram that illustrates components of the AISL system in some embodiments. The AISL system 6800 receives image data for a patient that includes a 3D image of the patient's heart, a patient substrate location, and optionally an ECG of the patient. The AISL component also receives a non-sinus rhythm ECG of the patient. The non-sinus rhythm ECG may be collected from the patient, for example, during a clinically induced (e.g., by pacing) arrhythmia. The AISL system outputs augmented image data that includes the 3D image, the patient substrate location, and an identified patient source location. The AISL system includes an augment image data component 6801, a generate calibrated library component 6802, an identify matching ECG component 6803, and an add source location component 6804. The AISL system also includes a patient-specific library 6805, a clinical library 6806, a model library 6807, and a calibrated library 6808. The augment image data component controls the overall processing of the AISL system. The generate calibrated library component generates a library of mappings that is calibrated to the patient. The identify matching component identifies an ECG of the calibrated library that matches a non-sinus rhythm ECG of the patient. The add source location component adds the patient source location to the image data to generate the augmented image data. The patient-specific library includes mappings of ECGs generated from simulations based on configuration parameters derived from the patient. The clinical library includes mappings of ECGs locations derived from ECGs collected from actual patients. The model library contains mappings of ECGs generated from simulations based on non-patient specific configuration parameters. The calibrated library includes mappings of ECGs that are calibrated to the patient such as by having ECGs similar to the ECG provided with the image data and having been generated using configuration parameters similar to that of the patient. Each of the libraries maps its ECGs to source locations associated with the ECGs.

Figure 69:
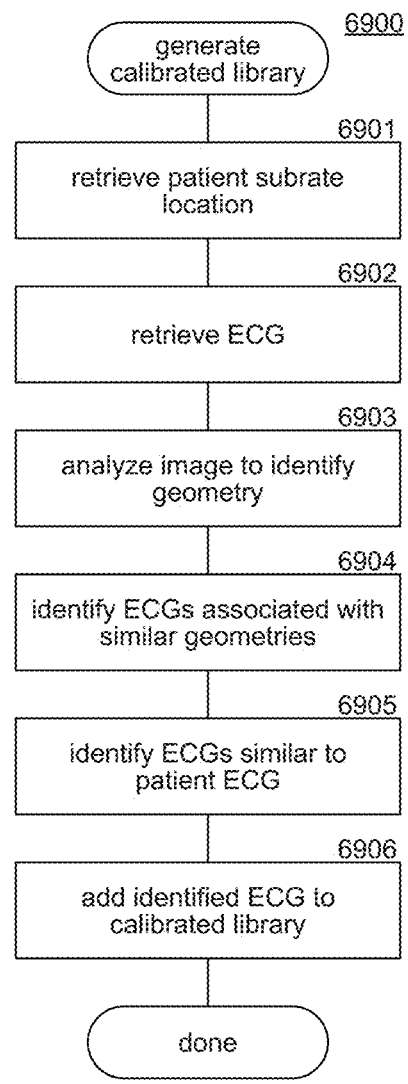
FIG. 69 is a flow diagram of a generate calibrated library component of the AISL system in some embodiments.

FIG. 69 is a flow diagram of a generate calibrated library component of the AISL system in some embodiments. The generate calibrated library 6900 is invoked to generate a calibrated library given image data received by the AISL system. In block 6901, the component retrieves the patient substrate location from the image data. In block 6902, the component retrieves the ECG from the image data. In block 6903, the component analyzes the image to identify the geometry of the patient's heart. In block 6904, the component identifies ECGs that are associated with heart geometries that are similar to that of the patient's heart geometry. In block 6905, the component identifies ECGs that are similar to the ECG of the image data. In block 686, the component adds to the calibrated library the mappings of the identified ECGs to source locations. The component then completes.

Figure 70:
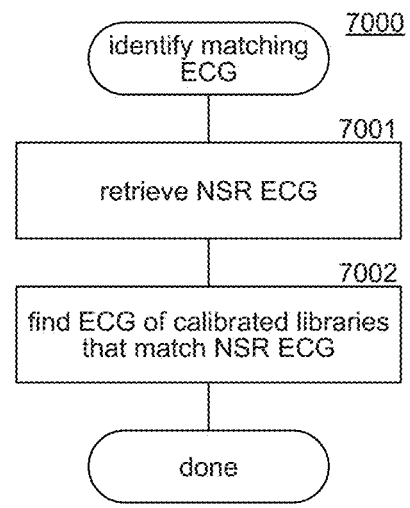
FIG. 70 is a flow diagram that illustrates the processing of an identify matching ECG component.

FIG. 70 is a flow diagram that illustrates the processing of an identify matching ECG component. The identify matching ECG component 7000 is invoked to identify an ECG or multiple ECGs that match the non-sinus rhythm ECG of the patient. In block 7001, the component retrieves the non-sinus rhythm ECG. In block 7002, the component identifies an ECG from the calibrated library that matches the non-sinus rhythm ECG of the patient. The component then completes.

Figure 71:
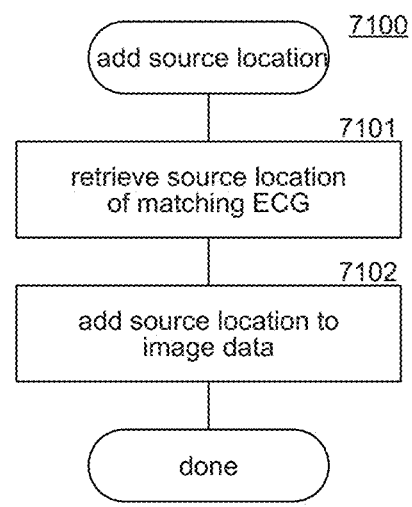
FIG. 71 is a flow diagram that illustrates the processing of an add source location component of the AISL system in some embodiments.

FIG. 71 is a flow diagram that illustrates the processing of an add source location component of the AISL system in some embodiments. The add source location component 7100 is invoked to add a source location to the image data to create augmented image data. In block 7101, the component retrieves the source location of the matching ECG. In block 7102, the component adds the source location to the image data and then completes. In some embodiments, the identify matching ECG component may identify multiple matching ECGs. In such as case, the component may generate a patient source location based on the source location of the multiple matching ECGs. For example, the component may take the average of the source locations. As another example, the component may apply a clustering technique to the source locations and take the average of the largest cluster. The component may also add multiple patient source locations to the image data, for example, one for each of the two largest clusters.

In some embodiments, the AISL system receives a 4D CT image of the patient that is captured when the ECG of the image data is collected. An image capture system may capture multiple 3D CT images during each heart cycle. For example, a 3D CT image may be captured at a capture interval of 25 milliseconds. The 4D CT image is a collection of the 3D CT images. If a cycle is 1 second and 3D CT images are captured for 30 cycles, then the 4D CT image will be a collection of 1200 3D CT images (i.e., 30*1000/25). The image capture system may start capturing 3D CT images at the same start point in each cycle such as the end of diastole as indicated by the P-wave on the ECG. The image capture system may analyze the patient ECG in real-time to identify the start point for each cycle. Since it is unlikely a cycle will be an exact multiple the capture interval, the image capture system may determine that the current cycle is near the start point of the next cycle (e.g., within 10 milliseconds) and capture the next 3D CT image at the start point of the next cycle. The image capture system may employ a variable rather than a fixed capture interval. The image capture system may the variable capture interval every cycle. For example, if the 40 3D CT images are to be captured every cycle and the last cycle was 0.8 seconds, the image capture system may set the capture interval to 20 milliseconds. However, if the last cycle (or the average of the last 10 cycles) was 1.2 seconds, the image capture system may send the capture interval to 30 milliseconds.

In some embodiments, the image data that is input to the AISL system may include a 4D CT image of one cycle in DICOM format and include the patient substrate location for the patient. An electrophysiologist may review the 4D CT image to identify the patient substrate location. The patient substrate location may be added to the image data by the electrophysiologist superimposing a marking of the patient substrate location on the 4D CT image or adding coordinates of the patient substrate location as metadata to the image data. The ECG collected during the capture of the 4D CT image may be added a metadata to the image data.

In some embodiments, a patient substrate location may be defined by a collection of locations that are each specified by a 3D coordinate in the reference frame of the 3D CT image. Each dimension (e.g., x, y, z) of a 3D coordinate may have a radius to indicate the size of the substrate. The AISL system may use the collection of locations to add, for each location, an indication of the substrate location and substrate volume (defined by the radii) onto the 3D CT image. The indication of the substrate location and substrate volume is referred to as a substrate mask. To add the substrate mask, the AISL system may identify voxels that are within each volume and set the intensity of each identified voxel to a substrate intensity as an indication that the voxel is part of a substrate. The substrate intensity may be specified as a Hounsfield unit (HU), which is a unit of attenuation of an x-ray as it passes through an object (e.g., bone). The substrate intensity may be an intensity that would not normally be found in a 3D CT image of the organ (e.g., 9000 HU). The AISL system may also add to the 3D CT image a source mask corresponding to the patient source location in a similar manner. The patient source location may be specified by a collection of source locations and source location volumes that are derived from mappings of ECGs to source locations. Each ECG may map to one or more source locations and source volumes. An augmented 3D CT image thus may include a substrate mask and/or a source mask. The substrate mask and the source mask may have different intensity values to differentiate them. Such an augmented 3D CT image can then be displayed to help inform treatment for the patient.

In some embodiments, the AISL system may position the source location more accurately on the 3D CT image by aligning the geometry of a simulation organ associated with the matching derived EM data to the geometry of the patient organ of the patient represented by the 3D CT image. To align the geometries, the AISL system may generate a transformation matrix that maps designated locations (or more generally designated volumes) within the simulation organ to the corresponding designated locations within the patient organ. The AISL system may then use the transformation matrix to transform the patient source location to a source location on the 3D CT image and add the transformed patient source location to the 3D CT image. The transformation may involve rotational, translational, scaling, and shearing of the 3D CT image.

When the organ is a heart, the designated locations may be, for example, the heart/valve plane, middle of the septal wall, LV/RV apex, aortic valve, and/or mitral valve. The AISL system may employ automated techniques to identify the designated locations with the patient organ. For example, the AISL system may employ a convolutional neural network that is trained with training data comprising 3D images labeled with a designated location (e.g., aortic valve). Alternatively, or additionally, the AISL system may receive an indication of the designated locations on the patient organ from person. The designated locations serve as "fiducial markers.

In some embodiments, the AISL system may receive a patient 4D CT image that represents 3D CT images collected over multiple cycles. The AISL system may use that patient 4D CT image when calibrating the mappings. For example, the AISL system may compare the movement of the patient's heart represented by the patient 4D CT image to movement of a heart mesh during simulation. In such a case, the patient specific and the model library may include the sequence of meshes from which the ECGs of the libraries were generated. Also, the clinical library may include clinical 4D CT images captured when the ECGs were collected from the clinical patients. The AISL system may base calibration on comparison of the patient 4D CT image and the clinical 4D CT images.

Figure 72:
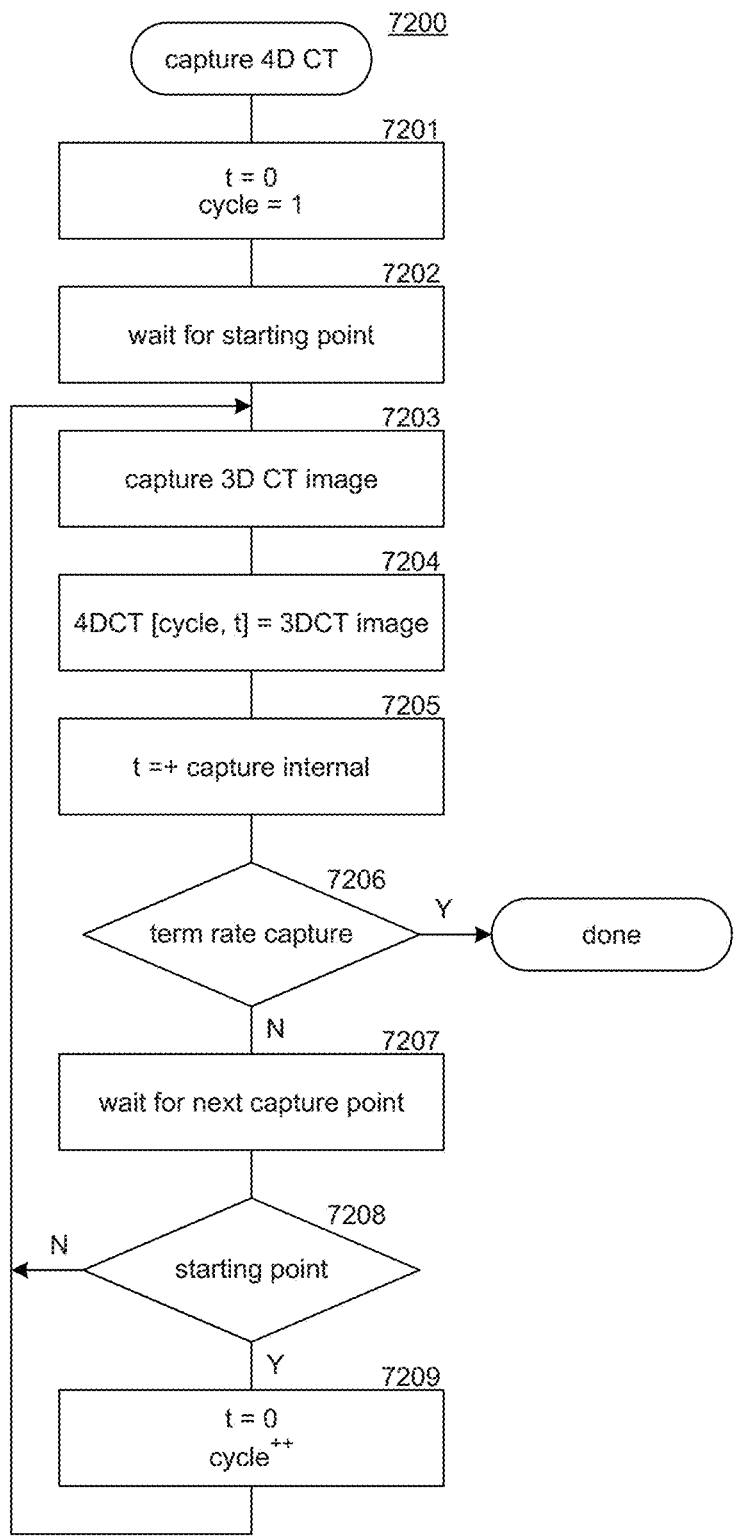
FIG. 72 is a flow diagram that illustrates the processing of a capture 4D CT image component in some embodiments.

FIG. 72 is a flow diagram that illustrates the processing of a capture 4D CT image component in some embodiments. The capture 4D CT image component 7200 receives an ECG of a patient, signals went to capture 3D CT image, and stores each 3D CT image as part of the 4D CT image. In block 7201, the component initializes the time of capture and cycle count. In block 7202, the component analyzes the ECG as it is being collected to identify the start point for the capture of the next cycle. In block 7203, the component directs the capturing of a 3D CT image. In block 7204, the component stores the 3D CT image in a 4D CT data structure that is indexed by the time and cycle count. In block 7205, the component increments the time by the capture interval. In decision block 7206, if the capturing of the 4D CT image is to be terminated, then the component completes, else the component continues at block 7207. In block 7207, the component waits for the next capture point which is at the expiration of the capture interval or at the starting point of the next cycle. In decision block 7208, if the capture point is the starting point of the next cycle, then the component continues at block 7209, else the component loops to block 7203 to capture the next 3D CT image. In block 7209, the component resets the time to zero and increments the cycle count and then loops to block 7203 to capture the next 3D CT image.

The following paragraphs describe various embodiments of aspects of the MLMO system and other system. An implementation of the systems may employ any combination of the embodiments. The processing described below may be performed by a computing system with a processor that executes computer-executable instructions stored on a computer-readable storage medium that implements the system.

In some embodiments, a method performed by one or more computing systems is provided for generating a classifier for classifying electromagnetic data derived from an electromagnetic source within a body. The method accesses a computational model of the electromagnetic source, wherein the computational model is used for modeling electromagnetic output of the electromagnetic source over time based on a source configuration of the electromagnetic source. For each of a plurality of source configurations, the method generates, using the computational model, a modeled electromagnetic output of the electromagnetic source for that source configuration. The method, for each modeled electromagnetic output, derives the electromagnetic data for the modeled electromagnetic output and generates a label for the derived electromagnetic data based on the source configuration for the modeled electromagnetic data. The method trains a classifier with the derived electromagnetic data and then labels it as training data. In some embodiments, the modeled electromagnetic output for a source configuration includes, for each of a plurality of time intervals, an electromagnetic mesh with a modeled electromagnetic value for each of a plurality of locations of the electromagnetic source. In some embodiments, the derived electromagnetic data, for a time interval, is an equivalent source representation of the electromagnetic output. In some embodiments, the equivalent source representation is generated using principal component analysis. In some embodiments, the method further identifies cycles within the derived electromagnetic data for a modeled electromagnetic output. In some embodiments, the same label is generated for each cycle. In some embodiments, the method further identifies a sequence of cycles that are similar, wherein the same label is generated for each sequence. In some embodiments, the deriving of the electromagnetic data for a modeled electromagnetic output includes normalizing the modeled electromagnetic output on a per-cycle basis. In some embodiments, the classifier is a convolutional neural network. In some embodiments, the convolutional neural network inputs a one-dimensional image. In some embodiments, the classifier is a recurrent neural network, an autoencoder, a restricted Boltzmann machine, or other type of neural network. In some embodiments, the classifier is a support vector machine. In some embodiments, the classifier is Bayesian. In some embodiments, the electromagnetic source is a heart, a source configuration represents a source location and other properties of a heart disorder, the modeled electromagnetic output represents activation of the heart, and the electromagnetic data is based on body-surface measurements such as an electrocardiogram. In some embodiments, the heart disorder is selected from a set consisting of inappropriate sinus tachycardia ("IST"), ectopic atrial rhythm, junctional rhythm, ventricular escape rhythm, atrial fibrillation ("AF"), ventricular fibrillation ("VF"), focal atrial tachycardia ("focal AT"), atrial microreentry, ventricular tachycardia ("VT"), atrial flutter ("AFL"), premature ventricular complexes ("PVCs"), premature atrial complexes ("PACs"), atrioventricular nodal reentrant tachycardia ("AVNRT"), atrioventricular reentrant tachycardia ("AVRT"), permanent junctional reciprocating tachycardia ("PJRT"), and junctional tachycardia ("JT").

In some embodiments, a method performed by a computing system is provided for classifying electromagnetic output collected from a target that is an electromagnetic source within a body. The method accesses a classifier to generate a classification for electromagnetic output of an electromagnetic source. The classifier is trained using training data generated from modeled electromagnetic output for a plurality of source configurations of an electromagnetic source. The modeled electromagnetic output is generated using a computational model of the electromagnetic source that models the electromagnetic output of the electromagnetic source over time based on a source configuration. The method collects target electromagnetic output from the target. The method applies the classifier to the target electromagnetic output to generate a classification for the target. In some embodiments, the training data is generated by running, for each of the source configurations, a simulation that generates an electromagnetic mesh for each of a plurality of simulation intervals, each electromagnetic mesh having an electromagnetic value for a plurality of locations of the electromagnetic source. In some embodiments, the electromagnetic source is a heart, a source configuration represents a source location of a heart disorder, and the modeled electromagnetic output represents activation of the heart, and the classifier is trained using electromagnetic data derived from an electrocardiogram representation of the electromagnetic output.

In some embodiments, one or more computing systems are provided for generating a classifier for classifying electromagnetic output of an electromagnetic source. The one or more computing systems include one or more computer-readable storage mediums and one or more processors for executing the computer-executable instructions stored in the one or more computer-readable storage mediums. The one or more computer-readable storage mediums store a computational model of the electromagnetic source. The computational model models electromagnetic output of the electromagnetic source over time based on a source configuration of the electromagnetic source. The one or more computer-readable storage mediums store computer-executable instructions for controlling the one or more computing systems to, for each of a plurality of source configurations, generate training data from the electromagnetic output of the computational model that is based on the source configuration and train the classifier using the training data. In some embodiments, the computer-executable instructions that generate the training data for a source configuration further control the one or more computing systems to generate derived electromagnetic data from the electromagnetic output for the source configuration and generate a label for the electromagnetic data based on the source configuration.

In some embodiments, a method performed by a computing system generating a simulated anatomy of an electromagnetic source within a body is provided. The method accesses seed anatomies of the electromagnetic source. Each seed anatomy has a seed value for each of a plurality of anatomical parameters of the electromagnetic source. The method accesses a set of weights that includes a weight for each seed anatomy. For each of the anatomical parameters, the method generates a simulated value for that anatomical parameter by combining the seed values for that anatomical parameter, factoring in the weights of the seed anatomies. In some embodiments, the method validates the simulated anatomy based on comparison to values for anatomical parameters found in a population. In some embodiments, the anatomical parameters include dimensions of the electromagnetic source and wherein a simulated value for a dimension is validated when a patient in the population includes value for that dimension that is approximately the same as the simulated value. In some embodiments, the anatomical parameters of the seed anatomies are collected by scanning actual electromagnetic sources within bodies. In some embodiments, the electromagnetic source is a heart. In some embodiments, the method generates a simulated value for an anatomical parameter based on a weighted average of the seed values for that anatomical parameter. In some embodiments, the method further generates a plurality of simulated anatomies wherein each simulated anatomy is based on a different set of weights.

In some embodiments, a computing system for generating simulated anatomies of a heart is provided. The computing system comprises one or more computer-readable storage mediums storing seed anatomies of a heart, each seed anatomy having a seed value for each of a plurality of anatomical parameters of a heart. The one or more computer-readable storage mediums also stores sets of weights that each includes a weight for each seed anatomy. The one or more computer-readable storage mediums store computer-executable instructions for controlling the computing system to, for each set of weights and for each of the anatomical parameters for that set of weights, generate a simulated value for that anatomical parameter by combining the seed values for that anatomical parameter, factoring in the weights of the seed anatomies. The computing system further comprises one or more processors for executing the computer-executable instructions stored in the one or more computer-readable storage mediums. In some embodiments, the instructions further control the computing system to validate each simulated anatomy based on comparison to values for anatomical parameters found in a population. In some embodiments, the anatomical parameters include thickness of walls of a heart and dimensions of a chamber of the heart. In some embodiments, a simulated value for a dimension is validated when a patient in the population includes value for that dimension that is approximately the same as the simulated value. In some embodiments, the seed anatomies represent extremes of hearts found in a population. In some embodiments, the anatomical parameters of the seed anatomies are collected by scanning hearts. In some embodiments, the generating of a simulated value for an anatomical parameter is based on a weighted average of the seed values for that anatomical parameter. In some embodiments, a method performed by a computing system for generating an arrhythmia model library for modeling a heart is provided. The method accesses simulated anatomies of anatomical parameters of the heart. The simulated anatomies are generated based on seed anatomies of anatomical parameters of the heart and sets of weights that include a weight for each seed anatomy. The method accesses configuration parameters that include one or more of torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics for the heart, sets of conductivities for the heart, arrhythmia source locations within the heart, and so on. The method establishes source configurations that are each based on a simulated anatomy and a combination of electrophysiology parameters. For each of a plurality of the source configurations, the method generates a mesh based on the simulated anatomy of that source configuration, the mesh having vertices, and for each vertex of the mesh, generates model parameters of a computational model of the heart based on the combination of electrophysiology parameters of that source configuration. The computational model for modeling electromagnetic propagation at that vertex is based on the electrophysiology parameters of that source configuration. In some embodiments, the method generates a simulated anatomy by accessing seed anatomies of a heart where each seed anatomy has a seed value for each of the anatomical parameters of the heart; accesses a set of weights that includes a weight for each seed anatomy; and for each of the anatomical parameters, generates a simulated value for that anatomical parameter by combining the seed values for that anatomical parameter, factoring in the weights of the seed anatomies. In some embodiments, the simulated anatomies are validated based on comparison to values for anatomical parameters found in a population. In some embodiments, the anatomical parameters of the seed anatomies are collected by scanning actual hearts. In some embodiments, for each of a plurality of source configurations, the method generates a modeled electromagnetic output of the heart for that source configuration using a computational model for the heart. In some embodiments, for each source configuration, the method generates training data for the modeled electromagnetic output that is based on that source configuration; and trains a classifier for classifying electromagnetic output of the heart using the training data.

In some embodiments, a computing system for generating a model library of models of an electromagnetic source within a body is provided. The computing system comprises one or more computer-readable storage mediums storing computer-executable instructions and one or more processors for executing the computer-executable instructions stored in the one or more computer-readable storage mediums. The instructions control the computing system to generate simulated anatomies of anatomical parameters of the electromagnetic source from seed anatomies and generate source configurations that are each based on a simulated anatomy and a combination of configuration parameters. The instructions control the computing system to, for each of a plurality of the source configurations, generate a mesh based on the simulated anatomy of that source configuration, the mesh having vertices; and for each vertex of the mesh, generate model parameters of a computational model of the electromagnetic source based on the combination of configuration parameters of that source configuration. In some embodiments, the computational model for modeling electromagnetic propagation at a vertex is based on the configuration parameters of a source configuration. In some embodiments, the simulated anatomies are generated based on anatomical parameters of the seed anatomies and sets of weights that include a weight for each seed anatomy. In some embodiments, the electromagnetic source is a heart and the configuration parameters include one or more of torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics for the heart, sets of conductivities for the heart, and arrhythmia source locations within the heart. In some embodiments, the simulated anatomies are validated based on comparison to values for anatomical parameters found in a population. In some embodiments, the anatomical parameters of the seed anatomies are collected by scanning actual electromagnetic sources. In some embodiments, the computer-executable instructions further control the computing system to, for each of a plurality of source configurations, generate a modeled electromagnetic output of the electromagnetic source for that source configuration using a computational model for the electromagnetic source. In some embodiments, computer-executable instructions further control the computing system to, for each source configuration, generate training data for the modeled electromagnetic output that is based on that source configuration; and train a classifier for classifying electromagnetic output of the electromagnetic source using the training data.

In some embodiments, a method performed by a computing system for generating a model library of models of an electromagnetic source within a body is provided. The method accesses simulated anatomies of anatomical parameters of the electromagnetic source. The method generates source configurations that are each based on a simulated anatomy and a combination of configuration parameters. For each of a plurality of the source configurations, the method generates a model based on the simulated anatomy of that source configuration, the combination of configuration parameters of that source configuration, and a computational model of the electromagnetic source. In some embodiments, the generating of a model includes generating a mesh based on the simulated anatomy of that source configuration and, for each vertex of the mesh, generating model parameters of a computational model of the electromagnetic source based on the combination of configuration parameters of that source configuration. In some embodiments, the computational model is for modeling electromagnetic propagation at a vertex based on the configuration parameters of a source configuration. In some embodiments, the electromagnetic source is a heart and the models are arrhythmia models. In some embodiments, the method further generates the simulated anatomies based on anatomical parameters of seed anatomies and sets of weights that include a weight for each seed anatomy. In some embodiments, the electromagnetic source is a heart and the configuration parameters include one or more of a human torso, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics for the heart, sets of conductivities for the heart, arrhythmia source locations within the heart, and so on.

In some embodiments, a method performed by a computing system for presenting weights for a simulated anatomy of a body part is provided. The method accesses seed anatomies of the body part. Each seed anatomy has a seed value for each of a plurality of anatomical parameters of the body part. For each of a plurality of seed anatomies of the body part, the method displays a seed representation of the body part based on seed values of anatomical parameters of that seed anatomy. The method accesses a set of weights that includes a weight for each seed anatomy. The method displays a simulated representation of the body part based on a simulated value for each anatomical parameter by, for each anatomical parameter, combining the seed values of the seed anatomies of that anatomical parameter, factoring in the weights of the seed anatomies. In some embodiments, the seed representations are displayed in a circular arrangement with the simulated representation displayed within the circular arrangement. In some embodiments, the method further displays, in association with each displayed seed representation for a seed anatomy, an indication of the weight associated with that seed anatomy. In some embodiments, the method further displays a line between each displayed seed representation and the displayed simulated representation, wherein the displayed indication of the weight for a seed anatomy is displayed in association with the displayed line between the displayed seed representation for that seed anatomy and the displayed simulated representation. In some embodiments, the method further provides a user interface element for specifying the weight for each seed anatomy. In some embodiments, the method provides a user interface element for specifying a plurality of sets of weights, with each set including a weight for each seed anatomy. In some embodiments, the plurality of sets of weights are specified by providing a range of weights and an increment. In some embodiments, the body part is a heart. In some embodiments, the body part is a lung. In some embodiments, the body part is a torso surface.

In some embodiments, a computing system for presenting a simulated anatomy of a body part is provided. The computing system comprises one or more computer-readable storage mediums storing computer-executable instructions and one or more processors for executing the computer-executable instructions stored in the one or more computer-readable storage mediums. The instructions control the computing system to, for each of a plurality of seed anatomies of the body part, display a seed representation of the body part based on seed values of anatomical parameters of that seed anatomy; and display a simulated representation of the body part based on a simulated anatomy with simulated values for anatomical parameters derived from a weighted combination of the seed values of the seed anatomies for the anatomical parameters. In some embodiments, the computer-executable instructions further control the computing system to generate the simulated anatomy by, for each anatomical parameter, generating a simulated value for that anatomical parameter by combining the seed values of the seed anatomies of that anatomical parameter, factoring in weights of the seed anatomies. In some embodiments, the seed representations are displayed in a circular arrangement with the simulated representation displayed within the circular arrangement. In some embodiments, the computer-executable instructions further control the computing system to display, in association with each displayed seed representation for a seed anatomy, an indication of a weight associated with that seed anatomy. In some embodiments, the computer-executable instructions further control the computing system to provide a user interface for specifying a plurality of sets of weights, with each set including a weight for each seed anatomy. In some embodiments, the plurality of sets of weights are specified by a range of weights and an increment.

In some embodiments, a method performed by a computing system for presenting a simulated anatomy of a heart is provided. For each of a plurality of seed anatomies of the heart, the method displays a seed representation of the heart based on seed values of anatomical parameters of that seed anatomy. The method displays a simulated representation of the heart based on a simulated anatomy derived, for each anatomical parameter, from a simulated value for that anatomical parameter generated from a weighted combination of the seed values of the seed anatomies for that anatomical parameter. In some embodiments, the seed representations are displayed in a circular arrangement with the simulated representation displayed within the circular (e.g., bullseye) arrangement. In some embodiments, the method further displays, in association with each displayed seed representation for a seed anatomy, an indication of a weight associated with that seed anatomy.

In some embodiments, a method performed by a computing system for converting a first polyhedral model to a second polyhedral model is provided. The first polyhedral model has a first polyhedral mesh with a volume containing first polyhedrons. Each vertex of the first polyhedrons has a model parameter. The method generates a representation of the surface of the first polyhedral model from the first polyhedrons. The method generates a second polyhedral mesh for the second polyhedral model by populating the volume with the surface with second polyhedrons that are different from the first polyhedrons. For each of a plurality of vertices of the second polyhedrons of the second polyhedral mesh, the method interpolates a model parameter for that vertex based on the parameters of vertices of the first polyhedrons that are proximate to that vertex. In some embodiments, the first polyhedrons are hexahedrons and the second polyhedrons are tetrahedrons. In some embodiments, the polyhedral meshes represent a body part. In some embodiments, the body part is a heart. In some embodiments, the first polyhedral mesh has an origin and further comprises, prior to interpolating the model parameters, mapping the second polyhedral mesh to the same origin. In some embodiments, each vertex of the first polyhedrons has multiple parameters and interpolates each model parameter. In some embodiments, the first polyhedral model and the second polyhedral model represent computational models of an electromagnetic source within a body, and the method further generates a modeled electromagnetic output of the electromagnetic source based on the second polyhedral model using a problem solver adapted to operate on meshes with second polyhedrons. In some embodiments, the electromagnetic source is a heart, and the method further generates a vectorcardiogram from the modeled electromagnetic output. In some embodiments, the first polyhedral model and the second polyhedral model are geometric models (e.g., of cardiac or torso anatomy). In some embodiments, the first polyhedral model and the second polyhedral model represent models of an electromagnetic source within a body, and the method further converts a plurality of first polyhedral models representing different source configurations. In some embodiments, the electromagnetic source is a heart and a source configuration specifies one or more of a fiber architecture, torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics, conductivities, arrhythmia source location or locations, and so on.

In some embodiments, a computing system for converting a first polyhedral model of a body part to a second polyhedral model of the body part is provided. The computing system comprises one or more computer-readable storage mediums storing computer-executable instructions and one or more processors for executing the computer-executable instructions stored in the one or more computer-readable storage mediums. The instructions for controlling the computing system to generate a representation of the surface of the first polyhedral model. The first polyhedral model has a first polyhedral mesh based on a first polyhedron. The instructions control the computing system to generate a second polyhedral mesh for the second polyhedral model by populating the volume with the surface based on a second polyhedron that is different from the first polyhedron. The instructions control the computing system to, for each of a plurality of vertices of second polyhedrons of the second polyhedral mesh, interpolate a model parameter for that vertex based on the parameters of vertices of first polyhedrons of the first polyhedral mesh that are proximate to that vertex. In some embodiments, the first polyhedron is a hexahedron and the second polyhedron is a tetrahedron. In some embodiments, the first polyhedral mesh has an origin wherein the computer-executable instructions further control the computing system to, prior to interpolating the model parameters, map the second polyhedral mesh to the same origin. In some embodiments, the first polyhedral model and the second polyhedral model represent computational models of the heart and the computer-executable instructions further control the computing system to generate a modeled electromagnetic output of the electromagnetic heart based on the second polyhedral model using a problem solver adapted to operate on meshes with second polyhedrons. In some embodiments, the computer-executable instructions further control the computing system to generate a vectorcardiogram from the modeled electromagnetic output. In some embodiments, the first polyhedral model and the second polyhedral model are geometric models (e.g., of cardiac or torso anatomy).

In some embodiments, a method performed by a computing system for converting a first polyhedral model to a second model is provided. The first polyhedral model has a first polyhedral mesh with a volume containing first polyhedrons. Each vertex of the first polyhedrons has a model parameter. The method generates a representation of the surface of the first polyhedral model from the first polyhedrons. For each of a plurality of points of a second model, the method interpolates a model parameter for that point based on the parameters of vertices of the first polyhedrons that are considered proximate to that vertex. In some embodiments, the second model is a second polyhedral model and the points are vertices of the second polyhedral model. In some embodiments, the second model is represented by regularly spaced grid points and the points are grid points.

In some embodiments, a method performed by a computing device for generating derived electromagnetic data for an electromagnetic source within a body is provided. The method accesses modeled electromagnetic output for a first model of the electromagnetic source over time. The first model is based on a first source configuration specifying a first anatomy. The modeled electromagnetic output is generated using a computational model of the electromagnetic source. The computational model is for generating modeled electromagnetic output of the electromagnetic source over time based on a model based on a source configuration. The method accesses a second model of the electromagnetic source based on a second source configuration specifying a second anatomy. The method generates derived electromagnetic data for the second model of the electromagnetic source based on the modeled electromagnetic output for the first model of the electromagnetic source, factoring in differences between the first anatomy and the second anatomy. In some embodiments, the electromagnetic source is a heart and the derived electromagnetic data is a cardiogram. In some embodiments, the cardiogram is a vectorcardiogram. In some embodiments, the cardiogram is an electrocardiogram. In some embodiments, the modeled electromagnetic output for a model includes, for each of a plurality of time intervals, an electromagnetic mesh with a modeled electromagnetic value for each of a plurality of vertices of the electromagnetic mesh. In some embodiments, the modeled electromagnetic output is a collection of voltage solutions.

In some embodiments, a computing system for generating a cardiogram for a heart is provided. The computing system comprises one or more computer-readable storage mediums storing a modeled electromagnetic output for a first arrhythmia model of the heart over time. The first arrhythmia model is based on a first anatomy. The modeled electromagnetic output is generated using a computational model of a heart, the computational model for generating modeled electromagnetic output of the heart over time based on an arrhythmia model. The one or more computer-readable storage mediums store a second arrhythmia model based on a second anatomy. The one or more computer-readable storage mediums store computer-executable instructions for controlling the computing system to generate a cardiogram for the second arrhythmia model based on the modeled electromagnetic output for the first arrhythmia model, factoring in differences between the first anatomy and the second anatomy. The computing system comprising one or more processors for executing the computer-executable instructions is stored in the one or more computer-readable storage mediums. In some embodiments, the cardiogram is a vectorcardiogram. In some embodiments, the cardiogram is an electrocardiogram. In some embodiments, the modeled electromagnetic output for an arrhythmia model includes, for each of a plurality of time intervals, an electromagnetic mesh with a modeled electromagnetic value for each of a plurality of vertices of the electromagnetic mesh. In some embodiments, the modeled electromagnetic output is a collection of voltage solutions.

In some embodiments, a method performed by a computing system for bootstrapping the generating of modeled electromagnetic output of an electromagnetic source within a body is provided. The method accesses first modeled electromagnetic output for a first model with a first source configuration of the electromagnetic source at first simulation intervals. The first modeled electromagnetic output is generated using a computational model of the electromagnetic source. The method initializes second modeled electromagnetic output for a second model with a second source configuration of the electromagnetic source to a first modeled electromagnetic output for one of the first simulation intervals. For each of a plurality of second simulation intervals, the method generates, using the computational model, second modeled electromagnetic output for the second model of the electromagnetic source based on the initialized second modeled electromagnetic output. In some embodiments, the electromagnetic source is a heart and the second source configuration is different from the first source configuration based on scar or fibrosis or pro-arrhythmic substrate location within the heart. In some embodiments, the electromagnetic source is a heart and the first model and the second model are arrhythmia models. In some embodiments, the modeled electromagnetic output for a model includes, for each of a plurality of time intervals, an electromagnetic mesh with a modeled electromagnetic value for each of a plurality of vertices of the electromagnetic mesh. In some embodiments, the method further generates, for each of a plurality of the first simulation intervals, the first modeled electromagnetic output for the first model, using the computational model. In some embodiments, the method initializes the second modeled electromagnetic output to the first modeled electromagnetic output for a first simulation interval after the first modeled electromagnetic output for the first simulation intervals has stabilized. In some embodiments, the electromagnetic source is a heart and the first modeled electromagnetic output has stabilized into a rhythm.

In some embodiments, a computing system for bootstrapping the generating of modeled electromagnetic output of a heart is provided. The computing system comprises one or more computer-readable storage mediums storing a first modeled electromagnetic output for a first arrhythmia model of the heart at first simulation intervals, the first modeled electromagnetic output generated using a computational model of a heart. The one or more computer-readable storage mediums also store computer-executable instructions for controlling the computing system to initialize second modeled electromagnetic output for a second arrhythmia model of the heart to a first modeled electromagnetic output for one of the first simulation intervals; and simulate, using the computational model, second modeled electromagnetic output for the second arrhythmia model based on the initialized second modeled electromagnetic output. The computing system also comprises one or more processors for executing the computer-executable instructions stored in the one or more computer-readable storage mediums. In some embodiments, the first arrhythmia model and the second arrhythmia model are based on different scar or fibrosis or pro-arrhythmic substrate locations within the heart. In some embodiments, the modeled electromagnetic output for an arrhythmia model includes, for each of a plurality of time intervals, an electromagnetic mesh with a modeled electromagnetic value for each of a plurality of vertices of the electromagnetic mesh. In some embodiments, the computer-executable instructions further control the computing system to, for each of a plurality of the first simulation intervals, generate using the computational model the first modeled electromagnetic output for the first arrhythmia model. In some embodiments, the computer-executable instructions control the computing system to initialize the second modeled electromagnetic output to the first modeled electromagnetic output for a first simulation interval after the first modeled electromagnetic output for the first simulation intervals has stabilized. In some embodiments, the first modeled electromagnetic output has stabilized into a rhythm.

In some embodiments, a method performed by a computing system for identifying derived electromagnetic data that matches electromagnetic data collected from a patient is provided. The electromagnetic data represents electromagnetic output from an electromagnetic source within a body. The method, for each of a plurality of model source configurations of the electromagnetic source, accesses a mapping of that model source configuration to electromagnetic data that is derived based on that model source configuration. The method accesses a patient source configuration representing a source configuration for the electromagnetic source within the patient. The method identifies model source configurations that match the patient source configuration. The method identifies, from the derived electromagnetic data to which the identified model source configurations are mapped, derived electromagnetic data that matches the patient electromagnetic data. In some embodiments, the derived electromagnetic data is derived from modeled electromagnetic output generated based on a model source configuration using a computational model of the electromagnetic source. In some embodiments, the modeled electromagnetic data for a model source configuration includes, for each of a plurality of time intervals, an electromagnetic mesh with a modeled electromagnetic value for each of a plurality of locations of the electromagnetic source. In some embodiments, the method further, when an identified model source configuration has an anatomical parameter value that does not match the value of that anatomical parameter of the patient source configuration, generates adjusted derived electromagnetic data based on the modeled electromagnetic output for that model source configuration and difference in the value. In some embodiments, a source configuration includes configuration parameters including anatomical parameters and electrophysiology parameters. In some embodiments, the electromagnetic source is a heart and the configuration parameters include a scar or fibrosis or pro-arrhythmic substrate location within the heart, an action potential for the heart, a conductivity for the heart, and an arrhythmia location. In some embodiments, the electromagnetic source is a heart and the anatomical parameters include dimensions of chambers of the heart, wall thicknesses of the heart, and orientation of the heart. In some embodiments, electromagnetic source is a heart and derived electromagnetic data is a cardiogram. In some embodiments, a model source configuration includes a disorder parameter relating to an attribute of the electromagnetic source such that derived electromagnetic data for the model source configuration is based on that attribute. In some embodiments, the electromagnetic source is a heart and the attribute is based on an arrhythmia. In some embodiments, the identifying of derived electromagnetic data that matches the patient electromagnetic data is based on a Pearson correlation coefficient, a root-mean-squared error, and so on. In some embodiments, the identifying of derived electromagnetic data that matches the patient electromagnetic data is based on root-mean-squared error. In some embodiments, a source configuration includes configuration parameters, the model source configurations include a value for each configuration parameter, and the patient source configuration includes a value for only a proper subset of the configuration parameters. In some embodiments, the derived electromagnetic data is based on a model orientation of the electromagnetic source and further comprise, when a patient orientation of the electromagnetic source of the patient is different from the model orientation, the identifying of the derived electromagnetic data factors in the difference between the model orientation and the patient orientation. In some embodiments, the electromagnetic source is a heart and the electromagnetic data is a vectorcardiogram, and the identifying of the derived electromagnetic data includes generating a rotation matrix based on the difference between the model orientation and the patient orientation and rotating a vectorcardiogram based on the rotation matrix.

In some embodiments, a method performed by a computing system for generating a classification for a patient based on patient electromagnetic data representing electromagnetic output of an electromagnetic source within the patient is provided. The method, for each of a plurality of clusters (e.g., groups) of model source configurations of the electromagnetic source, accesses a classifier for that cluster that is trained based on the model source configurations of that cluster to generate a classification for derived electromagnetic data. The method accesses a patient source configuration representing a source configuration for the electromagnetic source within the patient. The method identifies a cluster whose model source configurations matches the patient source configuration. The method applies the classifier for the identified cluster to the patient electromagnetic data to generate a classification for the patient. In some embodiments, the derived electromagnetic data is derived from modeled electromagnetic output generated based on a model source configuration using a computational model of the electromagnetic source. In some embodiments, a source configuration includes configuration parameters including anatomical parameters and electrophysiology parameters. In some embodiments, the electromagnetic source is a heart and the configuration parameters include a scar or fibrosis or pro-arrhythmic substrate location within the heart, an action potential for the heart, and a conductivity for the heart. In some embodiments, the electromagnetic source is a heart and the anatomical parameters include dimensions of chambers of the heart and wall thicknesses of the heart. In some embodiments, the electromagnetic source is a heart and derived electromagnetic data is a cardiogram. In some embodiments, the cardiogram is a vectorcardiogram. In some embodiments, a model source configuration matches the patient source configuration based on a cosine similarity. In some embodiments, the method further generates clusters of model source configurations; and for each of the clusters, for each of the model configuration sources of that cluster, generates a simulated electromagnetic output of the electromagnetic source based on that model configuration source; and generates derived electromagnetic data for that model source configuration from the simulated electromagnetic output based on that model source configuration. In some embodiments, a source configuration includes configuration parameters, the model source configurations include a value for each configuration parameter, and the patient source configuration includes a value for only a proper subset of the configuration parameters. In some embodiments, the derived electromagnetic data is based on a model orientation of the electromagnetic source, and the method further, when a patient orientation of the electromagnetic source of the patient is different from the model orientation, adjusts the patient electromagnetic data based on the difference between the model orientation and the patient orientation. In some embodiments, the electromagnetic source is a heart and the classification is based on source location of an arrhythmia.

In some embodiments, a computing system for identifying a model cardiogram that matches a patient cardiogram collected from a patient is provided. The computing system comprises one or more computer-readable storage mediums storing: for each of a plurality of model source configurations of a heart, a modeled cardiogram for that model source configuration; a patient source configuration representing the patient's heart; and computer-executable instructions that, when executed, control the computing system to: identify model source configurations that match the patient source configuration; and identify, from the modeled cardiograms for the identified model source configurations, those modeled cardiograms that match the patient cardiogram. The computing system includes one or more processors for executing the computer-executable instructions stored in the one or more computer-readable storage mediums. In some embodiments, a modeled cardiogram is generated from modeled electromagnetic output of a heart with a model source configuration using a computational model of the heart. In some embodiments, a cardiogram is adjusted based on differences in values of an anatomical parameter for a model source configuration and the patient source configuration. In some embodiments, the model source configurations include a scar or fibrosis or pro-arrhythmic substrate location within the heart, an action potential for the heart, a conductivity for the heart, and an arrhythmia location. In some embodiments, the model source configurations include dimensions of chambers of the heart, wall thicknesses of the heart, and orientation of the heart. In some embodiments, a source configuration includes configuration parameters, the model source configurations include a value for each configuration parameter, and the patient source configuration includes a value for only a proper subset of the configuration parameters. In some embodiments, modeled cardiograms are based on a model orientation of a heart and when a patient orientation of the heart is different from the model orientation, the identifying of modeled cardiogram factors in the difference between the model orientation and the patient orientation.

In some embodiments, a method performed by one or more computing systems for generating a patient classifier for classifying electromagnetic data derived from electromagnetic output of an electromagnetic source within a body is provided. The method accesses a model classifier for generating a classification for electromagnetic output of an electromagnetic source. The model classifier has model classifier weights learned based on training data that includes modeled derived electromagnetic data and model classifications. The modeled derived electromagnetic data is derived from modeled electromagnetic output generated using a computational model of the electromagnetic source that models the electromagnetic output of the electromagnetic source over time based on a source configuration. The method accesses patient training data that includes, for each of a plurality of patients, patient derived electromagnetic data and a patient classification for that patient. The method initializes patient classifier weights of the patient classifier based on the model classifier weights. The method trains the patient classifier with the patient training data and with the initialized patient classifier weights. In some embodiments, the classifier is a convolutional neural network. In some embodiments, the convolutional neural network inputs a one-dimensional image. In some embodiments, the model classifier is trained using training data that includes modeled derived electromagnetic data derived from modeled electromagnetic output generated based on source configurations that are identified as being similar to source configurations of the patients. In some embodiments, the electromagnetic source is a heart, a source configuration represents anatomical parameters and electrophysiology parameters of the heart, the modeled electromagnetic output represents activation of the heart, and the derived electromagnetic data is based on body-surface measurements. In some embodiments, a electrophysiology parameter is based on a heart disorder that is selected from a group consisting of but not limited to sinus rhythm, inappropriate sinus tachycardia, ectopic atrial rhythm, junctional rhythm, ventricular escape rhythm, atrial fibrillation, ventricular fibrillation, focal atrial tachycardia, atrial microreentry, ventricular tachycardia, atrial flutter, premature ventricular complexes, premature atrial complexes, atrioventricular nodal reentrant tachycardia, atrioventricular reentrant tachycardia, permanent junctional reciprocating tachycardia, and junctional tachycardia. In some embodiments, the electromagnetic data is a cardiogram. In some embodiments, the classification is a source location. In some embodiments, the patient derived electromagnetic data for a patient is derived from patient electromagnetic output of the electromagnetic source of that patient. In some embodiments, the method further receives target patient derived electromagnetic data for a target patient and applies the patient classifier to the target patient derived electromagnetic data to generate a classification for the target patient.

In some embodiments, a method performed by one or more computing systems for classifying patient derived electromagnetic data for a target patient is provided. The patient derived electromagnetic data is derived from patient electromagnetic output of an electromagnetic source within the patient's body. The method accesses a patient classifier to generate a classification for patient derived electromagnetic data of the electromagnetic source. The classifier is trained using weights of a model classifier and patient training data, the model classifier trained using modeled derived electromagnetic data and model classifications. The modeled derived electromagnetic data is generated from modeled electromagnetic output. The modeled electromagnetic output is generated for a plurality of source configurations using a computational model of the electromagnetic source. The patient training data includes patient derived electromagnetic data and patient classifications. The method receives the patient derived electromagnetic data for the target patient and applies the patient classifier to the received patient derived electromagnetic data to generate a patient classification for the target patient. In some embodiments, the electromagnetic source is a heart, a source configuration represents anatomical parameters and electrophysiology parameters of the heart, the modeled electromagnetic output represents activation of the heart, and the derived electromagnetic data is based on body-surface measurements.

In some embodiments, a computing system for generating a patient classifier for classifying a cardiogram is provided. The computing system comprises one or more computer-readable storage mediums storing computer-executable instructions and one or more processors for executing the computer-executable instructions stored in the one or more computer-readable storage mediums. The instructions control the computing system to initialize patient classifier weights of the patient classifier to model classifier weights of a model classifier. The model classifier is trained based on modeled cardiograms generated based on a computational model of the heart applied to model heart configurations. The instructions control the computing system to train the patient classifier with the patient training data and with the initialized patient classifier weights, the patient training data including, for each of a plurality of patients, a patient cardiogram and a patient classification for that patient. In some embodiments, the model classifier and the patient classifier are convolutional neural networks. In some embodiments, the convolutional neural networks input a one-dimensional image. In some embodiments, the model classifier and the patient classifier are neural networks. In some embodiments, the model classifier is trained using modeled cardiograms generated based on model heart configurations that are similar to patient heart configurations of the patients. In some embodiments, the computer-executable instructions further control the computing system to, for each of a plurality of clusters of similar patients, train a cluster patient classifier based on patient training data that includes cardiograms and patient classifications for the patients in that cluster. In some embodiments, the computer-executable instructions further control the computing system to identify similar patients based on comparison of patient heart configurations of the patients. In some embodiments, the computer-executable instructions further control the computing system to identify similar patients based on comparison of cardiograms of the patients. In some embodiments, the computer-executable instructions further control the computing system to identify a cluster of similar patients that are similar to a target patient and apply the cluster patient classifier for that identified cluster to a target patient cardiogram of the target patient to generate a target patient classification for the target patient.

In some embodiments, a method performed by a computing system for generating a classification for a target patient based on a target cardiogram of the target patient is provided. The method generates a patient classifier based on patient training data that includes cardiograms of patients and based on a transference from a model classifier generated based on model training data that includes modeled cardiograms. The modeled cardiograms are generated based on a computational model of the heart and model heart configurations. The method applies the patient classifier to the target cardiogram to generate a target classification for the target patient.

In some embodiments, a method performed by one or more computing systems for generating a patient-specific model classifier for classifying derived electromagnetic data derived from electromagnetic output of an electromagnetic source within a body is provided. The method identifies models that are similar to a target patient. For each model that is identified, the method applies a computational model of the electromagnetic source to generate modeled electromagnetic output of the electromagnetic source based on model source configuration for that model; derives modeled derived electromagnetic data from the generated modeled electromagnetic output for that model; and generates a label for that model. The method trains the patient-specific model classifier with the modeled derived electromagnetic data and the generated labels as training data. In some embodiments, the classifier is a convolutional neural network that inputs a one-dimensional image. In some embodiments, the similarity between a model and the target patient is based on source configurations. In some embodiments, the similarity between a model and the target patient is based on derived electromagnetic data. In some embodiments, the electromagnetic source is a heart, a source configuration represents anatomical parameters and electrophysiology parameters of the heart, the modeled electromagnetic output represents activation of the heart, and the derived electromagnetic data is based on body-surface measurements. In some embodiments, the electromagnetic data is a cardiogram. In some embodiments, the label represents a source location for a disorder of the electromagnetic source. In some embodiments, the training is based on a transference from a model classifier generated based on model training data that includes modeled derived electromagnetic data, the modeled derived electromagnetic data generated based on a computational model of the electromagnetic source and model source configurations. In some embodiments, the method further, for each of a plurality of clusters of similar target patients, trains a cluster-specific model classifier based on derived electromagnetic data for models that are similar to the target patients of that cluster. In some embodiments, the method further identifies a cluster whose target patients are similar to another target patient and applies the cluster-specific model classifier for that identified cluster to the target patient derived electromagnetic data of the other target patient to generate a target patient label for the other target patient. In some embodiments, the method further identifies the cluster of target patients based on comparison of patient source configurations of target patients. In some embodiments, the method further identifies the cluster of target patients based on comparison of patient derived electromagnetic data of the target patients.

In some embodiments, a computing system for generating a patient-specific model classifier for classifying a cardiogram of a target patient is provided. The computing system comprises one or more computer-readable storage mediums storing computer-executable instructions and one or more processors for executing the computer-executable instructions stored in the one or more computer-readable storage mediums. The instructions control the computing system to identify models that are similar to the target patient; and train the patient-specific model classifier based on training data that includes modeled cardiograms and model classifications of the identified models. The modeled cardiograms are generated using a computational model of the heart based on model heart configurations of the identified models. In some embodiments, the model classifications represent a source location for a heart disorder. In some embodiments, the training of the patient-specific model classifier is based on a transference from a model classifier generated based on model training data that includes modeled cardiograms. In some embodiments, the computer-executable instructions further control the computer system to, for each of a plurality of clusters of similar target patients, train a cluster-specific model classifier based on training data that includes modeled cardiograms and model classification of models that are similar to the target patients of that cluster. In some embodiments, the computer-executable instructions further control the computer system to identify a cluster whose target patients are similar to another target patient and apply the cluster-specific model classifier for that identified cluster to a target patient cardiogram of the other target patient to generate a target patient classification for the other target patient. In some embodiments, the computer-executable instructions control the computer system to identify the clusters of similar target patients based on comparison of patient heart configurations of target patients. In some embodiments, the computer-executable instructions control the computer system to identify the clusters of similar target patients based on comparison of patient cardiograms of the target patients.

In some embodiments, a method performed by a computing system for generating a representation of an electromagnetic source is provided. The method identifies modeled derived electromagnetic data that matches patient derived electromagnetic data of a patient. The modeled derived electromagnetic data is derived from modeled electromagnetic output of the electromagnetic source generated using a computational model of the electromagnetic source. The modeled electromagnetic output has, for each of a plurality of time intervals, an electromagnetic value for locations of the electromagnetic source. The method identifies the cycle within the modeled electromagnetic output from which the matching model derived electromagnetic data was derived. For each of a plurality of display locations of the electromagnetic source, the method generates a display electromagnetic value for that display location based on the electromagnetic values of the modeled electromagnetic output of the identified cycle. The method generates a display representation of the electromagnetic source that includes, for each of the plurality of display locations, a visual representation of the display electromagnetic value for that display location. In some embodiments, the display representation has geometry based on anatomical parameters of the electromagnetic source of the patient. In some embodiments, the visual representation of a display electromagnetic value is a shading based on magnitude of the display electromagnetic value. In some embodiments, the visual representation of a display electromagnetic value is a color selected based on magnitude of the display electromagnetic value. In some embodiments, the visual representation of a display electromagnetic value is an intensity of a color based on magnitude of the display electromagnetic value. In some embodiments, the display electromagnetic value is based on a difference between the electromagnetic value at the start of the cycle and the electromagnetic value at the end of the cycle. In some embodiments, the method further, for each of a plurality of display intervals of the identified cycle, generates and outputs a display representation for that display interval. In some embodiments, the display representations are output in sequence to illustrate activations of the electromagnetic source over time. In some embodiments, when multiple instances of derived electromagnetic data match the patient derived electromagnetic data, the generating of the display electromagnetic value for a display location is based on a combination of the electromagnetic values of the modeled electromagnetic output from which the matching instances of the modeled derived electromagnetic data were derived. In some embodiments, the combination is an average that is weighted based on closeness of the match. In some embodiments, the electromagnetic source is a heart.

In some embodiments, a method performed by a computing system for generating a representation of a heart is provided. The method identifies a modeled cardiogram that is similar to a cardiogram of a patient. For each of a plurality of display locations of the heart, the method generates a display electromagnetic value for that display location based on an electromagnetic value of modeled electromagnetic output of a heart from which the modeled cardiogram is derived. The modeled electromagnetic output is generated using a computational model of the heart. The method generates a display representation of the heart that includes, for each of the plurality of display locations, a visual representation of the display electromagnetic value for that display location. In some embodiments, the display representation has geometry based on anatomical parameters of the heart of the patient. In some embodiments, the visual representation of a display electromagnetic value is an intensity of a color based on magnitude of the display electromagnetic value. In some embodiments, the displayed electromagnetic value is based on a difference between the electromagnetic value at the start of a model cycle within the modeled electromagnetic output and the electromagnetic value at the end of the model cycle. In some embodiments, the model cycle is selected based on similarity to a patient cycle within the cardiogram. In some embodiments, the method further, for each of a plurality of display intervals of the modeled electromagnetic output, generates and outputs a display representation for that display interval. In some embodiments, the display representations are output in sequence to illustrate activations of the electromagnetic source over time.

In some embodiments, a computing system for displaying a representation of electrical activation of a heart of a patient is provided. The computing system comprises one or more computer-readable storage mediums storing computer-executable instructions and one or more processors for executing the computer-executable instructions stored in the one or more computer-readable storage mediums. The instructions control the computing system to identify a modeled cardiogram that is similar to a cardiogram of the patient. The instructions control the computing system to generate a display representation of the heart that includes, for each of a plurality of display locations of the heart, a visual representation of a display value for that display location. The display values are based on modeled electromagnetic output of a heart from which the modeled cardiogram is derived. The modeled electromagnetic output is generated using a computational model of the heart. The instructions control the computing system to display the display representation. In some embodiments, the display representation has geometry based on anatomical parameters of the heart of the patient.

In some embodiments, a method performed by a computing system for generating a surface representation of an electromagnetic force generated by an electromagnetic source within a body is provided. The method accesses a sequence of vectors representing magnitude and direction of the electromagnetic force over time. The vectors are relative to an origin. For each pair of adjacent vectors, the method identifies a region based on the origin and the pair of vectors; generates a region representation of the region; and displays the generated region representation of the region. In some embodiments, the method displays a representation of the electromagnetic source so that the displayed region representations visually emanate from the electromagnetic source. In some embodiments, the origin is within the electromagnetic source. In some embodiments, the electromagnetic source is a heart and the sequence of vectors is a vectorcardiogram. In some embodiments, the electromagnetic force has cycles and the region representations for a cycle form the surface representation for that cycle, and the method further simultaneously displays surface representations for multiple cycles. In some embodiments, the generated region representations are displayed in sequence to illustrate changes in the electromagnetic force over time.

In some embodiments, a computing system for displaying a representation of vectorcardiogram is provided. The computing system comprises one or more computer-readable storage mediums storing computer-executable instructions and one or more processors for executing the computer-executable instructions stored in the one or more computer-readable storage mediums. The instructions control the computing system to generate a surface representation of a portion of the vectorcardiogram where the surface representation is bounded by points representing x, y, and z values of vectors of the portion of the vectorcardiogram; and display the generated surface representation. In some embodiments, the computer-executable instructions further control the computing system to display a representation of the heart from which the vectorcardiogram is derived so that the displayed surface representation visually emanates from the displayed representation of the heart. In some embodiments, the vectors are relative to an origin that is within the heart. In some embodiments, the vectorcardiogram has cycles and the computer-executable instructions further control the computing system to simultaneously display the surface representations for multiple cycles. In some embodiments, the generated surface representation is incrementally displayed to illustrate changes in the vectorcardiogram over time. In some embodiments, the surface representation is displayed on a region-by-region basis.

In some embodiments, a method performed by a computing system is provided for identifying simulated cardiograms that are similar to a patient cardiogram. The simulated cardiograms are generated based on simulated pacings and the patient cardiogram is generated based on a patient pacing of a patient. The method identifies first simulated cardiograms whose simulated pacings are similar to the patient pacing. The method identifies, from the first simulated cardiograms, second simulated cardiograms generated based on a simulated heart with a simulation orientation that is similar to a patient orientation of the patient's heart. The method identifies, from the second simulated cardiograms, third simulated cardiograms that represent action potentials that are similar to the action potential represented by the patient cardiogram. The method identifies, from the third simulated cardiograms, calibrated simulated cardiograms that represent conduction velocities that are similar to the conduction velocity represented by the patient cardiogram. In some embodiments, the method labels each calibrated simulated cardiogram with a configuration parameter used when generating that calibrated simulated cardiogram. The method trains training a classifier with the calibrated simulated cardiograms and the labels as training data. In some embodiments, the method applies the trained classifier to the patient cardiogram to identify the configuration parameter for the patient. In some embodiments, the cardiogram is an electrocardiogram. In some embodiments, the cardiogram is a vectorcardiogram. In some embodiments, a pacing includes a pacing location and a pacing rate. In some embodiments, the similarity of action potentials is based on cardiograms that are normalized in magnitude and in duration. In some embodiments, the similarity of conduction velocities is based on cardiograms that are normalized in magnitude. In some embodiments, the simulated cardiograms are identified from a collection of simulated cardiograms generated based on a simulated structural disease similar to a patient structural disease of the patient. In some embodiments, the simulated cardiograms are identified from a collection of simulated cardiograms based on the similarity of cardiac geometry of a simulated cardiogram to patient cardiac geometry of the patient. In some embodiments, the similarity of orientations is based on simulated cardiac vectors that are similar to patient cardiac vectors of the patient, the cardiac vectors for cardiac cycle phases at cardiac locations. In some embodiments, the simulated cardiograms are identified from a collection of simulated cardiograms generated based on a simulated disease substrate similar to a patient disease substrate of the patient.

In some embodiments, a method performed by a computing system is provided for identifying simulated cardiograms that are similar to a patient cardiogram. The method determines morphological similarity of simulated cardiograms to the patient cardiogram based on morphology. The method identifies similar simulated cardiograms based on morphological similarity. In some embodiments, the determining of morphological similarity includes determining orientation similarity of simulated cardiograms to the patient cardiogram based on orientation and determining electrophysiological similarity of simulated cardiograms to the patient cardiogram. In some embodiments, the method determines pacing similarity of simulated cardiograms to the patient cardiogram wherein the identifying is further based on pacing similarity. In some embodiments, the electrophysiological similarity is based on action potential similarity and conduction velocity similarity. In some embodiments, the method trains a classifier using training data that includes the identified similar simulated cardiograms labeled with a configuration parameter. In some embodiments, the method determines cardiac geometry similarity of simulated cardiograms to the patient cardiogram wherein the identifying is further based on cardiac geometry similarity. In some embodiments, the cardiac geometry similarity is based on structural disease similarity and measurement similarity. In some embodiments, the method determines disease substrate similarity of simulated cardiograms to the patient cardiogram wherein the identifying is further based on disease substrate similarity.

In some embodiments, one or more computing systems is provided for identifying simulated cardiograms that are similar to a patient cardiogram. The one or more computing systems includes one or more computer-readable storage mediums for storing computer-executable instructions and one or more processors for executing the computer-executable instructions stored in the one or more computer-readable storage mediums. The instructions control the one or more computing systems to determine orientation similarity of simulated cardiograms to the patient cardiogram based on orientation, determine electrophysiological similarity of simulated cardiograms to the patient cardiogram, and identify similar simulated cardiograms based on orientation similarity and electrophysiological similarity. In some embodiments, the computer-executable instructions further control the one or more computing systems to determine disease substrate similarity of the simulated cardiograms to the patient cardiogram and to identify similar simulated cardiograms is further based on disease substrate similarity. In some embodiments, the computer-executable instructions further control the one or more computing systems to determine pacing similarity of the simulated cardiograms to the patient cardiogram and identify similar simulated cardiograms is further based on pacing similarity. In some embodiments, the electrophysiological similarity is based on action potential similarity and conduction velocity similarity. In some embodiments, the action potential similarity is based on cardiograms that are normalized in magnitude and in duration, and the conduction velocity similarity is based on cardiograms that are normalized in magnitude. In some embodiments, the computer-executable instructions further control the one or more computing systems to train a classifier using training data that includes the identified similar simulated cardiograms labeled with a configuration parameter.

In some embodiments, a method performed by a computing system is provided for mapping simulated cardiograms to patient cardiograms of a patient. The method identifies simulated cardiograms that match the patient cardiograms based on configuration parameters and pacing locations. The method trains a mapping function to map the identified simulated cardiograms to the patient cardiograms. The method applies the trained mapping function to simulated cardiograms to generate transformed simulated cardiograms. In some embodiments, the method trains a patient-specific model classifier based on the transformed simulated cardiograms.

In some embodiments, a method performed by one or more computing systems is provided for calibrating the orientation of a simulated vectorcardiogram ("VCG") to a patient VCG. The method displays a representation of the simulated VCG and representation of the patient VCG. The method receives from a user an indication to rotate one of the displayed representations. The method receives from the user an indication that the rotated representation and the other representation are aligned. The method generates a transformation matrix based on rotation of the rotated representation. In some embodiments, the representations displayed within a torso. In some embodiments, a representation of the simulated VCG is displayed with a representation of a heart based on cardiac geometry associated with the simulated VCG.

In some embodiments, a method performed by a computing system is provided for identifying simulated electromagnetic outputs of an electromagnetic source that are similar to a patient electromagnetic output of an electromagnetic source of a patient. The simulated electromagnetic outputs are generated based on simulated pacings of the electromagnetic source. The patient electromagnetic output is generated based on a patient pacing of the electromagnetic source of the patient. The method identifies pacing-similar simulated electromagnetic outputs whose simulated pacings are similar to the patient pacing. The method identifies configuration-similar simulated electromagnetic outputs generated based on a simulated electromagnetic source with a simulation configuration parameter that is similar to a patient configuration parameter of the electromagnetic source of the patient. The method identifies action-potential-similar simulated electromagnetic outputs that represent action potentials that are similar to the action potential represented by the patient electromagnetic source. The method identifies, from the identified pacing-similar, configuration-similar, and action-potential-similar simulated cardiograms, calibrated simulated electromagnetic outputs that represent conduction velocities that are similar to the conduction velocity represented by the patient electromagnetic output. In some embodiments, the patient pacing is performed using an invasive pacing device that administers electromagnetic pulses from inside the electromagnetic source. In some embodiments, the invasive pacing device is a catheter. In some embodiments, the patient pacing is performed using a non-invasive pacing device that administers electromagnetic pulses from outside the electromagnetic source. In some embodiments, the non-invasive pacing device generates an electromagnetic field to pace the electromagnetic source of the patient. In some embodiments, the non-invasive pacing device is a magnetic resonance scanner. In some embodiments, the identified calibrated simulated electromagnetic outputs are pacing-similar, configuration-similar, and action-potential-similar electromagnetic outputs.

A method performed by one or more computing systems for identifying a potential ablation pattern for an EM source of a patient is provided. The method accesses a patient EM output of the EM source. The method identifies non-ablation pattern information of a non-ablation pattern simulation. The non-ablation pattern information is identified based on similarity of simulated EM output of the non-ablation pattern simulation to the patient EM output. The method identifies an ablation pattern based on similarity of non-ablation pattern information to ablation pattern information associated with an ablation pattern simulation. The method outputs an indication of the identified ablation pattern as the potential ablation pattern for the EM source of the patient. In some embodiments, the EM source is a heart and the potential ablation pattern is for treating an arrhythmia of the patient. In some embodiments, the similarity is based on a mapping of mapping information associated with the non-ablation pattern simulation to the identified ablation pattern. In some embodiments, the mapping information includes the simulated EM output. In some embodiments, the mapping is a direct mapping. In some embodiments, the mapping is an indirect mapping. In some embodiments, the non-ablation pattern information includes a non-ablation pattern source configuration of the non-ablation pattern simulation and the ablation pattern information includes an ablation pattern source configuration of the ablation pattern simulation. In some embodiments, the indication of the identified ablation pattern is output to an ablation device. In some embodiments, the ablation device is a stereotactic body radiation therapy device. In some embodiments, the indication of the identified ablation pattern is displayed. In some embodiments, the identified ablation pattern is superimposed on an image of the EM source. In some embodiments, the image is based on an anatomical parameter collected as part of an ablation procedure. In some embodiments, the method further identifies the non-ablation pattern simulation from a calibrated collection of simulations.

In some embodiments, a method performed by one or more computing systems is provided for generating a mapping function to map patient information of a patient to an ablation pattern for treating arrhythmia of the patient. The method accesses ablation pattern simulations. Each ablation pattern simulation is generated based on a simulated source configuration and an ablation pattern. The simulated source configuration includes a simulated source location. For each ablation pattern simulation, the method generates a simulated feature vector that includes features based on the simulated source configuration but not based on the simulated source location and a feature based on a simulated cardiogram generated from a non-ablation pattern simulation based on the simulated source configuration but not based on an ablation pattern, and further labels the simulated feature vector with the simulated source location and the ablation pattern of that ablation pattern simulation. The method trains a classifier using the feature vectors and labels as training data. In some embodiments, the method further generates a patient feature vector with features based on a patient source configuration of the patient but not based on a source location and a feature based on a patient cardiogram of the patient, and further applies the classifier to the patient feature vector to identify a source location and an ablation pattern for treating the patient. In some embodiments, the method further outputs an indication of the identified source location and the identified ablation pattern for treating the patient. In some embodiments, the patient is treated using stereotactic body radiation therapy.

In some embodiments, one or more computing systems is provided for identifying an ablation pattern for a heart of a patient. The one or more computing systems comprise one or more computer-readable storage mediums storing computer-executable instructions and one or more processors for executing the computer-executable instructions stored in the one or more computer-readable storage mediums. The instructions, when executed control the one or more computing systems to, identify a simulated cardiogram generated from a non-ablation pattern simulation of a model library of non-ablation pattern simulations. Each non-ablation pattern simulation is generated based on a computational model of the heart and a heart configuration that includes a simulated source location. The instructions, when executed control the one or more computing systems to, identify an ablation pattern and a simulated source location associated with the simulated cardiogram, the ablation pattern associated with an ablation pattern simulation generated based on a computational model of the heart, based on a heart configuration that includes a source location, and based on the identified ablation pattern, the identified ablation pattern identified based on a mapping of the identified simulated cardiogram to the identified ablation pattern. The instructions, when executed control the one or more computing systems to, direct an ablation therapy for the patient based on the identified simulated source location and the identified ablation pattern. In some embodiments, the ablation therapy is for treating an arrhythmia. In some embodiments, the computer-executable instructions to direct an ablation therapy output to an ablation device an indication of the identified simulated source location and the identified ablation pattern. In some embodiments, the ablation device is a stereotactic body radiation therapy device. In some embodiments, the ablation device is a neuromodulation device. In some embodiments, the computer-executable instructions to direct an ablation therapy display an indication of the identified simulated source location of the heart configuration and the identified ablation pattern. In some embodiments, the computer-executable instructions to identify an ablation pattern identify multiple ablation patterns and the instructions to direct an ablation therapy output an indication of the identified simulated source location and the identified ablation patterns. In some embodiments, the heart configuration includes an anatomical parameter derived from an image of the patient collected as part of the ablation therapy.

In some embodiments, a method of treating a heart of a patient. The method includes identifying a source location within the heart of the patient and an ablation pattern. The identification is based on ablation pattern simulations. Each ablation pattern simulation is based on a source location (e.g., rotor location) and an ablation pattern. The identifying is based on a patient cardiogram of the patient. The method includes positioning a neuromodulation device at a target site of the heart based on the identified source location. The method includes applying energy based on the identified ablation pattern to the target site of the heart using the neuromodulation device. In some embodiments, the neuromodulation device is an ablation catheter and applying energy to the target site includes applying radiofrequency energy that ablates neural or myocardial structures at the target site. In some embodiments, the neuromodulation device is a cryoablation catheter and applying energy to the target site comprises applying cooling energy that cryoablates neural or myocardial structures at the target site. In some embodiments, the neuromodulation device comprises an implantable pulse generator and applying energy to the target site comprises applying electrical energy to neural or myocardial structures at the target site. In some embodiments, the neuromodulation device comprises a stereotactic body radiation therapy device and applying energy to the target site includes applying radiation to neural or myocardial structures at the target site.

In some embodiments, a method of treating a patient is provided. The method includes identifying a source location of an arrhythmia within the heart of the patient and an ablation pattern by directing a computing system to identify a simulated cardiogram that is similar to a patient cardiogram of the patient, the simulated cardiogram generated from a non-ablation pattern simulation of a model library of non-ablation pattern simulations. Each non-ablation pattern simulation is generated based on a computational model of the heart and a simulated heart configuration that includes a simulated source location. Each heart configuration of a simulation mapped to a simulated cardiogram generated based on the simulation. The identifying of the source location further directs the computing system to identify a simulated source location and an ablation pattern based on the identified simulated cardiogram. The simulated source location and the ablation pattern used in generating an ablation pattern simulation. The ablation pattern simulation is generated based on the computational model of the heart, based on the heart configuration that includes the simulated source location, and based on the ablation pattern. The method includes positioning a neuromodulation device at a target site based on the identified simulated source location and applying energy based on the identified ablation pattern using the positioned neuromodulation device. In some embodiments, the neuromodulation device is a stereotactic body radiation therapy device. the positioning includes a computing system sending instructions to the stereotactic body radiation therapy device. In some embodiments, the method includes identifying anatomical parameters of the patient from images collected by the stereotactic body radiation therapy device. In some embodiments, the neuromodulation device is an ablation catheter and applying energy includes applying radiofrequency energy that ablates neural or myocardial structures at the target site. In some embodiments, the neuromodulation device is a cryoablation catheter and applying energy comprises applying cooling energy that cryoablates neural or myocardial structures at the target site. In some embodiments, the neuromodulation device comprises an implantable pulse generator and applying energy comprises applying electrical energy to neural or myocardial structures at the target site.

In some embodiments, a method of treating a patient is provided. The method includes identifying a source location of an arrhythmia within the heart of the patient by directing a computing system to identify a simulated cardiogram that is similar to a patient cardiogram of the patient. The simulated cardiogram is generated from a simulation of a model library of simulations. Each simulation generated based on a computational model of the heart and a simulated heart configuration that includes a simulated source location. Each heart configuration of a simulation is mapped to a simulated cardiogram generated based on that simulation. The method further directs a computing system to identify a simulated source location of a simulated heart configuration used in generating the simulation from which the identified simulated cardiogram was generated. The method includes positioning a neuromodulation device at a target site based on the identified simulated source location. The method includes applying energy to the target site using the positioned neuromodulation device.

In some embodiments, a method for generating a model library of simulations of electrical activations of a heart. The method includes accessing simulated heart configurations that include a simulated source location and an ablation pattern. For each simulated heart configuration, the method includes running a simulation based on the simulated heart configuration. The method includes designating the simulation as being successful when the simulation does not result in an arrhythmia. In some embodiments, the method includes mapping ablation patterns of simulated heart configurations used to generate successful simulations to simulated cardiograms generated based on simulations based on simulated heart configurations that do not include an ablation pattern.

In some embodiments, a method performed by a computing system for storing results of an ablation procedure is provided. The method applies a computational targeting procedure to identify an ablation target of a heart of a patient. The computational targeting procedure is based on mappings of cardiograms to source locations of an arrhythmia. The computational targeting procedure inputs a cardiogram of the patient and outputs the source location as the ablation target. The method receives the result of the ablation procedure performed on the patient based on the identified ablation target. The method generates an ablation procedure record of the result of the ablation procedure. The ablation procedure record identifies the patient and interested parties in the ablation procedure and includes a reference to the result of the ablation procedure. The method published the ablation procedure record for recording in a distributed ledger for access by permissioned parties. In some embodiments, the distributed ledger is a blockchain. In some embodiments, one or more interested party stores the result of the ablation procedure and an electronic medical record of the patient. In some embodiments, an interested party that stores the result of an ablation procedure controls access by a party to the result. In some embodiments, the ablation procedure is one of a plurality of ablation procedures performed on the patient during an ablation study of the patient and the ablation procedure records for the patient are stored in the same block of the distributed ledger. In some embodiments, each block of the distributed ledger stores ablation procedure records of only one patient. In some embodiments, the method further provides to a miner of the distributed ledger access to the computational targeting procedure based on mining activity of the miner. In some embodiments, the method further provides a token to the miner based on the mining activity and exchanging the token for access to the computational targeting procedure. In some embodiments, the distributed ledger is a blockchain and further comprising selecting a miner for mining a block based on a proof-of-stake consensus algorithm. In some embodiments, the computational targeting procedure includes applying a classifier that inputs the cardiogram of the patient and outputs the source location, the classifier trained using the mappings as training data. In some embodiments, the mappings are generated using a computational model of the heart that models electromagnetic output of the heart over time based on a heart configuration that includes a source location. In some embodiments, the mappings include cardiograms collected from patients. In some embodiments, the method further provides a contributor access to the computational targeting procedure based on the contributor providing computational resources for training the classifier. In some embodiments, the computational targeting procedure includes identifying a cardiogram of the mappings that is similar to the cardiogram of the patient and selecting the source location of the identified mapping as the ablation target. In some embodiments, the mappings are generated using a computational model of the heart that models electromagnetic output of the heart over time based on a heart configuration that includes a source location. In some embodiments, mappings include cardiograms collected from patients. In some embodiments, the mappings are generated using a computational model of the heart that models electromagnetic output of the heart over time based on a heart configuration that includes a source location. In some embodiments, the method further provides a contributor access to the computational targeting procedure based on the contributor providing computational resources for generating the mappings. In some embodiments, mappings include cardiograms collected from patients. In some embodiments, the method further provides a contributor access to the computational targeting procedure based on the contributor providing cardiograms collected from patients.

In some embodiments, a computing system for storing results of a procedure performed on a patient. The computing system comprises one or more computer-readable storage mediums for storing computer-executable instructions and one or more processors for executing the computer-executable instruction stored in the one or more computer-readable storage medium. The instructions when executed control the computing system to perform as follows. The computing system receives the result of the procedure performed on an electromagnetic source of the patient based on a procedure target. The procedure target is identified by applying a computational targeting procedure that inputs electromagnetic data derived from the electromagnetic source of the patient and outputs a procedure target. The computing system generates a procedure record that includes a reference to the result of the procedure. The computing system publishes the procedure record in a distributed ledger for access by permissioned parties. In some embodiments, the distributed ledger is a blockchain. In some embodiments, the procedure is one of a plurality of procedures performed on the patient during a procedure study of the patient. In some embodiments, the procedure is one of a plurality of procedures performed on the patient during a study of the patient and the procedure records for the patient are stored in the same block of the distributed ledger. In some embodiments, the computing system further provides to a miner of the distributed ledger access to the computational targeting procedure based on mining activity of the miner. In some embodiments, the instructions further provide a token to the miner based on the mining activity and exchange the token for access to the computational targeting procedure. In some embodiments, wherein the computational targeting procedure includes instructions to apply a classifier that inputs the electromagnetic data of the patient and outputs the target location, the classifier trained using the mappings as training data. In some embodiments, the mappings are generated using a computational model of the electromagnetic source that models electromagnetic output of the electromagnetic source over time based on an electromagnetic source configuration that includes a source location. In some embodiments, the mappings include electromagnetic data collected from patients. In some embodiments, the computing system further provides a contributor access to the computational targeting procedure based on the contributor providing computational resources for training the classifier. In some embodiments, the computational targeting procedure includes identifying electromagnetic output of the mappings that is similar to the electromagnetic output of the patient and selecting the source location of the identified mapping as the procedure target. In some embodiments, the mappings are generated using a computational model of the electromagnetic source that models electromagnetic output of the electromagnetic source over time based on an electromagnetic source configuration that includes a source location. In some embodiments, the mappings include electromagnetic data collected from patients. In some embodiments, the mappings are generated using a computational model of the electromagnetic source that models electromagnetic output of the electromagnetic source over time based on an electromagnetic configuration that includes a source location. In some embodiments, the computing system provides a contributor access to the computational targeting procedure based on the contributor providing computational resources for generating the mappings. In some embodiments, the mappings include electromagnetic data collected from patients. In some embodiments, the computing system provides a contributor access to the computational targeting procedure based on the contributor providing electromagnetic data collected from patients.

In some embodiments, a method performed by one or more computing systems is provided for identifying simulated electromagnetic data of an electromagnetic source that are similar to a patient electromagnetic data of a patient electromagnetic source of a patient. The simulated electromagnetic data is generated based on simulated pacing locations of the electromagnetic source and the patient electromagnetic data generated based on a patient pacing locations of the patient electromagnetic source. The identifies simulated electromagnetic data whose simulated pacing locations are similar to the patient pacing locations. The method identifies simulated electromagnetic data generated based on with a simulation configuration parameter that is similar to a patient configuration parameter of the electromagnetic source of the patient. The method identifies simulated electromagnetic data generated based on simulated action potentials that are similar to patient action potentials of the patient. The method identifies simulated electromagnetic data generated based on simulated conduction velocities that are similar to patient conduction velocities of the patient. The method generates a calibrated collection of simulated electromagnetic data based on the identified simulated electromagnetic data. In some embodiments, the method identifies simulated electromagnetic data that is similar to patient electromagnetic data of the patient. In some embodiments, the pacing lead is placed with an invasive pacing device that administers electromagnetic pulses from inside the electromagnetic source. In some embodiments, the invasive pacing device is a catheter, an implantable cardioverter, or a pacemaker. In some embodiments, the patient pacing is performed using a non-invasive pacing device that administers electromagnetic pulses from outside the electromagnetic source. In some embodiments, the non-invasive pacing device generates an electromagnetic field to pace the electromagnetic source of the patient. In some embodiments, the non-invasive pacing device is a magnetic resonance device. In some embodiments, the electromagnetic source is a heart.

In some embodiments, a method is provided for identifying simulated electromagnetic data of an electromagnetic source that are similar to a patient electromagnetic data of a patient electromagnetic source of a patient. The method, for each of a plurality of patient pacing locations of the patient electromagnetic source, includes pacing the patient electromagnetic source by sending electromagnetic impulses to the pacing location and collecting the patient electromagnetic data during the pacing. The method includes submitting patient pacing locations and patient electromagnetic data collected while pacing at patient pacing locations to one or more computing devices that generate a calibrated collection of simulations. The one or more computing devices identifies simulations of a model library of simulations of the electromagnetic source based on similarity between pacing locations, source configurations, action potentials, conduction velocities, and patient electromagnetic data of the simulations and of the patient. The identified simulations form the calibrated collection of simulations. In some embodiments, the method includes submitting to the one or more computing devices a patient cardiogram of the patient and receiving an indication of a source configuration parameter of a simulation of the calibrated collection based on similarity between the simulated cardiograms and the patient cardiogram. In some embodiments, the method includes, for each patient pacing location, placing a pacing lead at that patient pacing location wherein the electromagnetic impulse is sent via the pacing lead. In some embodiments, the placing of a patient pacing lead is performed using an invasive pacing device that administers electrical impulses from inside the patient electromagnetic source. In some embodiments, wherein the invasive pacing device is a catheter, an implantable cardioverter, or a pacemaker. In some embodiments, the electromagnetic source is a heart. In some embodiments, the electromagnetic impulses are generated via a non-invasive pacing device. In some embodiments, the non-invasive pacing device is a magnetic resonance device. In some embodiments, the method includes receiving from the one or more computing devices an indication of a source parameter of a source configuration identified based on the calibrated collection. In some embodiments, the source parameter is a source location. In some embodiments, the method includes conducting a procedure on the patient electromagnetic source based on the source location. In some embodiments, two of the patient pacing locations are distant pacing location.

In some embodiments, a method performed by one or more computing systems is provided for augmenting image data with a patient source location of a heart disorder of a heart of a patient. The method receives image data that includes a 3D image of the heart of the patient and a patient substrate location. The method receives a patient cardiogram of the patient. The method identifies a patient source location of a heart disorder for the patient based on the patient cardiogram and mappings of cardiograms to source locations. The method adds the patient source location to the image data to generate the augmented image data. In some embodiments, the method identifies the patient source location by applying a machine learning algorithm that inputs a cardiogram and outputs a source location wherein the machine learning algorithm having been trained based on the mappings. In some embodiments, the method identifies the patient source location by comparing the patient cardiogram to the cardiograms of the mappings to identify a cardiogram that is similar to the patient cardiogram. In some embodiments, the mappings include mappings based on one or more of clinical data collected from actual patients, simulations of electrical activity of a heart based on varying configuration parameters, and simulations of electrical activity of the patient heart based on configuration parameters derived from the patient. In some embodiments, the method further, prior to identifying the patient source location, calibrates the mappings to the patient heart so that the identifying is based on the calibrated mappings. In some embodiments, the calibrating is based on geometry of the heart of the patient. In some embodiments, the calibrating is based on a cardiogram of the patient. In some embodiments, the method further provides the augmented image data to a planning system for informing care of the patient based on the image data. In some embodiments, the 3D image is included in a file in a standard format. In some embodiments, the standard format is a Digital Imaging and Communications in Medicine ("DICOM") format. In some embodiments, the patient substrate location and patient source locations are included in the file as metadata. In some embodiments, the patient substrate location and the patient source location are external to the file. In some embodiments, the patient substrate location and the source location are superimposed on the 3D image of the file. In some embodiments, the method further displays the 3D image with the patient substrate location and the source location superimposed on the displayed 3D image.

In some embodiments, one or more computing systems are provided for augmenting image data with a patient source location of a disorder of an organ of a patient. The one or more computing systems include one or more computer-readable storage mediums that stores computer-executable instructions for controlling the one or more computing systems and one or more processors for executing the computer-executable instructions stored in the one or more computer-readable storage mediums. The instructions receive image data that includes a 3D image of the organ of the patient and a patient substrate location. The 3D image is in a Digital Imaging and Communications in Medicine ("DICOM") format. The instructions receive patient derived EM data derived from EM output of the organ of the patient. The instruction identify a patient source location of a disorder of the organ of the patient based on the patient derived EM data and mappings of derived EM data to source locations. The instructions add the patient source location to the image data to generate augmented image data. In some embodiments, the organ is a heart, derived EM data is a cardiogram, and the patient derived EM data is a non-sinus rhythm cardiogram. In some embodiments, the instructions that identify the patient source location apply a machine learning algorithm that inputs a cardiogram and outputs a source location wherein the machine learning algorithm was trained based on the mappings. In some embodiments, the instructions that identify the patient source location compare the patient cardiogram to the cardiograms of the mappings to identify a cardiogram that is similar to the patient cardiogram. In some embodiments, the mappings include mappings based on one or more of clinical data collected from actual patients, simulations of electrical activity of a heart based on varying configuration parameters, and simulations of electrical activity of the patient heart based on configuration parameters derived from the patient. In some embodiments, the instructions further, prior to identification of the patient source location, calibrate the mappings to the patient heart so that the identification is based on the calibrated mappings. In some embodiments, the instructions further provide the augmented image data to a planning system for informing care of the patient based on the annotated image data. In some embodiments, the instructions further display the 3D image with the patient substrate location and the patient source location superimposed on the displayed 3D image.

In some embodiments, one or more computing systems are provided for augmenting image data with a patient source location of a heart disorder of a heart of a patient. The one or more computing systems include one or more computer-readable storage mediums that stores computer-executable instructions for controlling the one or more computing systems and one or more processors for executing the computer-executable instructions stored in the one or more computer-readable storage mediums. The instructions access image data that includes a 3D image of the heart of the patient and a patient substrate location and access a patient cardiogram of the patient. The instructions identify a patient source location of a heart disorder for the patient based on the patient cardiogram. The instructions augment the image data with the patient source location to generate the augmented image data. In some embodiments, the identification is based on mappings of cardiograms to source locations. In some embodiments, the instructions that identify the patient source location apply a machine learning algorithm that inputs a cardiogram and outputs a source location wherein the machine learning algorithm was trained based on the mappings. In some embodiments, the instructions that identify the patient source location compare the patient cardiogram to the cardiograms of the mappings to identify a cardiogram that is similar to the patient cardiogram. In some embodiments, the mappings include mappings based on one or more of clinical data collected from actual patients, simulations of electrical activity of a heart based on varying configuration parameters, and simulations of electrical activity of the patient heart based on configuration parameters derived from the patient. In some embodiments, the instructions, prior to identification of the patient source location, calibrate the mappings to the patient heart so that the identifying is based on the calibrated mappings. In some embodiments, the instructions provide the augmented image data to a planning system for informing care of the patient based on the image data. In some embodiments, the instructions provide the augmented image data to a system that supports treating patients. In some embodiments, the instructions provide the augmented image data to a planning system for informing care of the patient based on the image data. In some embodiments, the image data is a Digital Imaging and Communications in Medicine ("DICOM") format. In some embodiments, the image data includes a patient substrate volume indicating volume of the substrate at the substrate location and the instructions further access a 4D image of the heart of the patient, the 4D image including a sequence of 3D images collected during a cycle of the heart and add a substrate mask to the 4D image at the substrate location with the substrate volume. In some embodiments, the patient substrate location is specified by a 3D coordinate and the patient substrate volume is represented by an indication of a radius for each dimension of the 3D coordinate. In some embodiments, the 4D image has voxels with intensity values and the instructions further include instructions to set the intensity values of voxels corresponding to the substrate mask to a substrate intensity value. In some embodiments, the identification of the patient source location is based on mappings of cardiograms to source locations, wherein the patient source location is a source location mapped to a cardiogram that is similar to the patient cardiogram, wherein each cardiogram is associated with a 3D image, and wherein the instructions further include instructions to adjust the patient source location based on differences in the geometry of a heart represented by the 3D image associated with a cardiogram that is similar to the patient cardiogram and the geometry of the heart of the patient represented by the 3D image of the heart of the patient. In some embodiments, the adjustment is based on aligning designated locations of the geometries. In some embodiments, the designated location of the 3D image of the heart of the patient is specified by fiducial markers added to that 3D image. In some embodiments, the instructions further include instructions to identify a patient source volume associated with patient source location; access a 4D image of the heart of the patient, the 4D image including a sequence of 3D images collected during a cycle of the heart; and add a source mask to the 4D image at the patient source location with the patient source volume. In some embodiments, the patient source location is specified by a 3D coordinate and the patient source volume is represented by an indication of a radius for each dimension of the 3D coordinate. In some embodiments, the 4D image has voxels with intensity values and the instructions further include instructions to set the intensity values of voxels corresponding to the source mask to a source intensity value.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

In some embodiments, the MLMO system can be employed to classify electromagnetic output of an electromagnetic source based on different types of classifications. For example, the classifications may include location of a heart disorder (e.g., rotor location), scar or fibrosis or pro-arrhythmic substrate location, heart geometry (e.g., ventricle orientation), and so on. To generate the training data, the MLMO system labels the training data with the classification type that the classifier is to generate. Accordingly, the invention is not limited except as by the appended claims.

The invention claimed is:

1. A method performed by one or more computing systems for augmenting image data with a patient source location of a heart disorder of a heart of a patient, the method comprising:
running simulations of electrical activity of simulated hearts that each specifies a source location and simulated cardiac geometry; each simulation generates a sequence of voltage solutions, each voltage solution represented as three-dimensional (3D) mesh based on a simulated cardiac geometry with voltages associated with vertices of the 3D mesh;
for each simulation, generating a mapping of a simulated cardiogram to that simulation, the simulated cardiogram generated based on the voltage solutions of that simulation;
receiving image data that includes a 3D image of the heart of the patient and that includes a patient substrate location;
receiving a patient cardiogram of the patient;
identifying a patient source location of a heart disorder for the patient based on the patient cardiogram and the mappings of simulated cardiograms to simulations;
adding the patient source location to the image data to generate the augmented image data; and
displaying a 3D graphic of a heart based on the image data, the 3D graphic having a coloring based on a weighted accumulation of differences in voltages of the voltage solutions over time.

2. The method of claim 1 further comprising, prior to identifying the patient source location, calibrating the mappings to the patient heart so that the identifying is based on the calibrated mappings.

3. The method of claim 2 wherein the calibrating is based on geometry of the heart of the patient.

4. The method of claim 1 further comprising providing the augmented image data to a planning system for informing care of the patient based on the image data.

5. The method of claim 1 wherein the 3D image is included in a file in a standard format.

6. The method of claim 5 wherein the standard format is a Digital Imaging and Communications in Medicine ("DICOM") format.

7. The method of claim 6 wherein the patient substrate location and patient source locations are included in the file as metadata.

8. The method of claim 6 wherein the patient substrate location and the patient source location are external to the file.

9. The method of claim 6 wherein the patient substrate location and the source location are superimposed on the 3D image.

10. One or more computing systems for augmenting image data with a patient source location of a disorder of an organ of a patient, the one or more computing systems comprising:
   one or more computer-readable storage mediums that stores computer-executable instructions for controlling the one or more computing systems to:
      receive image data that includes a 3D image of the organ of the patient and a patient substrate location, the 3D image being in a Digital Imaging and Communications in Medicine ("DICOM") format;
      receive patient derived electromagnetic ("EM") data derived from EM output of the organ of the patient;
      for each of a plurality of source locations,
         run a simulation of EM output of the organ based on a patient-specific source configuration based on an organ geometry derived from the 3D image, wherein at least some of the simulations are bootstrapped with the EM output of another simulation; and
         generate derived EM data based on the simulated EM output;
      identify a patient source location of a disorder of the organ of the patient based on similarity of the patient derived EM data to a simulated derived EM data and the source locations of the simulation; and
      add the patient source location to the image data to generate augmented image data; and
   one or more processors for executing the computer-executable instructions stored in the one or more computer-readable storage mediums.

11. The one or more computing systems of claim 10 wherein the organ is a heart, derived EM data is a cardiogram, and the patient derived EM data is a non-sinus rhythm cardiogram.

12. The one or more computing systems of claim 11 wherein the instructions further display the 3D image with the patient substrate location and the patient source location superimposed on the displayed 3D image.

13. One or more computing systems for generating and displaying image data augmented with a patient source location of a heart disorder of a heart of a patient, the one or more computing systems comprising:
   one or more computer-readable storage mediums for storing computer-executable instructions for controlling the one or more computing systems to:
      access image data that includes a 3D image of the heart of the patient and a patient substrate location;
      access a patient cardiogram of the patient;
      identify a patient source location of a heart disorder for the patient based on the patient cardiogram;
      augment the image data with the patient source location to generate the augmented image data, wherein the identification of the patient source location is based on mappings of cardiograms to source locations, wherein the patient source location is a source location mapped to a cardiogram that is similar to the patient cardiogram, wherein each cardiogram is associated with a 3D image;
      adjust the patient source location based on differences in the geometry of a heart represented by the 3D image associated with a cardiogram that is similar to the patient cardiogram and the geometry of the heart of the patient represented by the 3D image of the heart of the patient; and
      display the 3D image of the heart of the patient that includes an indication of the patient substrate location and an indication of the adjusted patient source location to inform treatment of the patient; and
   one or more processors for executing the computer-executable instructions stored in the one or more computer-readable storage mediums.

14. The one or more computing systems of claim 13 wherein the identification is based on mappings of cardiograms to source locations.

15. The one or more computing systems of claim 14 wherein the mappings include mappings based on one or more of clinical data collected from actual patients, simulations of electrical activity of a heart based on varying configuration parameters, and simulations of electrical activity of the patient heart based on configuration parameters derived from the patient.

16. The one or more computing systems of claim 14 wherein the instructions, prior to identification of the patient source location, calibrate the mappings to the patient heart so that the identifying is based on the calibrated mappings.

17. The one or more computing systems of claim 13 wherein the instructions provide the augmented image data to a planning system for informing care of the patient based on the image data.

18. The one or more computing systems of claim 13 wherein the instructions provide the augmented image data to a system that supports treating patients.

19. The one or more computing systems of claim 13 wherein the image data is a Digital Imaging and Communications in Medicine ("DICOM") format.

20. The one or more computing systems of claim 13 wherein the adjustment is based on aligning designated locations of the geometries.

21. The one or more computing systems of claim 20 wherein the designated location of the 3D image of the heart of the patient is specified by fiducial markers added to that 3D image.

* * * * *